United States Patent
Josse et al.

(10) Patent No.: US 11,833,059 B2
(45) Date of Patent: Dec. 5, 2023

(54) EXPANDABLE INTER-BODY DEVICE, EXPANDABLE PLATE SYSTEM, AND ASSOCIATED METHODS

(71) Applicant: Warsaw Orthopedic, Inc., Warsaw, IN (US)

(72) Inventors: Loic Josse, Palm Beach Gardens, FL (US); Bertrand Peultier, Les Hopitaux Neufs (FR); Jerome Nayet, Saint-Genis-Pouilly (FR)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/391,403

(22) Filed: Aug. 2, 2021

(65) Prior Publication Data
US 2022/0133499 A1 May 5, 2022

Related U.S. Application Data

(63) Continuation-in-part of application No. 17/246,932, filed on May 3, 2021, which is a continuation-in-part
(Continued)

(30) Foreign Application Priority Data

Nov. 5, 2020 (WO) .................. PCT/IB2020/000932
Nov. 5, 2020 (WO) .................. PCT/IB2020/000942
Nov. 5, 2020 (WO) .................. PCT/IB2020/000953

(51) Int. Cl.
*A61F 2/44* (2006.01)
*A61B 17/80* (2006.01)
*A61F 2/30* (2006.01)

(52) U.S. Cl.
CPC .......... *A61F 2/4455* (2013.01); *A61F 2/4425* (2013.01); *A61F 2002/30507* (2013.01);
(Continued)

(58) Field of Classification Search
CPC .......... A61F 2/44; A61F 2/442; A61F 2/4425; A61F 2/4455; A61F 2/4611;
(Continued)

(56) References Cited

U.S. PATENT DOCUMENTS 1,677,337 A    7/1928 Grove
3,847,154 A   11/1974 Nordin
(Continued)

FOREIGN PATENT DOCUMENTS

CN    107 137 166 A     9/2017
DE     44 16 605 C1     6/1995
(Continued)

OTHER PUBLICATIONS

International Search Report and Written Opinion in Application No. PCT/US2022/016831 dated Sep. 29, 2022.
(Continued)

*Primary Examiner* — Jessica Weiss
(74) *Attorney, Agent, or Firm* — FOX ROTHSCHILD LLP

(57) ABSTRACT

The present disclosure provides for spinal implants and plates including, for example, expandable plates deployable between a contracted position and an expanded position. The expandable plate may include an expandable body including a first portion and a second portion. The first portion may include a receiving cavity facing the proximal end, and a first through aperture extending in the proximal-to-distal direction. The second portion may include a lower end having a size and shape that corresponds to the receiving cavity, and a second through aperture extending in the proximal-to-distal direction. The expandable plate may include a locking screw and a nut. In at least some embodiments, in a locked position, the locking screw extends through the first through aperture and second through aper-
(Continued)

ture, and is secured to the nut. In various embodiments, in an expanded position the first portion and second portion are farther away from one another relative to a contracted position.

20 Claims, 119 Drawing Sheets

Related U.S. Application Data of application No. 17/123,889, filed on Dec. 16, 2020, now Pat. No. 11,564,724.

(52) U.S. Cl.
CPC ............... *A61F 2002/30594* (2013.01); *A61F 2002/443* (2013.01)

(58) Field of Classification Search
CPC .. A61F 2002/30507; A61F 2002/30594; A61F 2002/443
USPC ........ 623/17.11–17.16; 606/70–71, 280–299
See application file for complete search history.

(56) References Cited

U.S. PATENT DOCUMENTS

| | | | |
|---|---|---|---|
| 4,401,112 A | 8/1983 | Rezaian |
| 4,553,273 A | 11/1985 | Wu |
| 4,636,217 A | 1/1987 | Ogilvie et al. |
| 4,716,894 A | 1/1988 | Lazzeri et al. |
| 4,759,769 A | 7/1988 | Hedman et al. |
| 5,059,193 A | 10/1991 | Kuslich |
| 5,171,278 A | 12/1992 | Pisharodi |
| 5,228,811 A | 7/1993 | Potter |
| 5,284,483 A | 2/1994 | Johnson et al. |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,653,763 A | 8/1997 | Errico et al. |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,941,885 A | 8/1999 | Jackson |
| 5,971,987 A | 10/1999 | Huxel et al. |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,491,724 B1 | 12/2002 | Ferree |
| 6,520,991 B2 | 2/2003 | Huene |
| 6,520,993 B2 | 2/2003 | James et al. |
| 6,524,238 B2 | 2/2003 | Velikaris et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,188,626 B2 | 3/2007 | Foley et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,255,700 B2 | 8/2007 | Kaiser et al. |
| 7,316,532 B2 | 1/2008 | Matthys-Mark |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,635,366 B2 * | 12/2009 | Abdou ............... A61B 17/8872 606/71 |
| 7,637,909 B2 | 12/2009 | Lechot et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,824,428 B2 | 11/2010 | Mikkonen et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |

(56) References Cited

U.S. PATENT DOCUMENTS

| | | |
|---|---|---|
| 7,875,076 B2 | 1/2011 | Mathieu et al. |
| 7,883,542 B2 | 2/2011 | Zipnick |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |
| 8,262,570 B2 | 9/2012 | White et al. |
| 8,262,662 B2 | 9/2012 | Beardsley et al. |
| 8,262,710 B2 * | 9/2012 | Freedman .......... A61B 17/7059 606/280 |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,898 B2 * | 11/2013 | Prandi ................ A61B 17/8061 606/280 |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,285 B2 * | 5/2014 | Lewis ................ A61B 17/8875 606/86 R |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,548 B2 * | 7/2015 | Matityahu .......... A61B 17/8061 |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |

(56) References Cited

U.S. PATENT DOCUMENTS

| | | |
|---|---|---|
| 9,364,341 B2 | 6/2016 | Gowan |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Arnin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Arnin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |

(56) References Cited

U.S. PATENT DOCUMENTS

| | | |
|---|---|---|
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |

(56) References Cited

U.S. PATENT DOCUMENTS

| | | |
|---|---|---|
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 11,285,014 B1 | 3/2022 | Josse et al. |
| 11,376,134 B1 | 7/2022 | Dewey et al. |
| 11,723,780 B2 | 8/2023 | Seifert et al. |
| 2002/0045943 A1 | 4/2002 | Uk |
| 2002/0045945 A1 | 4/2002 | Liu et al. |
| 2002/0055741 A1* | 5/2002 | Schlapfer ............... A61B 17/80 606/71 |
| 2002/0116066 A1 | 8/2002 | Chauvin et al. |
| 2002/0128713 A1 | 9/2002 | Ferree |
| 2002/0151976 A1 | 10/2002 | Foley et al. |
| 2002/0183762 A1 | 12/2002 | Anderson et al. |
| 2003/0050701 A1 | 3/2003 | Michelson |
| 2003/0130739 A1 | 7/2003 | Gerbec et al. |
| 2003/0163132 A1* | 8/2003 | Chin ............... A61B 17/7059 606/280 |
| 2004/0102778 A1* | 5/2004 | Huebner ........... A61B 17/1735 606/71 |
| 2004/0172134 A1 | 9/2004 | Berry |
| 2004/0186570 A1 | 9/2004 | Rapp |
| 2004/0193158 A1 | 9/2004 | Lim et al. |
| 2004/0204713 A1* | 10/2004 | Abdou ............... A61B 17/8004 606/301 |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2005/0209698 A1 | 9/2005 | Gordon et al. |
| 2005/0228398 A1 | 10/2005 | Rathbun et al. |
| 2006/0122701 A1 | 6/2006 | Kiester |
| 2006/0129244 A1 | 6/2006 | Ensign |
| 2006/0260446 A1 | 11/2006 | Chang |
| 2006/0276901 A1 | 12/2006 | Zipnick et al. |
| 2007/0173840 A1* | 7/2007 | Huebner ............... A61B 17/80 606/304 |
| 2007/0218750 A1 | 9/2007 | Corrao et al. |
| 2007/0233150 A1 | 10/2007 | Blain et al. |
| 2007/0270859 A1 | 11/2007 | Companioni et al. |
| 2008/0058804 A1 | 3/2008 | Lechot et al. |
| 2008/0132959 A1 | 6/2008 | Mikkonen et al. |
| 2008/0140207 A1 | 6/2008 | Olmos et al. |
| 2009/0024158 A1 | 1/2009 | Viker |
| 2009/0292361 A1 | 11/2009 | Lopez |
| 2010/0076440 A1 | 3/2010 | Pamichev et al. |
| 2010/0082109 A1 | 4/2010 | Greenhalgh et al. |
| 2010/0152853 A1 | 6/2010 | Kirschman |
| 2010/0191336 A1 | 7/2010 | Greenhalgh |
| 2010/0211176 A1 | 8/2010 | Greenhalgh |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0153020 A1 | 6/2011 | Abdelgany et al. |
| 2011/0218572 A1 | 9/2011 | Lechmann et al. |
| 2012/0004732 A1 | 1/2012 | Goel et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0143195 A1 | 6/2012 | Sander |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215313 A1 | 8/2012 | Saidha et al. |
| 2012/0215316 A1 | 8/2012 | Mohr et al. |
| 2013/0158664 A1 | 6/2013 | Palmatier et al. |
| 2013/0184823 A1 | 7/2013 | Malberg |
| 2013/0190876 A1 | 7/2013 | Drochner et al. |
| 2013/0211526 A1 | 8/2013 | Alheidt et al. |
| 2013/0226191 A1 | 8/2013 | Thoren et al. |
| 2013/0231747 A1 | 9/2013 | Olmos et al. |
| 2013/0304136 A1 | 11/2013 | Gourlaouen-Preissler et al. |
| 2013/0317312 A1 | 11/2013 | Eastlack et al. |
| 2014/0018816 A1 | 1/2014 | Fenn et al. |
| 2014/0107790 A1 | 4/2014 | Combrowski |
| 2014/0114321 A1 | 4/2014 | Davenport et al. |
| 2014/0114420 A1 | 4/2014 | Robinson |
| 2014/0148904 A1 | 5/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0249631 A1 | 9/2014 | Weiman |
| 2014/0277471 A1 | 9/2014 | Gray et al. |
| 2014/0277473 A1 | 9/2014 | Perrow |
| 2014/0277487 A1 | 9/2014 | Davenport et al. |
| 2014/0277500 A1 | 9/2014 | Logan et al. |
| 2014/0303674 A1 | 10/2014 | Sasing |
| 2014/0364855 A1 | 12/2014 | Stoll et al. |

(56) References Cited

U.S. PATENT DOCUMENTS

| | | |
|---|---|---|
| 2015/0223945 A1 | 8/2015 | Weiman et al. |
| 2015/0230931 A1 | 8/2015 | Greenhalgh |
| 2015/0238236 A1 | 8/2015 | Sasing |
| 2015/0354635 A1 | 12/2015 | McClymont et al. |
| 2015/0374507 A1 | 12/2015 | Wolters et al. |
| 2016/0008924 A1 | 1/2016 | Canourgues et al. |
| 2016/0022434 A1 | 1/2016 | Robinson |
| 2016/0051373 A1* | 2/2016 | Faulhaber ............ A61F 2/4455 623/17.16 |
| 2016/0058571 A1 | 3/2016 | McLaughlin et al. |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0095718 A1 | 4/2016 | Burkhardt et al. |
| 2016/0199073 A1 | 7/2016 | Nino et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0112630 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1 | 1/2018 | Hessler et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116891 A1 | 5/2018 | Beale et al. |
| 2018/0193160 A1 | 7/2018 | Hsu et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0325574 A1 | 11/2018 | Bjork et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133779 A1 | 5/2019 | McLaughlin et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262009 A1 | 8/2019 | Cheng |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328539 A1 | 10/2019 | Suh et al. |
| 2019/0328540 A1 | 10/2019 | Seifert et al. |
| 2019/0329388 A1 | 10/2019 | Erickson et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0069316 A1 | 3/2020 | DeSoutter et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |

(56) References Cited

U.S. PATENT DOCUMENTS

| | | |
|---|---|---|
| 2020/0214754 A1 | 7/2020 | Bowen et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2022/0015924 A1 | 1/2022 | Freedman et al. |
| 2022/0047312 A1 | 2/2022 | Seykora et al. |
| 2022/0133336 A1 | 5/2022 | Tsai et al. |
| 2022/0133498 A1 | 5/2022 | Josse et al. |
| 2022/0387184 A1* | 12/2022 | Josse .................. A61F 2/30749 |
| 2023/0027836 A1* | 1/2023 | Predick .............. A61B 17/8023 |

FOREIGN PATENT DOCUMENTS

| | | |
|---|---|---|
| EP | 0 767 636 A1 | 4/1997 |
| EP | 0 880 950 A1 | 12/1998 |
| EP | 0 857 042 B1 | 11/2001 |
| EP | 1 442 732 A1 | 8/2004 |
| EP | 1 124 512 B1 | 9/2004 |
| EP | 1 107 711 B1 | 10/2004 |
| EP | 1 506 753 A1 | 2/2005 |
| EP | 1 459 711 B1 | 7/2007 |
| EP | 2954860 A2 | 12/2015 |
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| GB | 2 377 387 A | 1/2003 |
| KR | 102192022 B1 | 12/2020 |
| WO | 92/14423 A1 | 9/1992 |
| WO | 97/ 00054 A1 | 1/1997 |
| WO | 99/ 26562 A1 | 6/1999 |
| WO | 99/66867 A1 | 12/1999 |
| WO | 00/12033 A1 | 3/2000 |
| WO | 00/25706 A1 | 5/2000 |
| WO | 00/ 49977 A1 | 8/2000 |
| WO | 02/19952 A1 | 3/2002 |
| WO | 03/105673 A2 | 12/2003 |
| WO | 2006116850 A1 | 11/2006 |
| WO | 2012139022 A2 | 10/2012 |
| WO | 2014/133755 A1 | 9/2014 |
| WO | 2015063721 A1 | 5/2015 |
| WO | 2015198335 A1 | 12/2015 |
| WO | 2016057940 A1 | 4/2016 |
| WO | 2017/168208 A1 | 10/2017 |
| WO | 2018049227 A1 | 3/2018 |
| WO | 2021055323 A1 | 3/2021 |

OTHER PUBLICATIONS

International Search Report and Written Opinion, PCT/IB2020/000942, dated Aug. 10, 2021.
International Search Report and Written Opinion in Application No. PCT/US2022/016809 dated Jul. 27, 2022.
International Search Report and Written Opinion in Application No. PCT/US2022/027695 dated Jul. 27, 2022.
International Search Report and Written Opinion in Application No. PCT/US2022/030094 dated Sep. 16, 2022.
International Search Report and Written Opinion in Application No. PCT/US2022/027200 dated Aug. 19, 2022.
International Search Report, and Written Opinion for Application. No. PCT/US2019/019067, dated Jun. 3, 2019.
International Search Report and Written Opinion for Application No. PCT/US2019/019060, dated Jun. 5, 2019.
International Search Report and Written Opinion, PCT/IB2020/000932, dated Jul. 29, 2021.
Chinese Office Action in Application No. 201980010758.4 dated Jun. 16, 2023.
Chinese Office Action in Application No. 201980010758.4 dated Sep. 16, 2023.

* cited by examiner

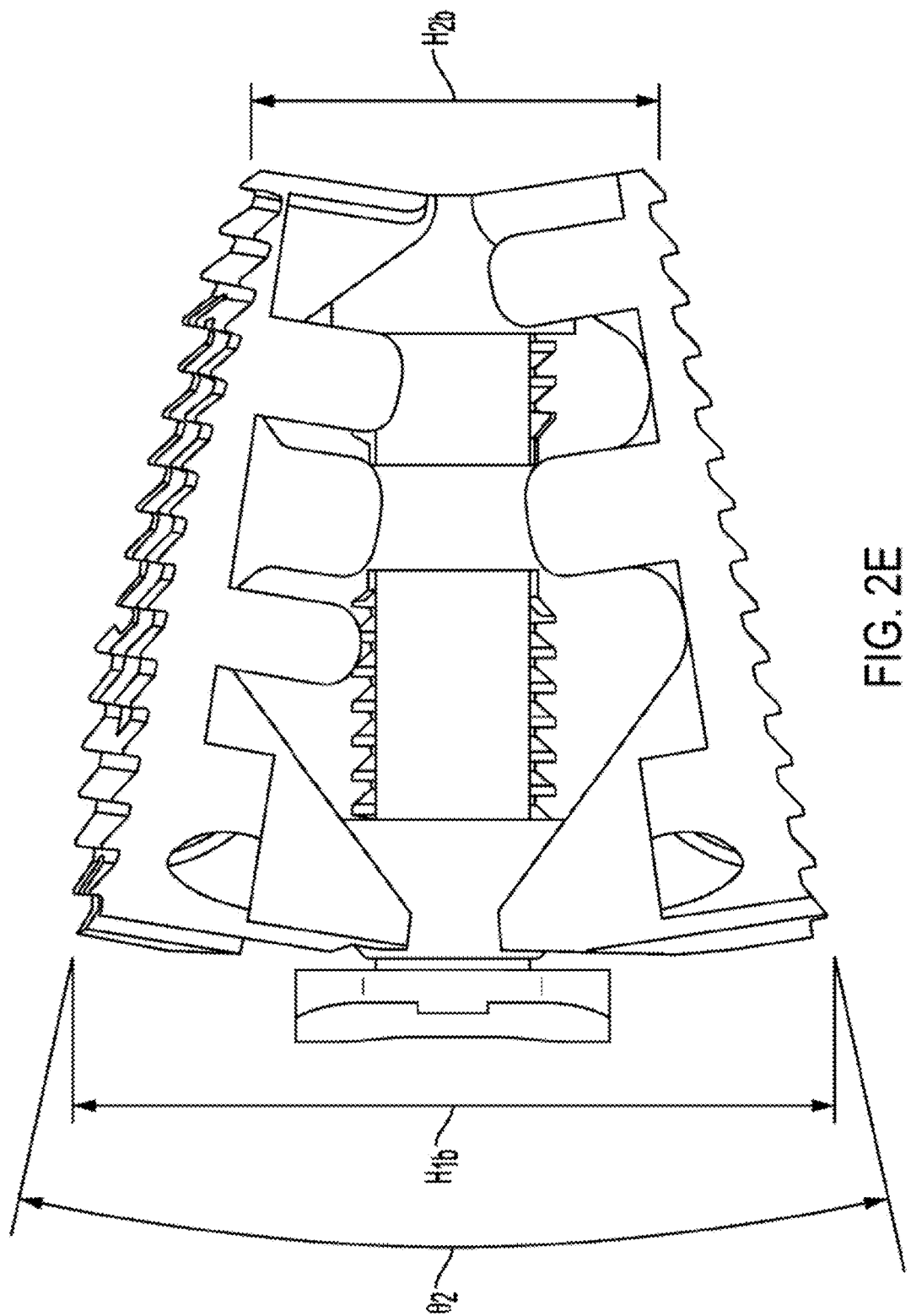

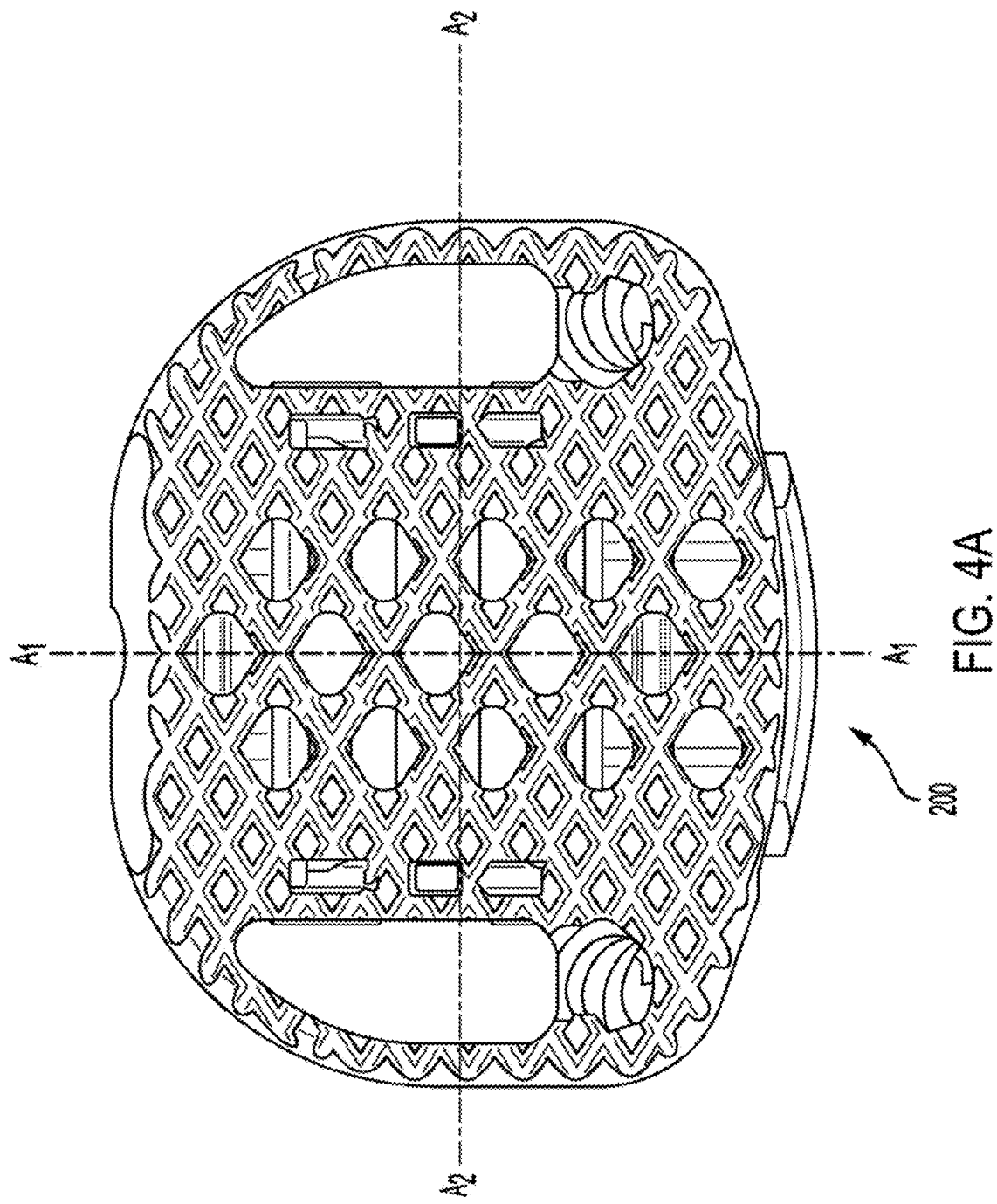

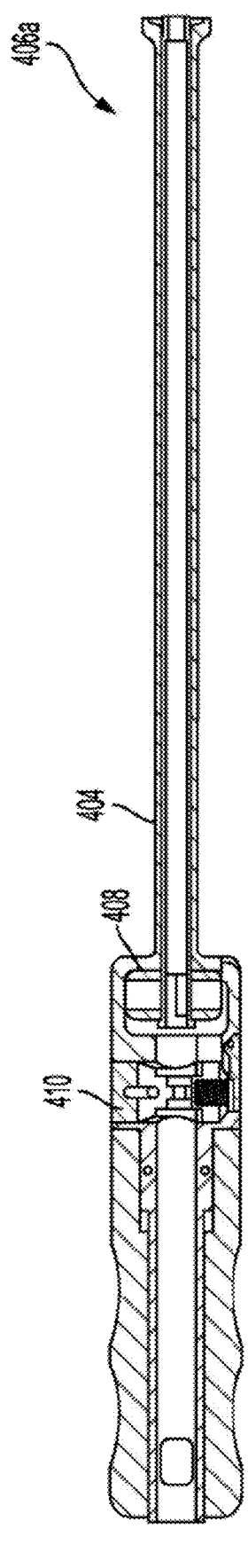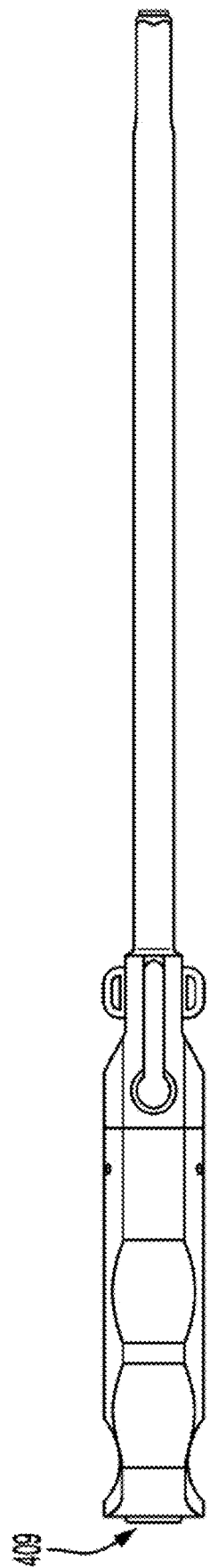

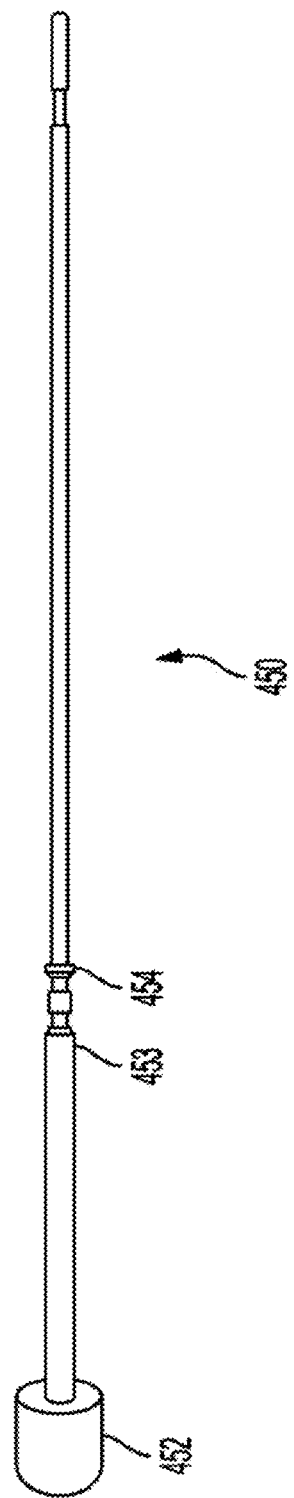

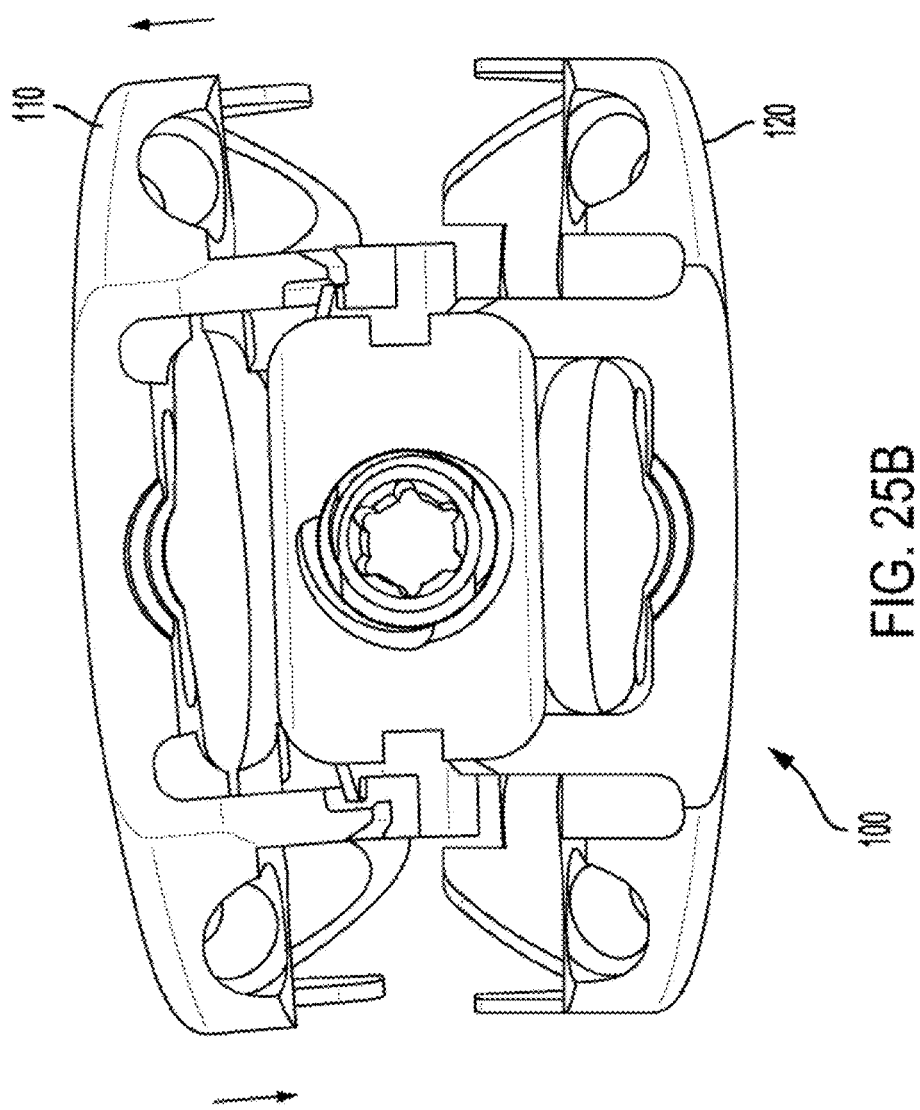

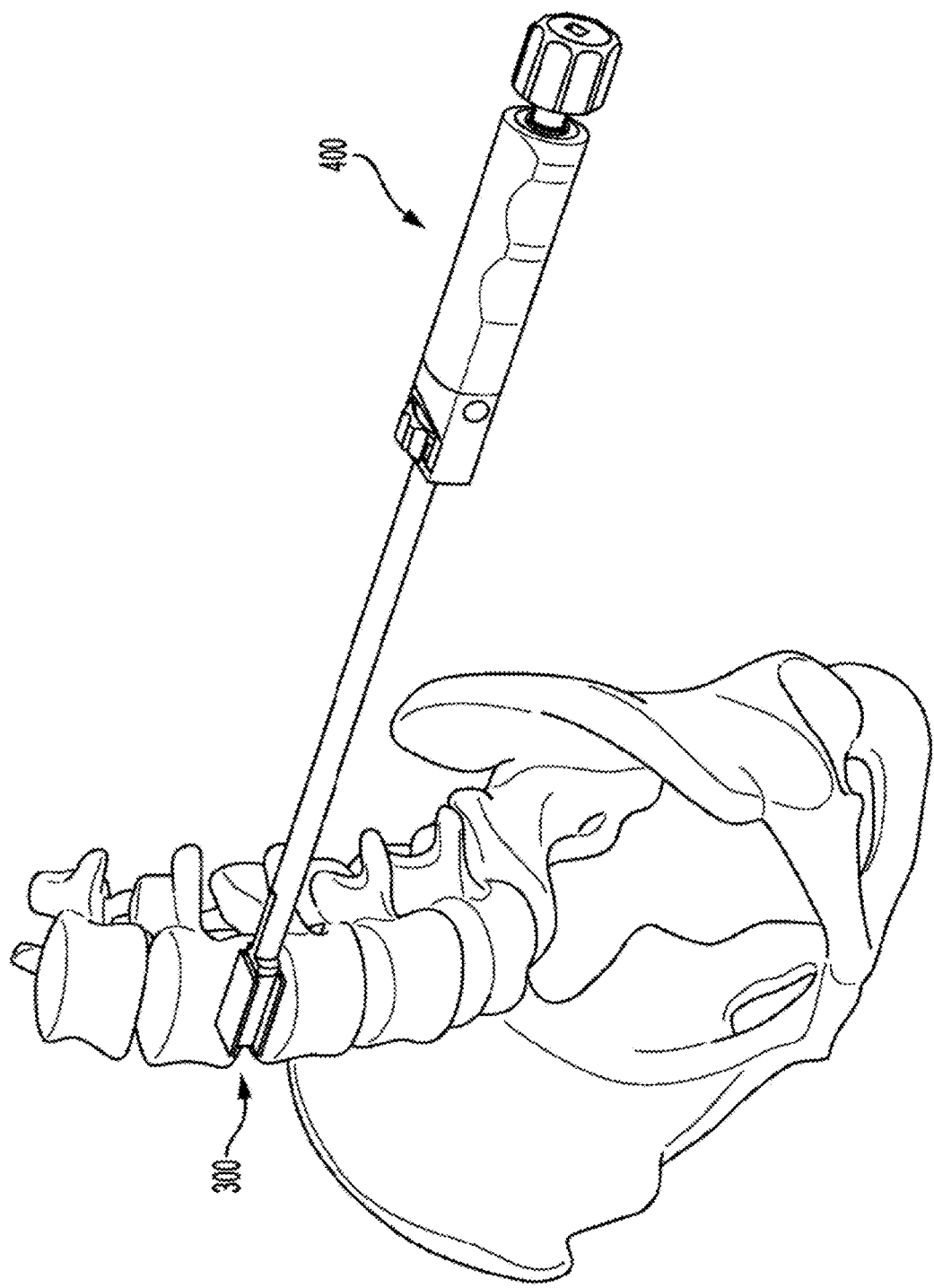

1600

EXPANDABLE INTER-BODY DEVICE, EXPANDABLE PLATE SYSTEM, AND ASSOCIATED METHODS

CROSS-REFERENCE TO RELATED APPLICATIONS

This application is a continuation in part of U.S. patent application Ser. No. 17/246,932, titled Expandable Inter-Body Device, System, and Method, filed May 3, 2021 which is a continuation in part of U.S. patent application Ser. No. 17/123,889, titled Expandable Inter-Body Device, System, and Method, filed Dec. 16, 2020 which claims priority to and incorporates by reference co-related patent applications, PCT/IB2020/000953, titled Expandable Inter-Body Device, System, and Method, filed Nov. 5, 2020; PCT/IB2020/000932, titled Screwdriver and Complimentary Screws, filed Nov. 5, 2020; and PCT/IB2020/000942, titled Expandable Inter-Body Device, System, and Method, filed Nov. 5, 2020. The contents of each are hereby incorporated in their entireties.

FIELD

The present disclosure generally relates to medical devices for the treatment of musculoskeletal disorders, and more particularly to a surgical device that includes an expandable spinal implant, systems for implanting and manipulating the expandable spinal implant, and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, they may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody devices may be introduced to a space between adjacent vertebral bodies (the interbody space) to properly space the vertebral bodies and provide a receptacle for bone growth promoting materials, e.g., grafting.

More recently, interbody devices have been introduced that provide additional capability beyond static spacing of the vertebral bodies. For example, some devices have expansion capability such that the implant may be introduced to the interbody space in a collapsed state and then expanded to produce additional spacing and, in some cases, introduce or restore curvature to the spine by expanding selectively. However, many existing expandable interbody designs have limited ranges of expansion.

An additional problem exists related to subsidence of spinal surfaces due to existing interbody devices having inadequately-sized load-bearing surfaces. In the case of expandable devices, the loads on the load-bearing surfaces, including loads generated during expansion of the implant, are often significant. An expandable implant with relatively large surface areas is needed to bear the loads, including the loads generated during implant expansion, in an attempt to avoid a need for follow-on surgery due to subsidence of spinal surfaces.

A further problem is instability of existing expandable interbody devices as they are expanded. Often, the load-bearing surfaces move relative to one another, as well as relative to an inserter, as the interbody device is expanded such that there is a risk of undesired shifts in the positioning of the interbody device within the interverterbral space. Additionally, and depending at least partly on the particular insertion technique employed, anatomical features such as the iliac crest and rib cage pose challenges to the adjustment of inter-body designs in situ.

The present disclosure seeks to address these and other shortcomings in the existing relevant arts.

SUMMARY

The techniques of this disclosure generally relate to highly adjustable interbody devices that are expandable to selectively increase/decrease a spacing distance between endplates of the interbody device and adjustable to selectively increase/decrease an angle of inclination between endplates of the interbody device. Additionally, at least in some embodiments, the techniques of this disclosure relate to a plate that may further be an expandable plate configured to be positioned external to and adjacent to a disc space that is securely connected to an adjustable interbody device configured to be positioned within the disc space. For example, an interbody device may be positioned between superior and inferior endplates and the expandable plate may be securely connected to the interbody device and be positioned outside of the disc space such that bone screws may selectively penetrate into the superior and inferior endplates.

The details of one or more aspects of the disclosure are set forth in the accompanying drawings and the description below. Other features, objects, and advantages of the techniques described in this disclosure will be apparent from the description and drawings, and from the claims.

In one aspect, the disclosure provides for an expandable plate and/or expandable implant deployable between a contracted position and an expanded position. In various embodiments, the expandable plate may include an expandable body having a thickness in a proximal-to-distal direction between a proximal end and a distal end, a width in a widthwise direction, and a height in a longitudinal direction, for example. In various embodiments, the expandable body may include a first portion and a second portion, for example. In various embodiments, the first portion may include a receiving cavity facing the proximal end, and a first through aperture extending in the proximal-to-distal direction, for example. In various embodiments, the second portion may include a lower end having a size and shape that corresponds to the receiving cavity, and a second through aperture extending in the proximal-to-distal direction, for example. In various embodiments the expandable plate may include a locking screw and a nut, for example. In at least some embodiments, in a locked position, the locking screw extends through the first through aperture and second through aperture, and is secured to the nut, for example. In at least some embodiments, the expandable plate may be configured to couple to an implant, such as a spinal implant for example.

In another aspect, the present disclosure provides for a spinal implant. The spinal implant may include a superior endplate having a first outside surface and a first inside surface opposite the first outside surface, the first inside surface including first proximal ramps and first distal ramps disposed opposite the first proximal ramps, for example. The spinal implant may include an inferior endplate including a second outside surface and a second inside surface opposite the second outside surface, the second outside surface including second proximal ramps and second distal ramps disposed opposite the second proximal ramps, for example. In various embodiments, an endplate including a plurality of bone screw apertures and a central aperture may be provided, for example. In various embodiments, a moving mechanism may be coupled to the superior endplate and the inferior endplate, for example. Additionally, the moving mechanism may include a buttress block and a first trolley and a second trolley disposed on opposite sides of the buttress block, and a rotatable first set screw and a rotatable second set screw opposite the first set screw, for example. In various embodiments, the first set screw and second set screw may be configured to rotate in a first rotation direction and a second rotation direction about a rotation axis projecting in a longitudinal direction of the moving mechanism, for example. Additionally, in various embodiments, the first trolley may be operably coupled to the first set screw and movable toward and away the buttress block in the longitudinal direction of the moving mechanism by rotation of the first set screw along the rotation axis, for example. Additionally, the second trolley may be operably coupled to the second set screw and movable toward and away the buttress block in the longitudinal direction of the moving mechanism by rotation of the second set screw along the rotation axis, for example. In various embodiments, the moving mechanism may be configured to operably adjust a spacing between the superior and inferior endplates upon simultaneous rotation of the first and second set screws along the rotation axis, for example. In various embodiments, the moving mechanism may be configured to operably adjust an angle of inclination between the superior and inferior endplates upon rotating either one of the first set screw and second set screw along the rotation axis, for example. In various embodiments, the spinal implant further comprises an expandable plate deployable between a contracted position and an expanded position, for example. In various embodiments, the expandable body may have a thickness in a proximal-to-distal direction between a proximal end and a distal end, a width in a widthwise direction, and a height in a longitudinal direction, for example. In various embodiments, the expandable body may include a first portion and a second portion, for example. In various embodiments, the first portion may include a receiving cavity facing the proximal end, and a first through aperture extending in the proximal-to-distal direction, for example. In various embodiments, the second portion includes a lower end having a size and shape that corresponds to the receiving cavity, and a second through aperture extending in the proximal-to-distal direction, for example. In various embodiments, a locking screw and a nut may be provided, for example. In at least some embodiments, in a locked position, the locking screw extends through the first through aperture and second through aperture, and is secured to the nut, for example. At least in some embodiments, the expandable plate is disposed proximate the anterior endplate, for example.

In another aspect, a method for installing an expandable plate and an expandable spinal implant, is disclosed. The method may include the steps of providing an expandable spinal implant and providing a plate that may further be an expandable plate, for example. In various embodiments, the expandable plate may include an expandable body having a thickness in a proximal-to-distal direction between a proximal end and a distal end, a width in a widthwise direction, and a height in a longitudinal direction, for example. In various embodiments, the expandable body may include a first portion and a second portion, for example. In various embodiments, the first portion may include a receiving cavity facing the proximal end, and a first through aperture extending in the proximal-to-distal direction, for example. In various embodiments, the second portion may include a lower end having a size and shape that corresponds to the receiving cavity, and a second through aperture extending in the proximal-to-distal direction, for example. In various embodiments the expandable plate may include a locking screw and a nut, for example. In at least some embodiments, in a locked position, the locking screw extends through the first through aperture and second through aperture, and is secured to the nut, for example. In at least some embodiments, the expandable plate may be configured to couple to an implant, such as a spinal implant for example. The method may further include the steps of inserting the expandable spinal implant between adjacent boney structures and installing a first bone screw that extends through either one of the first bone screw aperture and second bone screw aperture, for example.

BRIEF DESCRIPTION OF DRAWINGS

FIGS. 2E and 2F are side views of the embodiment of FIGS. 1A and 1B in an expanded position in accordance with the principles of the present disclosure;

FIG. 4A is a top down view of the embodiment of FIGS. 2A-2C in accordance with the principles of the present disclosure;

FIGS. 19A-19C are side views of first surgical tool and adjustment rod of an expandable spinal implant system, respectively, in accordance with the principles of the present disclosure;

FIG. 25A and FIG. 25B illustrate a first bent position and a second bent position, respectively, of one embodiment of an expandable spinal implant in accordance with the principles of the present disclosure;

FIG. 34 is a perspective view of one embodiment of an expandable spinal implant system in accordance with the principles of the present disclosure;

DETAILED DESCRIPTION

Figure 1A:
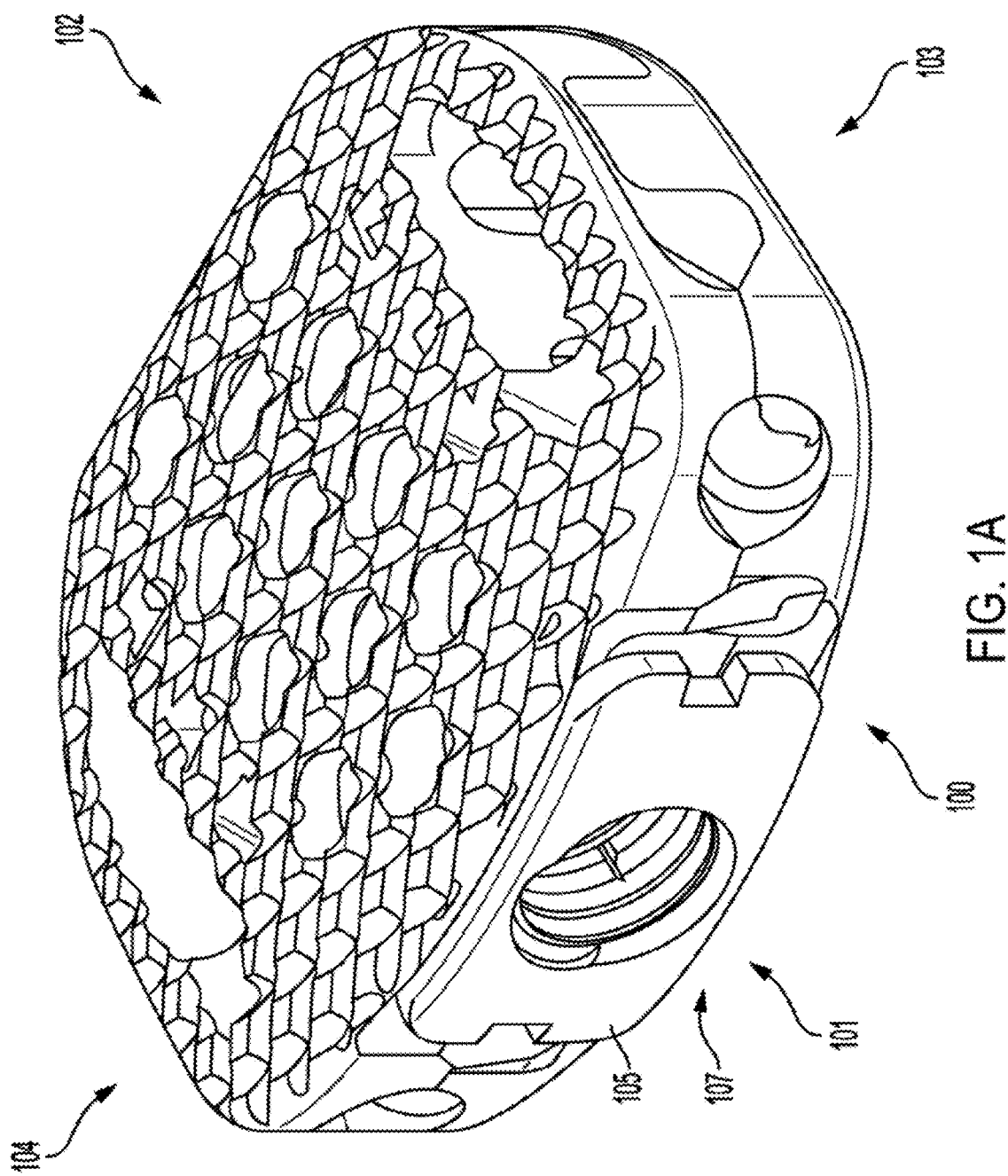
FIG. 1A is a perspective view of one embodiment of an expandable spinal implant in a fully contracted position in accordance with the principles of the present disclosure.

The exemplary embodiments of, for example, an anterior expandable inter-body device, lateral expandable inter-body device, inter-body device systems, and inter-body device methods of use are discussed in terms of medical devices for the treatment of musculoskeletal disorders and more particularly, in terms of various inter-body devices suitable as spinal implants for anterior surgical techniques, oblique surgical techniques, and lateral surgical techniques. Exemplary embodiments are also discussed with related emphasis on specialized adjustment instruments such as, for example, an instrument capable of adjusting a spacing of the aforementioned various interbody devices between adjacent vertebrates of a spine by expansion and contraction as well as adjusting an angle of inclination with respect to the coronal plane and/or sagittal plane of a patient. Disclosed devices and systems may be capable of adjusting the curvature of a patient's spine for lordosis correction and a kyphosis correction. Likewise, an instrument capable of installing various anchoring screws is described in conjunction with disclosed inter-body devices.

As used herein, standard anatomical terms of location have their ordinary meaning as they would be understood by a person of ordinary skill in the art unless clearly defined or explained otherwise. It should be understood that various aspects disclosed herein may be combined in different combinations than the combinations specifically presented in the description and accompanying drawings. For example, characteristics of one embodiment may be combined or substituted with characteristics of another different embodiment unless those characteristics are clearly explained as being mutually exclusive. It should also be understood that, depending on the example, certain acts or events of any of the processes or methods described herein may be performed in a different sequence, may be added, merged, or left out altogether (e.g., all described acts or events may not be necessary to carry out the disclosed techniques and methods). In addition, while certain aspects of this disclosure are described as being performed by a single module or unit for purposes of clarity, it should be understood that the techniques of this disclosure may be performed by a combination of units or modules associated with, for example, a medical device.

In some embodiments, the present system includes an expandable spinal implant suitable for insertion for oblique techniques, postero-lateral procedures and/or transforaminal lumbar interbody fusions (sometimes referred to as TLIF procedures), direct posterior (sometimes referred to as PLIF procedures), direct lateral (sometimes referred to as DLIF procedures), anterior lumbar interbody fusions (sometimes referred to as ALIF procedures), or variations of these procedures, in which the present implant is inserted into an intervertebral space and then expanded in order to impart and/or augment a lordotic and/or kyphotic curve of the spine.

In some embodiments, the spinal implant system may also be employed to restore and/or impart sagittal balance to a patient by increasing and/or restoring an appropriate lordotic and/or kyphotic angle between vertebral bodies at a selected level where the spinal implant is implanted and expanded. Additionally, some embodiments may also be employed to restore and/or impart coronal balance for correction of, for example, scoliosis. In the various embodiments described, the spinal implant system may be useful in a variety of complex spinal procedures for treating spinal conditions beyond one-level fusions. Furthermore, the spinal implant system described in the enclosed embodiments may also be used as a fusion device with an expandable height for tailoring the implant to a particular interbody disc space to restore the spacing between adjacent vertebral bodies and facilitate spinal fusion between the adjacent vertebral bodies.

In some embodiments, and as mentioned above, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral oblique, and/or antero lateral oblique approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components, e.g., a "proximal end" of an end plate and a "proximal end" of a wedge, indicate similar spatial orientation and/or positioning, i.e., that each "proximal end" is situated on or directed towards the same end of the device. Further, the use of various spatial terminology herein should not be interpreted to limit the various insertion techniques or orientations of the implant relative to the positions in the spine.

As used in the specification and including the appended claims, "treating" or "treatment" of a disease or condition refers to performing a procedure that may include administering one or more drugs, biologics, bone grafts (including allograft, autograft, xenograft, for example) or bone-growth promoting materials to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise. The term "bone growth promoting material" as used herein may include, but is not limited to: bone graft (autograft, allograft, xenograft) in a variety of forms and compositions (including but not limited to morselized bone graft); osteoinductive material such as bone morphogenetic proteins (BMP) (including but not limited to INFUSE® available from Medtronic) and alternative small molecule osteoinductive substances; osteoconductive materials such as demineralized bone matrix (DBM) in a variety of forms and compositions (putty, chips, bagged (including but not limited to the GRAFTON® family of products available from Medtronic)); collagen sponge; bone putty; ceramic-based void fillers; ceramic powders; and/or other substances suitable for inducing, conducting or facilitating bone growth and/or bony fusion of existing bony structures. Such bone growth promoting materials may be provided in a variety of solids, putties, liquids, colloids, solutions, or other preparations suitable for being packed or placed into or around the various implants 100, 200, 300 and embodiments described herein.

The components of the expandable spinal implant systems described herein can be fabricated from biologically acceptable materials suitable for medical applications, including metals, synthetic polymers, ceramics and bone material and/or their composites. For example, the components of expandable spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE'), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaprolactone and their combinations.

Various components of spinal implant system may be formed or constructed of material composites, including but not limited to the above-described materials, to achieve various desired characteristics such as strength, rigidity, elasticity, compliance, biomechanical performance, durability and radiolucency or imaging preference. The components of expandable spinal implant system, individually or collectively, may also be fabricated from a heterogeneous material such as a combination of two or more of the above-described materials. The components of the expandable spinal implant systems may be monolithically formed, integrally connected or include fastening elements and/or instruments, as described herein. For example, in some embodiments the expandable spinal implant systems may comprise expandable spinal implants 100, 200, 300 comprising PEEK and/or titanium structures with radiolucent markers (such as tantalum pins and/or spikes) selectively placed in the implant to provide a medical practitioner with placement and/or sizing information when the expandable spinal implant 100, 200, 300 is placed in the spine. The components of the expandable spinal implant system may be formed using a variety of subtractive and additive manufacturing techniques, including, but not limited to machining, milling, extruding, molding, 3D-printing, sintering, coating, vapor deposition, and laser/beam melting. Furthermore, various components of the expandable spinal implant system may be coated or treated with a variety of additives or coatings to improve biocompatibility, bone growth promotion or other features. For example, the endplates 110, 120, may be selectively coated with bone growth promoting or bone ongrowth promoting surface treatments that may include, but are not limited to: titanium coatings (solid, porous or textured), hydroxyapatite coatings, or titanium plates (solid, porous or textured).

The expandable spinal implant system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the expandable spinal implant system may be employed with surgical procedures, as described herein, and/or, for example, corpectomy, discectomy, fusion and/or fixation treatments that employ spinal implants to restore the mechanical support function of vertebrae. In some embodiments, the expandable spinal implant system may be employed with surgical approaches, including but not limited to: anterior lumbar interbody fusions (ALIF), posterior lumbar interbody fusion (PLIF), oblique lumbar interbody fusion, transforaminal lumbar interbody fusion (TLIF), various types of anterior fusion procedures, and any fusion procedure in any portion of the spinal column (sacral, lumbar, thoracic, and cervical, for example).

Figure 30A:
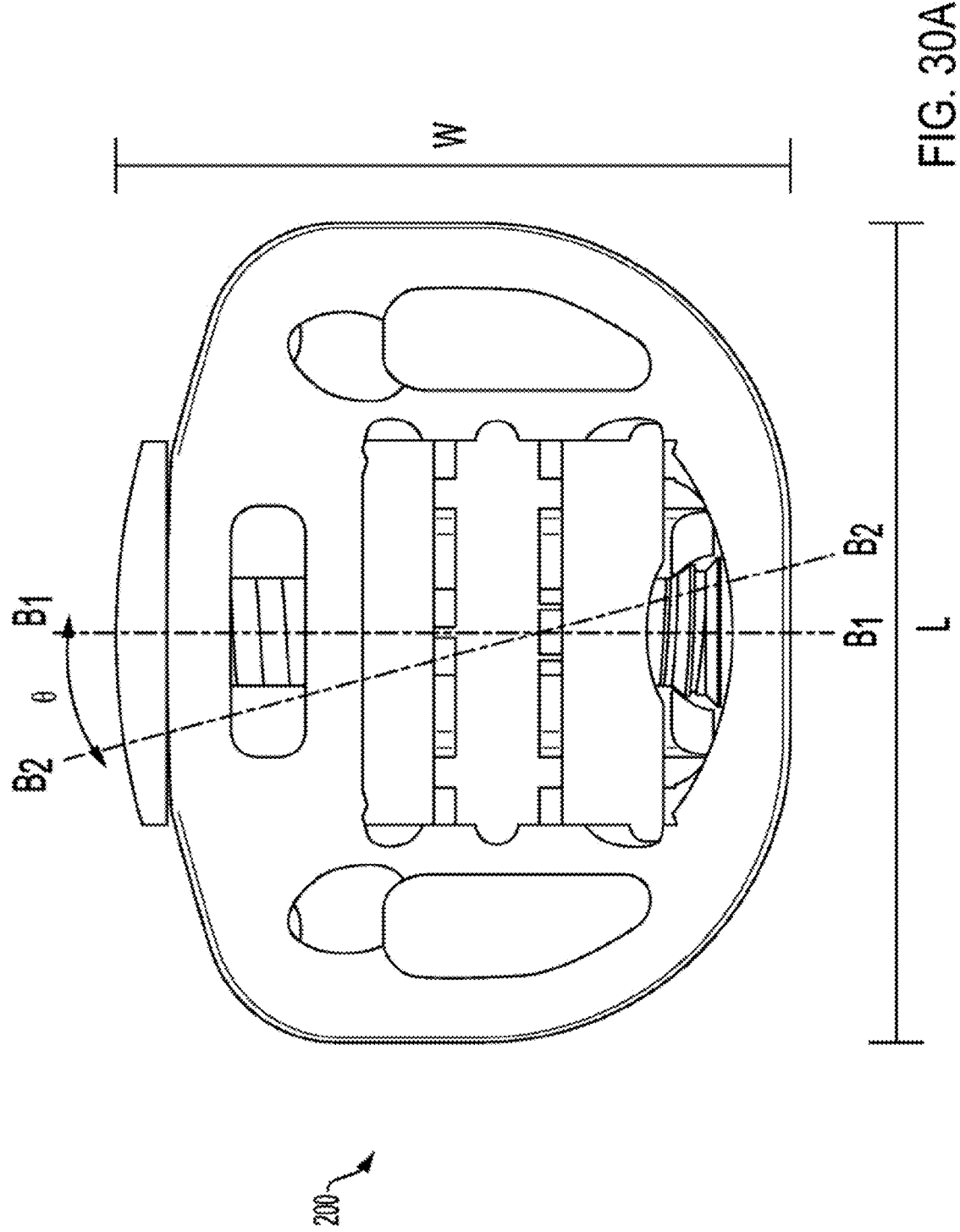
FIG. 30A is a top down view of one embodiment of an expandable spinal implant in accordance with the principles of the present disclosure.
Figure 30B:
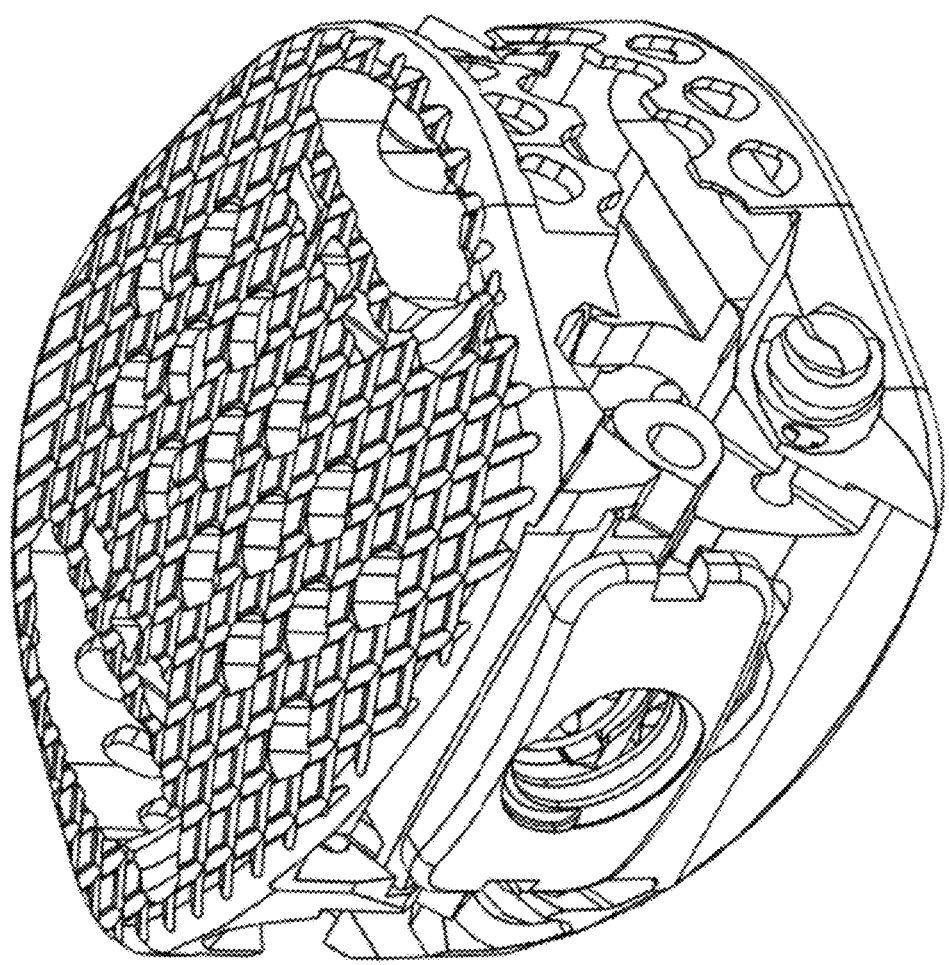
FIG. 30B is perspective view of one embodiment of an expandable spinal implant in accordance with the principles of the present disclosure.
Figure 30C:
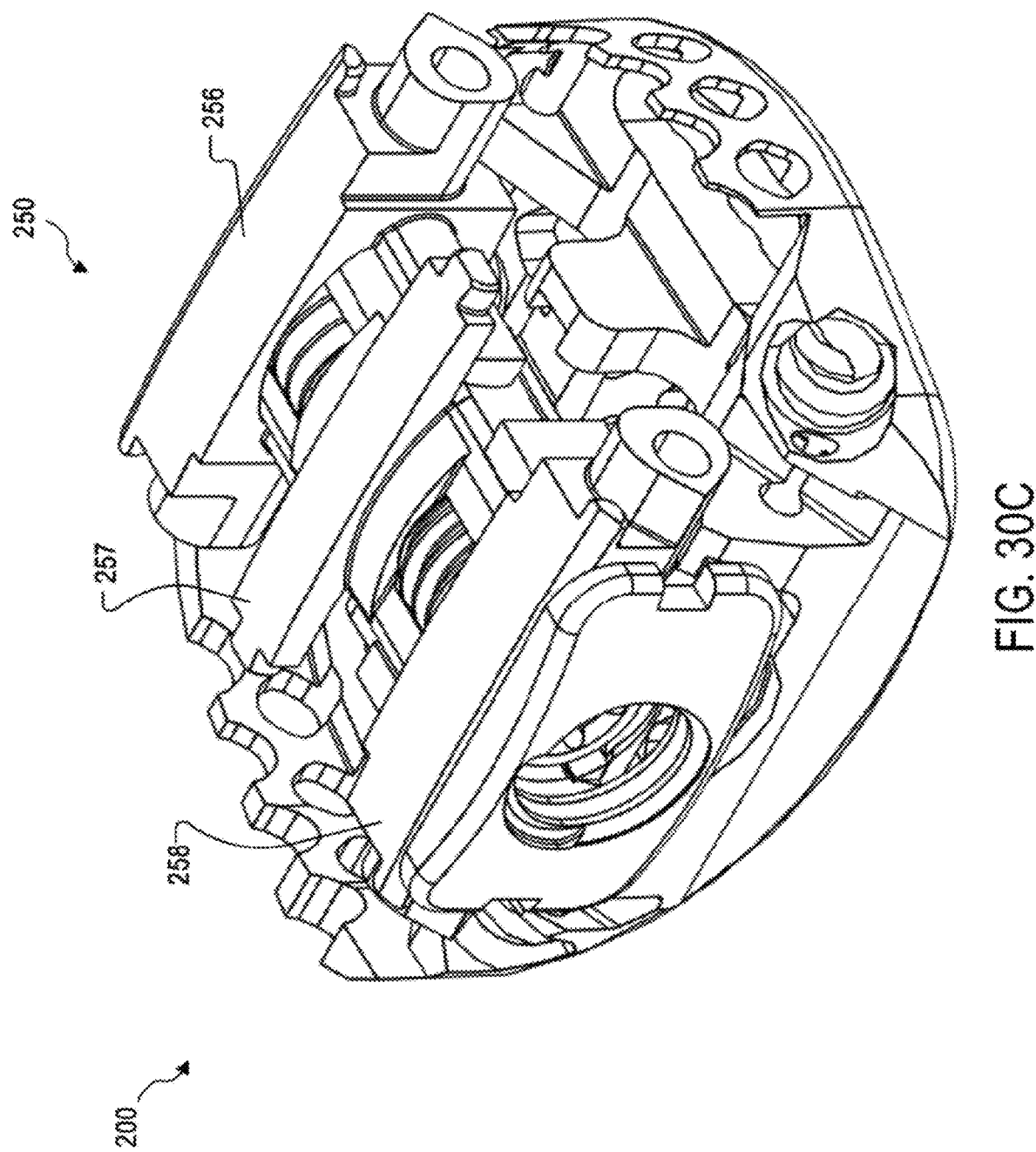
FIG. 30C is a perspective view of one embodiment of an expandable spinal implant with a top endplate removed in accordance with the principles of the present disclosure.
Figure 30D:
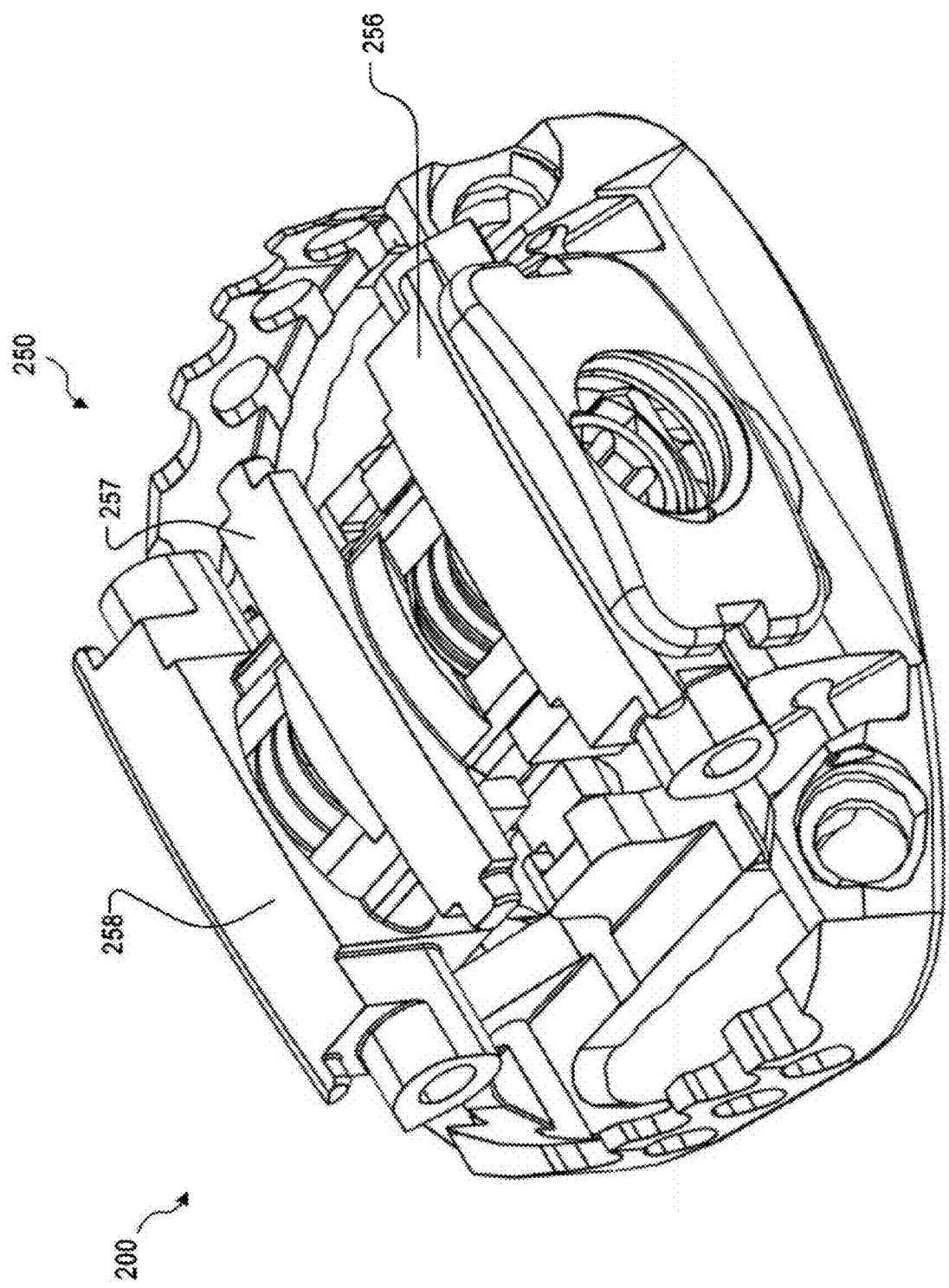
FIG. 30D is an alternate perspective view of one embodiment of an expandable spinal implant with a top endplate removed in accordance with the principles of the present disclosure.
Figure 30E:
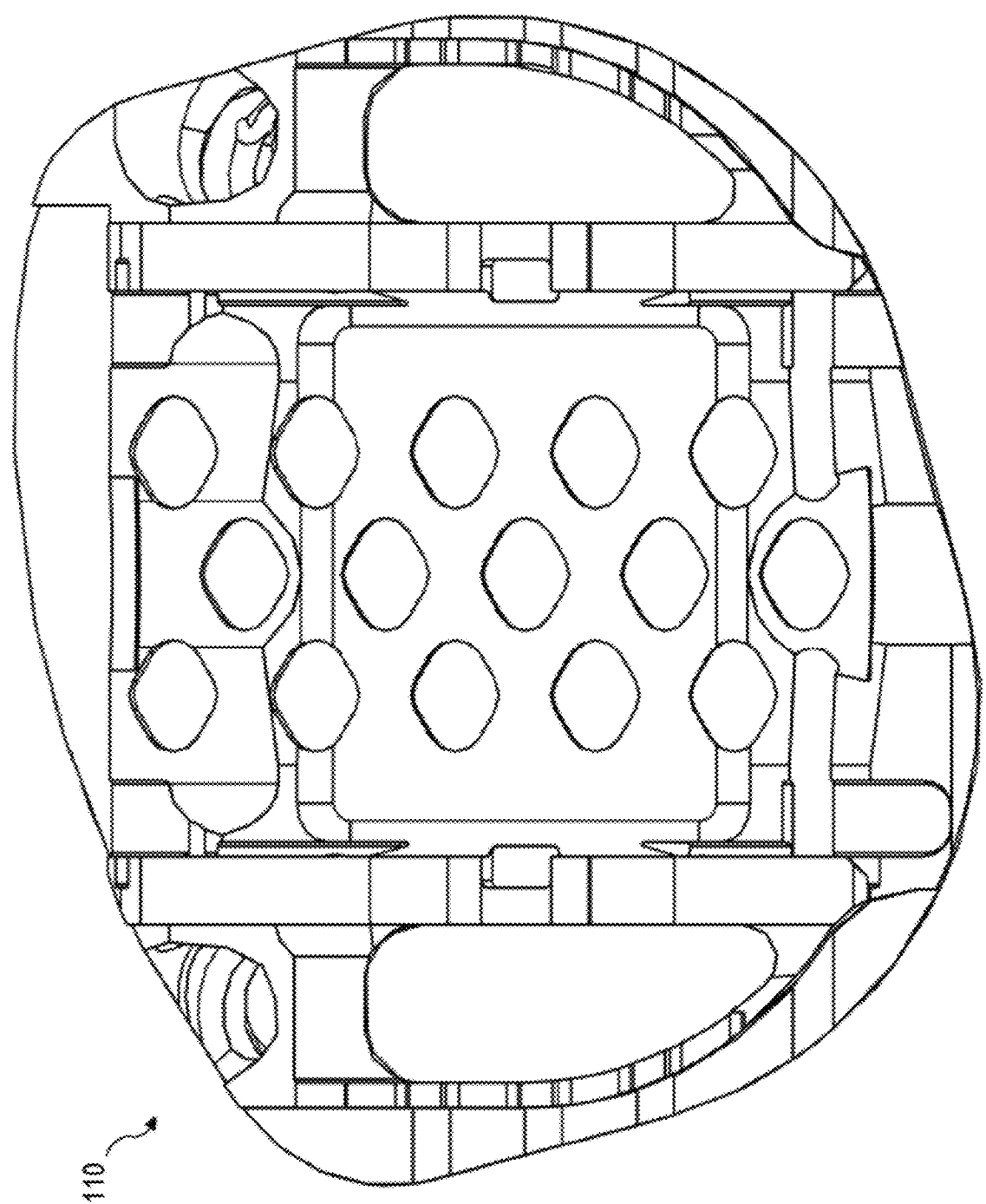
FIG. 30E is a top down view of one embodiment of a top endplate in accordance with the principles of the present disclosure.
Figure 30F:
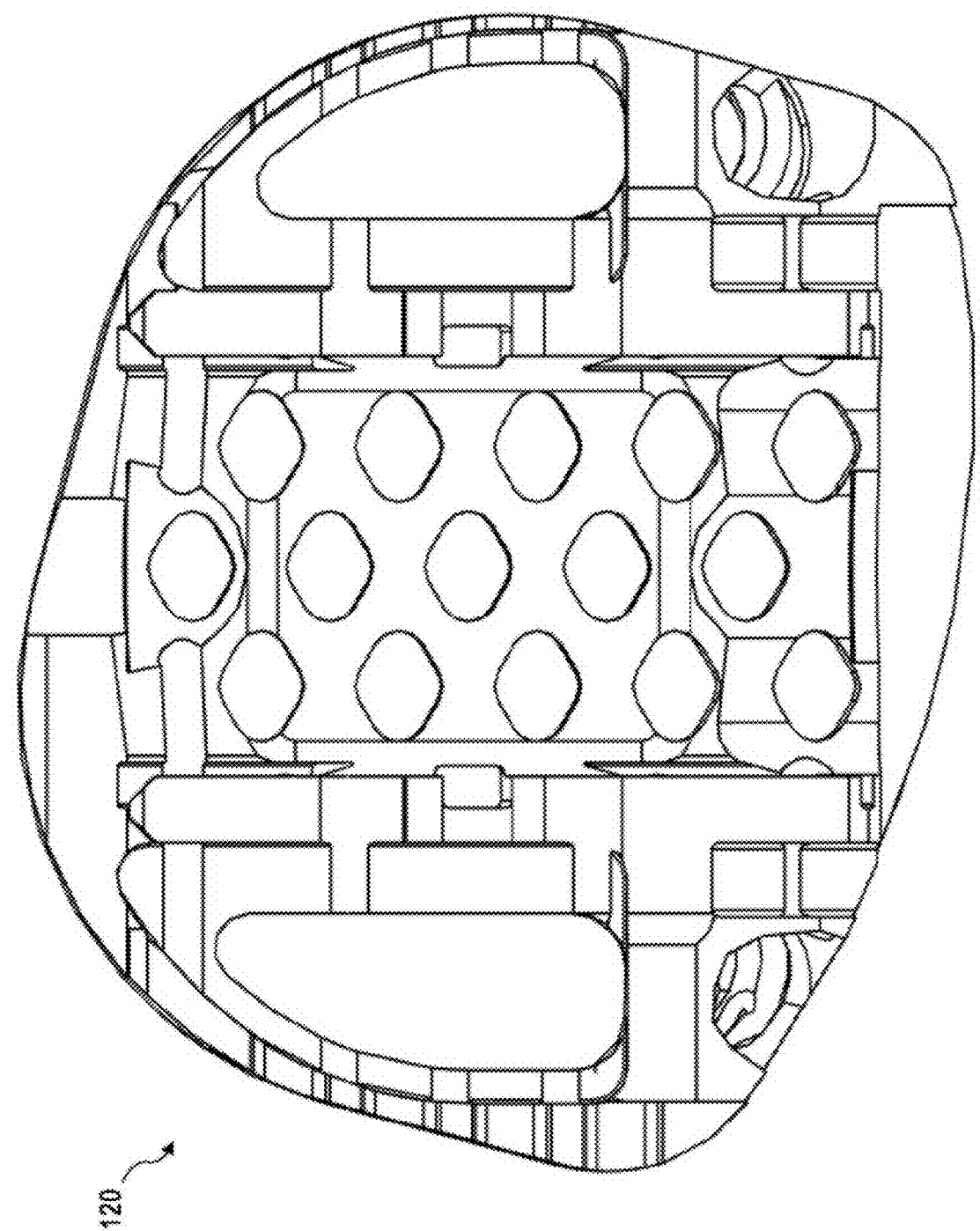
FIG. 30F is a top down view of one embodiment of a bottom endplate in accordance with the principles of the present disclosure.
Figure 31:
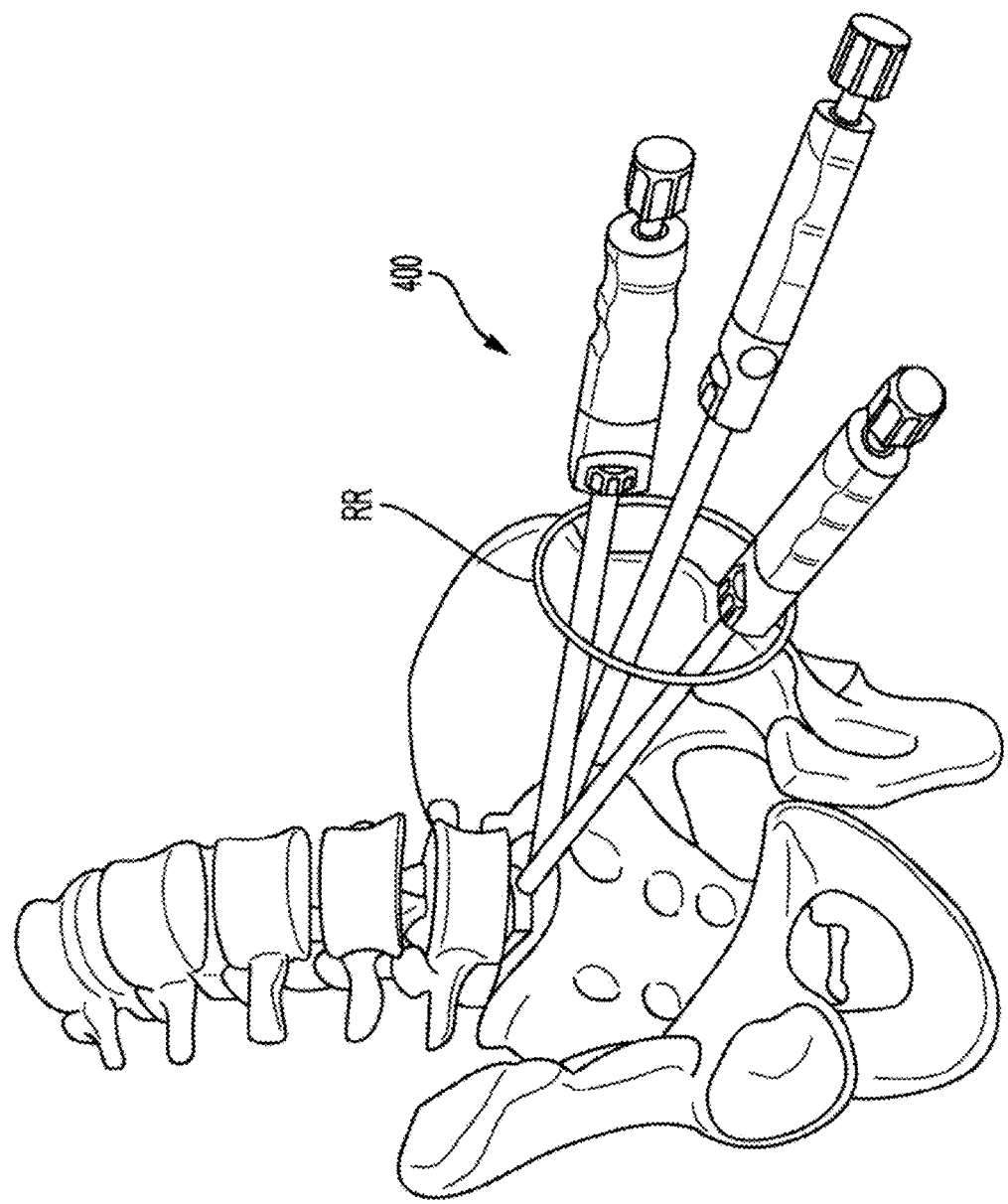
FIG. 31 is a perspective view of one embodiment of an expandable spinal implant system illustrating three alternate angular positions of an insertion tool in accordance with the principles of the present disclosure.
Figure 53:
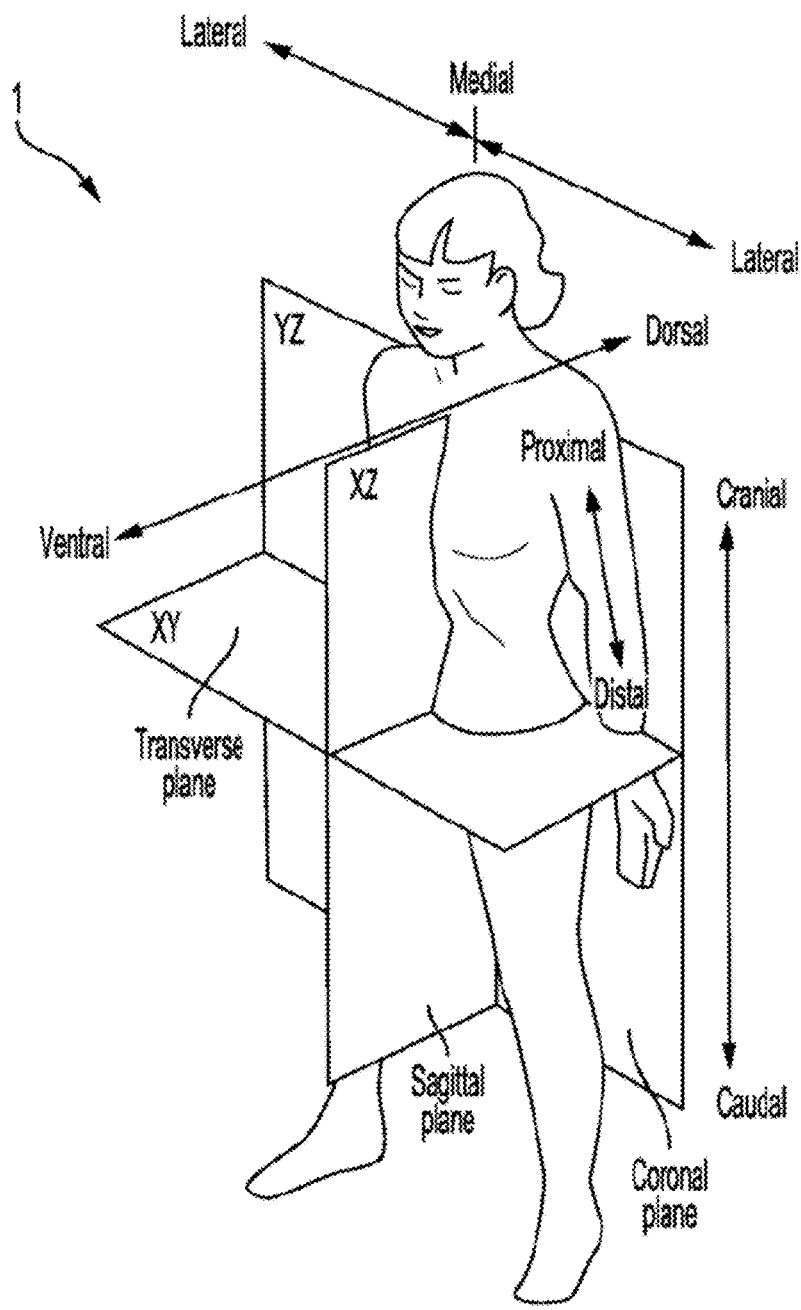
FIG. 53 is a reference diagram illustrating various cardinal directions and planes with respect to a patient that the exemplary embodiments of FIGS. 1-44B may operate, adjust, and/or move along in accordance with the principles of the present disclosure.

Generally in FIGS. 1-44B, five exemplary embodiments of an expandable spinal implants 100, 200, 300, 600, and 700 are shown (spinal implant 100 is highlighted in exemplary FIGS. 1-28, implant 200 is highlighted in exemplary FIGS. 29-31, implant 300 is highlighted in exemplary FIGS. 32-35, implant 600 is highlighted in exemplary FIGS. 36-39B, implant 700 is highlighted in FIGS. 40-44B). Exemplary embodiments of surgical tools 400, 450, and 500 are highlighted in exemplary FIGS. 8, 18-23C and disclosed in conjunction with an inter-body spinal implant system. For example, surgical tools 400, 450, and 500 are discussed concurrently with exemplary spinal implant 100. It shall be understood that the same or similar surgical tools highlighted in exemplary FIGS. 8, 18-23C may be employed with expandable spinal implants 200, 300, 600, and 700. Similar and/or identical numbering of corresponding elements may be used interchangeably between the various exemplary embodiments of an expandable spinal implants 100, 200, 300, 600, and 700 for ease of understanding and convenience in explanation. For example, moving mechanism 250 is predominately discussed concurrently with exemplary spinal implant 100 and is highlighted in exemplary FIGS. 9A-15 although the same or similar moving mechanism 250 may be employed with expandable spinal implants 200, 300, 600, and 700. FIG. 53 is provided solely as a reference illustration showing a patient 1 and various standard medical terms and orientations with respect to cardinal directions and planes of the body of patient 1 in which expandable spinal implants 100, 200, 300, 600, and 700 may act.

Referring generally to FIGS. 1-28 a first exemplary expandable spinal implant 100, moving mechanism 250, first surgical tool 400, and second surgical tool 500 are illustrated. Spinal implant 100 may be configured to be inserted in an intervertebral disc space between adjacent vertebral bodies accordingly to a variety of surgical techniques, e.g., anterior techniques, oblique techniques, and lateral techniques.

Figure 1B:
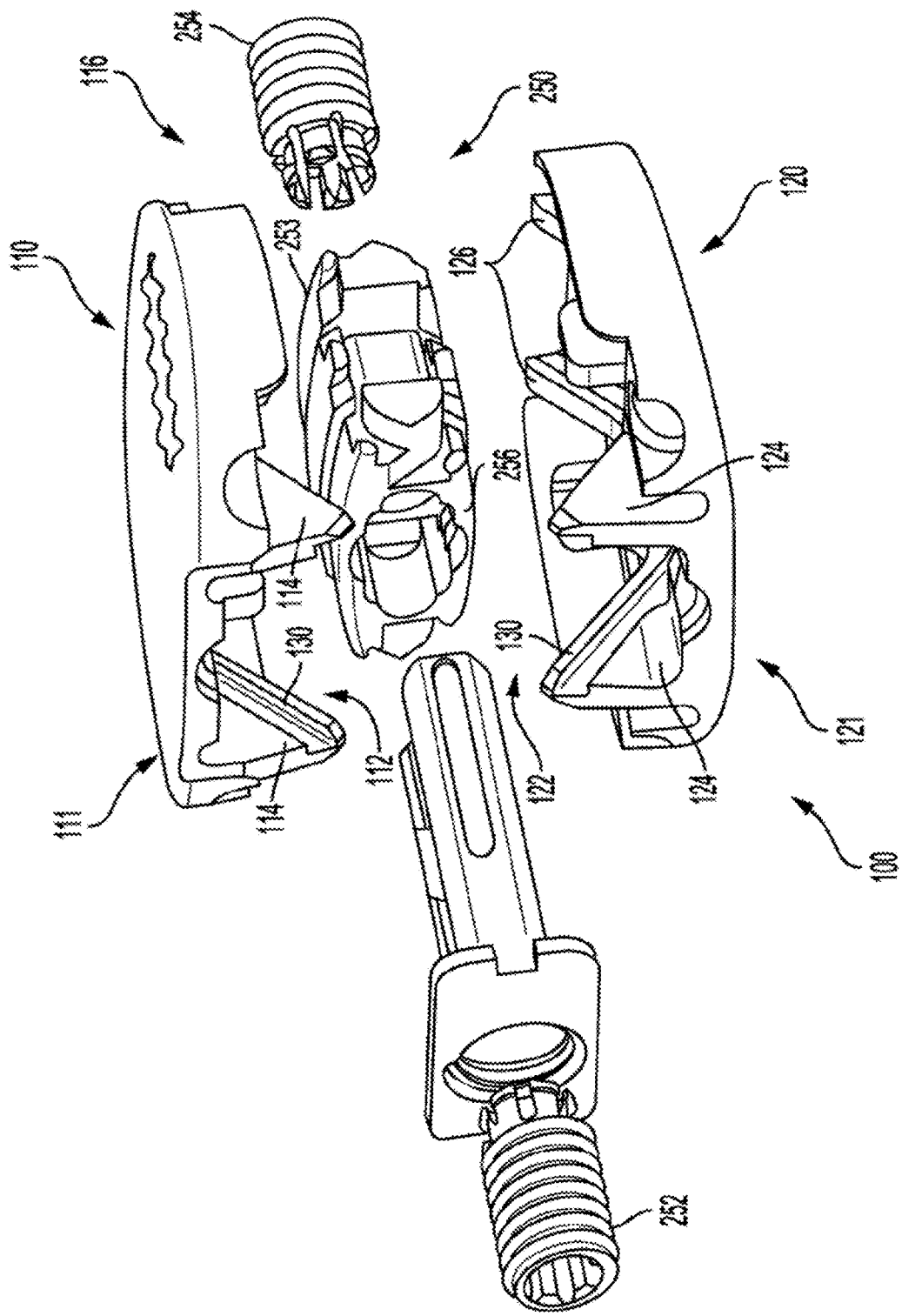
FIG. 1B is an exploded parts view of the embodiment of FIG. 1A in accordance with the principles of the present disclosure.

FIG. 1A shows the spinal implant 100 in a perspective view and FIG. 1B shows the spinal implant 100 in an exploded parts view. Exemplary spinal implant 100 includes a top endplate 110 (first endplate) and a bottom endplate 120 (second endplate) and a moving mechanism 250, which will be described in greater detail below. Spinal implant 100 includes a proximal end 101 and a distal end 102 opposite the proximal end 101, and a first lateral end 103 and a second lateral end 104 opposite the first lateral end 103. The first and second lateral ends 103, 104 extend between the proximal end 101 and the distal end 102. The proximal end 101 includes an exposed screw guide endplate 105 defining a corresponding screw guide aperture 107, which are disposed between endplates 110 and 120. The screw guide endplate 105 and guide aperture 107 will be described in greater detail below.

Top endplate 110 may include a first outside surface 111 and a first inside surface 112 opposite the first outside surface 111. Similarly, bottom endplate 120 may include a second outside surface 121 and a second inside surface 122. The outside surfaces 111, 121 may be configured to be positioned between and/or contact vertebral bodies in a patients spine and have various surface characteristics. For example, in some embodiments, outside surfaces 111 and 122 may have a substantially linear surface profiles extending across faces of textured surfaces thereof. In other embodiments, outside surfaces 111 and 122 may have curved surface profiles extending across faces of textured surfaces thereof. Further details of endplates 110, 120 will be described in greater detail below. Inside surfaces 111, 122, may surround moving mechanism 250 and have various contours, guides, cavities, and other operable characteristics that facilitate movement and/or provide mechanical advantage to other operable and movable corresponding parts to facilitate contraction, angular adjustment, lateral bending, absorption of compression forces, shear forces, etc. as will be explained in greater detail below.

In the exemplary embodiment, top endplate 110 includes a pair of first proximal ramps 114 and a pair of first distal ramps 116 opposite the first proximal ramps 114. Each ramp of the first proximal ramps 114 includes an inclined surface extending away from inside surface 112 and moving mechanism 250. Similarly, each ramp of first distal ramps 116 includes an inclined surface extending away from inside surface 112 and moving mechanism 250. Bottom endplate 120 includes a pair of second proximal ramps 124 and a pair of second distal ramps 126 opposite the second proximal ramps 124. Each ramp of the second proximal ramps 124 includes an inclined surface extending away from inside surface 122 and moving mechanism 250. Similarly, each ramp of second distal ramps 126 includes an inclined surface extending away from inside surface 112 and moving mechanism 250. Furthermore, each ramp 114, 116, 124, 126 includes a corresponding guide wall 130 extending along an inside surface thereof and extending in a direction substantially parallel to the inclined surface of the corresponding ramp.

Exemplary spinal implant 100 includes a moving mechanism 250 that is operably coupled to top endplate 110 and bottom endplate 120 as will be explained in greater detail below. Moving mechanism 250 includes a first set screw 252 and a corresponding first trolley 256 operably coupled thereto, and a second set screw 254 and a corresponding second trolley 258 operably coupled thereto. A first functional feature of moving mechanism 250 is that it is further configured to increase and decrease a spacing between the top and bottom endplates 110, 120 upon simultaneous rotation of the first and second set screws 252, 254 in a clockwise and counterclockwise direction, respectively. A second functional feature of moving mechanism 250 is that it is further configured to increase and decrease an angle of inclination between the top and bottom endplates 110, 120 upon rotation of the first set screw 252 in a clockwise and counterclockwise direction, respectively. Additional functions and attributes of moving mechanism 250 will be described in greater detail below.

Figure 1C:
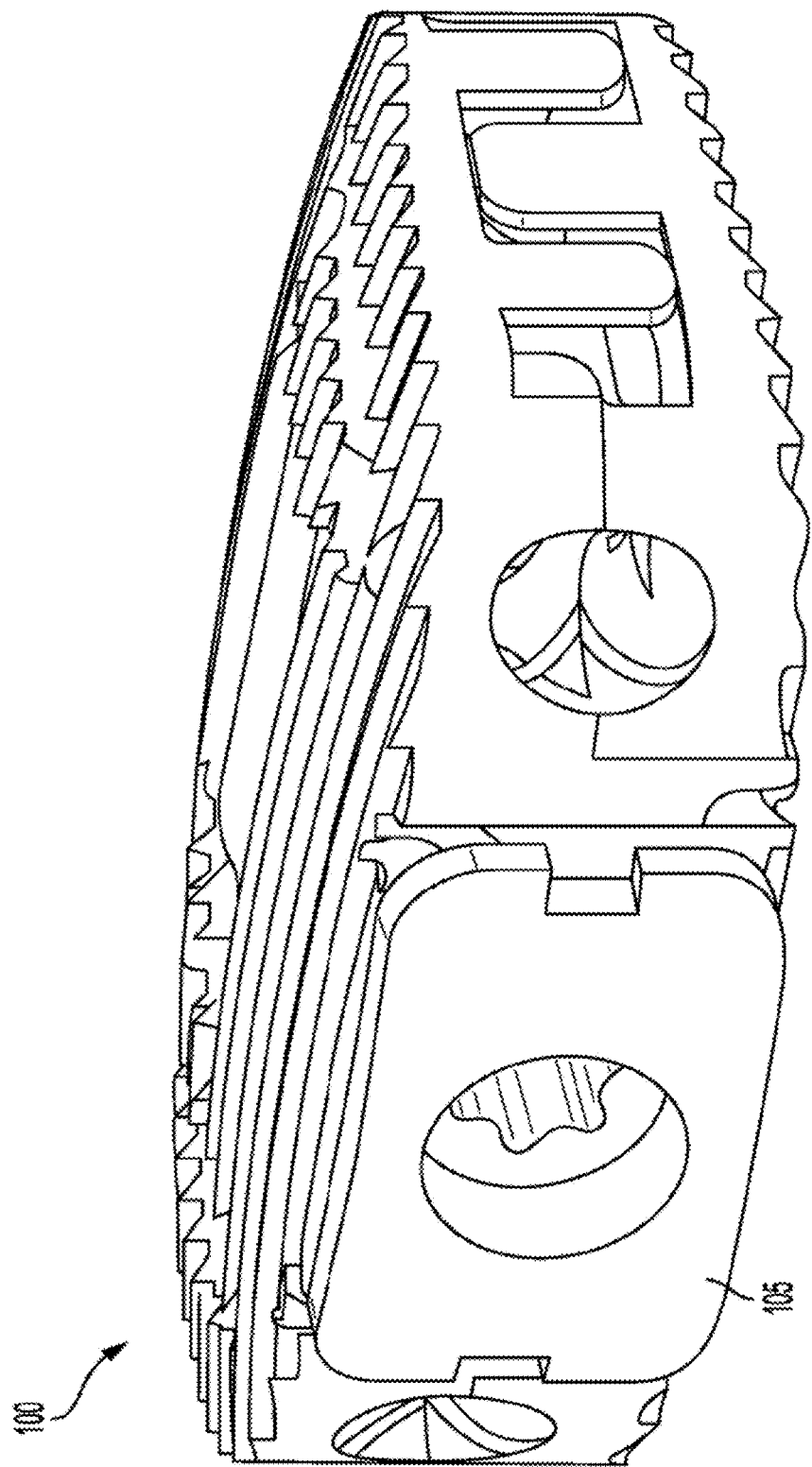
FIG. 1C is a perspective view of one embodiment of an expandable spinal implant in a contracted or closed configuration in accordance with the principles of the present disclosure.
Figure 1D:
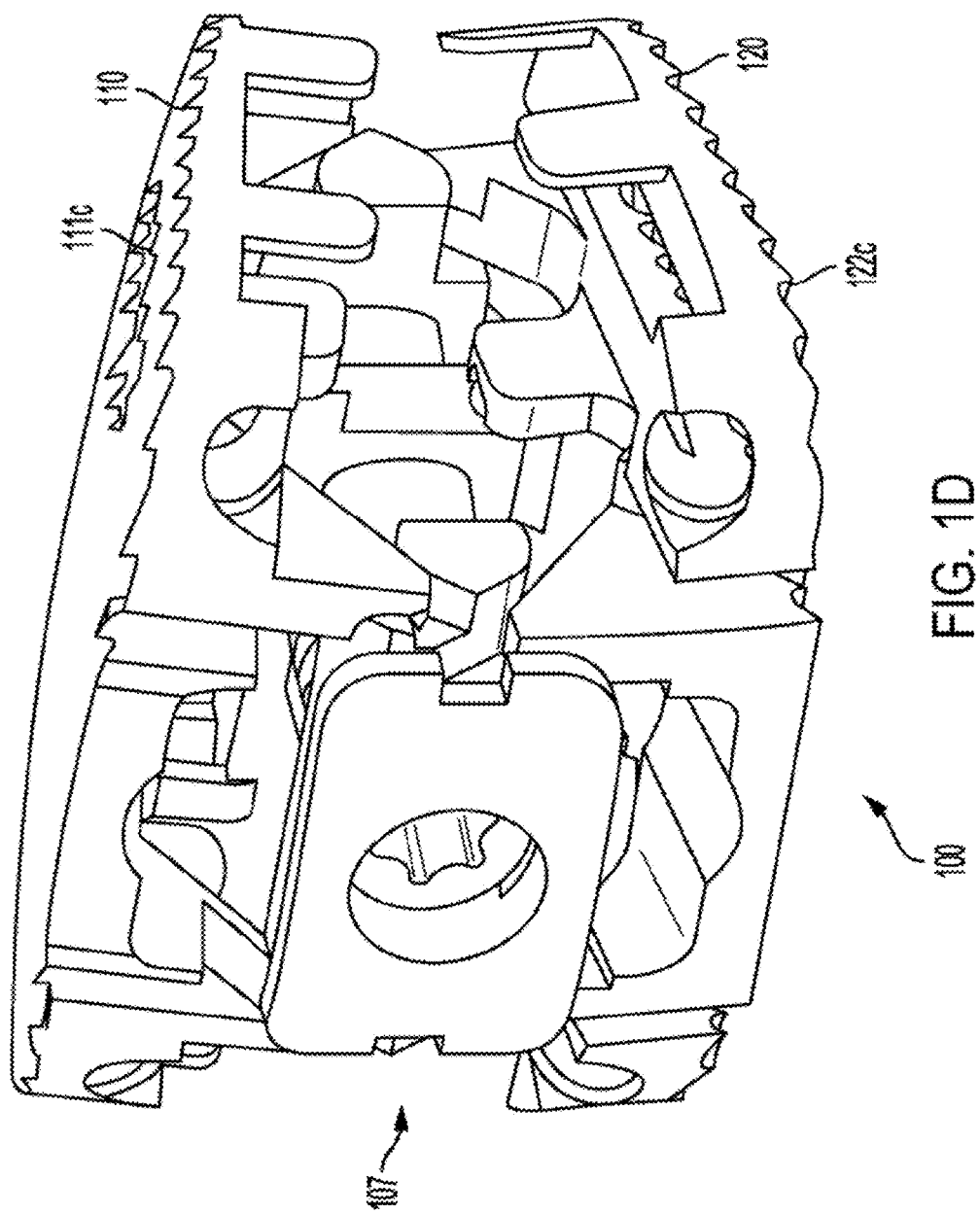
FIG. 1D is a perspective view of one embodiment of an expandable spinal implant in an expanded or opened configuration in accordance with the principles of the present disclosure.

FIG. 1C is a perspective view of spinal implant 100 in a contracted position and FIG. 1D is a perspective view of spinal implant 100 in an expanded position. In the contracted position of FIG. 1C, top endplate 110 and bottom endplate 120 are contracted to a fully closed position. In the expanded position of FIG. 1B, top endplate 110 and bottom endplate 120 are expanded to a mid-way position, i.e., endplates 110 and 120 can additionally expand if desired. In some embodiments, top endplate 110 may be referred to as an anterior wedge or anterior endplate and bottom endplate 120 may be referred to as a posterior wedge or posterior endplate.

As explained above, spinal implant 100 includes a proximal end 101 and a distal end 102 opposite the proximal end 101, and a first lateral end 103 and a second lateral end 104 opposite the first lateral end 103. It shall be understood that reference to other parts of spinal implant 100 may be in terms of the above orientation with reference to spinal implant 100 generally, e.g., endplate 110 may also include a proximal end 101 and a distal end 102 opposite the proximal end 101, and a first lateral end 103 and a second lateral end 104 opposite the first lateral end 103.

Figure 2A:
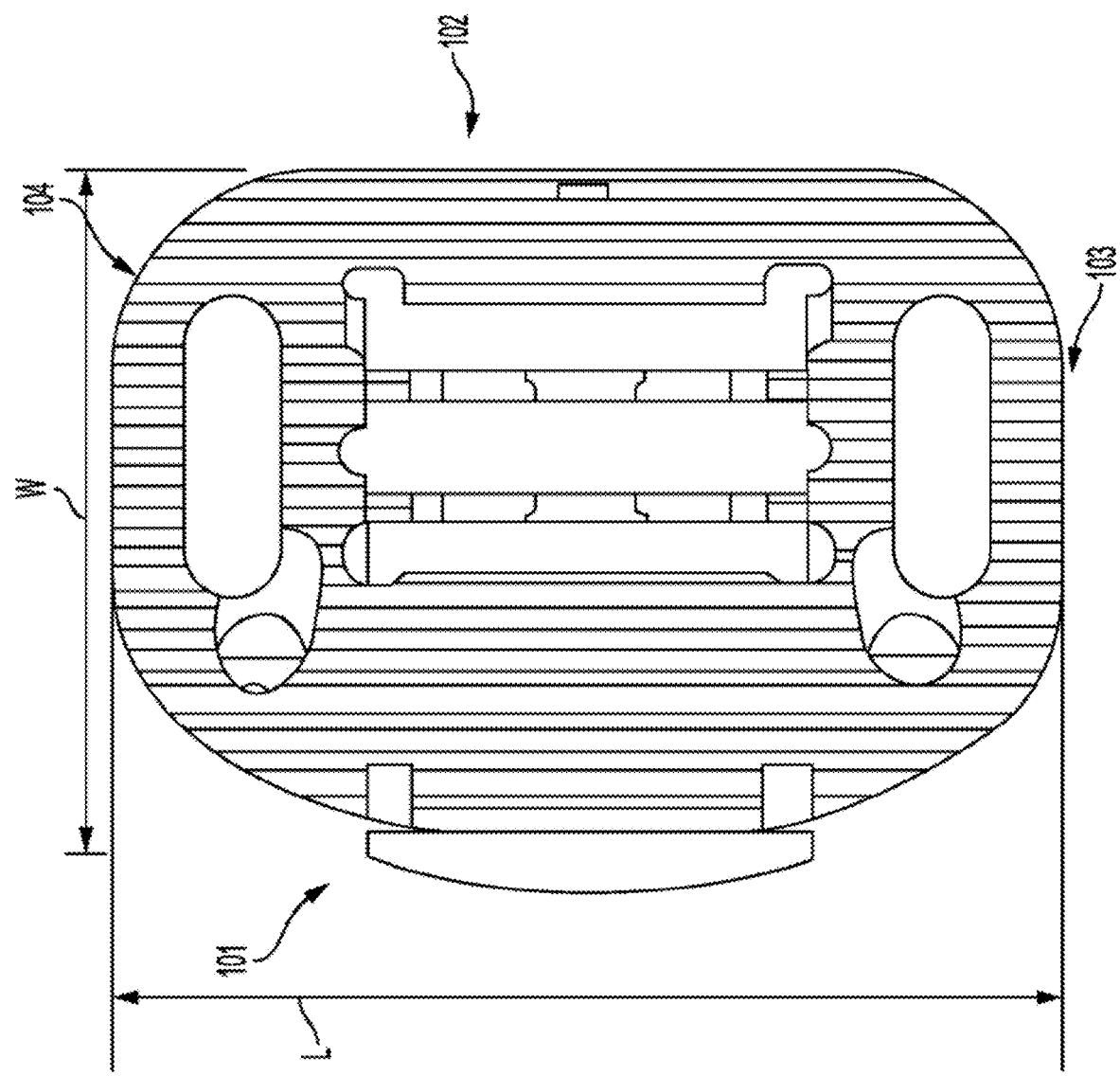
FIGS. 2A and 2B are a top down views of the embodiment of FIGS. 1A and 1B in accordance with the principles of the present disclosure.
Figure 2B:
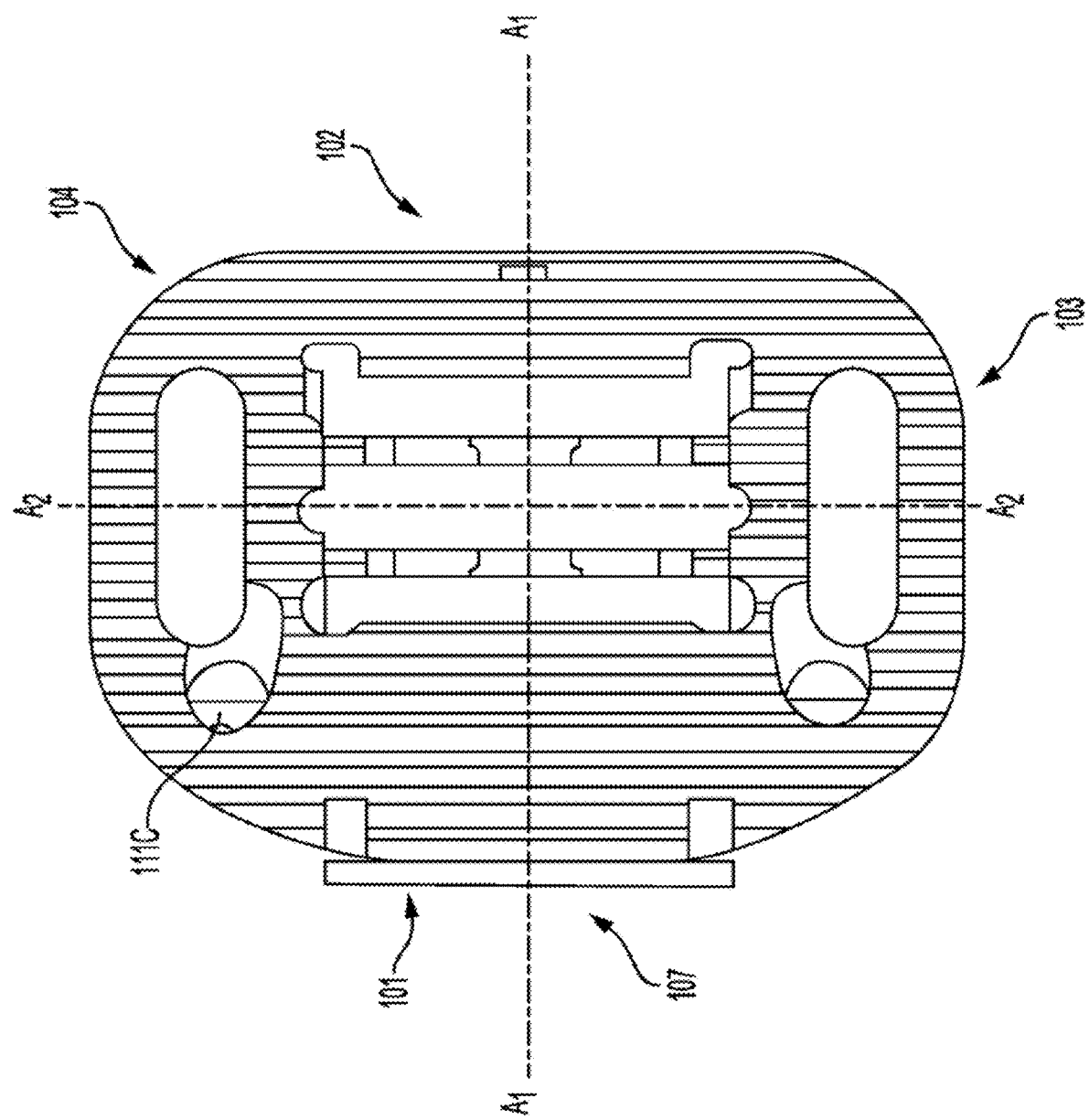

FIGS. 2A and 2B illustrate a top down view of spinal implant 100. Spinal implant 100 has a length L and a width W predominately defined by a footprint of endplates 110, 120. Spinal implant 100 has a first reference axis $A_1$ and a second reference axis $A_2$. First reference axis $A_1$ may be understood as a projection passing through a central portion of guide aperture 107 in a direction parallel to an end surface of first and second lateral ends 103, 104, e.g., first reference axis $A_1$ may pass through the center of spinal implant 100 in a width wise direction. Second reference axis $A_2$ may be understood as a projection intersecting first reference axis $A_1$ and passing through the center of spinal implant 100 in a length wise direction. Top endplate 110 may have a plurality of channels 111c spaced apart from one another and extending in a length wise direction thereof, e.g., in a direction parallel with reference axis $A_2$. Similarly, bottom endplate 120 may have a plurality of channels 122c spaced apart from one another and extending in a length wise direction thereof, e.g., in a direction parallel with reference axis $A_2$. In the exemplary embodiment, channels 111c, 122c may each have an inclined edge portion that assists with positioning the spinal implant 100 between vertebral bodies and provides a surface for promoting bone growth thereon.

Figure 2C:
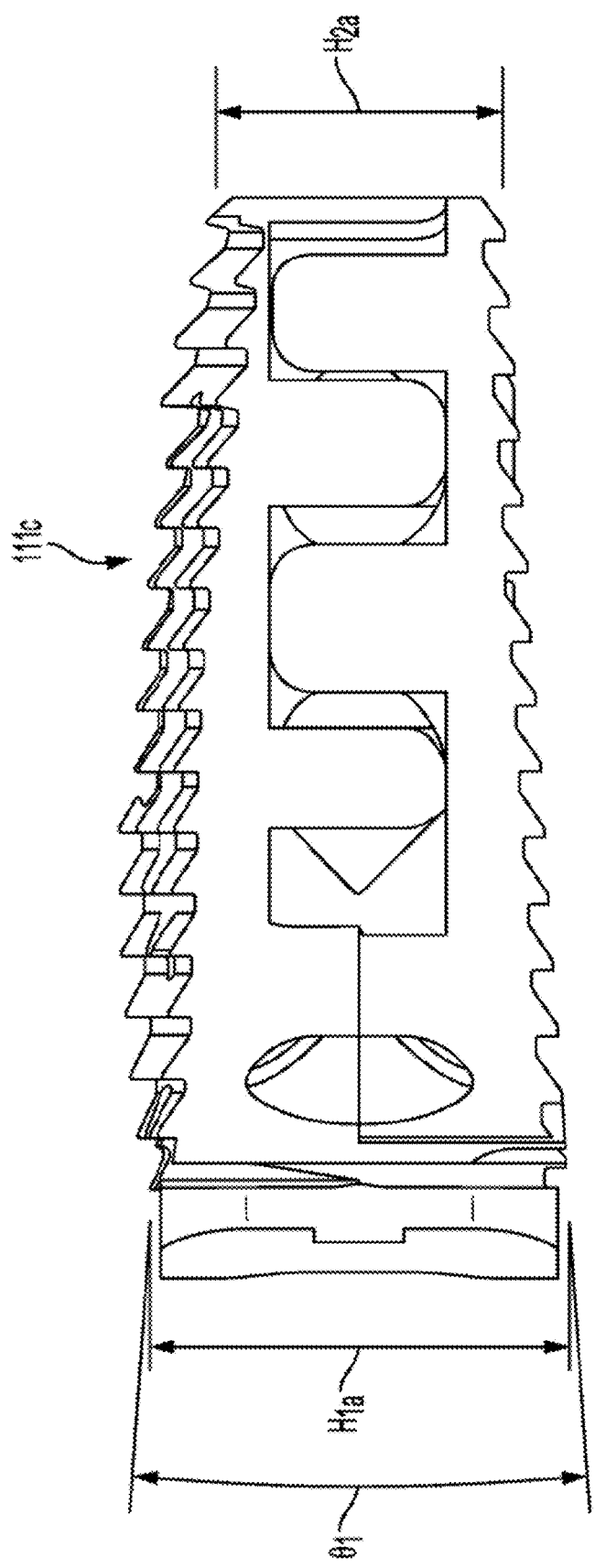
FIGS. 2C and 2D are side views of the embodiment of FIGS. 1A and 1B in a contracted position in accordance with the principles of the present disclosure.
Figure 2D:
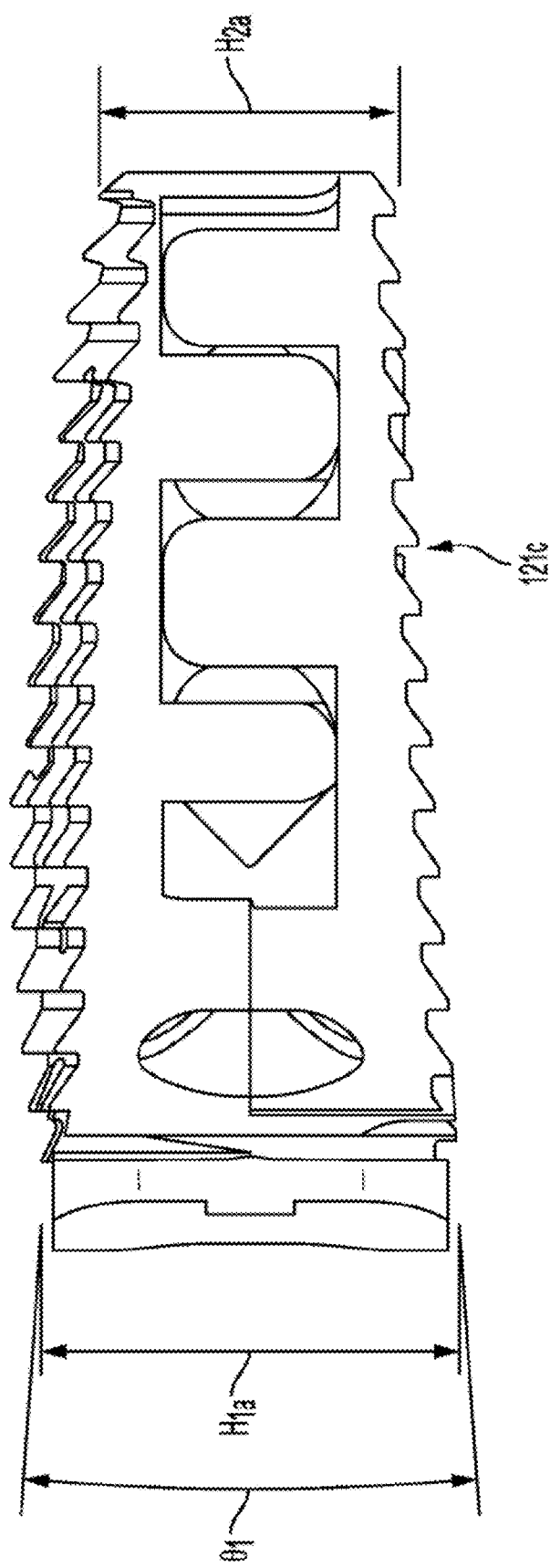
Figure 2F:
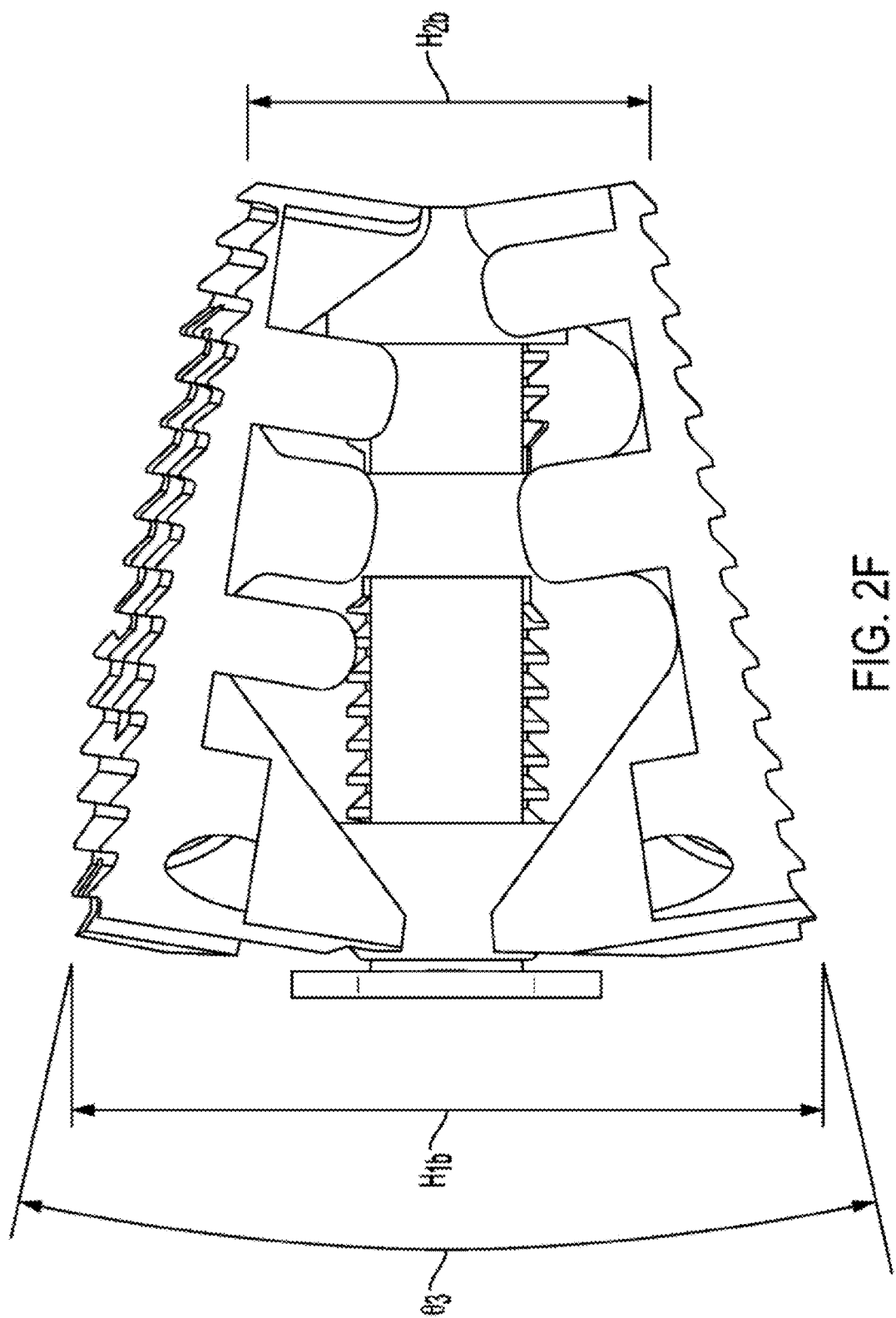

FIGS. 2C and 2D illustrate spinal implant 100 in a side view in a contracted position and FIGS. 2E and 2F illustrate spinal implant 100 in a side view in an expanded position. It shall be understood that FIGS. 2C-2F schematically illustrate spinal implant 100 with some internal parts being illustrated or simplified and others being omit for ease of explanation. For example, FIGS. 2C-2F are illustrated schematically solely to assist in explaining various positions of first and second endplates 110, 120 with respect to one another. In the contracted position, a first height $H_{1A}$ of proximal end 101 may be about 10 mm and in the expanded position a second height $H_{1B}$ of proximal end 101 may be about 22 mm. In the contracted position, a first height $H_{2A}$ of distal end 102 may be about 7 mm and in the expanded position a second height $H_{2B}$ of distal end 102 may be about 12 mm. Additionally, in the contracted position, a first angle of inclination $\theta_1$ between endplates 110, 120 may be about 7° and in the expanded position a second angle of inclination $\theta_2$ between endplates 110, 120 may be about 25°. Although specific ranges are provided herein with reference to exemplary spinal implant 100, other embodiments may have alternate corresponding dimensions, i.e., height, from those provided above. Likewise, other embodiments may have alternate corresponding angles of inclination between endplates 110, 120.

Figure 3A:
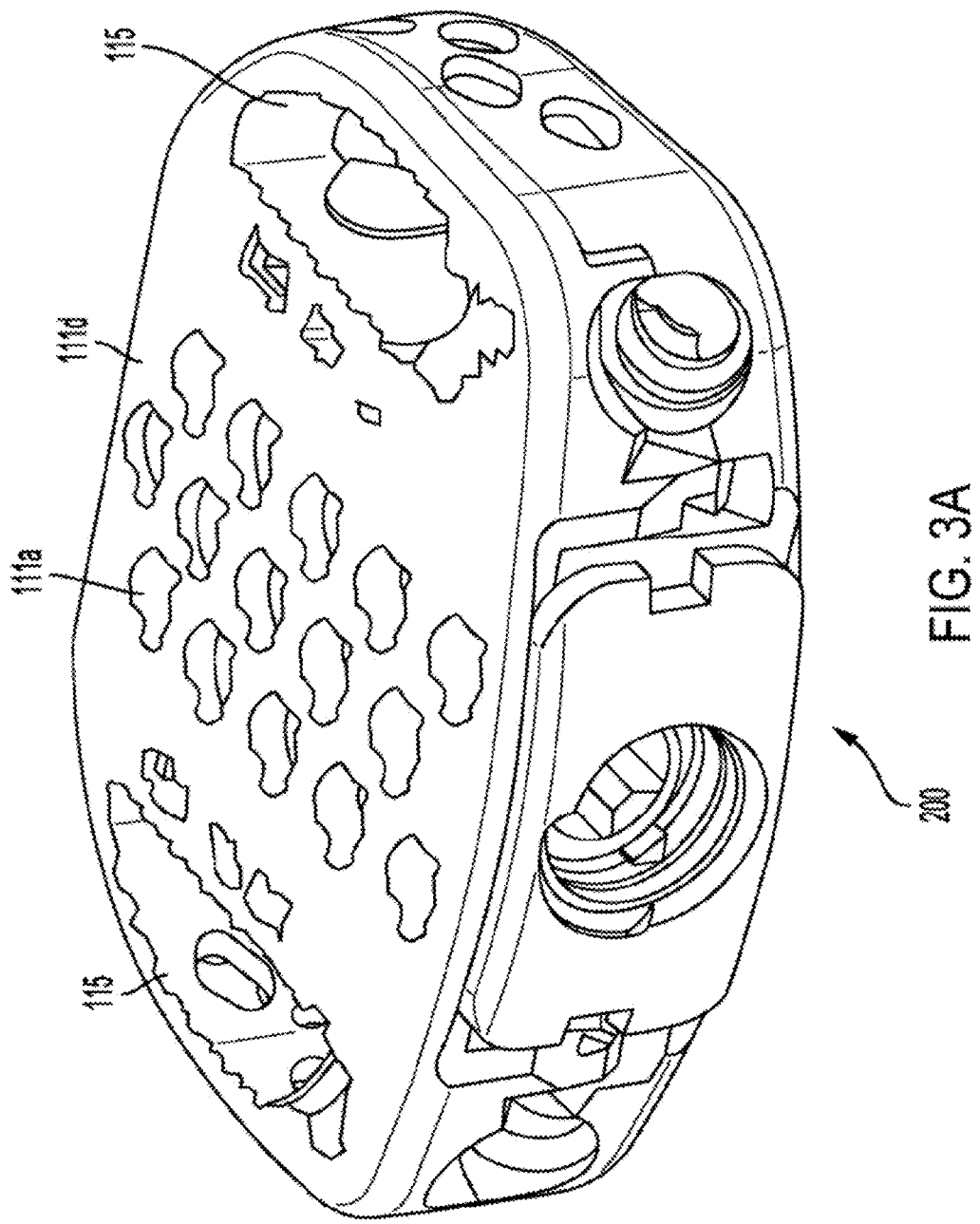
FIG. 3A is a perspective view of one embodiment of an expandable spinal implant in a closed configuration in accordance with the principles of the present disclosure.
Figure 3B:
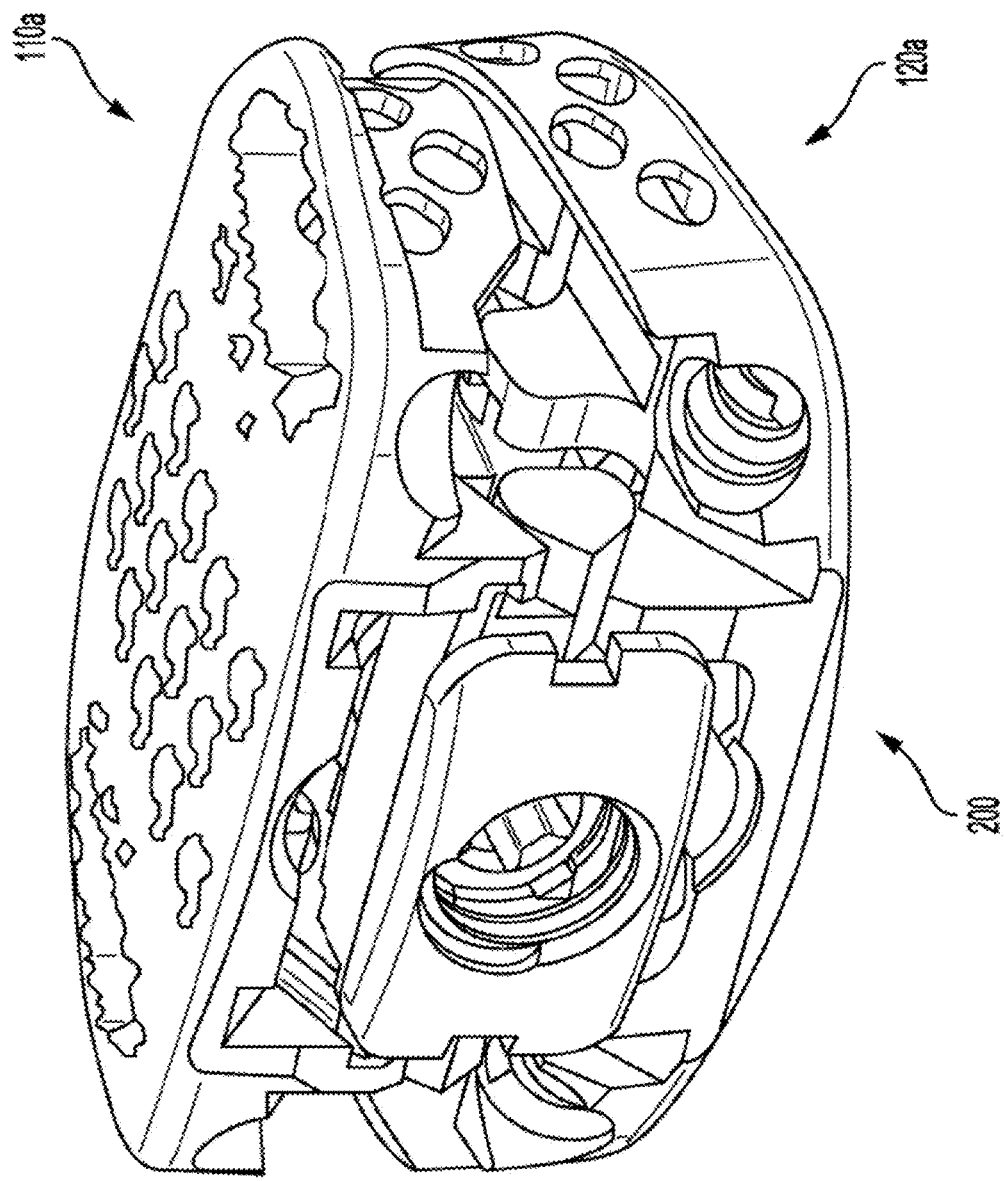
FIG. 3B is a perspective view of one embodiment of an expandable spinal implant in an expanded configuration in accordance with the principles of the present disclosure.

FIGS. 3A and 3B are perspective view of an alternate embodiment of a second spinal implant 200. Spinal implant 200 may have the same characteristics or similar characteristics as spinal implant 100. As illustrated, spinal implant 200 includes a top patterned endplate 110a and a bottom patterned endplate 120a. Top patterned endplate 110a includes an outside surface 111 and an inside surface 112 opposite the outside surface 111. Similarly, bottom patterned endplate 120a includes a first outside surface 121 and a first inside surface 122 opposite the outside surface 111. As illustrated, the outside surface 111 includes a plurality of raised diamond shaped surfaces 111d (a diamond tread pattern) and a plurality of first openings 111a that may each have a diamond like shape, a circular shape, and/or a diamond like shape including chamfered or rounded corners. Although not visible in FIGS. 3A and 3B, it shall be understood that bottom patterned endplate 120a may also have a plurality of raised diamond shaped surfaces and a plurality of openings the same as or similar to the plurality of raised diamond shaped surfaces 111d and the plurality of first openings 111a of top patterned endplate 110a.

As illustrated, the plurality of first openings 111a are circular and disposed in a central region of top patterned endplate 110a, although they may have alternate shapes and/or be disposed in alternate locations in other embodiments. For example, first and second outside surfaces 111 and 122 may comprise various anti-migration, anti-expulsion, and/or osseointegration features including, but not limited to: ridges, teeth, pores, and coatings (including but not limited to porous titanium coatings such as those provided on Capstone PTC™ implants available from Medtronic). The endplates 110a, 120a may further comprise at least one second opening 115 defined therein, and configured to allow bone growth materials to be packed, placed, or loaded into spinal implant 200. In the exemplary embodiment a pair of second openings 115 are shown with each having a D like shape.

Figure 4B:
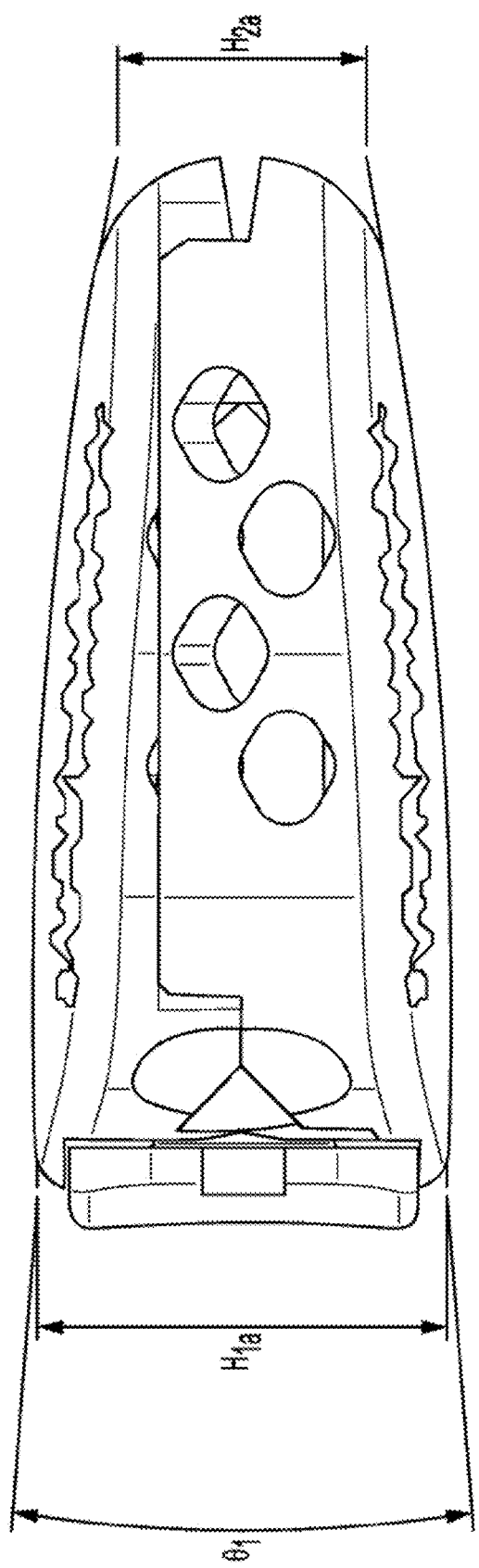
FIG. 4B is a side view of the embodiment of FIGS. 2A-2C in a contracted position in accordance with the principles of the present disclosure.
Figure 4C:
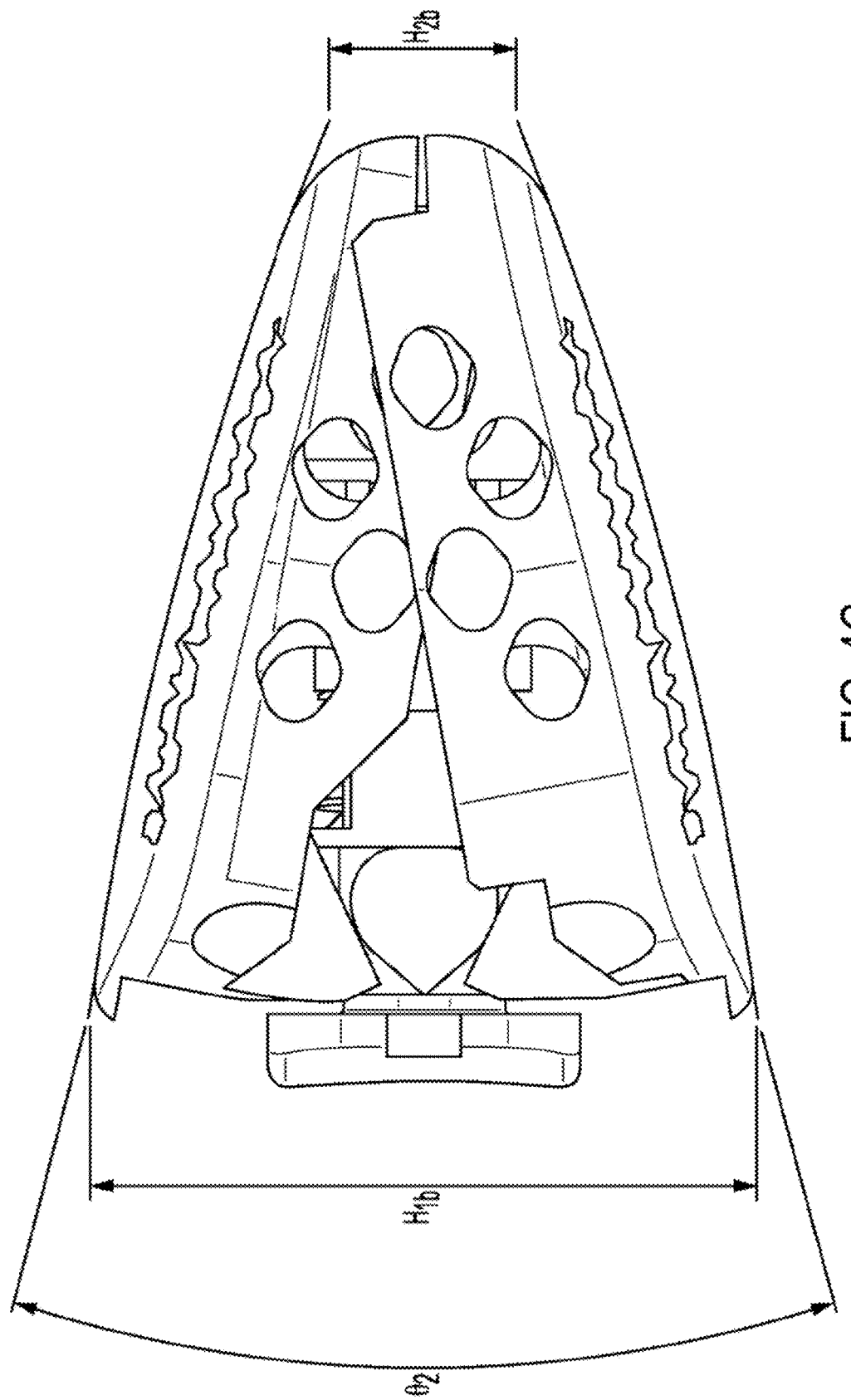
FIG. 4C is a side view of the embodiment of FIGS. 2A-2C in a partially expanded and inclined position in accordance with the principles of the present disclosure.
Figure 4D:
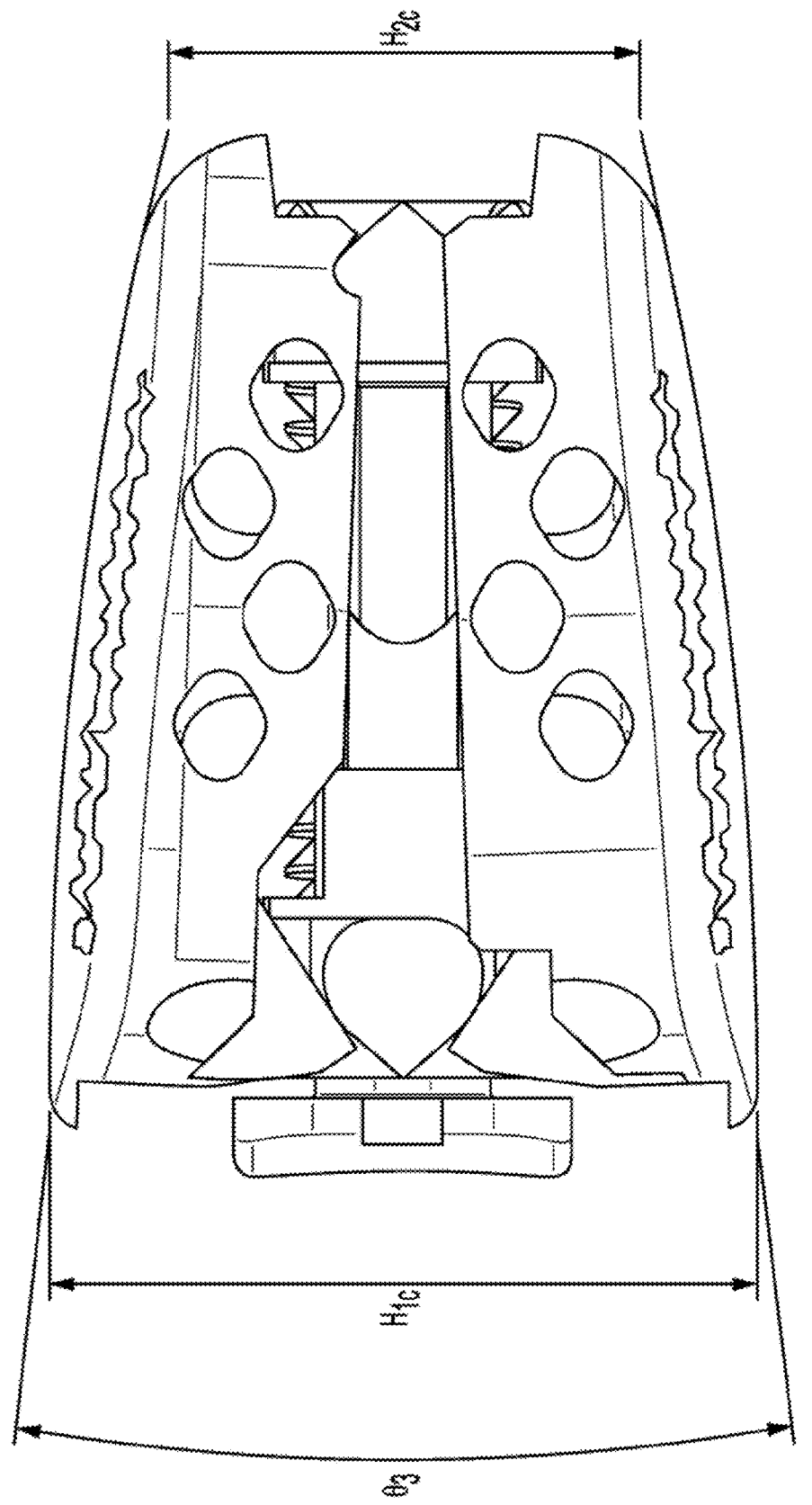
FIG. 4D is a side view of the embodiment of FIGS. 2A-2C in a fully expanded position in accordance with the principles of the present disclosure.

FIG. 4A illustrates spinal implant 200 in a top down view and each of FIGS. 4B-4D illustrate spinal implant 200 in a side view in a different respective position. FIG. 4B illustrates spinal implant 200 in a first position, FIG. 4C illustrates spinal implant 200 in a second position and FIG. 4D illustrates spinal implant 200 in a third position. In the first position, a first height $H_{1A}$ of proximal end 101 may be about 10 mm, in the second position a second height $H_{1B}$ of proximal end 101 may be about 18 mm, and in the third position a third height Hic of proximal end 101 may be about 18 mm. In the first position, a first height $H_{2A}$ of distal end 102 may be about 6 mm, in the second position a second height $H_{2B}$ of distal end 102 may be about 5 mm, and in the third position a third height Hic of distal end 102 may be about 11.8 mm (approximately 12 mm). Additionally, in the first position, a first angle of inclination $\theta_1$ between endplates 110a, 120a may be about 9°, in the second position a second angle of inclination $\theta_2$ between endplates 110a, 120a may be about 30°, and in the third position a third angle of inclination $\theta_3$ between endplates 110a, 120a may be about 13°. In some embodiments, the first position may correspond to a fully contracted position, the second position may correspond to a maximum inclination angle, and the third position may correspond to a fully expanded position. Although specific ranges are provided herein with reference to exemplary spinal implant 100, other embodiments may have alternate corresponding dimensions, i.e., height, from those provided above. Likewise, other embodiments may have alternate corresponding angles of inclination between endplates 110a, 120a.

Figure 5A:
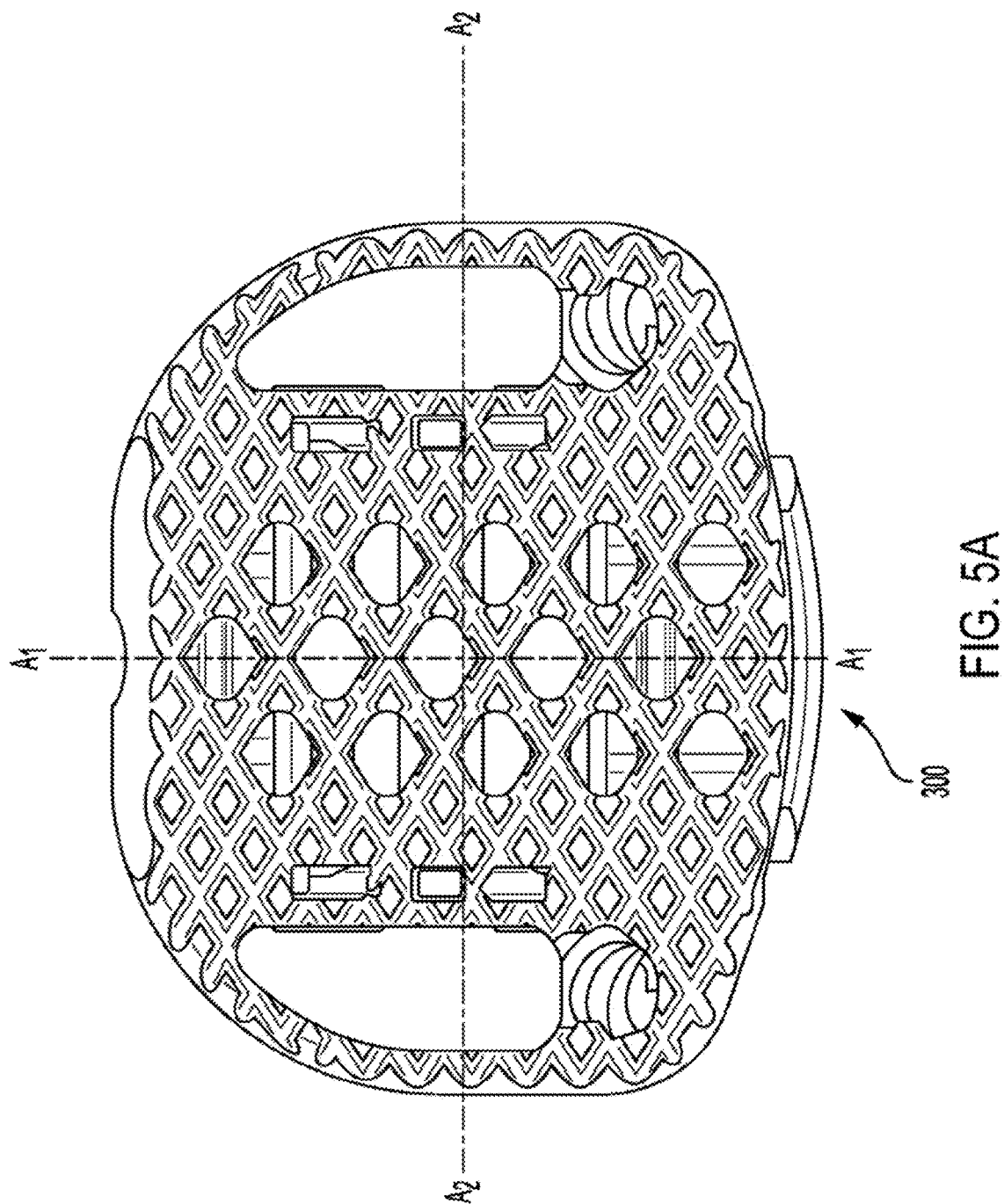
FIG. 5A is a top down view of one embodiment in accordance with the principles of the present disclosure.
Figure 5B:
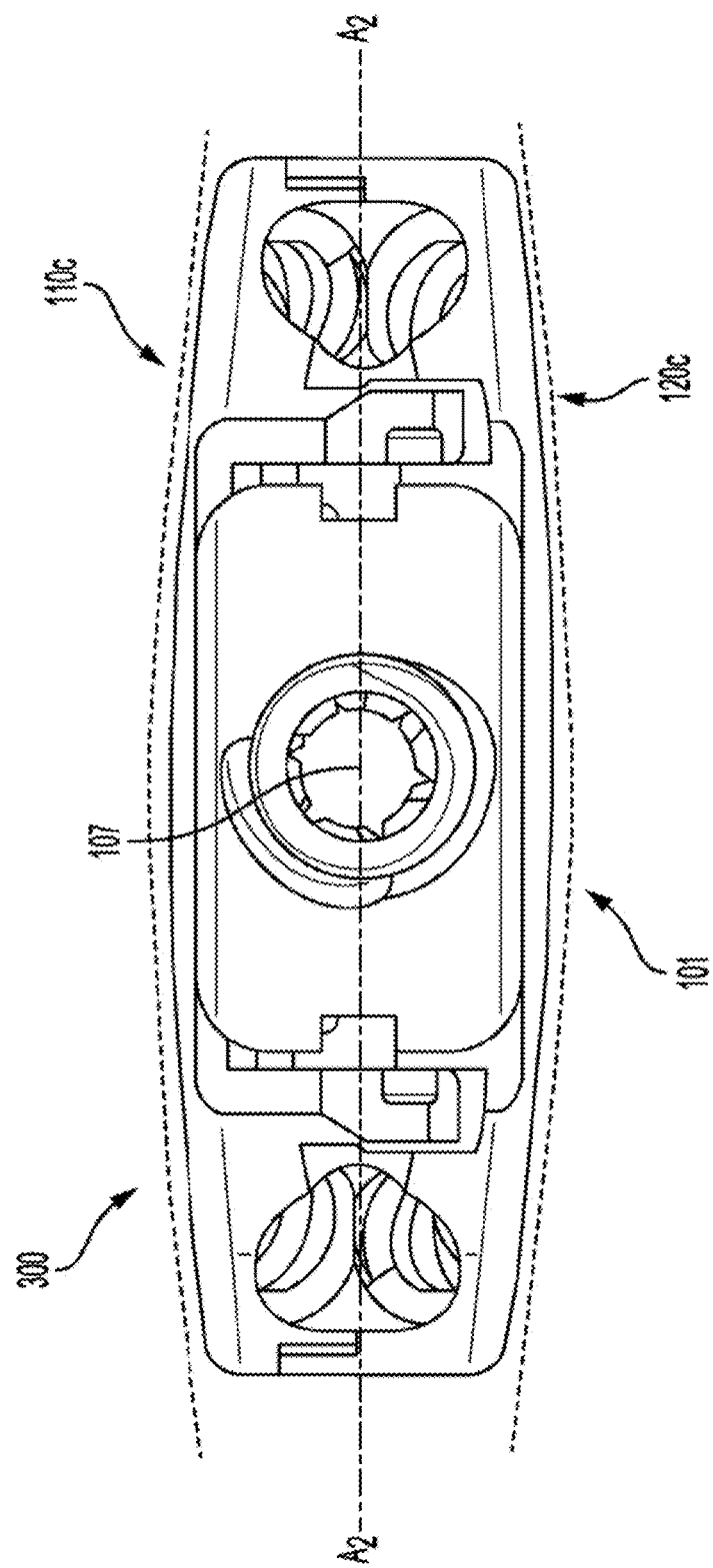
FIG. 5B is a front side view of the embodiment of FIG. 5A in accordance with the principles of the present disclosure.
Figure 5C:
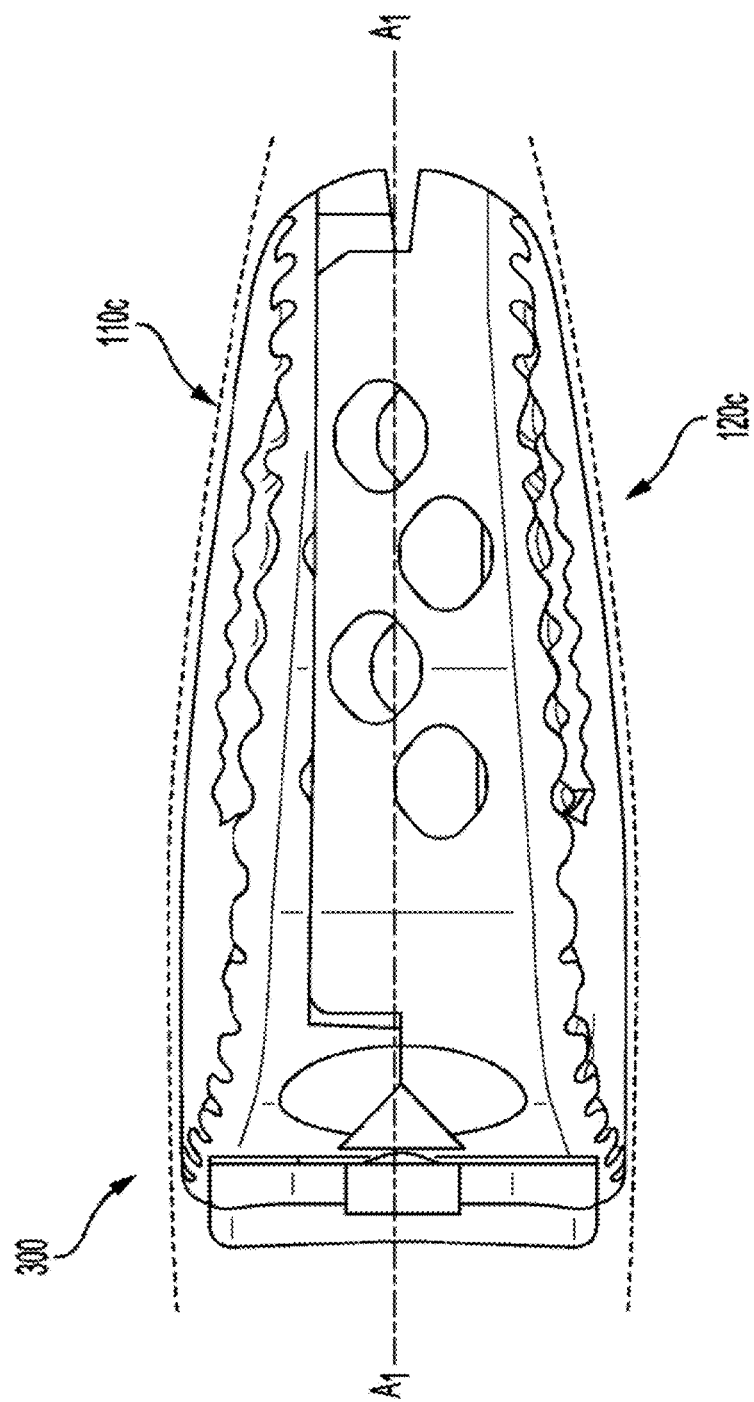
FIG. 5C is an alternate side view of the embodiment of FIG. 5A in accordance with the principles of the present disclosure.

FIG. 5A is a top down view of a spinal implant 300. Spinal implant 300 may have the same characteristics or similar characteristics as spinal implant 200 and spinal implant 100. FIGS. 5B and 5C are alternate side views of the embodiment of FIG. 5A. As illustrated spinal implant 300 includes a first reference axis $A_1$ and a second reference axis $A_2$. First reference axis $A_1$ passes through the center of spinal implant 300 in a width wise direction and second reference axis $A_2$ passes through the center of spinal implant 300 in a length wise direction. First and second reference axes $A_1$ and $A_2$ may be understood as linear projections that are perpendicular with respect to one another. Additionally, first reference axis $A_1$ may pass through the center of guide aperture 107 and other components operably disposed therein, e.g., moving mechanism 250 as will be discussed in greater detail below.

As illustrated, spinal implant 300 includes a top curved endplate 110c and a bottom curved endplate 120c. The top curved endplate 110c features a concave surface profile with respect to the first and second reference axes $A_1$ and $A_2$ projecting thereunder. The concave surface profile is emphasized by the curved line thereabove. The bottom curved endplate 120 features a convex surface profile with respect to the first and second reference axes $A_1$ and $A_2$ projecting thereabove. The convex surface profile is emphasized by the curved line therebelow.

Figure 6A:
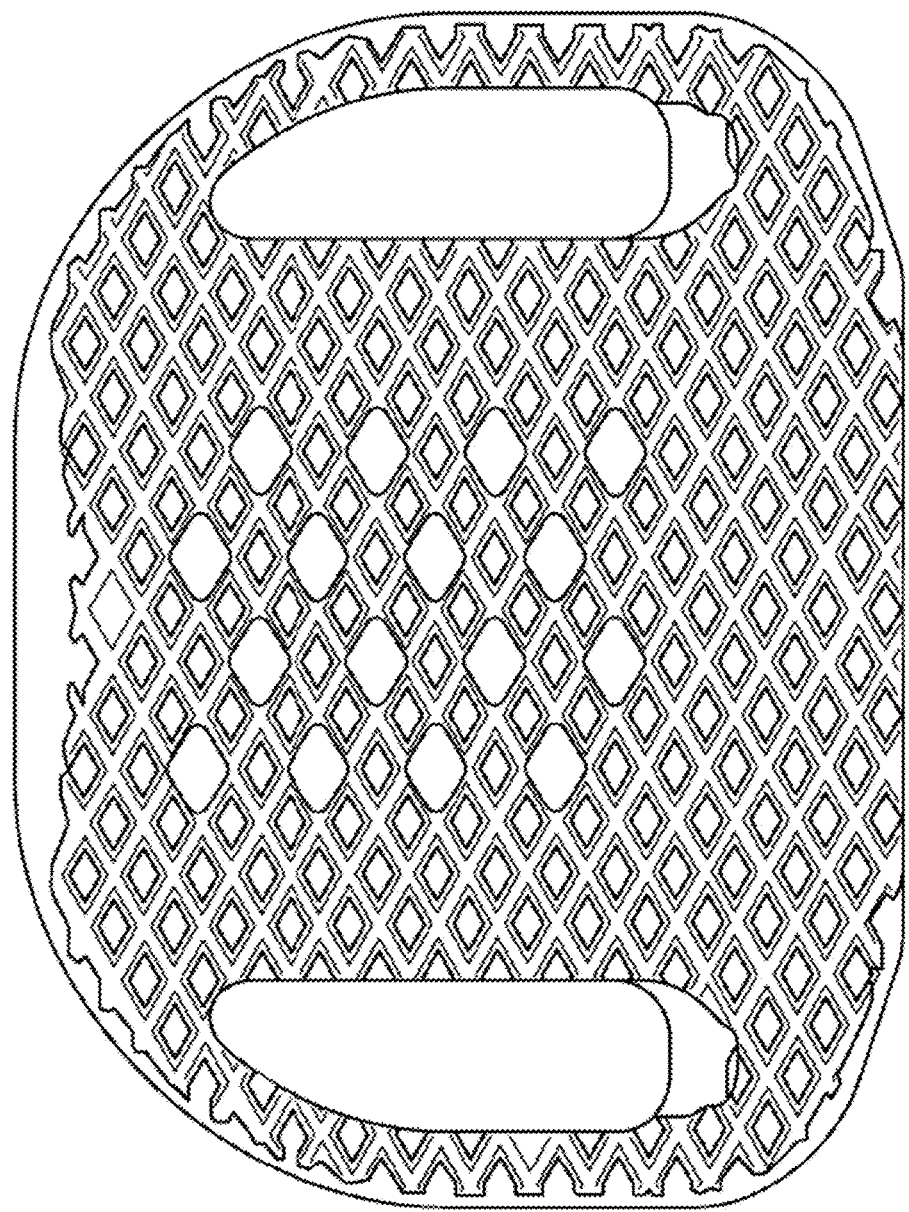
FIGS. 6A-6C are top down views of three exemplary footprint sizes of a top endplate in accordance with the principles of the present disclosure.
Figure 6B:
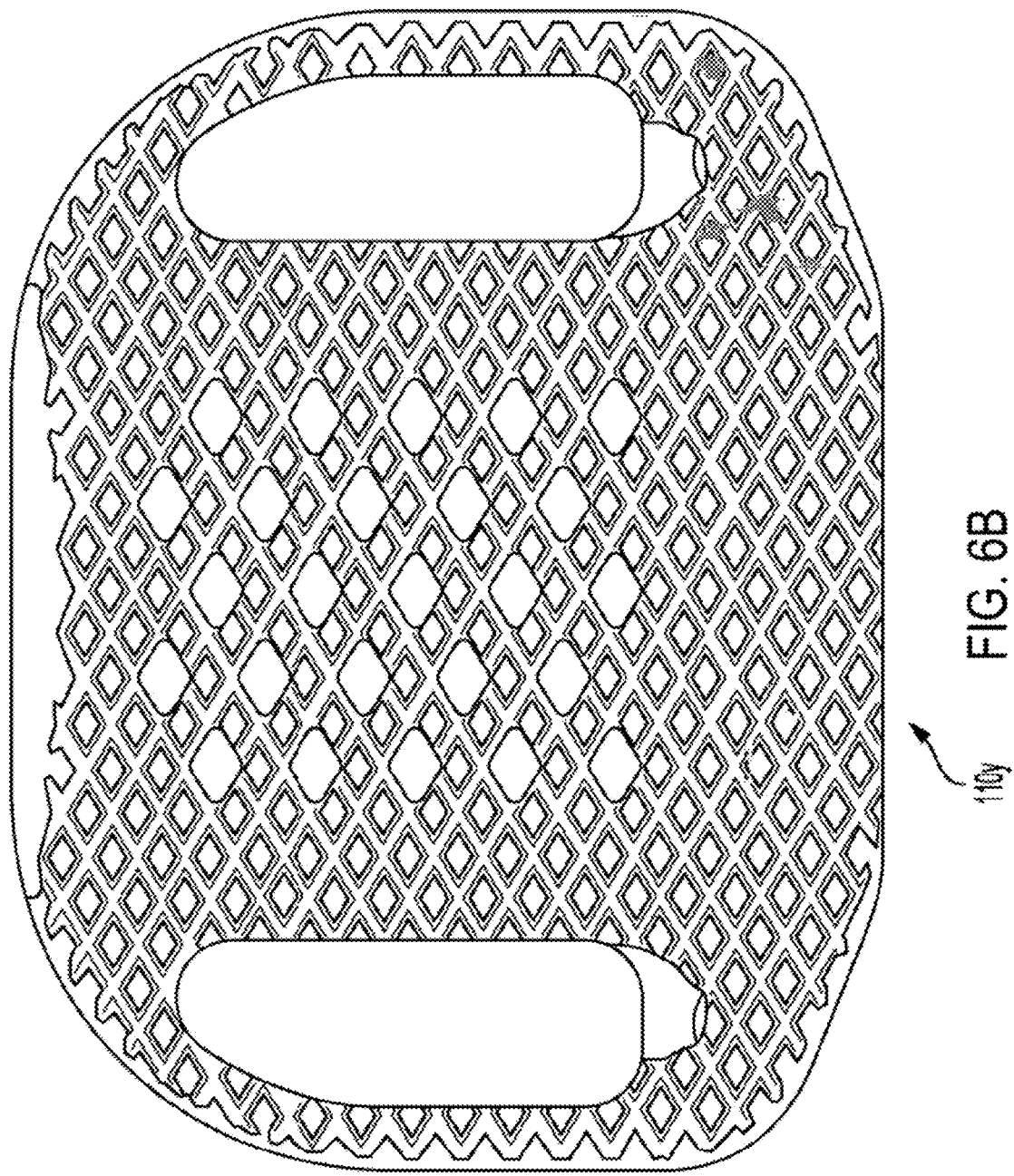
Figure 6C:
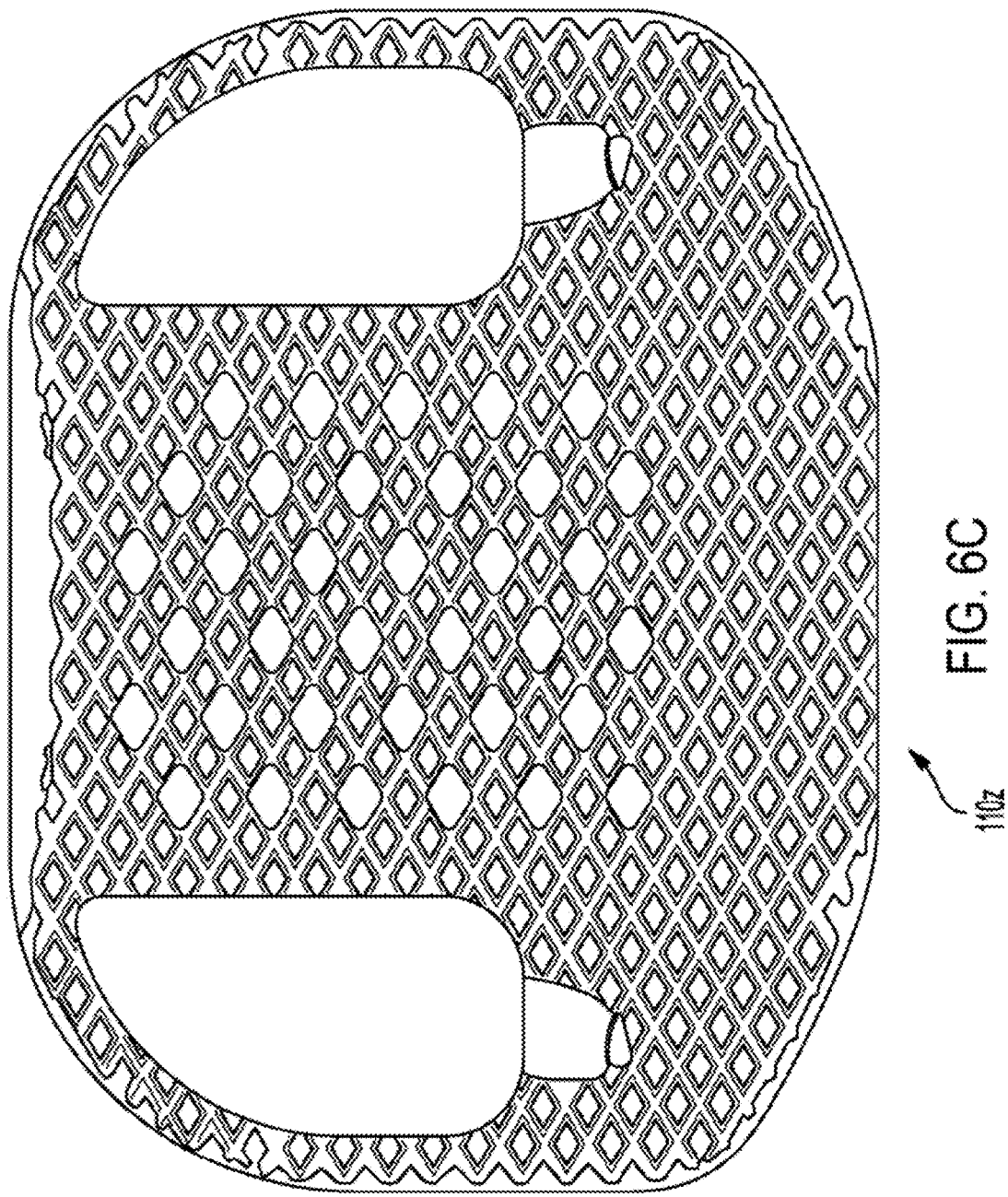
Figure 7A:
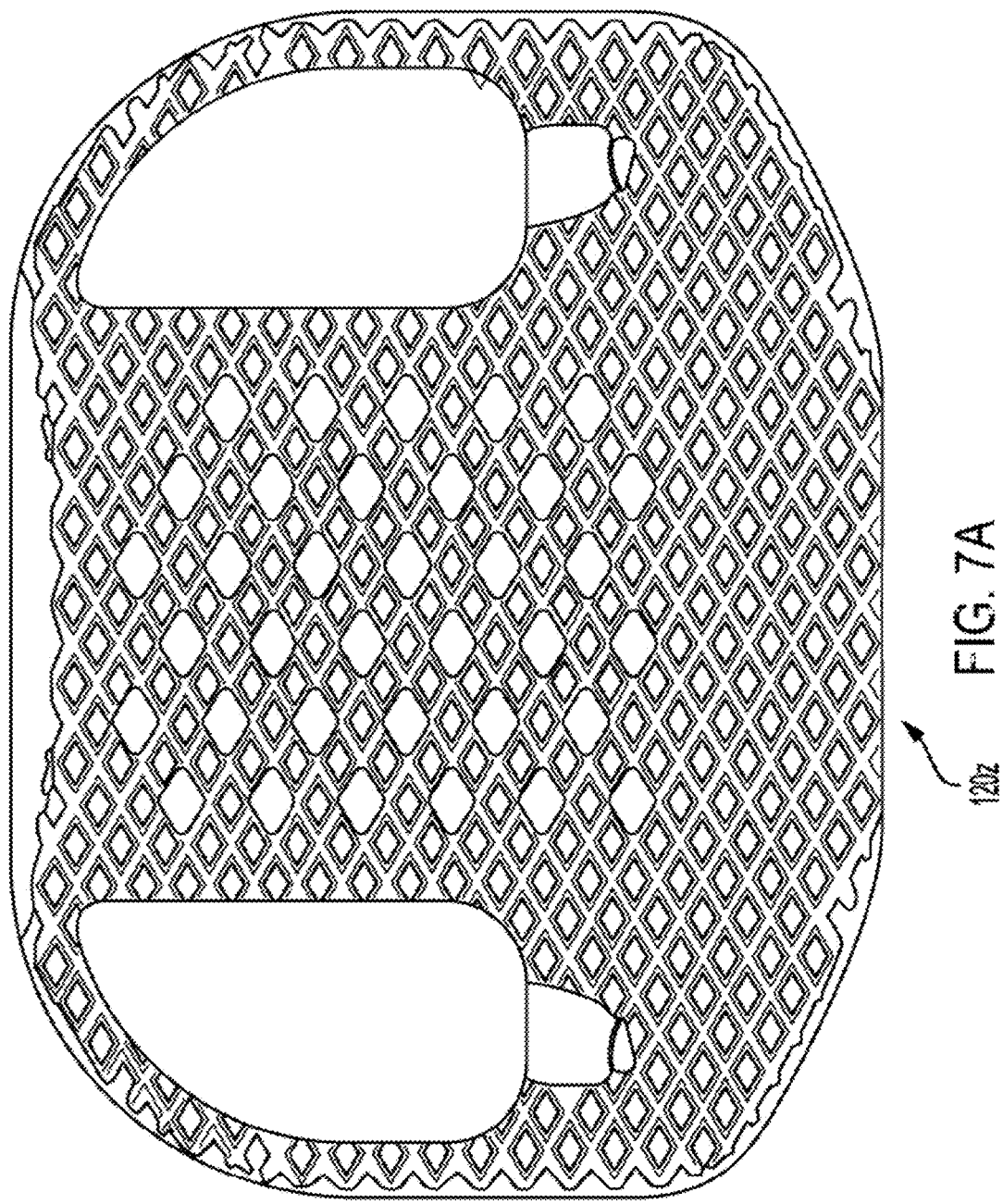
FIGS. 7A-7C are top down views of three exemplary footprint sizes of a bottom endplate in accordance with the principles of the present disclosure.
Figure 7B:
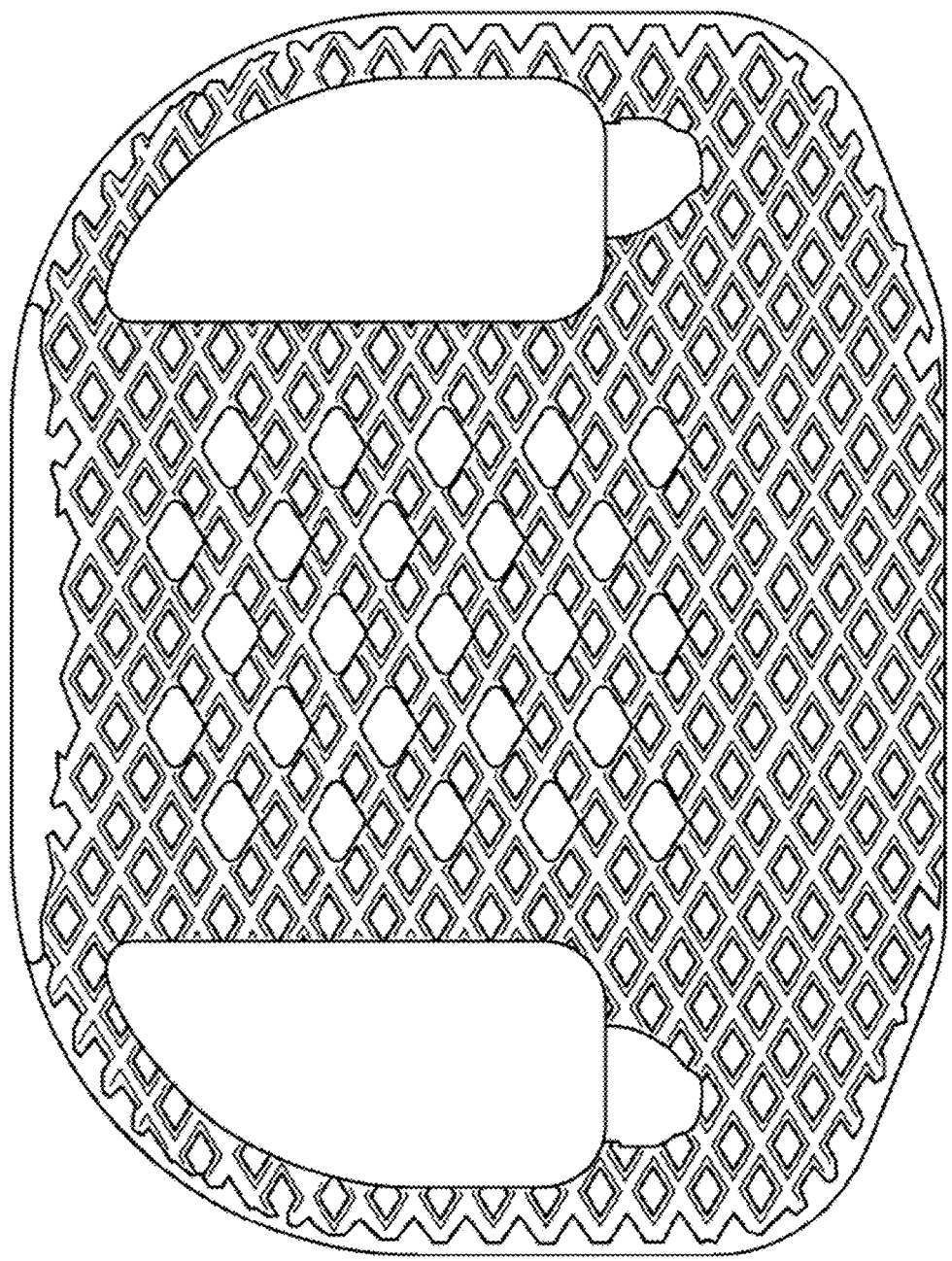
Figure 7C:
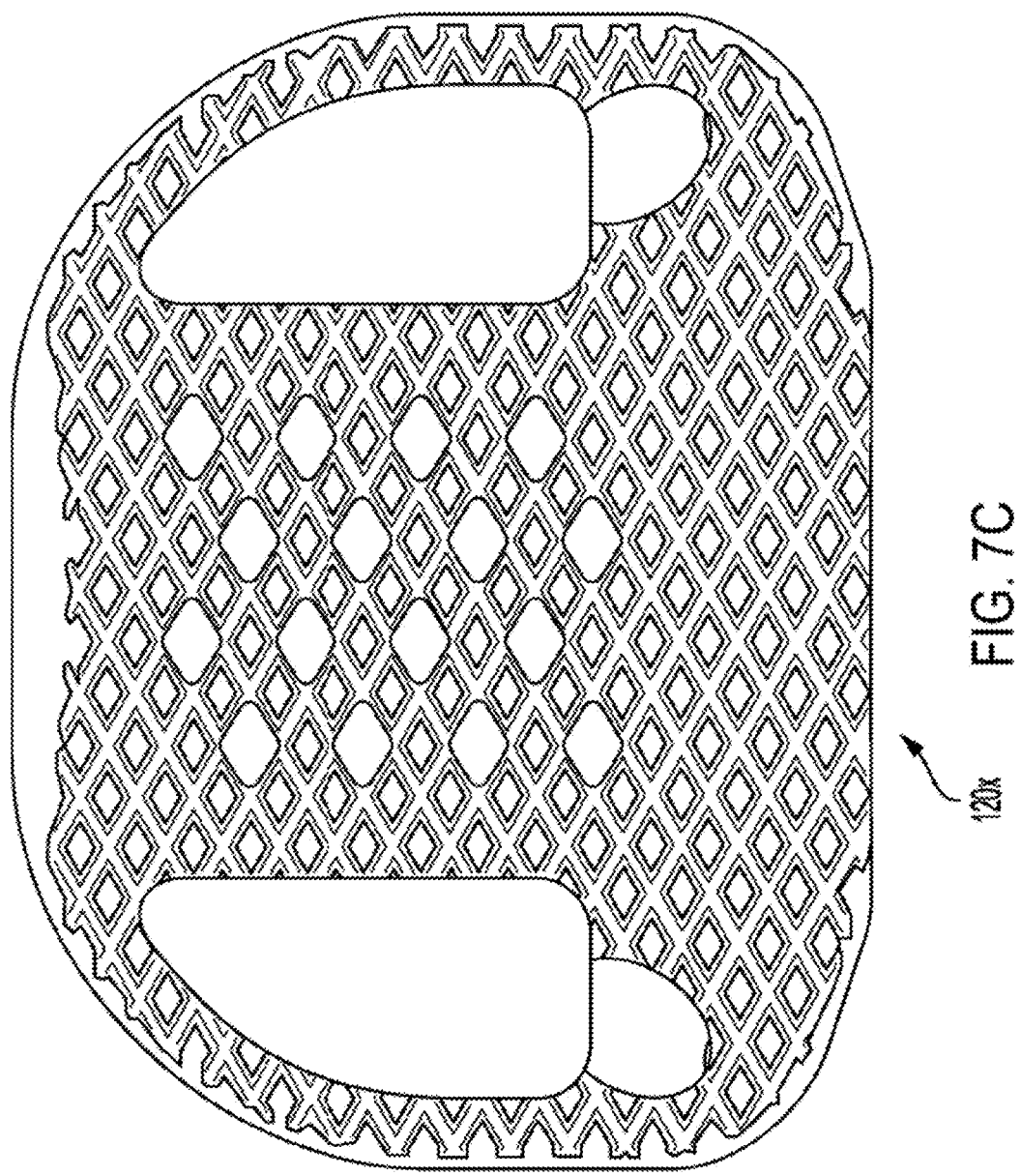

FIGS. 6A-6C are top down views of three exemplary footprint sizes of a first top endplate 110x, second top endplate 110y, and third top endplate 110z. It shall be understood that first, second, and third top endplates 110x, 110y, and 110z may be substituted for endplates 110, 110a, and 110c in accordance with the principles of the present disclosure. FIGS. 7A-7C are top down views of three exemplary footprint sizes of a first bottom endplate 120x, second bottom endplate 120y, and third bottom endplate 120z. It shall be understood that first, second, and third bottom endplates 120x, 120y, and 120z may be substituted for endplates 120, 120a, and 120c in accordance with the principles of the present disclosure. First top endplate 110x and first bottom endplate 120x may have a length of about 32 mm and a width of about 25 mm. Second top endplate 110y and second bottom endplate 120y may have a length of about 37 mm and a width of about 29 mm. Third top endplate 110z and third bottom endplate 120z may have a length of about 42 mm and a width of about 32 mm. It shall be understood that first top endplate 110x and first bottom endplate 110y are suitable for patients with relatively small vertebrae, second top endplate 110y and second bottom endplate 110y are suitable for patients with relatively larger vertebrae than the previous example, and third top endplate 110z and third bottom endplate 110z are suitable for patients with relatively larger vertebrae than the previous two examples. In this way, spinal implants 100, 200, and 300 may be configured to have any of the exemplary footprint sizes explained above depending on a particular patient's vertebral anatomy. For example, as part of an initial assessment a surgeon may assess which of the available footprint sizes is best suited for a particular patient's vertebral anatomy. It shall be understood that the above exemplary footprint sizes are non-limiting exemplary embodiments and that other footprint sizes may be used with any of spinal implants 100, 200, 300 provided the chosen footprint size is suitable for a particular patient's anatomy. However, the three exemplary footprint sizes explained above are generally suitable for the majority of patients.

Figure 8:
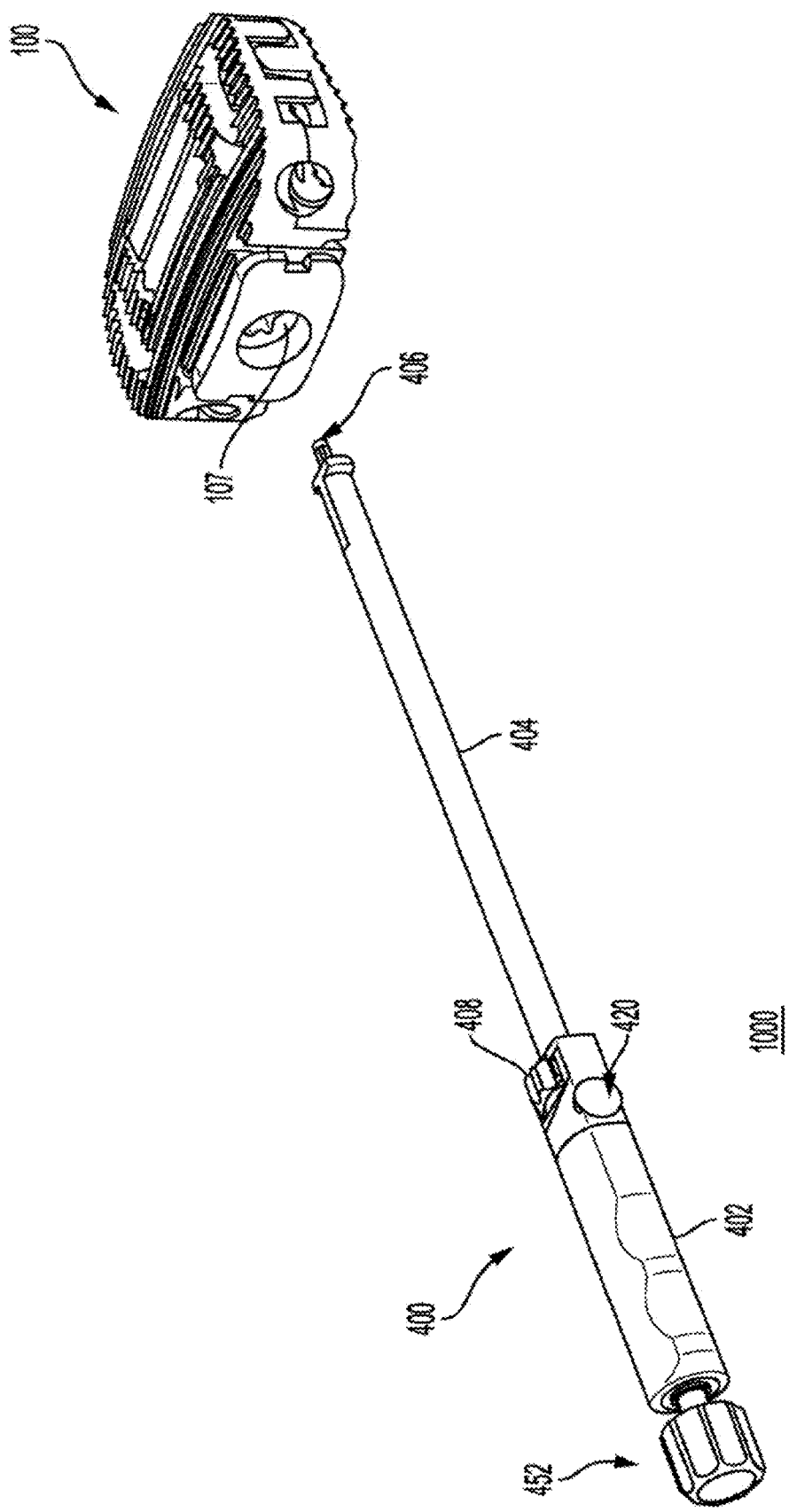
FIG. 8 is perspective view of one embodiment of an expandable spinal implant system in accordance with the principles of the present disclosure.
Figure 9A:
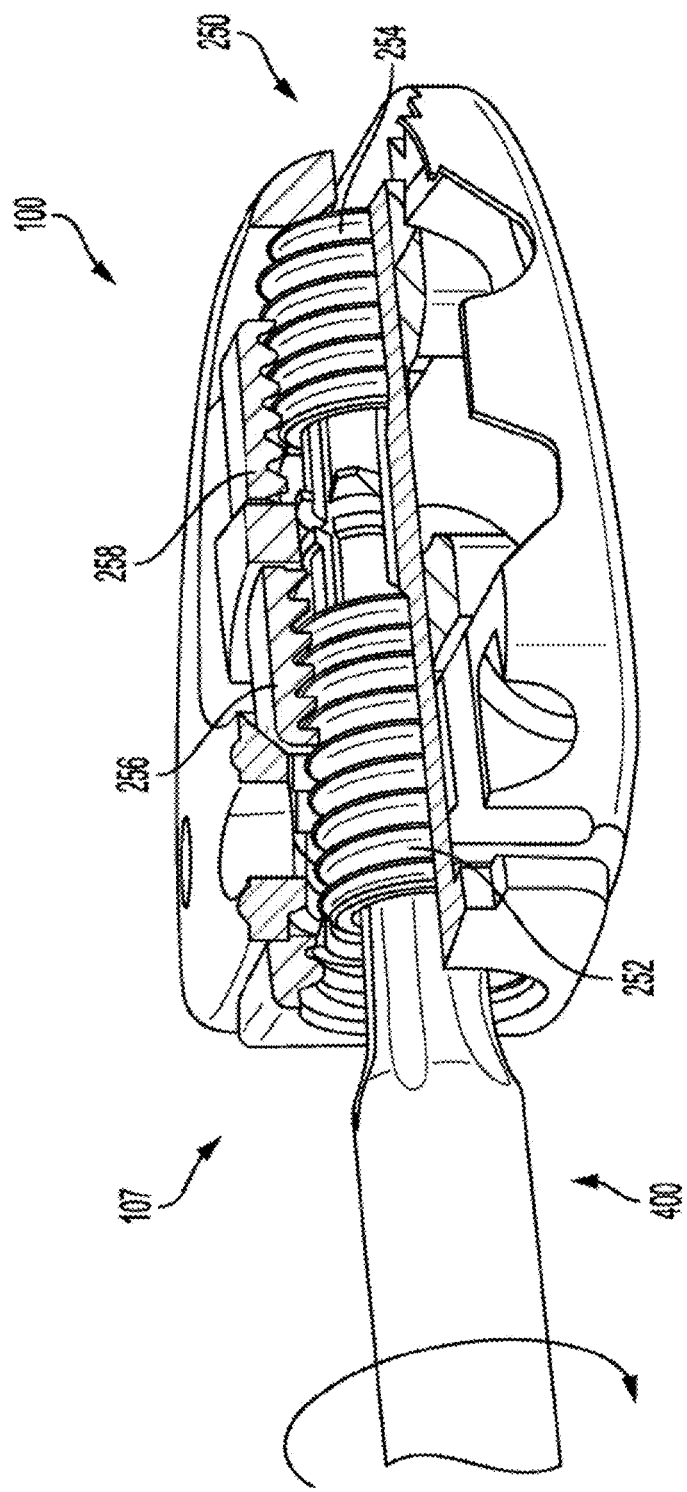
FIG. 9A is a cutout perspective showing a surgical tool in a first adjustment position where an exemplary spinal implant is in a contracted position.
Figure 9B:
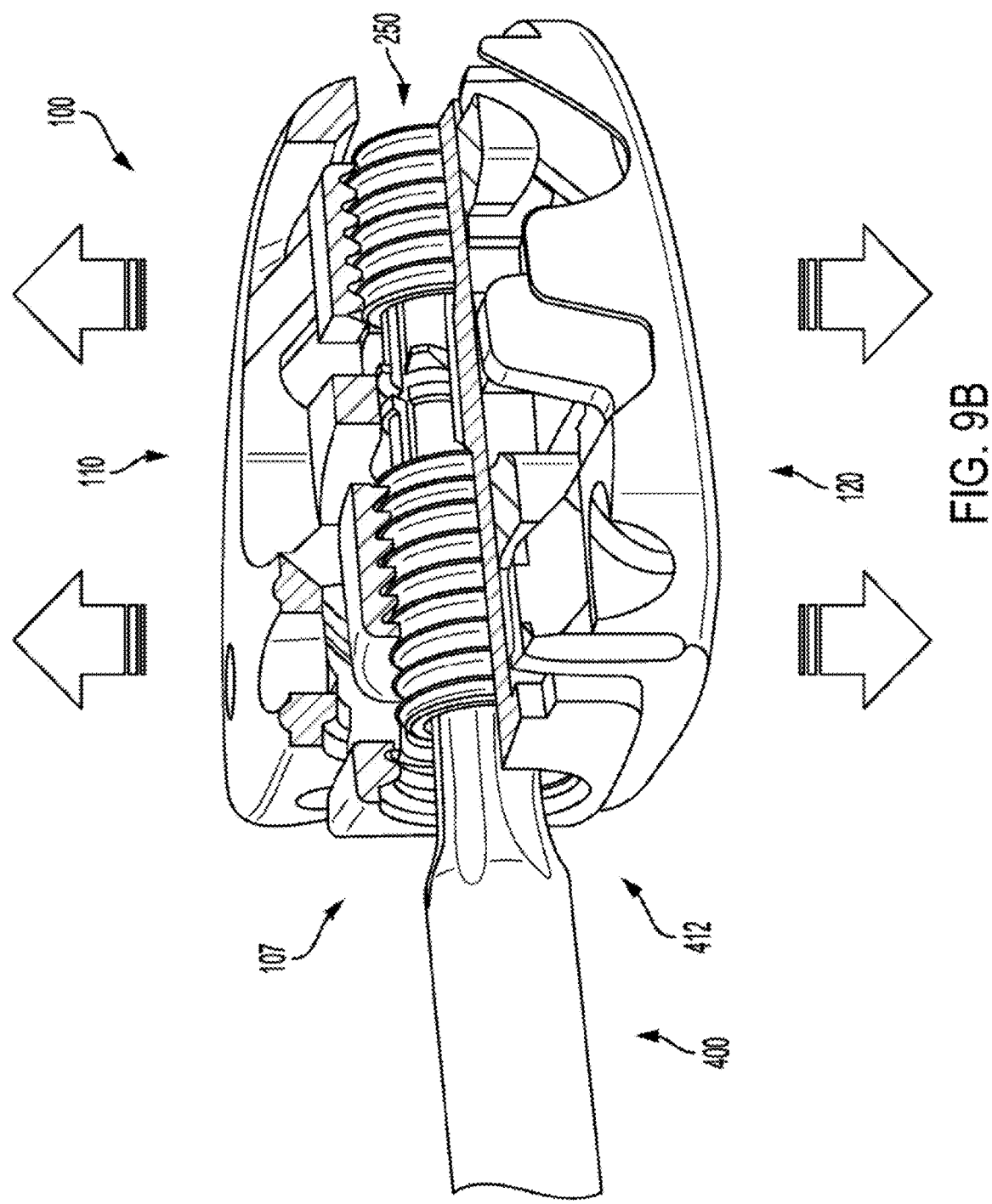
FIG. 9B is a cutout perspective showing the surgical tool in the first adjustment position after adjusting the exemplary spinal implant from the contracted position to a first expanded position.

FIG. 8 is a perspective view of one embodiment of an expandable spinal implant system 1000 in accordance with the principles of the present disclosure. First surgical tool 400 includes a handle 402, shaft 404, tip 406, locking mechanism 408, and adjustment knob 452. Tip 406 is configured to be inserted inside of guide aperture 107 and operably connected to spinal implant 100. First surgical tool 400 is configured to perform a variety of functions for operably manipulating spinal implant 100. For example, first surgical tool 400 is configured to operably engage with spinal implant 100 via a secured connection such that a spinal implant 100 may be inserted between vertebral bodies of a patient according to anterior surgical techniques, oblique surgical techniques, and lateral surgical techniques. Additionally, first surgical tool 400 is configured to operably engage with spinal implant 100 to adjust spinal implant 100 from a contracted position to an expanded position and vice-versa. Furthermore, first surgical tool 400 is configured to operably engage with spinal implant 100 to adjust an angle of inclination between endplates 110, 120. Further still, spinal implant 100 may be adjusted in situ between vertebral bodies after spinal implant 100 is inserted into a patient. Additional attributes of the surgical tool will be disclosed below with reference to FIGS. 18A-19B FIG. 9A is a cutout perspective showing first surgical tool 400 in a first adjustment position where the spinal implant 100 is in a contracted position and FIG. 9B is a cutout perspective showing first surgical tool 400 in the first adjustment position after adjusting the spinal implant 100 from the contracted position to a first expanded position. As illustrated, tip 406 is inserted through guide aperture 107 and into moving mechanism 250. Moving mechanism 250 includes a first set screw 252 and a second set screw 254 having respective internal cavities configured to operably receive tip 406. In some embodiments, first set screw 252 may be referred to as an anterior screw and second set screw 254 may be referred to as a posterior screw. The first and second set screws 252, 254 have a helical thread pitch that corresponds to keyed projections of first and second trolleys 256, 258, respectively. In the exemplary embodiment, the second set screw 254 has a reverse thread pitch and a shorter length than first set screw 252. In some embodiments, the thread pitch may be an M6 thread pitch, however other embodiments may have other thread pitches.

Each internal cavity of set screws 252, 254 comprises an internal circumferential surface that is keyed to the outside circumferential surface 456 of tip 406 of first surgical tool 400. For example, the outside circumferential surface 456 may resemble the geometry of the tip of a torx driver, hex driver, or the like and the internal circumferential surfaces of the first and second set screws 252, 254 may resemble the geometry of the cavity of the head of a torx screw, hex screw, or the like. In some embodiments, the internal circumferential surfaces of the first and second set screws 252, 254 may be configured for a Torx T20 driver or the like, however other embodiments may be differently sized. In other embodiments, the connection between the outer circumferential surface 456 and the inner circumferential surfaces of first and second set screws 252, 254 may comprise a variety of drive interfaces including but not limited to: multi-lobular drives; hexalobular drives; cross or Phillips head drives; straight or "flat head" drives; square or other polygonal drives; and/or combinations thereof. It shall be understood that any suitable geometrical shape or surface profile may be used by the exemplary embodiments disclosed herein provided the outside circumferential surface 456 is operably keyed to engage with the internal circumferential surfaces of the first and second set screws 252, 254.

In the exemplary embodiment, outside circumferential surface 456 is engaged with both the first and second set screws 252, 254 and when first surgical tool 400 is rotated in a first direction (clockwise direction) the outside circumferential surface 456 translates both set screws 252, 254 thereby causing the first and second trolleys 256, 258 to move away from one another in opposite directions. In turn, the first and second trolleys 256, 258 cause the top and bottom endplates 110, 120 to move apart from one another an equal amount in the expansion direction indicated by the arrows. The expansion direction may be a generally vertical direction projecting away from and perpendicular to the generally horizontal direction of a rotation axis of the moving mechanism. Likewise, when first surgical tool 400 is rotated in a second direction (counter-clockwise direction) the outside circumferential surface 456 translates both set screws 252, 254 thereby causing the first and second trolleys 256, 258 to move towards one another (not illustrated). In turn, the first and second trolleys 256, 258 urge the top and bottom endplates 110, 120 to move towards one another an equal amount in a contraction direction (not illustrated). The contraction direction may be a generally vertical direction projecting towards and perpendicular to the generally horizontal direction of the rotation axis of the moving mechanism. In summary, when positioning the first surgical tool 400 in the first position and rotating the first surgical tool 400 in either the first or second direction the moving mechanism 250 operably adjusts a spacing between the top and bottom endplates by simultaneous rotation of the first and second set screws 252, 254 along the rotation axis.

Figure 10A:
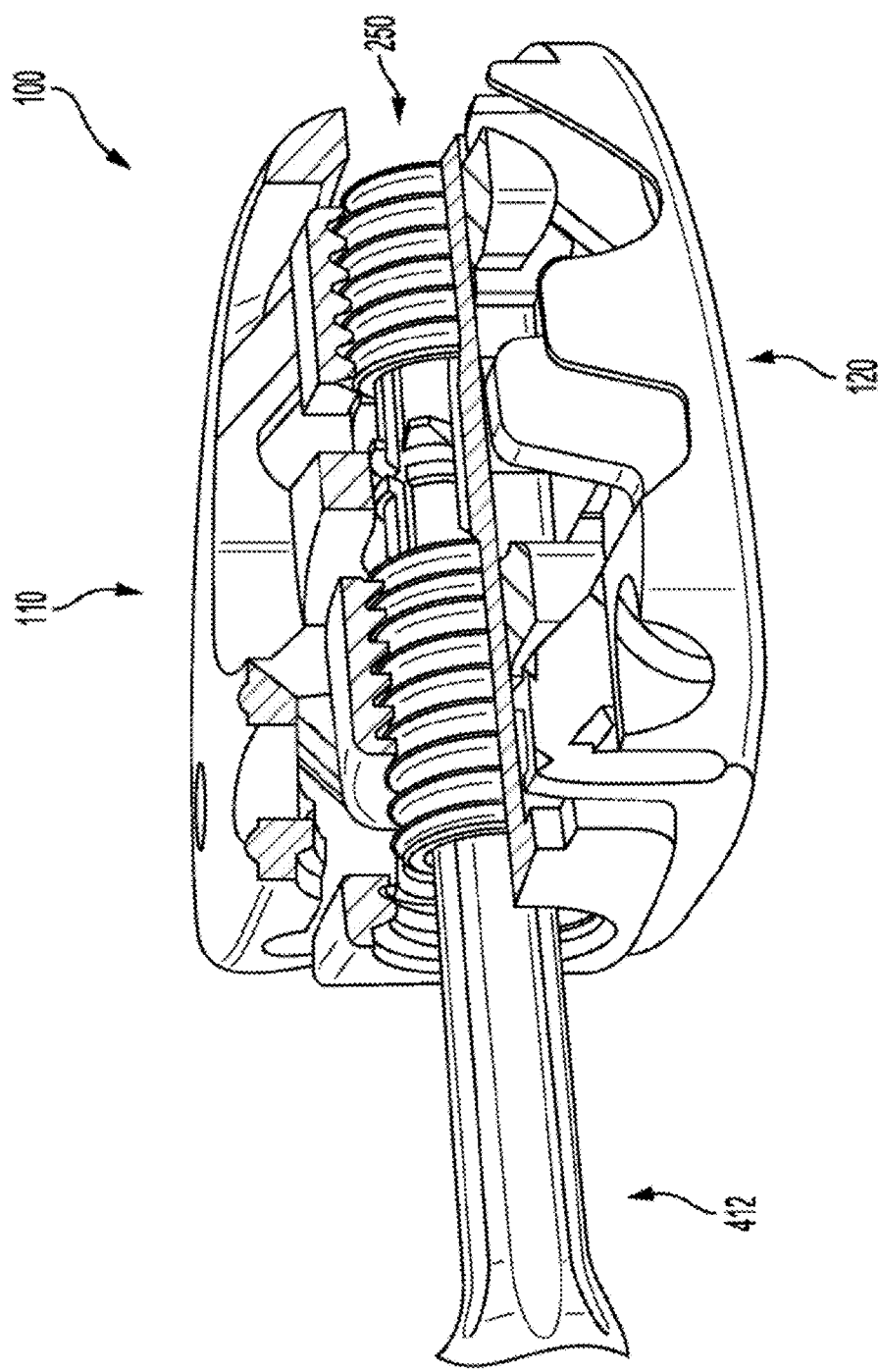
FIG. 10A is a cutout perspective showing the surgical tool in a second adjustment position where the exemplary spinal implant is in the first expanded position of FIG. 9B.
Figure 10B:
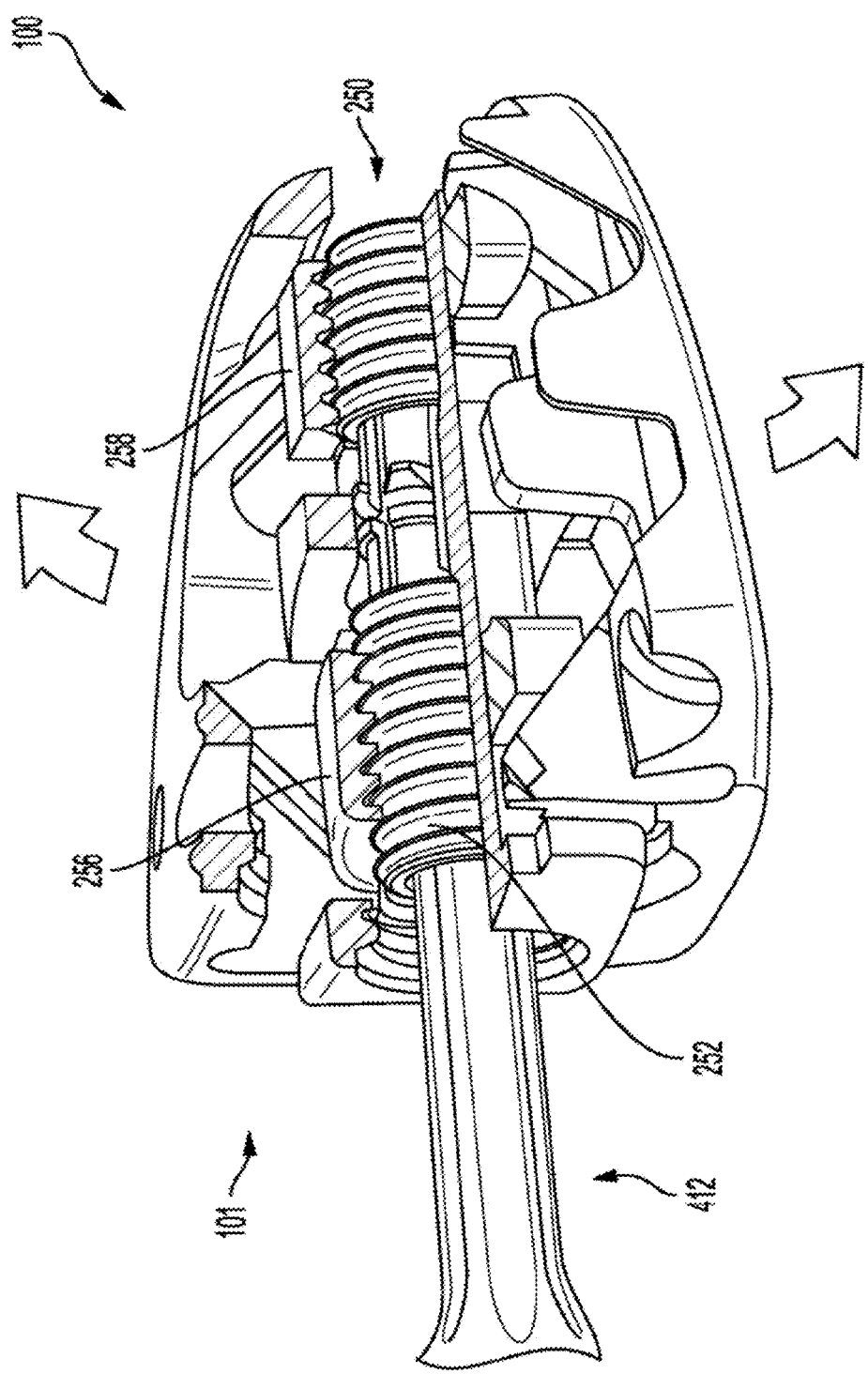
FIG. 10B is a cutout perspective showing the surgical tool in the second position after adjusting the exemplary spinal implant from the first expanded position to an expanded and angled position.

FIG. 10A is a cutout perspective showing first surgical tool 400 in a second adjustment position where the spinal implant 100 is in the first expanded position of FIG. 9B. As illustrated, first surgical tool 400 is retracted from moving mechanism 250 such that the outside circumferential surface 456 is only engaged with the first set screw 252, i.e., first surgical tool 400 is in the second position. When first surgical tool 400 is in the second position and rotated in a first direction (clockwise direction) the outside circumferential surface 456 translates only the first set screw 252 thereby causing only the first trolley 256 to move towards the proximal end 101 of spinal implant 100 and allowing the second trolley 258 to remain stationary in place. In turn, the first trolley 256 urges the proximal end 101 of top and bottom endplates 110, 120 thereby causing top and bottom endplates 110, 120 to move apart from one another at the proximal end 101 in the direction shown by the arrows thereby increasing an angle of inclination between the top and bottom endplates 110, 120. Likewise, when first surgical tool 400 is in the second position and is rotated in the second direction (counter-clockwise direction) the outside circumferential surface 456 translates only the first set screw 252 thereby causing the first trolley 256 to move towards the stationary second trolley 258. In effect, the top and bottom endplates 110, 120 move towards one another at the proximal end 101 (not illustrated) thereby decreasing an angle of inclination between the top and bottom endplates 110, 120. In summary, when positioning the first surgical tool 400 in the second position and rotating the first surgical tool 400 in either the first or second direction the moving mechanism 250 operably adjusts an angle of inclination between the top and bottom endplates 110, 120 upon rotating the first set screw along the rotation axis.

Figure 11A:
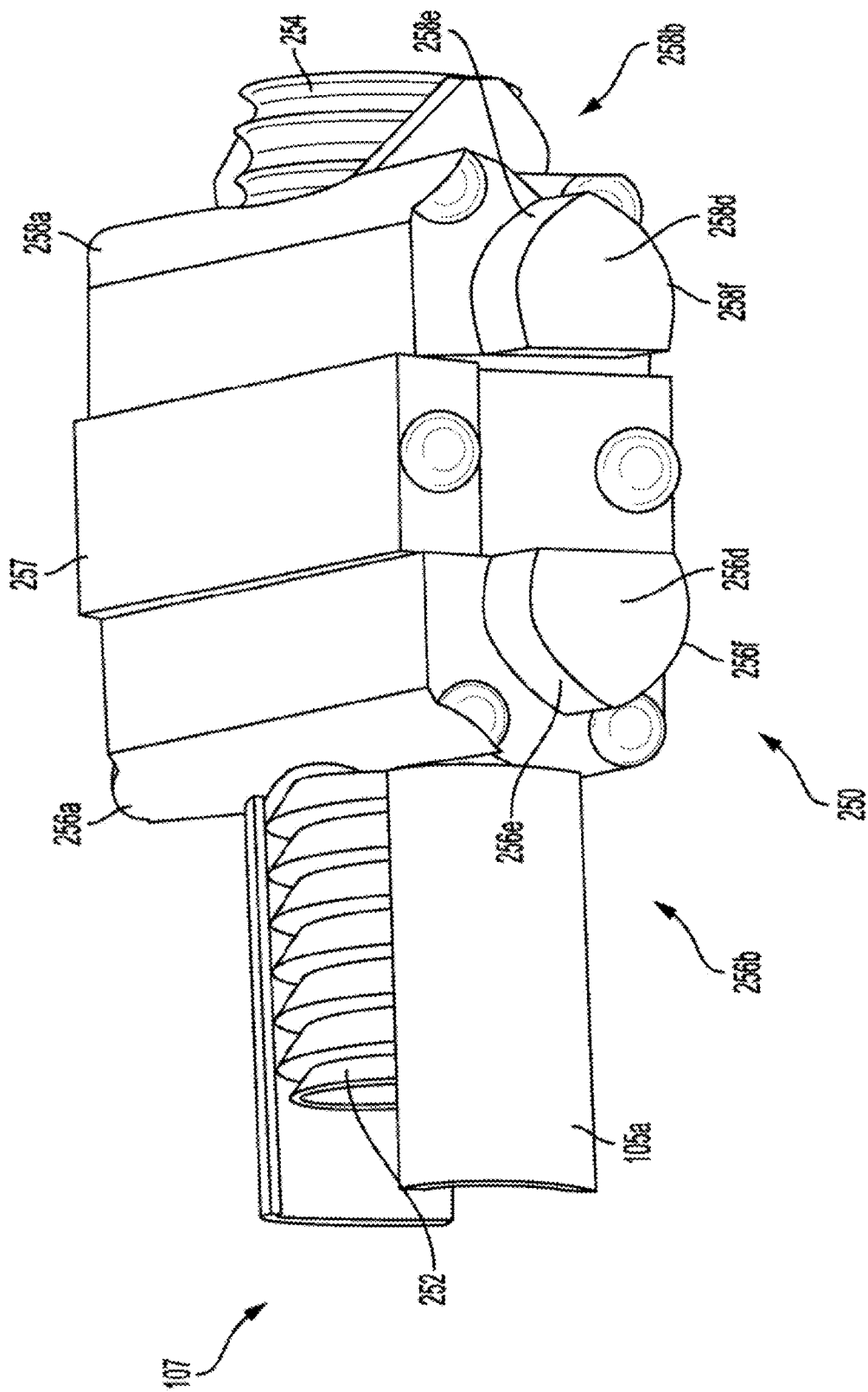
FIGS. 11A and 11B are perspective views of a moving mechanism in a contracted position and an expanded position, respectively, in accordance with the principles of the present disclosure.
Figure 11B:
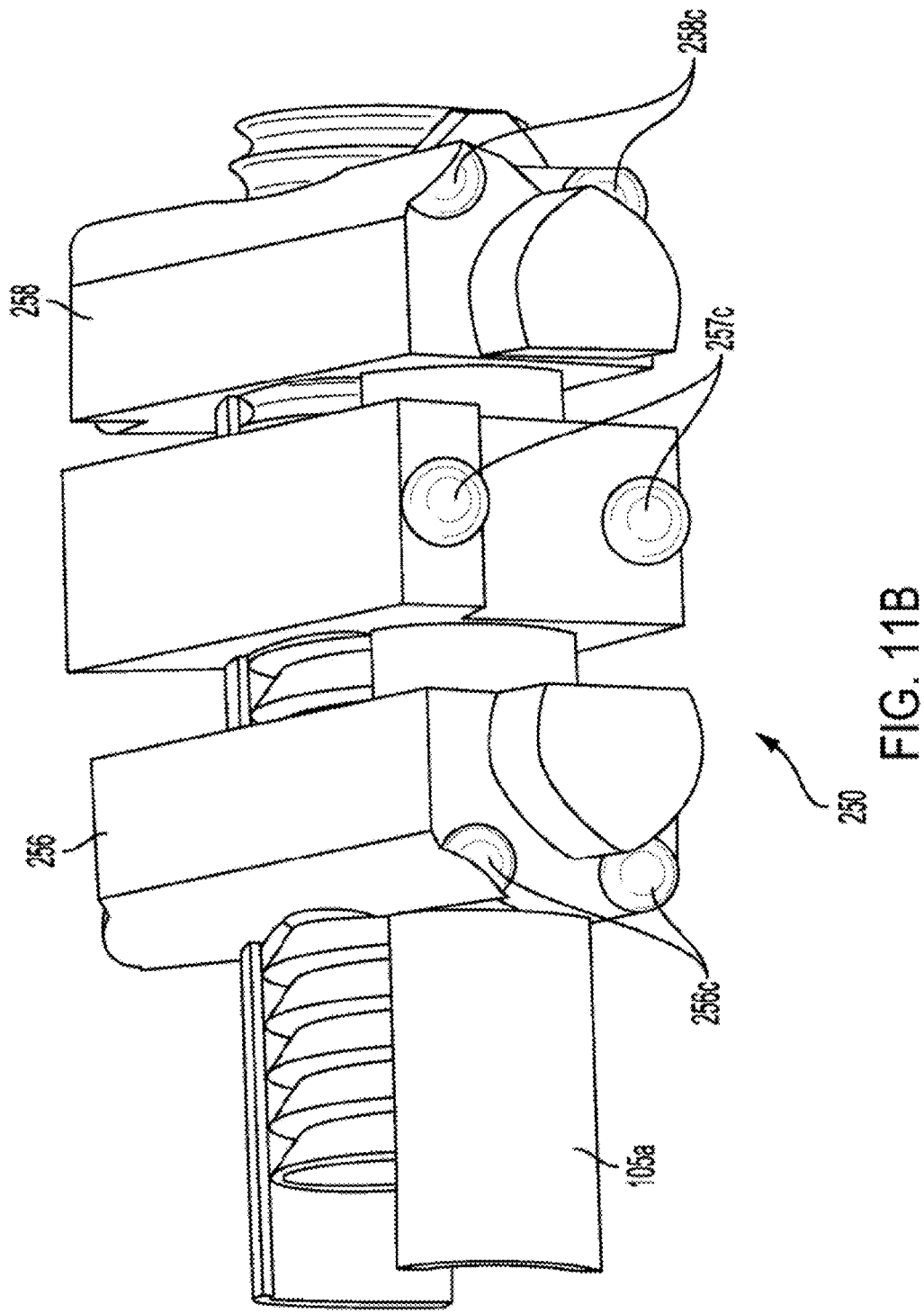

FIGS. 11A and 11B are perspective views of a moving mechanism 250 in a contracted position and an expanded position, respectively. Moving mechanism 250 is suitable for use in any exemplary embodiments disclosed herein. As illustrated moving mechanism 250 includes a screw guide housing 105a coupled to screw guide endplate 105 (not illustrated) and a central buttress block 257. Screw guide housing 105a may operably retain first and second screws 252, 254 therein and thereby define a rotation axis of moving mechanism 250 projecting in a longitudinal direction thereof. First and second trolleys 256, 258 are operably coupled to first and second set screws 252, 254 and are further configured to move along outside surfaces of screw guide housing 105a upon rotation of first and second set screws 252, 254.

First trolley 256 includes a first beveled edge 256a and a second beveled edge 256b opposite the first beveled edge 256a, the first and second beveled edges 256a, 256b are disposed on opposite sides of the rotation axis of the moving mechanism 250. Second trolley 258 includes a third beveled edge 258a and a fourth beveled edge 258b (not illustrated) opposite the third beveled edge 258a, the third and fourth beveled edges 258a, 258b are disposed on opposite sides of the rotation axis of the moving mechanism 250. Additionally, first trolley 256 has a first side surface and a second side surface opposite the first side surface, the first and second side surfaces being on opposite sides of the rotation axis of the moving mechanism 250. Likewise, second trolley 256 has a third side surface and a fourth side surface opposite the third side surface, the third and fourth side surfaces being on opposite sides of the rotation axis of the moving mechanism 250. Furthermore, buttress block 257 has a seventh and eighth side surface opposite the seventh side surface, the seventh and eighth side surfaces being on opposite sides of the rotation axis of the moving mechanism 250.

First trolley 256 includes a first plurality of projections 256c, the second trolley 258 includes a second plurality of projections 258c, and the buttress block 257 includes a third plurality of projections 257c. In the exemplary embodiment, first trolley 256 has two projections 256c projecting perpendicularly out from first side surface and two projections 256c projecting perpendicularly out from second side surface. Likewise, second trolley 258 has two projections 258c projecting perpendicularly out from third side surface and two projections 258c projecting perpendicularly out from fourth side. Furthermore, buttress block 257 has two projections 257c projecting perpendicularly out from seventh side surface and two projections 258c projecting perpendicularly out from eighth side surface. The first and second plurality of projections 256c, 258c may be conically shaped projections having a dome like shape or a hemispherical shape, for example. In the non-limiting exemplary embodiment, each projection of the first and second plurality of projections 256c, 258c comprises a hemispherical projection having a flat surface that coincides with a corresponding surface of one of the first through fourth beveled edges 256a, 256b, 258a, 258b. However, other embodiments may have other shapes and/or surface profiles as may be consistent with the disclosure herein.

First trolley 256 includes a first plurality of wedges 256d and second trolley 258 includes a second plurality of wedges 258d. For example, first trolley 256 includes a first wedge 256d projecting away from the first side surface in a transverse direction of the moving mechanism 250 and a second wedge 256d projecting away from the second side surface in the transverse direction of the moving mechanism. Likewise, second trolley 258 includes a third wedge 258d projecting away from the third side surface in a transverse direction of the moving mechanism 250 and a fourth wedge 258d projecting away from the fourth side surface in the transverse direction of the moving mechanism. In the exemplary embodiment, each wedge of the first plurality of wedges 256d includes a corresponding upper contact surface 256e and a corresponding lower contact surface 256f and each respective upper contact surface 256e meets a corresponding lower contact surface 256f at an apex point (not labeled). Likewise each wedge of the second plurality of wedges 258d includes a corresponding upper contact surface 258e and a corresponding lower contact surface 258f and each respective upper contact surface 258e meets a corresponding lower contact surface 258f at an apex point (not labeled). In the exemplary embodiment, each upper contact surface 256e, 258e and each lower contact surface 256f, 258f has a curved surface profile. For example, each upper contact surface 256e, 258e is concave with respect to a corresponding apex point and each lower contact surface 256f, 258f is convex with respect to a corresponding apex point.

Figure 12A:
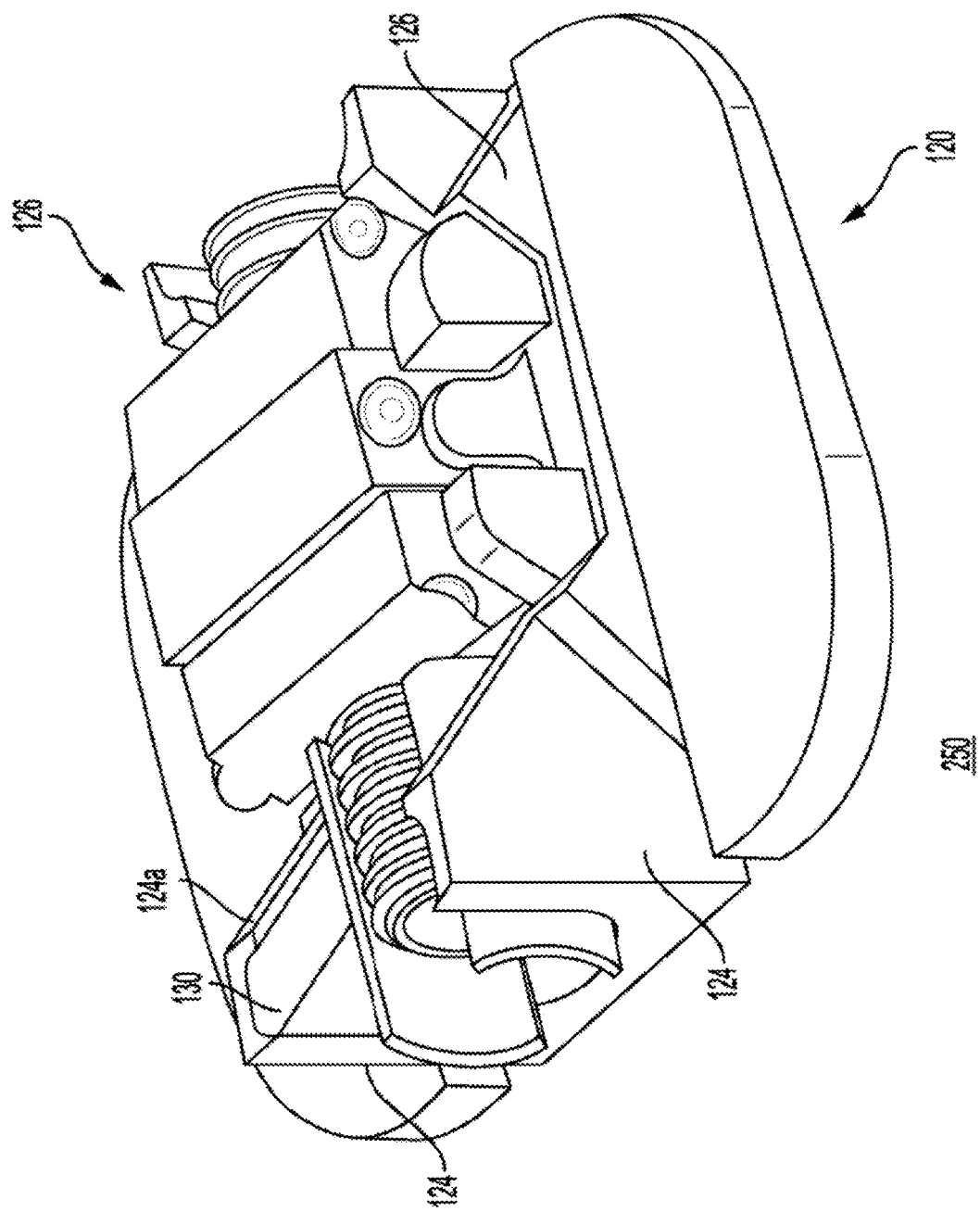
FIGS. 12A and 12B are perspective views of the moving mechanism of FIGS. 11A and 11B in the contracted position and the expanded position, respectively, with a bottom endplate in accordance with the principles of the present disclosure.
Figure 12B:
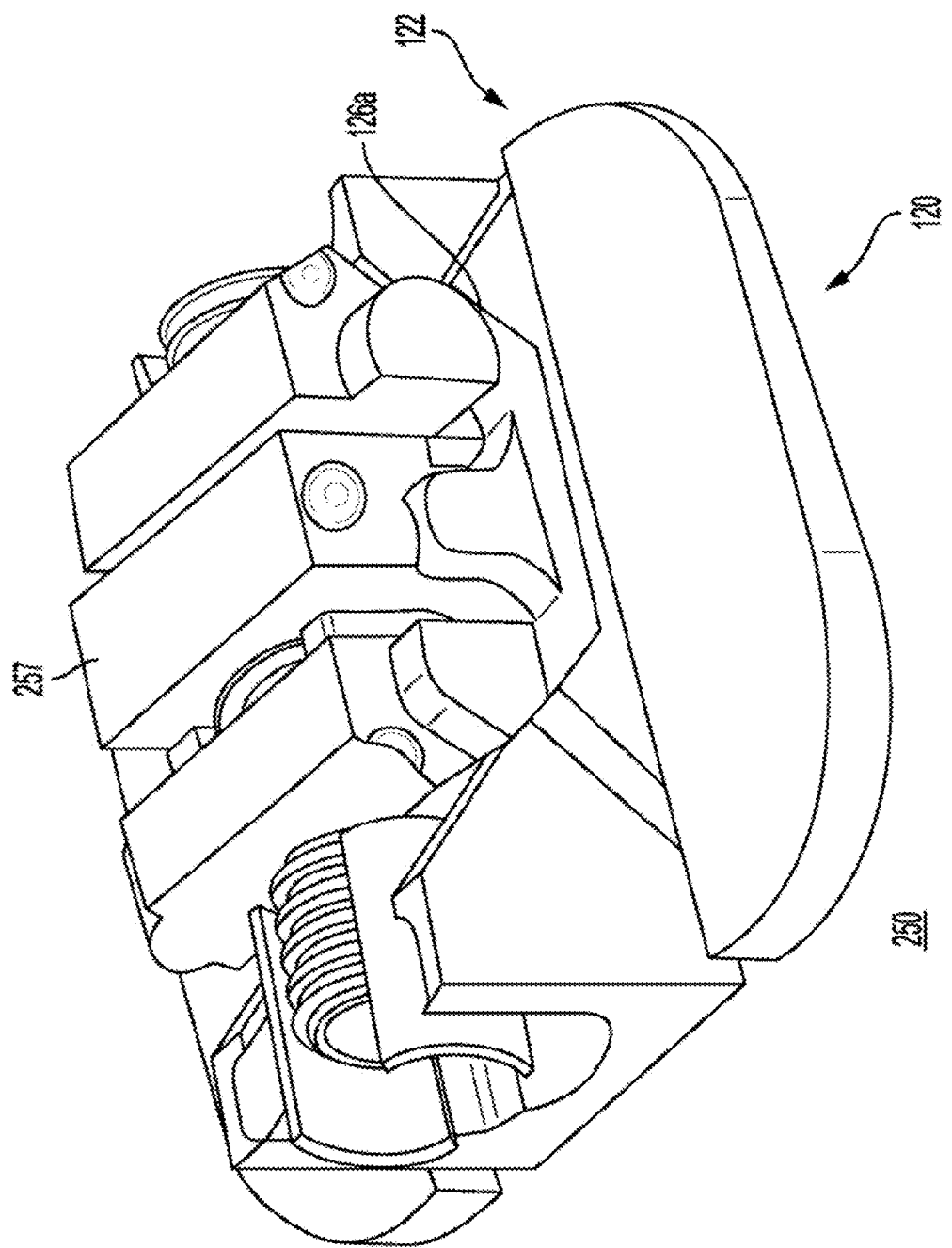
Figure 13A:
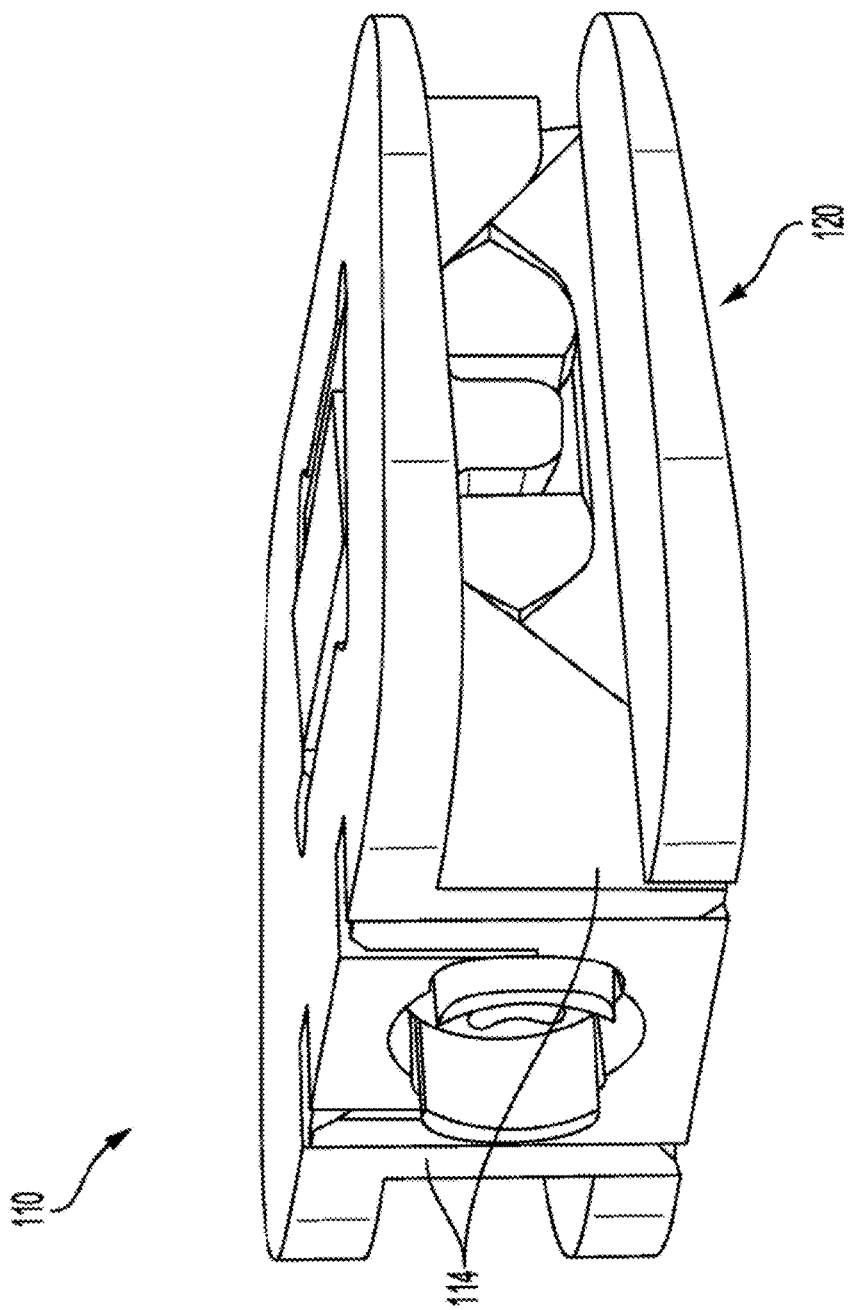
FIGS. 13A and 13B are perspective views of the moving mechanism of FIGS. 12A and 12B in the contracted position and the expanded position, respectively, with a top endplate and the bottom endplate in accordance with the principles of the present disclosure.
Figure 13B:
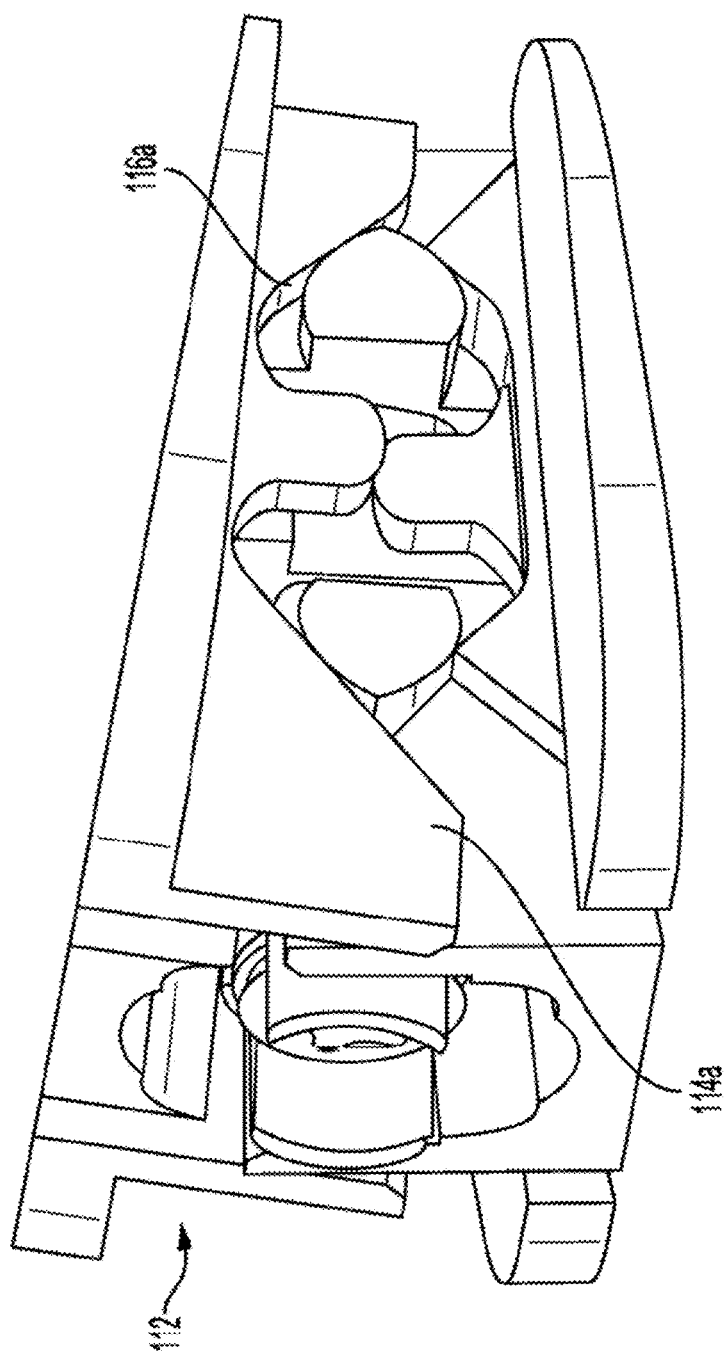

FIGS. 12A and 12B are perspective views of moving mechanism 250 of FIGS. 11A and 11B in the contracted position and the expanded position, respectively, shown with an exemplary bottom endplate 120. FIGS. 13A and 13B are perspective views of the moving mechanism 250 of FIGS. 12A and 12B in the contracted position and the expanded position, respectively, with a top endplate 110 and a bottom endplate 120. It shall be understood that FIGS. 12A-13B schematically moving mechanism 250 with some internal parts being illustrated or simplified and others being omit for ease of explanation. For example, FIGS. 12A-13B are illustrated schematically solely to assist in explaining operable characteristics of moving mechanism 250. FIGS. 12A and 12B show bottom endplate 120 having a pair of second proximal ramps 124 and a pair of second distal ramps 126 disposed opposite the pair of second proximal ramps 124. Each ramp of second proximal ramps 124 may include a first inclined contact surface 124a extending away from buttress block 257 and inclined with respect to an inside surface 122 of endplate 120. Similarly, each ramp of second distal ramps 126 may include a second inclined contact surface 126a extending away from buttress block 257 and inclined with respect to an inside surface 122 of endplate 120. In the exemplary embodiment, the first inclined contact surfaces extend a first length (first distance) and the second inclined contact surfaces extend a second length (second distance) and the first length is greater than the second length.

FIGS. 13A and 13B show top endplate 110 having a pair of first proximal ramps 114 and a pair of first distal ramps 116 disposed opposite the pair of first proximal ramps 114. Each ramp of first proximal ramps 114 may include a third inclined contact surface 114a extending away from buttress block 257 and inclined with respect to an inside surface 112 of endplate 110. Similarly, each ramp of first distal ramps 116 may include a fourth inclined contact surface 116a extending away from buttress block 257 and inclined with respect to an inside surface 112 of endplate 110. In the exemplary embodiment, the third inclined contact surfaces extend a third length (third distance) and the fourth inclined contact surfaces extend a fourth length (fourth distance) and the third length is greater than the fourth length.

Figure 17:
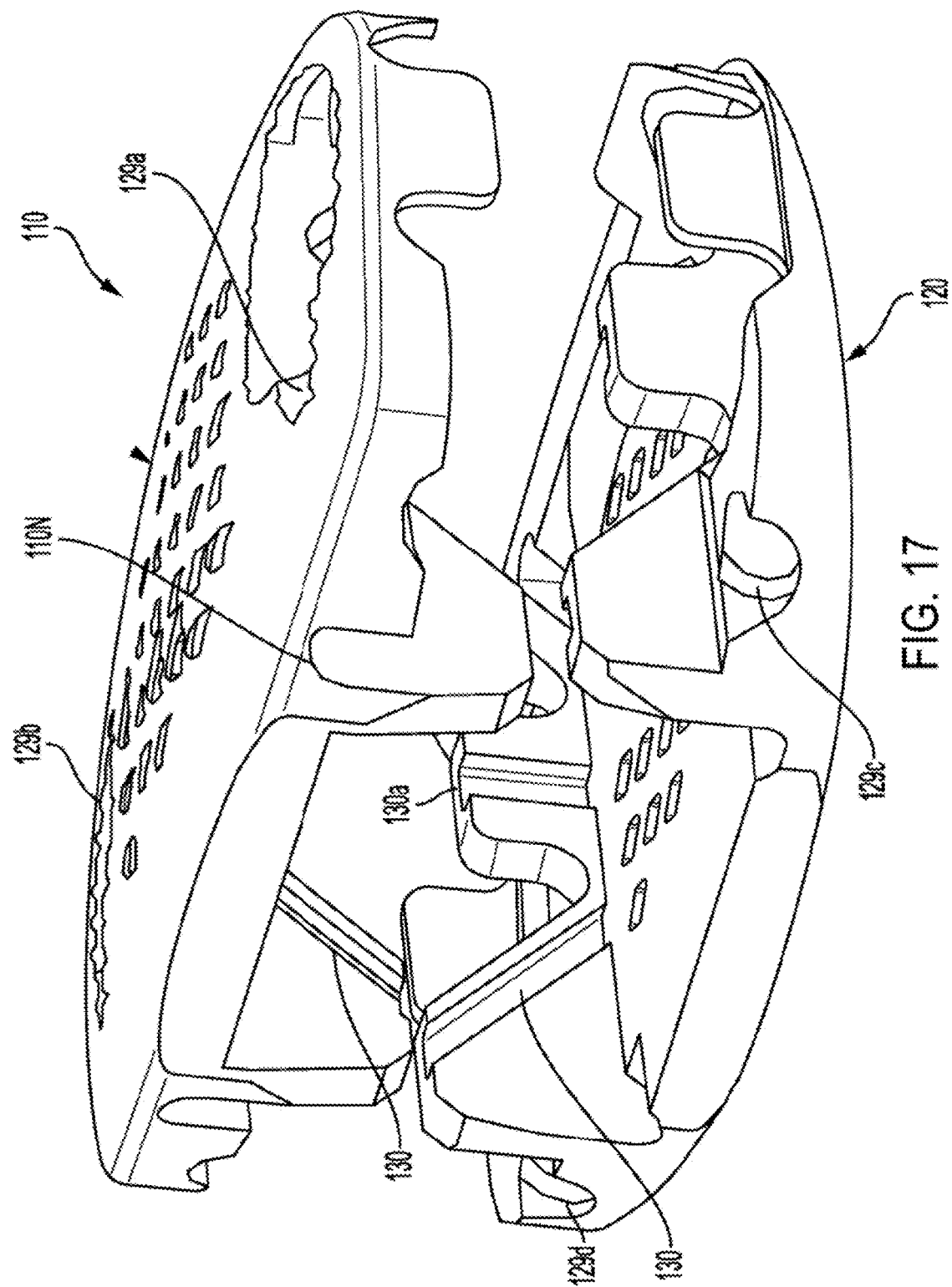
FIG. 17 is an exploded view of the top endplate and bottom endplate of FIG. 16 in accordance with the principles of the present disclosure.

Each ramp of ramps 114, 116, 124, 126 may have an inside surface disposed adjacent to and facing the rotation axis of moving mechanism 250 and an outside surface opposite the inside surface and facing away from the rotation axis of moving mechanism 250. Additionally, each ramp of ramps 114, 116, 124, 126 may include a corresponding guide wall 130, which is best illustrated in FIGS. 12A and 17. Each guide wall 130 may extend along the inside surface of a corresponding ramp in a parallel direction to the corresponding contact surface. For example, with reference to FIGS. 12A-13B, guide wall 130 extends along the inside surface of proximal ramp 124 in a direction that is substantially parallel to first inclined contact surface 124a. As best understood with reference to FIGS. 12A-12B, each bottom most projection 256c of the first trolley 256 is disposed inside of a corresponding guide wall 130 of the second proximal ramps 124. Likewise, each bottom most projection 258c of the second trolley 258 is disposed inside of a corresponding guide wall 130 of the second distal ramps 126. Similarly, although not directly visible, in FIGS. 13A-13B each top most projection 256c of the first trolley 256 is disposed inside of a corresponding guide wall 130 of first proximal ramps 114. Likewise, each top most projection 258c of second trolley 258 is disposed inside of a corresponding guide wall 130 of first distal ramps 116.

With reference to FIGS. 13A and 13B, when first surgical tool 400 is in the first position and translates first and second screws 252, 254 in the first direction the first and second trolleys 256, 258 move away from one another in opposite directions and the top endplate 110 and bottom endplate 120 move away from one another as the spinal implant 100 expands. For example, in some embodiments, beveled edges 256a, 256b of the first trolley 256 act against endplates 110, 120 at a proximal end 101 thereof and the first plurality of wedges 256d contact and slide along a corresponding ramp of the first and second first proximal ramps 114, 124. However, in other embodiments, 256e and 256f may act against inclined contact surface 124a in lieu of providing beveled edges 256a, 256b. In some embodiments, beveled edges 258a, 258b of the second trolley 258 act against endplates 110, 120 at a distal end 102 thereof and the second plurality of wedges 258d contact and slide along a corresponding ramp of the first and second first distal ramps 116, 126. However, in other embodiments, 258e and 258f may push against inclined contact surface 126a in lieu of providing beveled edges 256a, 256b. Additionally, each projection 256c of the first trolley 256 slides along a corresponding guide wall 130 of the first and second first proximal ramps 114, 124 and each projection 258c of the second trolley 258 slides along a corresponding guide wall 130 of the first and second distal ramps 116, 126. Furthermore, during the expansion of spinal implant 100 each projection 257c of buttress block 257 may slide vertically in a corresponding vertical guide wall 130a (see FIG. 17) of the top and bottom endplates 110, 120. In this way, the spinal implant 100 moves from a contracted position to an expanded position. It shall be understood that movement of spinal implant from the expanded position to the contracted position occurs in substantially the same way.

When first surgical tool 400 is in the second position and translates only the first screw 252 in the first direction the first trolley 256 moves away from buttress block 257 and stationary second trolley 258 and an angle of inclination between the top endplate 110 and bottom endplate 120 increases. For example, beveled edges 256c of first trolley 256 may push against endplates 110, 120 at a proximal end 101 thereof and/or the first plurality of wedges 256d may contact and slide along a corresponding ramp of the first and second first proximal ramps 114, 124 as explained above. Additionally, each projection 256c of the first trolley 256 slides along a corresponding guide wall 130 of the first and second first proximal ramps 114, 124 as explained above. The second trolley 258 remains stationary with beveled edges 258a, 258b remaining in contact with endplates 110, 120 at a distal end 102 thereof and the second plurality of wedges 258d remaining in contact with a corresponding ramp of the first and second distal ramps 116, 126. Due to first trolley 256 acting against endplates 110, 120 by moving away from buttress block 127 and second trolley 258 remaining stationary the second plurality of wedges 258d pivot along a corresponding ramp of the first and second distal ramps 116, 126 and each projection 258c of the second trolley 258 pivots and/or incrementally slides along a corresponding guide wall 130 of the first and second first distal ramps 116, 126. Furthermore, during the expansion of spinal implant 100 each projection 257c of buttress block 257 may slide vertically up and down in a corresponding vertical guide wall 130a (see FIG. 17) of the top and bottom endplates 110, 120 as necessary. In this way, a distance between endplates 110, 120 at the proximal end 101 is increased and a distance between endplates 110, 120 at the distal end 102 is minutely decreased thereby adjusting an angle of inclination between top endplate 110 and bottom endplate 120. Those with skill in the art, will appreciate that in disclosed exemplary embodiments first set screw 252 is longer than second set screw 254 thereby providing more room for travel of the first trolley 256 such that the first trolley 256 may enable a greater distance of travel between endplates 110, 120 at the proximal end 101 than second trolley 258 enables at the distal end 102.

Figure 14A:
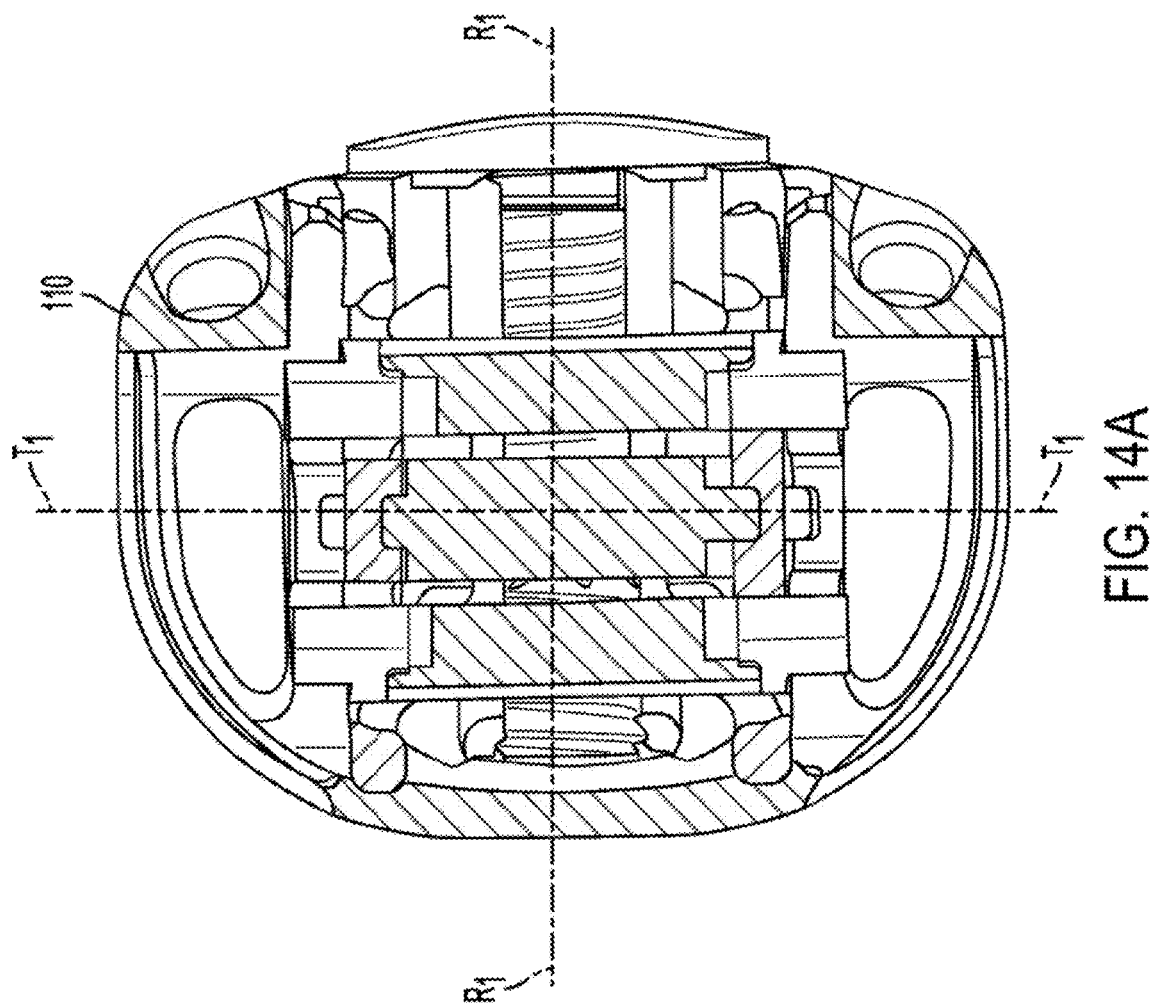
FIGS. 14A and 14B are cut-out views of a moving mechanism in accordance with the principles of the present disclosure.
Figure 14B:
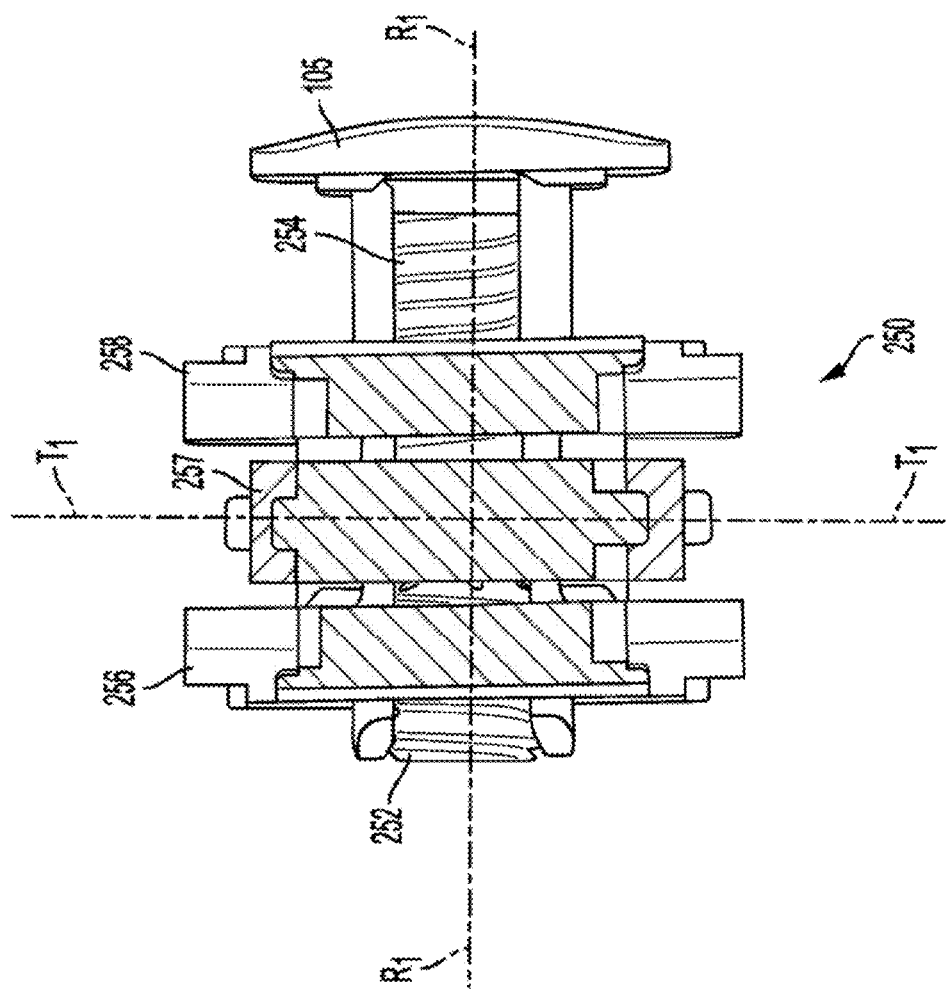

FIGS. 14A and 14B are cut-out views of a moving mechanism 250 in relation to a top endplate 110. As shown, moving mechanism 250 includes a rotation axis $R_1$ projecting in a longitudinal direction thereof and extending in a transverse direction of endplate 110 (from proximal side 101 to distal side 102). Rotation axis $R_1$ projects through the center of set screws 252, 254. Moving mechanism 250 includes a transverse axis $T_1$ intersecting a center of rotation axis and projecting perpendicular to rotation axis $R_1$ through buttress block 257.

Figure 15:
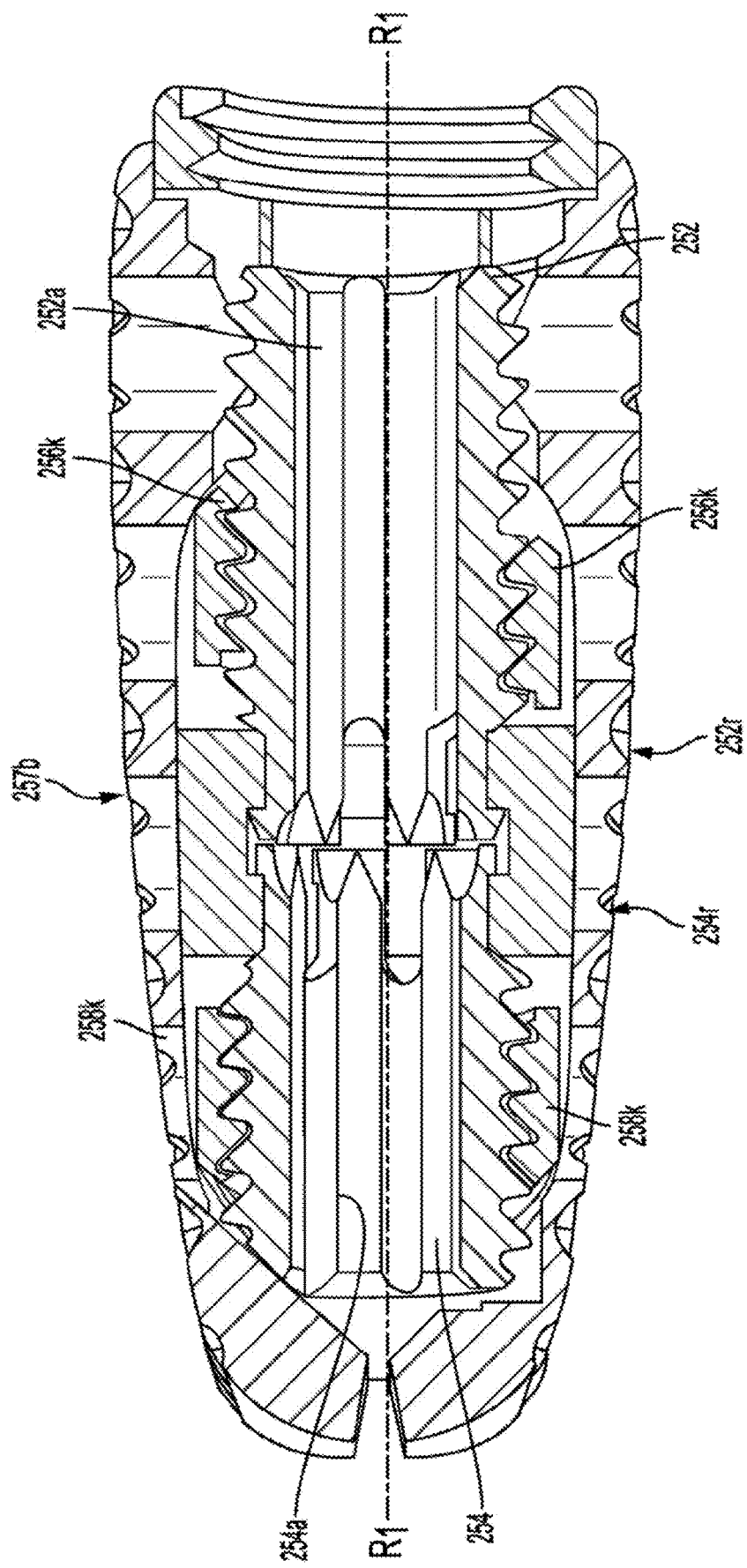
FIG. 15 is a cross section of the moving mechanism of FIGS. 14A and 14B along a longitudinal axis thereof in accordance with the principles of the present disclosure.

FIG. 15 illustrates a cross section of moving mechanism 250 taken along rotation axis $R_1$. As shown, first set screw 252 is operably coupled with first trolley 256 by a plurality of keyed projections 256k (thread pattern) that correspond to the pitch pattern of first set screw 252. Second set screw 254 is operably coupled with second trolley 258 by a plurality of keyed projections 258k (thread pattern). First set screw 252 includes a first internal circumferential surface 252a and second set screw 254 includes a second internal circumferential surface. The buttress block 257 includes an interior retention cavity 257b where a first retaining portion 252r of first set screw 252 and a second retaining portion 254r of second set screw 254 are retained. Interior retention cavity 257b may be an internal cavity spanning the inside circumference of buttress block 257 and configured to enable first set screw 252 and second set screw 254 to freely rotate along the rotation axis $R_1$ while preventing first set screw 252 and second set screw 254 from traveling in the longitudinal direction of moving mechanism 250.

Figure 16:
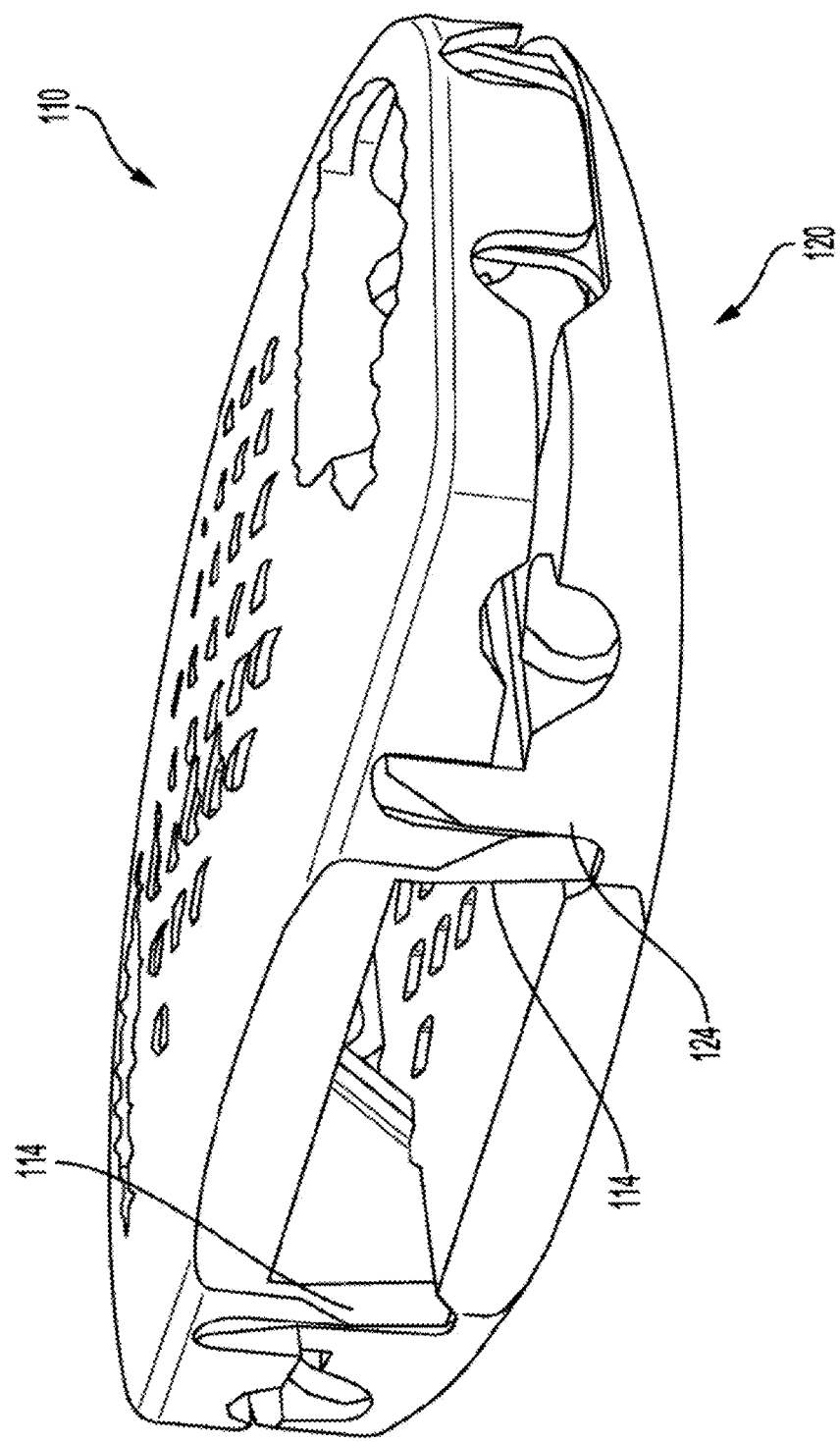
FIG. 16 is a perspective view of a top endplate and bottom endplate of one embodiment of an expandable spinal implant in accordance with the principles of the present disclosure.

FIG. 16 is a perspective view of a top endplate 110 and bottom endplate 120 of spinal implant 100 and FIG. 17 is an exploded view of the top endplate 110 and bottom endplate 120 of FIG. 16. In the exemplary embodiment, when spinal implant 100 is in the closed position, inside surface 112 of top endplate 110 and inside surface 124 of bottom endplate 120 are nested or partially nested with respect to one another. For example, FIG. 16 shows first proximal ramps 114 of top endplate 110 inset from second proximal ramps 124 of bottom endplate 120. Additionally, top endplate 110 includes a first plurality of recesses 110n that allow corresponding components of bottom endplate 120a to nest inside of when spinal implant 100 is in the contracted position. For example, FIG. 16 shows second proximal ramps 124 nested inside of recess 110n. In some embodiments, recesses 110n may be referred to as nested recesses for convenience in explanation.

Top endplate 110 and/or bottom endplate 120 may optionally include at least one anchoring aperture 129. In the exemplary embodiment, top endplate 110 includes a pair of top anchoring apertures 129a, 129b, that pass through top endplate 110 at an inclined angle with respect to outside surface 111 of top endplate 110. Similarly, bottom endplate 120 includes a pair of bottom anchoring apertures 129c, 129d that pass through bottom endplate 120 at an inclined angle with respect to outside surface 121 of endplate 120. Each anchoring aperture 129 of the plurality of anchoring apertures 129a-129d is disposed adjacent an outside surface of a corresponding ramp 114, 116 however exemplary embodiments are not limited to the specific location shown in FIG. 17.

Figure 18A:
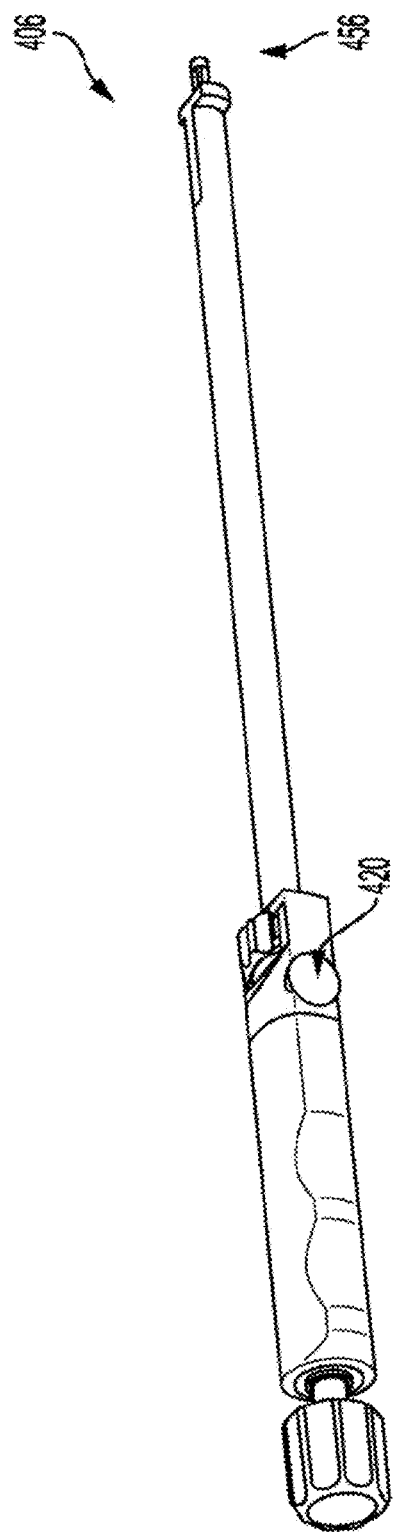
FIGS. 18A-18B are perspective views of a first surgical tool of an expandable spinal implant system in accordance with the principles of the present disclosure.
Figure 18B:
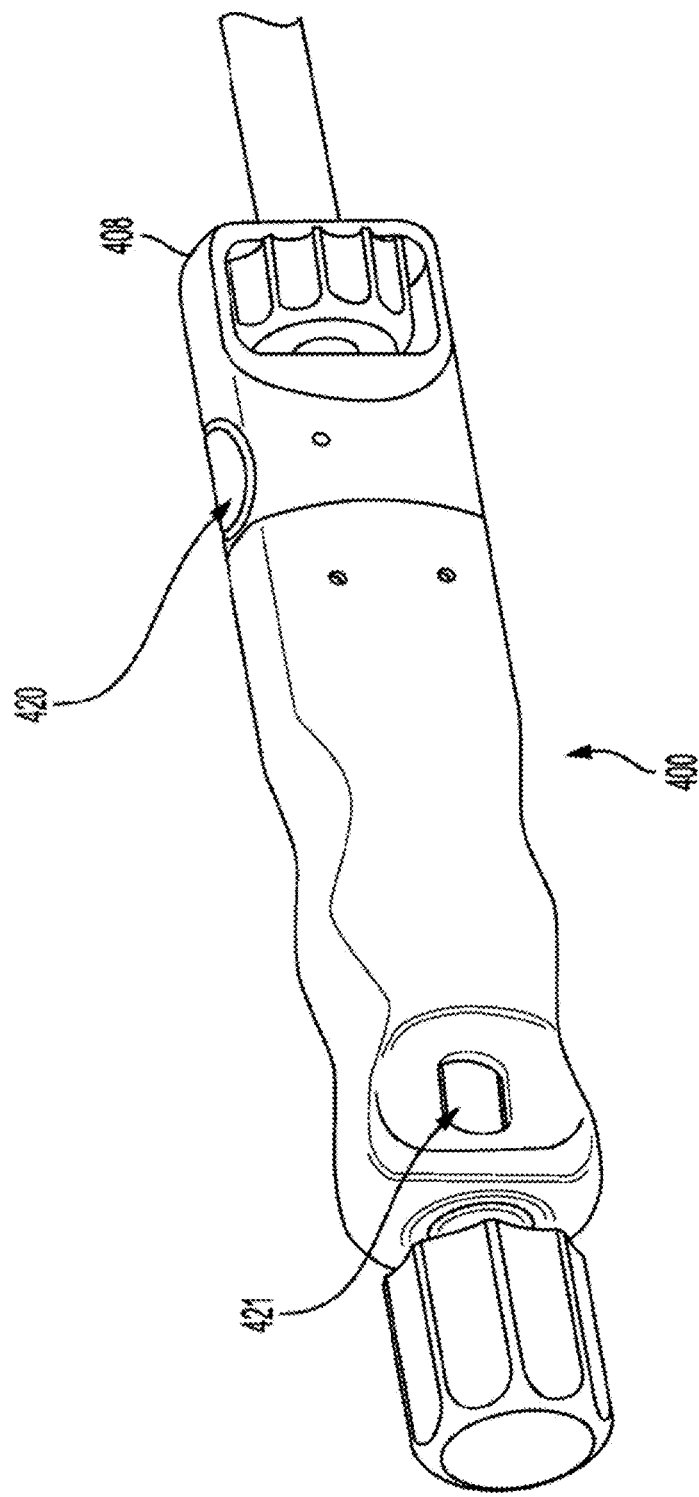

FIGS. 18A-18B are perspective views of a first surgical tool 400 of an adjustable spinal implant system in accordance with the principles of the present disclosure. FIGS. 19A-19B are side views of the first surgical tool 400 and a corresponding adjustment rod 450 configured for insertion inside of first surgical tool 400. Tip 406 is configured to connect to spinal implant 100 such that spinal implant 100 is securely attached to first surgical tool 400 by engaging locking mechanism 408. Similarly, tip 406 is configured to disconnect from spinal implant 100 such that spinal implant 100 is no longer securely attached to first surgical tool 400 by disengaging locking mechanism 408. For example, FIG. 19A shows tip 406 in a first locking position with tip grips 406a being expanded for gripping onto spinal implant 100 and FIG. 19B shows tip 406 in a second locking position with tip grips 406a being retracted. Locking mechanism 408 is configured to toggle between the first locking position and second locking position. In some embodiments, when locking mechanism 408 is engaged in the first locking position spinal implant 100 is fixedly coupled to first surgical tool 400 such that it will not rotate. This may be advantageous for initial positioning of spinal implant 100 between vertebral bodies during surgery. Additionally, first surgical tool 400 includes a positioning mechanism 410 configured to position adjustment rod 450 in a first position and a second position (see FIG. 19A). First surgical tool 400 may also include a push button 420 to toggle between positioning adjustment rod 450 in a first position to engage both first and second set screws 252, 254 and a second position to engage only the first set screw 252 (see FIG. 18B). Furthermore, in some embodiments first surgical tool 400 may include a window 421 to identify whether both first and second set screws 252 254 are engaged for parallel expansion/contraction of spinal implant 100 or whether only the first set screw 252 is engaged for adjusting an angle of inclination of spinal implant 100.

In the exemplary embodiment, first surgical tool 400 includes a central shaft aperture 409 extending through handle 402, shaft 404, and tip 406. Central shaft aperture 409 is configured to receive adjustment rod 450 therein such that adjustment knob 452 is rotatable therein and protrudes, at least partly, from both ends. Adjustment rod 450 includes an adjustment knob 452, first and second positioning surfaces 453, 454 and keyed circumferential surface 456. When adjustment rod 450 is positioned within central shaft aperture 409, adjustment knob 452 protrudes from one end and keyed circumferential surface 456 protrudes from the other end (see FIG. 14). With adjustment rod 450 inserted within central shaft aperture 409 positioning mechanism 410 can extend and retract adjustment rod 450 in the longitudinal direction of shaft 409. As explained above with respect to FIGS. 13A and 13B, when first surgical tool 400 is in the first position, keyed circumferential surface 456 may rotate first and second set screws 252, 254 along the rotation axis and when first surgical tool 400 is in the second position, keyed circumferential surface 456 may rotate only the first set screw 252 along the rotation axis. In some embodiments, positioning mechanism 410 is configured to be toggled between a first position and a second position where it can act against positioning surfaces 453, 454 to extend and retract adjustment rod 450 in the longitudinal direction of shaft 409. For example, in the first position positioning mechanism 410 may extend adjustment rod 450 from tip 406 to an extended position where circumferential surface 456 may engage with internal circumferential surfaces of the first and second set screws 252, 254. In the second position, positioning mechanism 410 may retract adjustment rod 450 through tip 406 to a partially retracted position where circumferential surface 456 may only engage with internal circumferential surface of the first set screw 252. An internal gearing of positioning mechanism 410 may include internal locking pins and surfaces that act against positioning surfaces 453, 454 such that when an exposed turn dial knob of positioning mechanism 410 is turned to a particular position, the internal locking pins and surfaces act against the inclined and recessed surfaces of positioning surfaces 453, 454.

Additionally, in some embodiments, first surgical tool 400 may be configured to receive adjustment rods 450 of varying lengths having varying outside circumferential surfaces 456 and positioning surfaces 453, 454. For example, first surgical tool 400 may be configured to receive a first relatively shorter adjustment rod 450 optimized for use for a spinal implant 100 using corresponding relatively smaller endplates 110, 120 of FIGS. 6A-7C and a corresponding smaller moving mechanism 250 having a relatively shorter longitudinal axis optimized for such relatively shorter endplates 110x, 120x. For example still, first surgical tool 400 may be configured to receive a second relatively longer adjustment rod 450 optimized for use for a spinal implant 100 using corresponding relatively larger endplates 110z, 120z of FIGS. 6A-7C and a corresponding larger moving mechanism 250 having a relatively longer longitudinal axis optimized for such relatively longer endplates 110z, 120z.

Additionally, in some embodiments, first surgical tool 400 may be configured to receive multiple types of adjustment rods 450. In at least one embodiment, first surgical tool 400 may receive a first adjustment rod 450 with an outside circumferential surface 456 that is configured to engage (1) both the first and second set screws 252, 254 at the same time and (2) the first set screw 252. For example, the first adjustment rod 450 may be toggled between (1) a first position where outside circumferential surface 456 is fully extended and configured to engage both the first and second set screws 252, 254, and (2) a second position where outside circumferential surface 456 is partially extended (and/or partially retracted) to engage only the first set screw 252. In an alternate embodiment, first surgical tool 400 may receive a second adjustment rod 450 with an outside circumferential surface 456 that is configured to engage only one set screw 252, 254 at a time. For example, the outside circumferential surface 456 may have an engagement surface with a longitudinal length that corresponds to a single set screw 252, 254 such that it only engages with a single set screw 252, 254 at a time. For example, the second adjustment rod 450 may be toggled between (1) a first position where outside circumferential surface 456 is fully extended and configured to engage the second set screw 254 independently of the first set screw 252 and (2) a second position where outside circumferential surface 456 is partially extended (and/or partially retracted) to engage only the first set screw 252. At least one advantage of having first surgical tool 400 being configured to receive multiple types of adjustment rods 450 of varying lengths and having outside circumferential surfaces of different lengths is that a surgeon can quickly and easily select the appropriate adjustment rod 450. For example, a surgeon may select first adjustment rod 450 to expand/contract a spacing between endplates 110, 120 by the same or substantially the same amount while maintaining the angle of inclination between endplates 110, 120, i.e., by engaging both first and second set screws 252, 254. Additionally, a surgeon may select second adjustment rod 450 to selectively increase/decrease an angle of inclination between endplates of spinal implant 100 at the proximate side 101 and the distal side 102 independently, i.e., by only engaging one of first and second set screws 252, 254 at a time. For example still, the second adjustment rod 450 may be configured to adjust spinal implant 100 to enable anterior expansion separately from enabling posterior expansion which may enable spinal implant 100 to be placed in kyphosis as is consistent with above explained embodiments.

Furthermore, in some embodiments, first surgical tool 400 is configured to operate in three modes. In the first mode, tip grips 406a are securely connected to spinal implant 100. In the second mode, adjustment rod 450 may be positioned in a first position such that upon selective rotation of adjustment knob 452 a spacing between endplates 110, 120 selectively increase/decrease in minute increments. For example, by rotating each of first set screw 252 and second set screw 254. In the third mode, adjustment rod 450 may be positioned in a second position such that upon selective rotation of adjustment knob 452 an angle of inclination between endplates 110, 120 may selectively increase/decrease in minute increments. For example, by only rotating first set screw 252 an angle of inclination between endplates 110, 120 may increase/decrease by moving one side of the endplates 110,120 towards/away from each other and moving the opposite side of the endplates 110,120 in an opposite direction. In some embodiments, this may also happen by only rotating second set screw 254. For example, first surgical tool 400 may have a relatively short circumferential engagement surface 456 that will only engage a single one of the internal circumferential surfaces of first or second set 252, 254 at a time.

Figure 20:
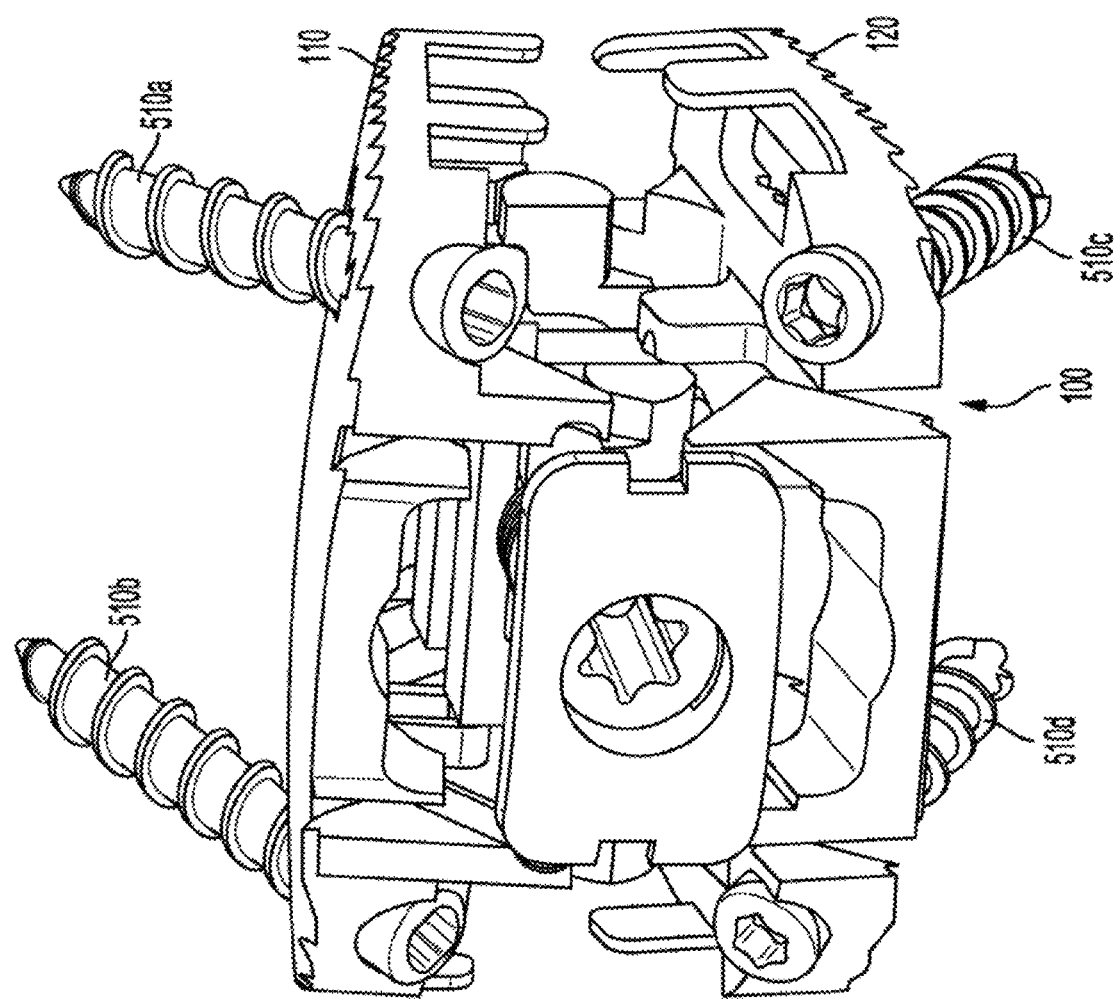
FIG. 20 illustrates a perspective view of one embodiment of an expandable spinal implant system having anchoring screws in accordance with the principles of the present disclosure.

FIG. 20 illustrates a perspective view of one embodiment of an expandable spinal implant 100 including a plurality of anchoring screws 510. In some embodiments, anchoring screws 510 may be referred to as bone screws. In the exemplary spinal implant 100, top endplate 110 includes a first anchoring screw 510a, and a second anchoring screw 510b opposite the first anchoring screw 510a that each extend through a corresponding aperture. For example, first and second anchoring screws 510a, 510b pass through a corresponding aperture of top endplate 110 configured to orient them at an inclined angle with respect to outside surface 111 of top endplate 110. Similarly, bottom endplate 120 includes a third anchoring screw 510c, and a fourth anchoring screw 510d that each extend through a corresponding aperture. Anchoring screws 510c, 510d project from a proximal end 101 of spinal implant 100 at an inclined angle towards distal end 102. For example, third and fourth anchoring screws 510c, 510d pass through a corresponding aperture of bottom endplate 120 configured to orient them at an inclined angle with respect to outside surface 121 of bottom endplate 120. However, it shall be understood that in other embodiments at least one aperture may orient a corresponding anchoring screw 510a, 510b, 510c, 510d at any angle with respect to the corresponding endplate 110, 120 consistent with the disclosure herein. Anchoring screws 510a-510d are configured to anchor into corresponding adjacent vertebral bodies.

Figure 21A:
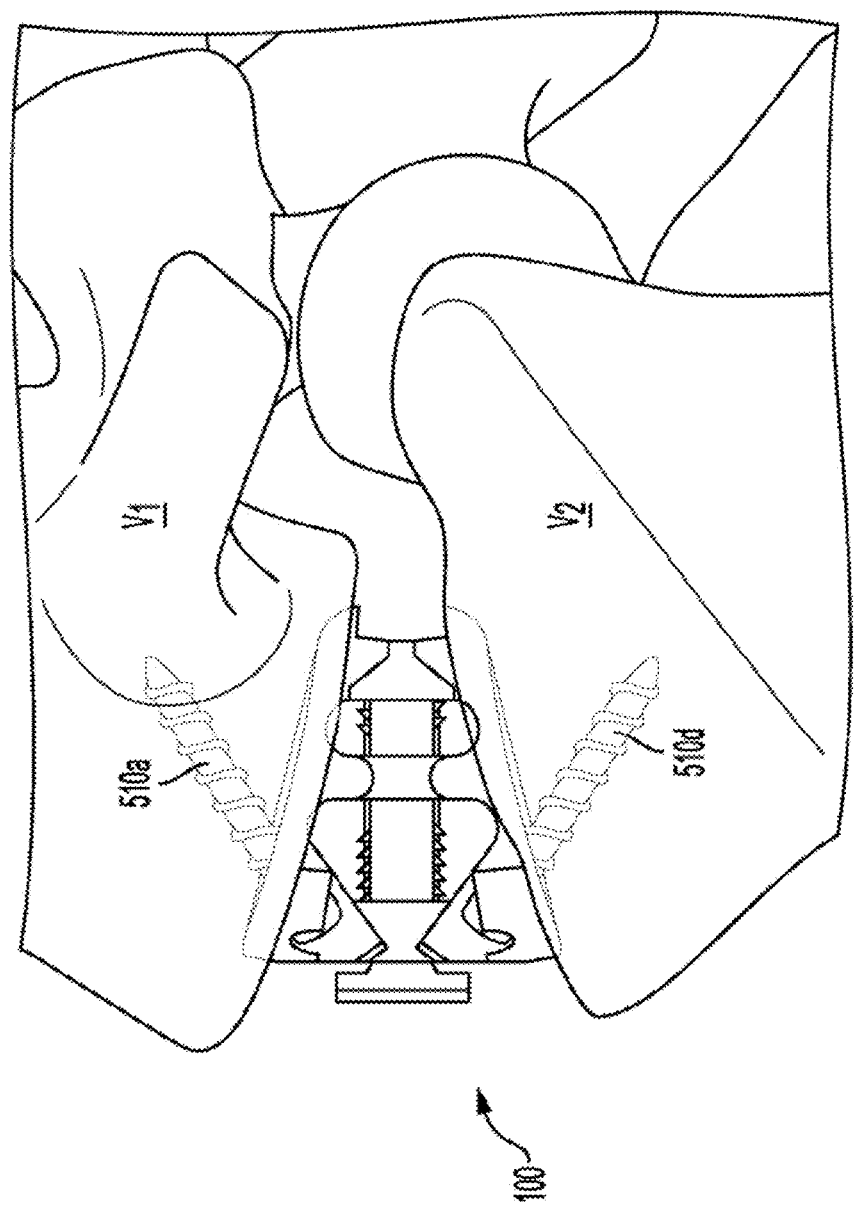
FIGS. 21A-21B illustrate a lateral side view and front side view, respectively, of one embodiment of an expandable spinal implant system having anchoring screws in accordance with the principles of the present disclosure.
Figure 21B:
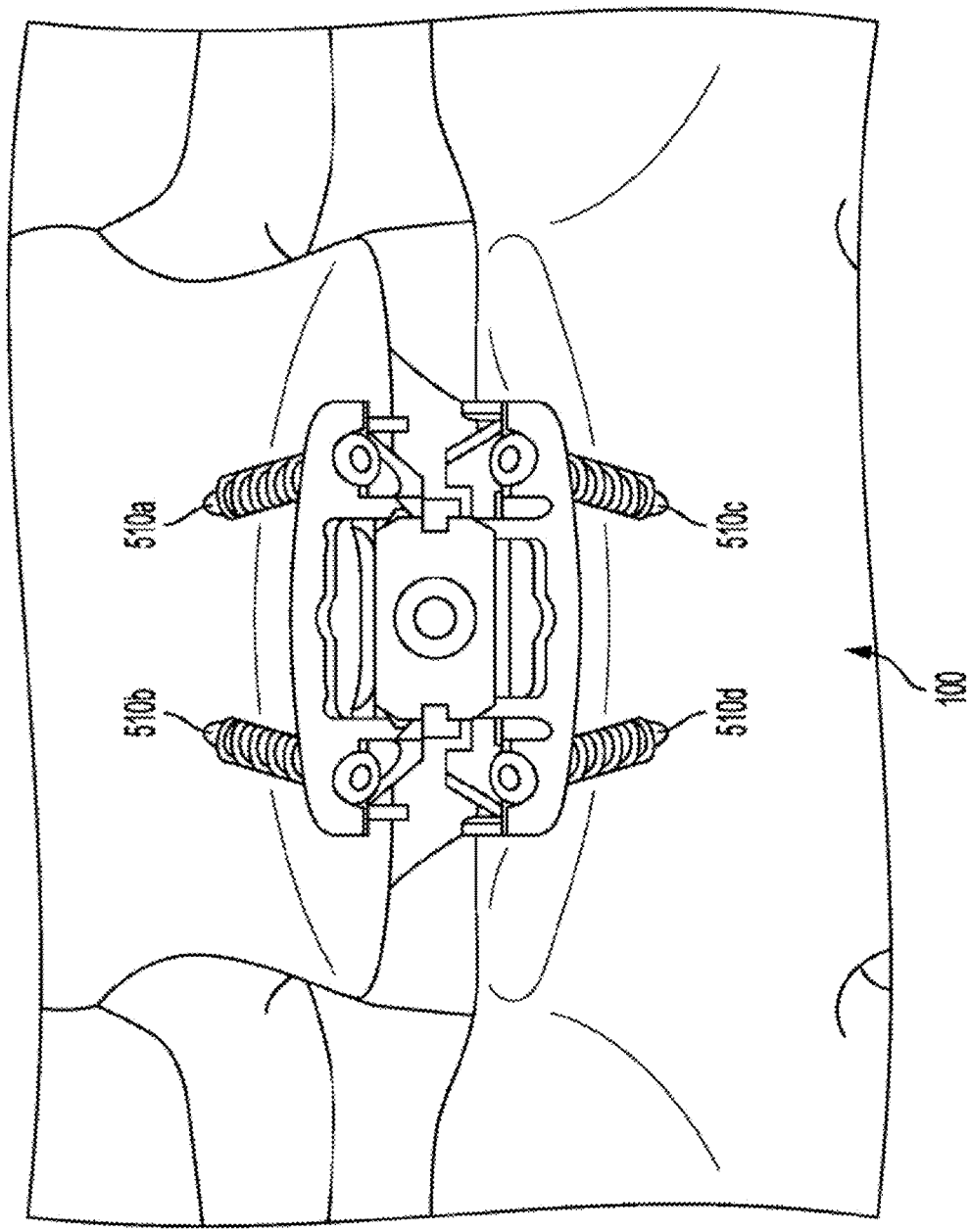

FIGS. 21A-21B illustrate a lateral side view and front side view, respectively, of one embodiment of an expandable spinal implant system in which anchoring screws 510a-510d are anchored into adjacent vertebral bodies. As illustrated, anchoring screws 510a, 510b project out from top endplate 110 of spinal implant 100 from a proximal end 101 at an inclined angle towards distal end 102 thereby anchoring into a top vertebral body $V_1$. Similarly, anchoring screws 510*a*, 510*b* project out from bottom endplate 120 of spinal implant 100 from a proximal end 101 at an inclined angle towards distal end 102 thereby anchoring into a bottom vertebral body $V_2$. As used herein, a pair of vertebral bodies, adjacent vertebral bodies, and/or first and second vertebral bodies may refer to, e.g., top vertebral body $V_1$ and bottom vertebral body $V_2$.

Figure 22A:
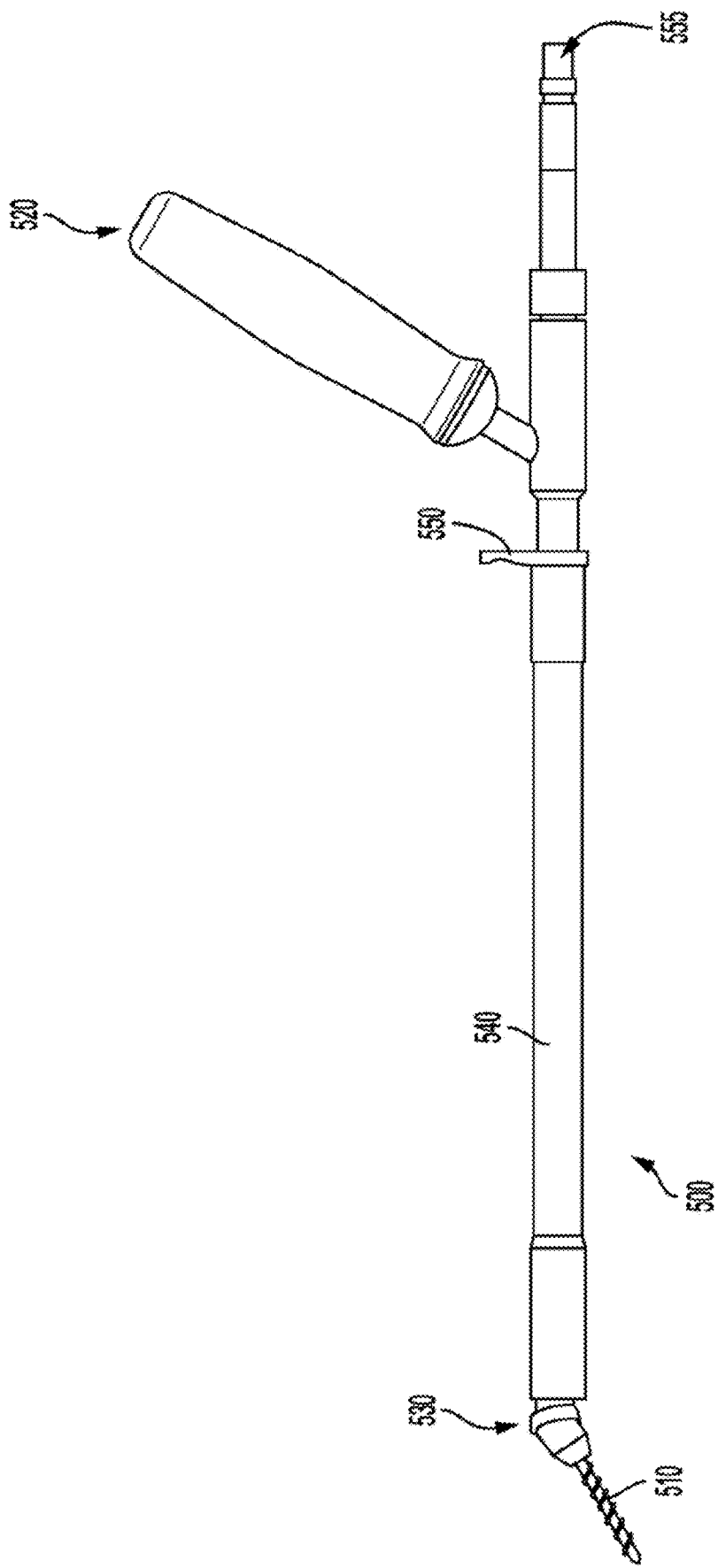
FIG. 22A is a side view of a second surgical device suitable for use with the embodiment of FIG. 20 in accordance with the principles of the present disclosure.
Figure 22B:
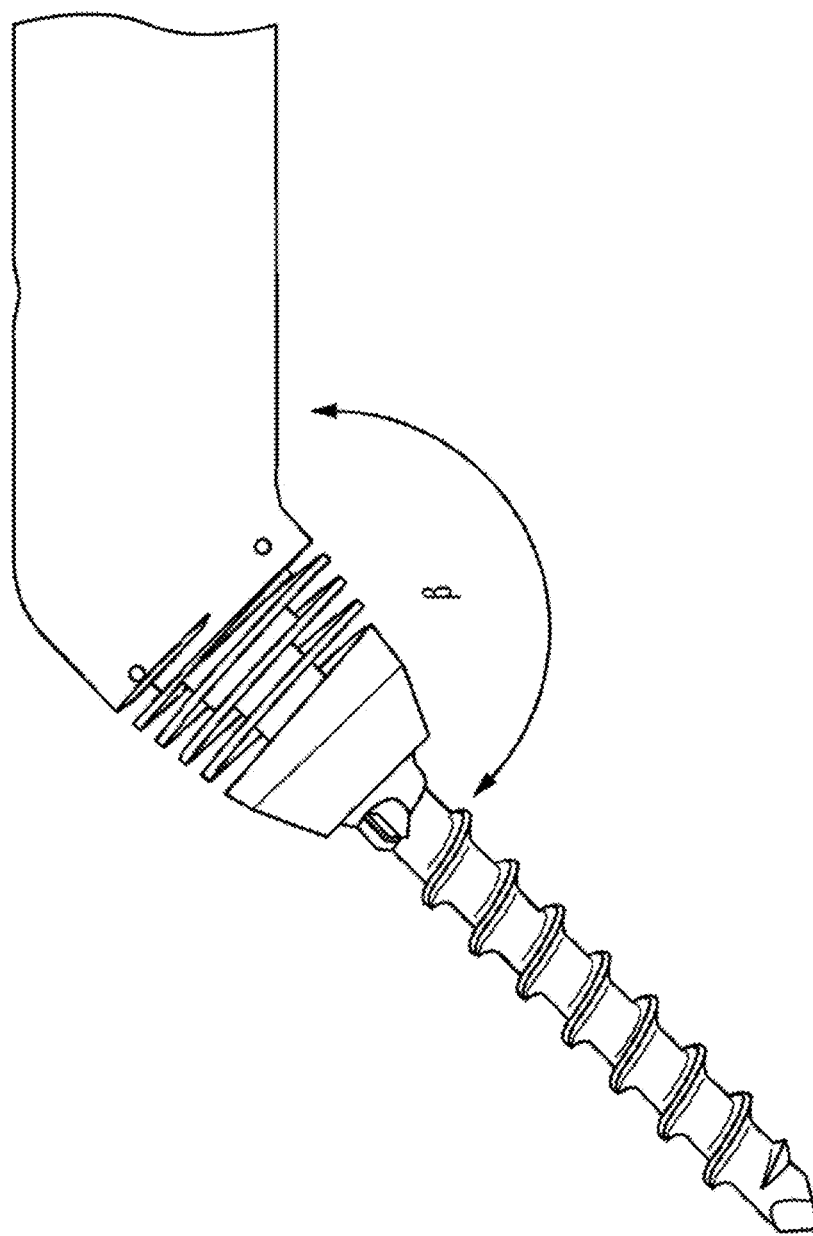
FIG. 22B is a side view of an enlarged region of FIG. 22A in accordance with the principles of the present disclosure.

FIG. 22A is a side view of a second surgical tool 500 suitable for use with disclosed embodiments and systems herein, e.g., to drive anchoring screws 510*a*-510*d*. FIG. 22B is a side view of an enlarged region of FIG. 22A. Exemplary, second surgical tool 500 includes a ratcheting drive shaft 555, a positioning handle 520, a tip portion 530, a drive shaft housing 540, and a trigger 550. Ratcheting drive shaft 555 may be configured to connect and disconnect with a ratcheting handle (not shown) and rotate within ratcheting drive shaft housing 540. For example, the drivable connection may comprise a variety of drive interfaces including but not limited to: multi-lobular drives; hexalobular drives; cross or Phillips head drives; straight or "flat head" drives; square or other polygonal drives; and/or combinations thereof. Positioning handle 520 may be configured to assist with maintaining and controlling the second surgical tool 500, e.g., in view of torque transmitted through ratcheting drive shaft 555. Tip portion 530 is angled at a degree β with respect to a longitudinal direction of drive shaft housing 540. In some embodiments, tip portion 530 is angled such that the degree β corresponds to the inclination of anchoring screws 510*a*-510*d* and the inclination of anchoring aperture 129. For example, anchoring apertures 129 may be inclined about 30°-50°, and more particularly about 40°, with respect to an outside surface 111, 121 of endplates 110, 120. This arrangement may be advantageous for driving anchoring screws 510*a*-510*d* while spinal implant 100 is positioned between adjacent vertebral bodies. Tip portion 530 may secure anchoring screw 510 in an internal cavity therein such that anchoring screw 510 may not disconnect during initial positioning of anchoring screw 510. For example, tip portion 530 may have a flexible elastic member configured to securely retain a head portion of anchoring screw 510. Tip portion 530 may, however, release anchoring screw 510 when anchoring screw is sufficiently anchored into an anatomical feature, such as a vertebrae for example. This feature may be particularly advantageous during surgery for maintaining the anchoring screw 510 in tip portion 530 such that anchoring screw 510 does not uncouple from tip portion 530 when initially positioning anchoring screw 510 in an anchoring aperture, for example anchoring aperture 129. Additionally, in some embodiments tip portion 530 is operably coupled with trigger 550 such that trigger 550 may disconnect anchoring screw 510 when anchoring screw 510 is installed. In some embodiments, trigger 550 may not be necessary because tip portion 530 may self-release anchoring screw 510 after installation.

Figure 23A:
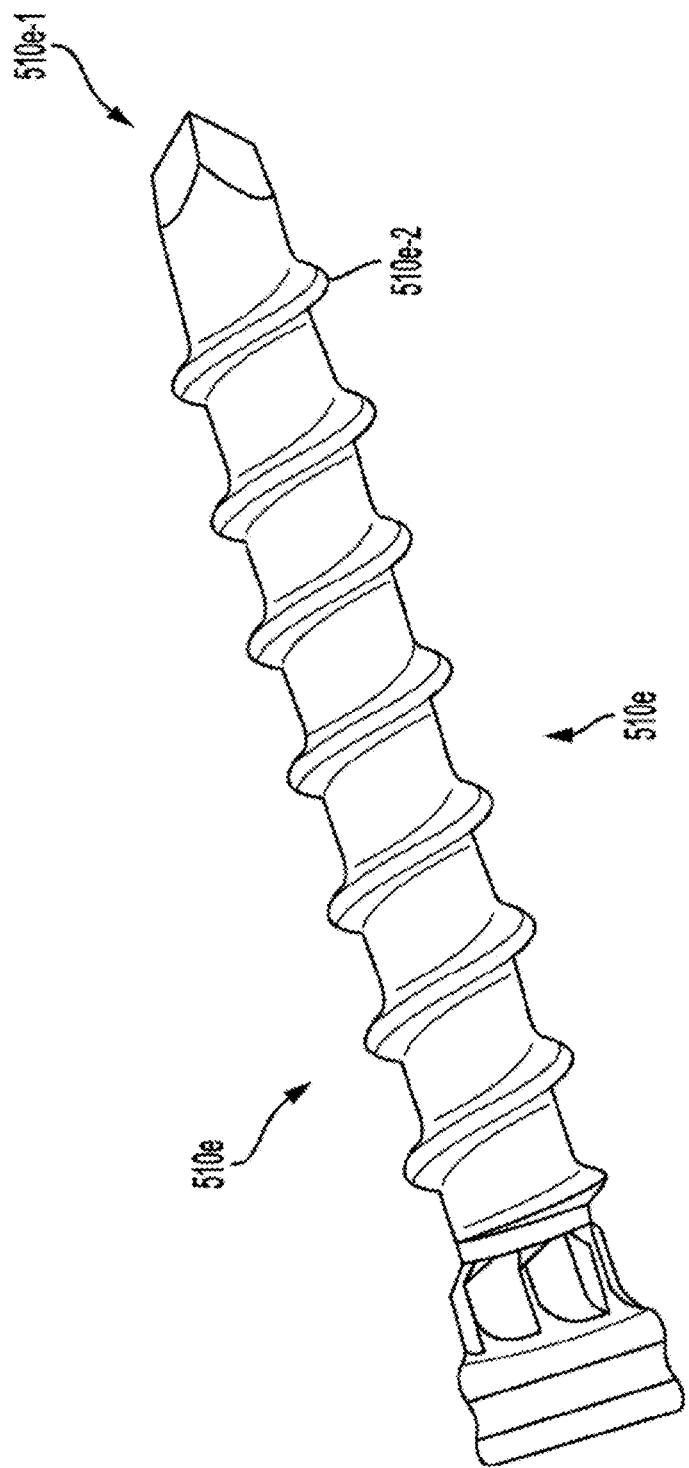
FIGS. 23A-23C are various perspective views of exemplary anchoring screws suitable for use with the embodiment of FIG. 20 in conjunction with the second surgical tool of FIGS. 22A-22B in accordance with the principles of the present disclosure.
Figure 23B:
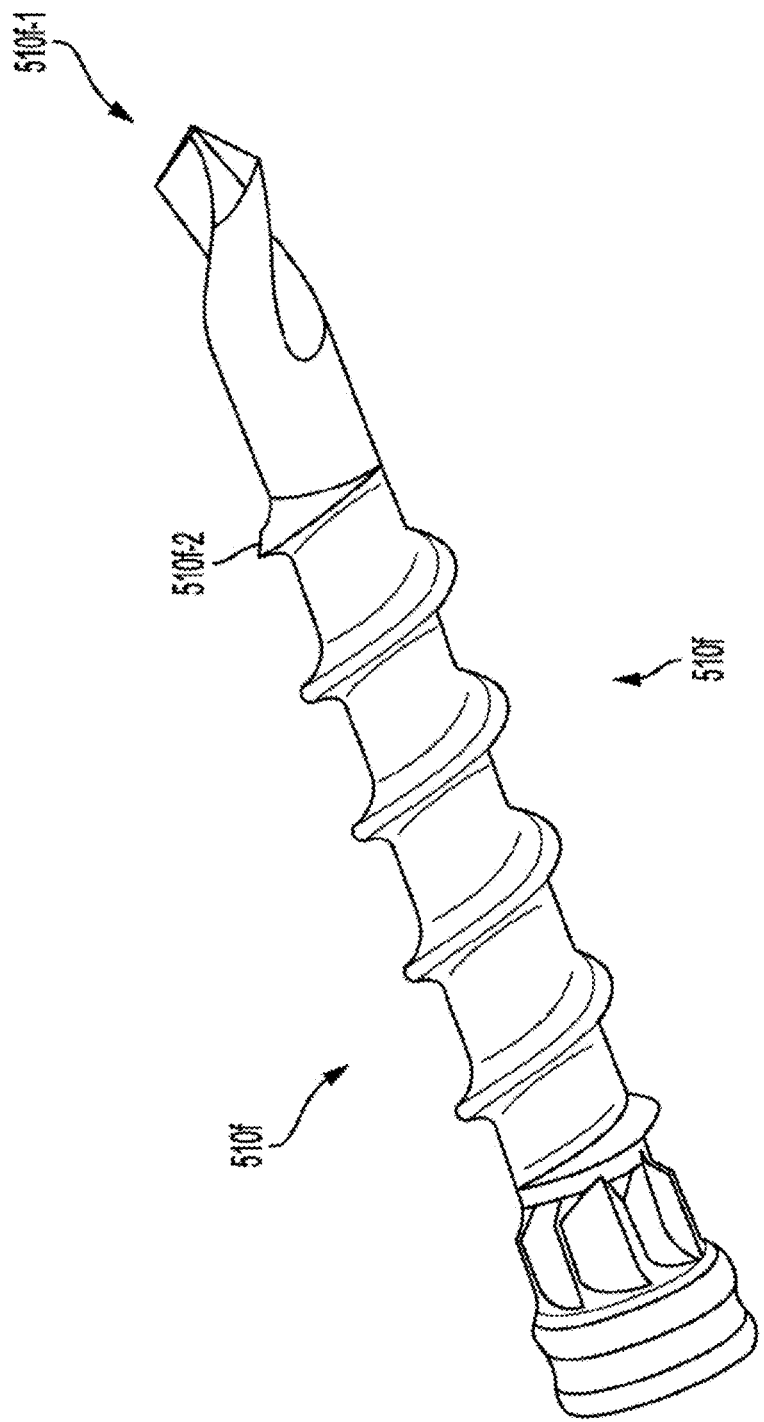
Figure 23C:
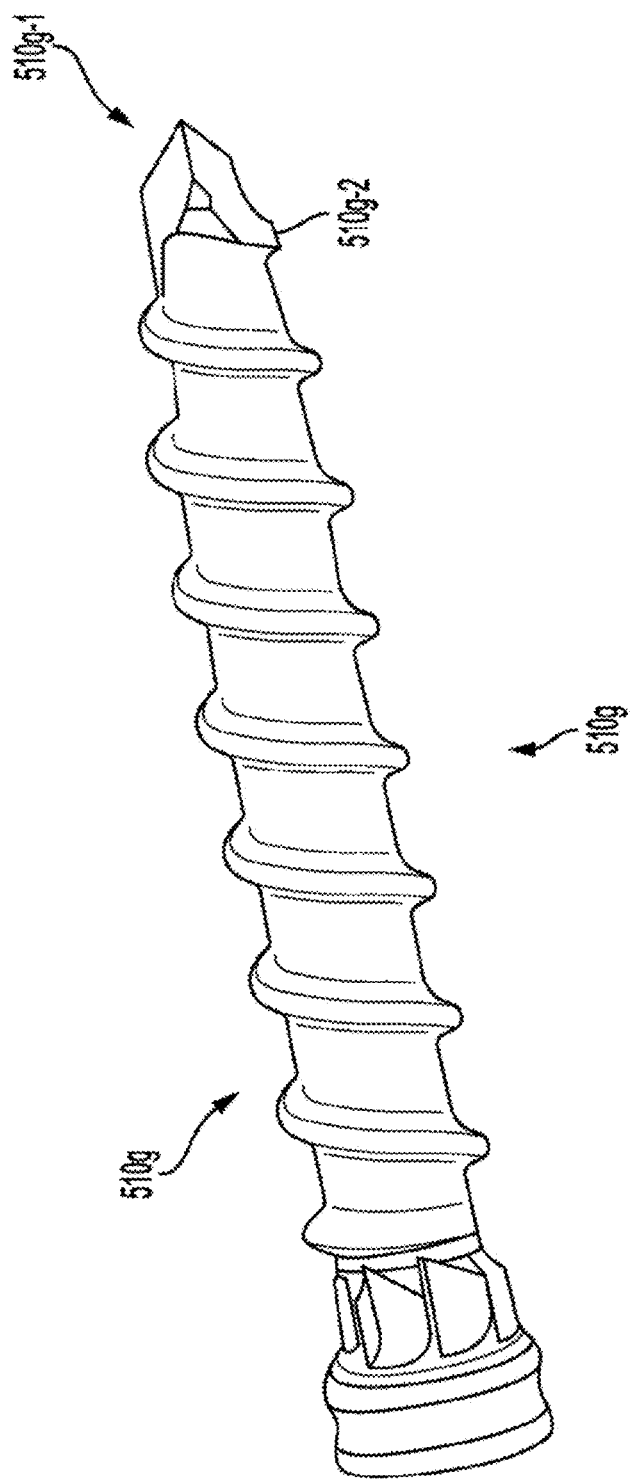

FIGS. 23A-23C are various perspective views of exemplary anchoring screws suitable for use with disclosed embodiments herein in conjunction with the second surgical tool 500. FIG. 23A shows a trocar tip anchoring screw 510*e*, FIG. 23B shows a flutes or fluted tip anchoring screw 510*f*, and FIG. 23C shows a speed anchoring screw 510*g*. Each anchoring screw 510*e*-510*g* may have a thread pitch and sizing that corresponds to a size of anchoring aperture 129. Trocar tip anchoring screw 510*e* includes an angled tip portion 510*e*-1 and a thread pattern including threads 510*e*-2. Threads 510*e*-2 may be spaced back from angled tip portion 510*e*-1 which may facilitate with aligning anchoring screw 510*e* with anchoring aperture 129. For example, in some embodiments, threads 510*e*-2 are spaced back about 3 mm from angled tip portion 510*e*-1. Fluted tip anchoring screw 510*f* includes a cutting tip 510*f*-1 and a thread pattern included threads 510*f*-2. Cutting tip 510*f*-1 may extend a relatively long distance from the beginning of threads 510*f*-2 such that the cutting tip 510*f*-1 may pre-drill into an adjacent vertebral body before the threads 510*f*-2 engage with anchoring aperture 129. For example, in some embodiments, threads 510*f*-2 are spaced back about 8 mm from cutting tip 510*f*-1. Speed anchoring screw 510*g* includes a conical tip 510*g*-1 and a thread pattern including threads 510*g*-2. Different from trocar tip anchoring screw 510*e* and fluted tip anchoring screw 510*f*, threads 510*g*-2 of speed anchoring screw 510*g* may begin immediately adjacent conical tip 510*g*-1.

Figure 24A:
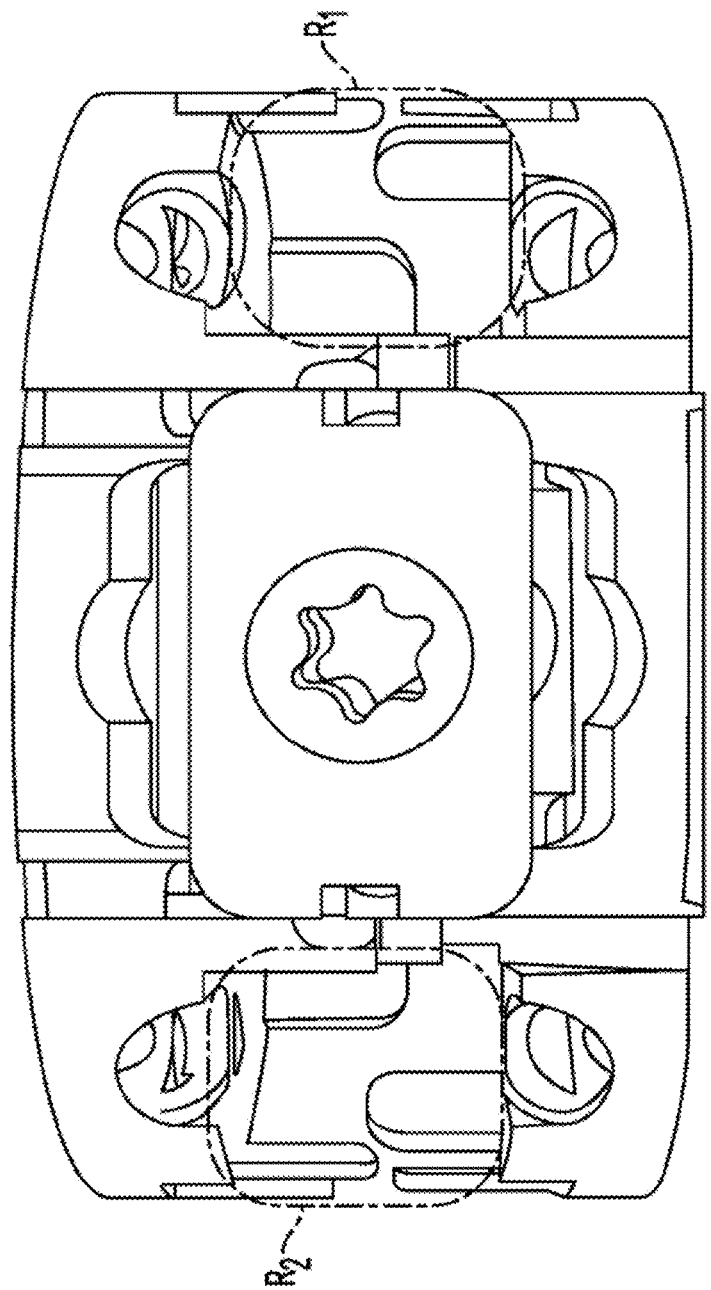
FIGS. 24A-24D are various side views and top down views of exemplary bone grafts in accordance with the principles of the present disclosure.
Figure 24B:
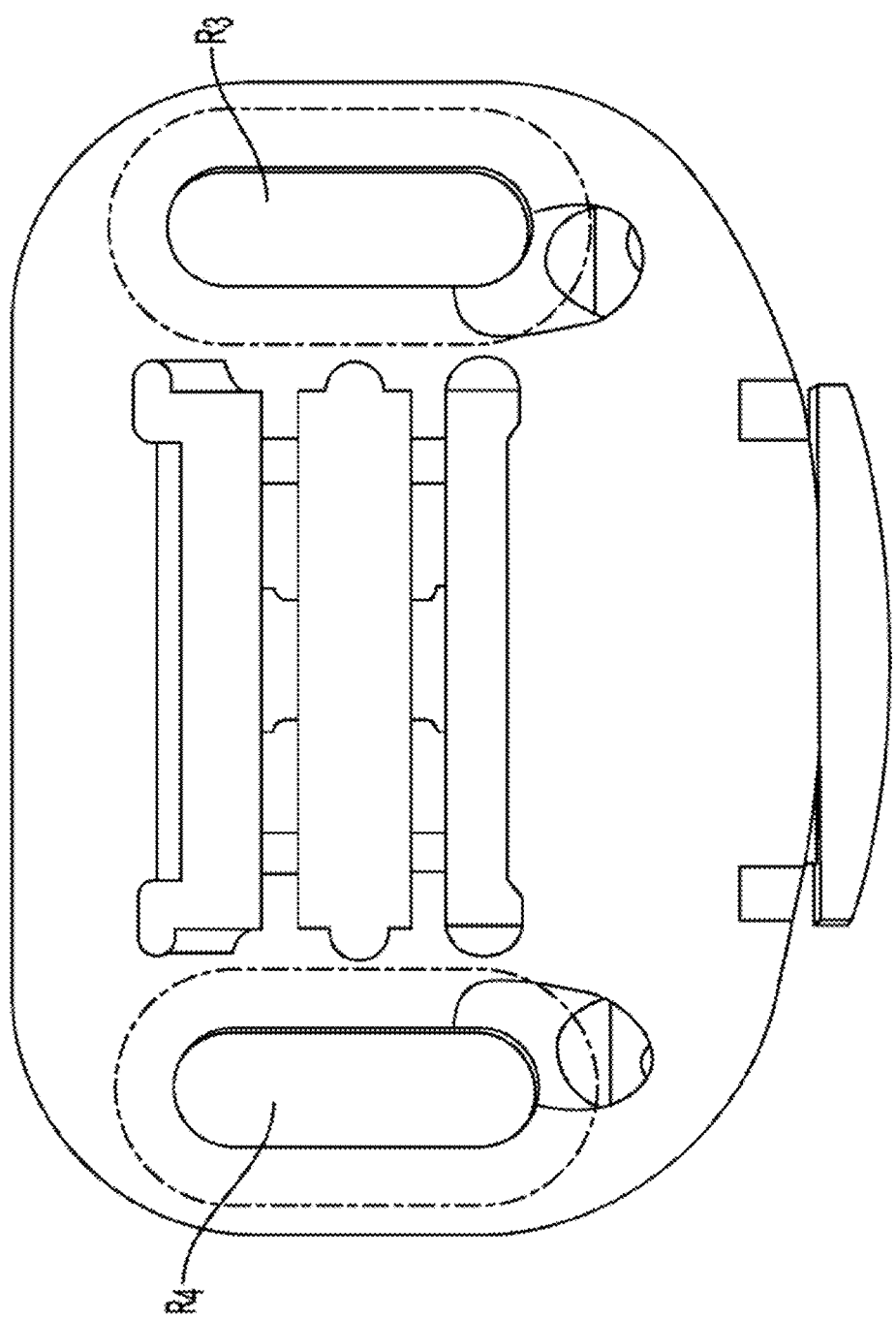
Figure 24C:
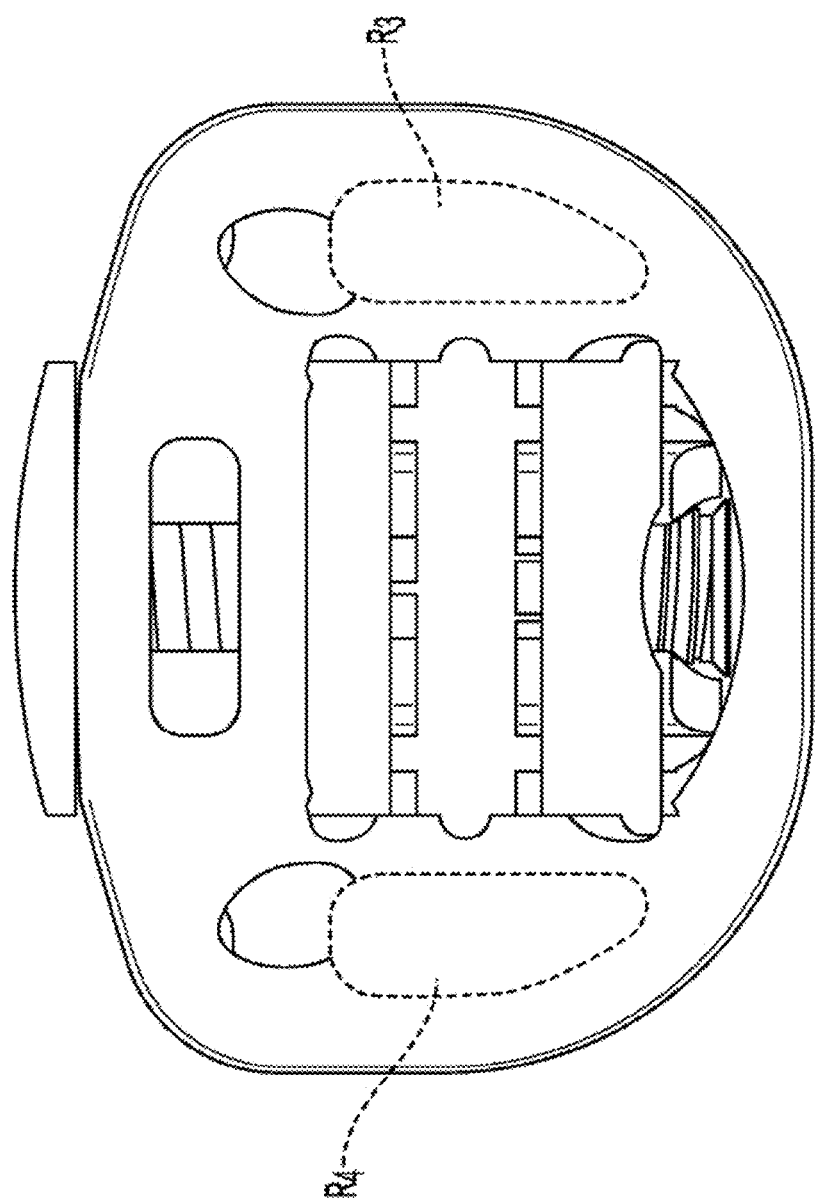
Figure 24D:
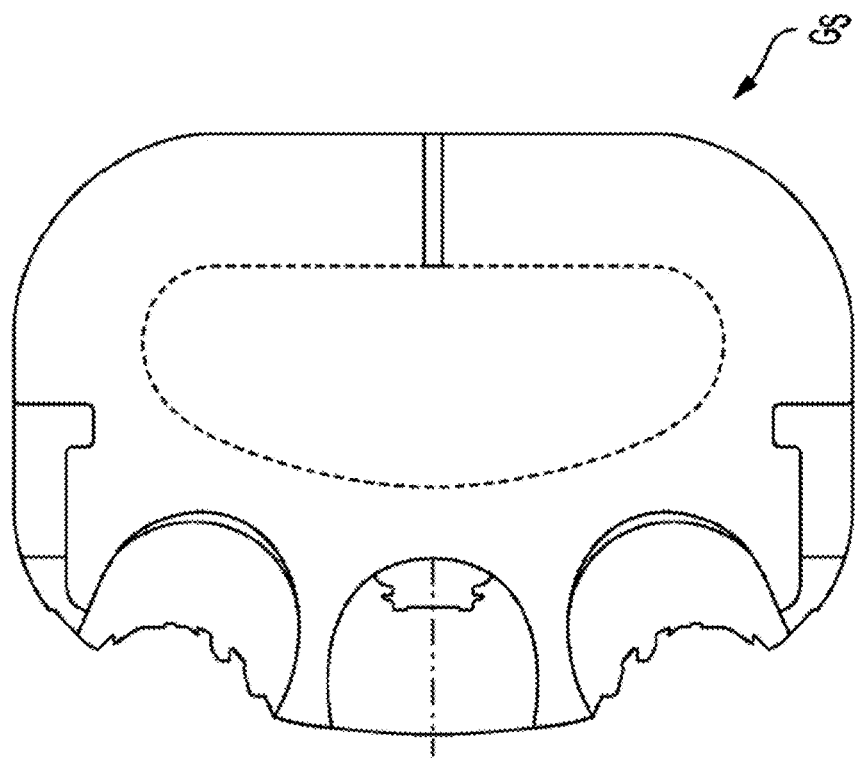

FIGS. 24A-24D are various side views and top down views of exemplary bone graft areas in accordance with the principles of the present disclosure. In the side view of FIG. 24A, first and second regions $R_1$, and $R_2$ are shown where bone growth material may be grafted and/or bone growth promoting materials may be used. In the top down view of FIG. 24B, third and fourth regions $R_3$, $R_4$ are shown where bone growth material may be grafted and/or bone growth promoting materials may be used. In some embodiments, third and fourth regions $R_3$, $R_4$ overlap vertically with first and second regions $R_1$, and $R_2$. In FIGS. 24C and 24D an exemplary grafting section GS is shown. Grafting section GS may be grafted to an endplate 110, 120. In some embodiments, grafting section GS may be filled with a bone growth material having a resultant surface area ranging from about 140 $mm^2$ to about 180 mm, and more particularly about 160 $mm^2$. For example, the bone growth material may extend through the grafting section GS three dimensionally and have a corresponding surface area ranging from about 140 $mm^2$ to about 180 $mm^2$, and more particularly about 160 $mm^2$. Consistent with disclosed embodiments herein, the open arrangement of spinal implant 100 and endplates 110, 120 in particular is advantageous for direct segmental fusion techniques. For example, the superior and inferior vertebral endplates allow the creation of a fusion bone bridge to solidify a segment. Additionally, the expandable and contractible nature of spinal implant 100 lends to bone packing techniques after positioning and adjusting spinal implant 100 between vertebral bodies. For example, after spinal implant 100 is positioned between adjacent vertebral bodies, spinal implant 100 may be packed with bone material in situ. In some embodiments, the endplate 110 may be considered a direct superior vertebral endplate and endplate 120 may be considered an inferior vertebral endplate where such endplates are configured to allow for a fusion bone bridge there through to solidify a segment.

In some embodiments, the spinal implant system includes an agent, including but not limited to the bone growth promoting materials described herein, which may be disposed, packed, coated or layered within, on or about the components and/or surfaces of the spinal implant system. In some embodiments the bone growth promoting material may be pre-packed in the interior of spinal implant 100, and/or may be packed during or after implantation of the implant via a tube, cannula, syringe or a combination of these or other access instruments. Additionally, bone growth promoting material may be further tamped into spinal implant 100 before, during or after implantation. In some embodiments, the bone growth promoting material and/or directly grafted material may enhance fixation of spinal implant 100 with adjacent bony structures. In some embodiments, the agent may include one or a plurality of therapeutic agents and/or pharmacological agents for release, including sustained release, to treat, for example, pain, inflammation and degeneration.

Figure 25A:
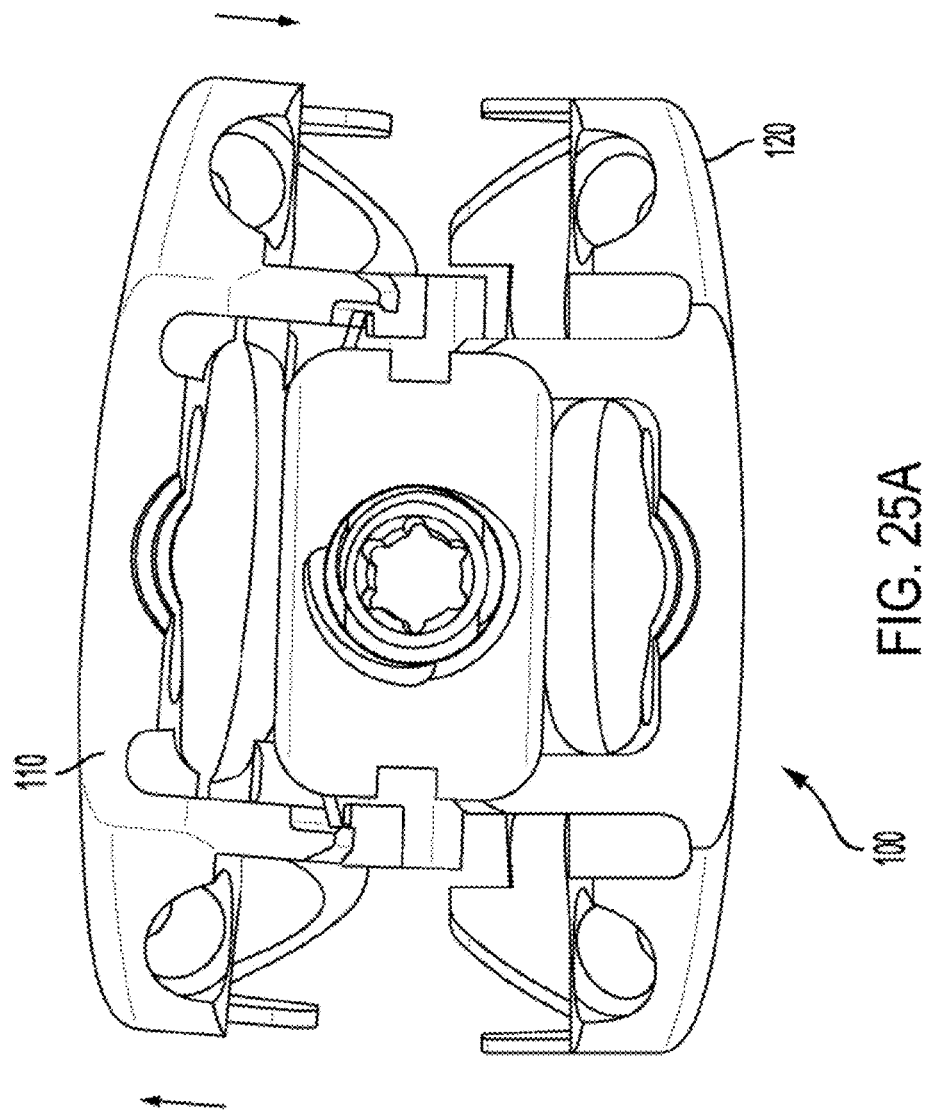

FIGS. 25A and 25B illustrate spin implant 100 in a first bent position and a second bent position, respectively. FIG. 25A shows spinal implant 100 where top endplate 110 is bent in a first lateral direction with respect to bottom endplate 120. FIG. 25B shows spinal implant 100 where top endplate 110 is bent in a second lateral direction, opposite the first lateral direction, with respect to bottom endplate 120. As explained in greater detail above, the various disclosed projections, guide walls, cavities, recesses, etc. are configured such that spinal implant 100 may allow for lateral bending to some predetermined degree. For example, projections 256c, 257c, 258c may pivot laterally in guide walls 130 to accommodate some degree of lateral bending. In this way, top endplate 110 and bottom endplate 120 may be configured to laterally bend with respect one another in a first direction and a second direction by a predetermined amount. However, in other embodiments it may be desirable for spinal implant 100 to be rigid in the lateral direction and for no lateral bending to be permissible.

Figure 26:
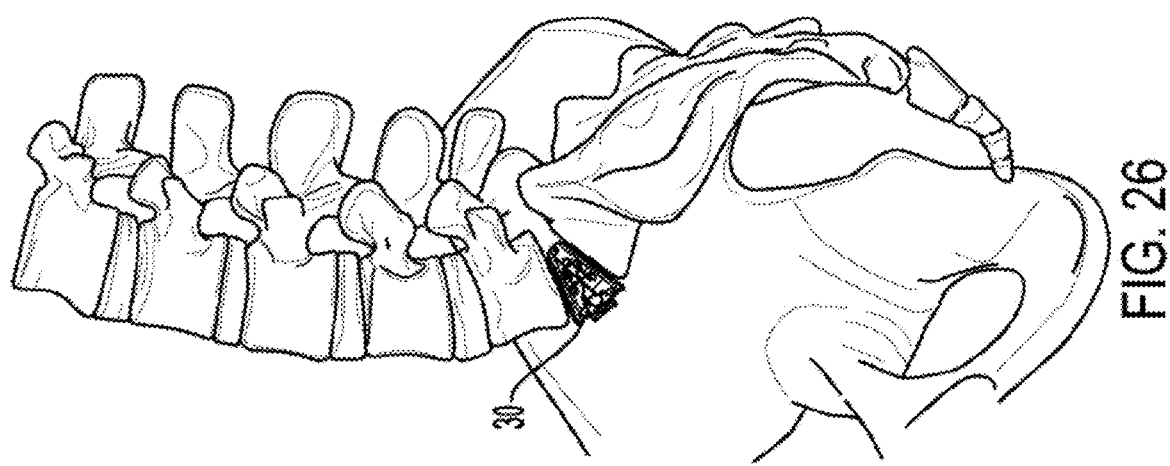
FIGS. 26-28 illustrate a left side view, right side view, and front side view, respectively, of an installed expandable spinal implant positioned between adjacent vertebral bodies in accordance with the principles of the present disclosure.
Figure 27:
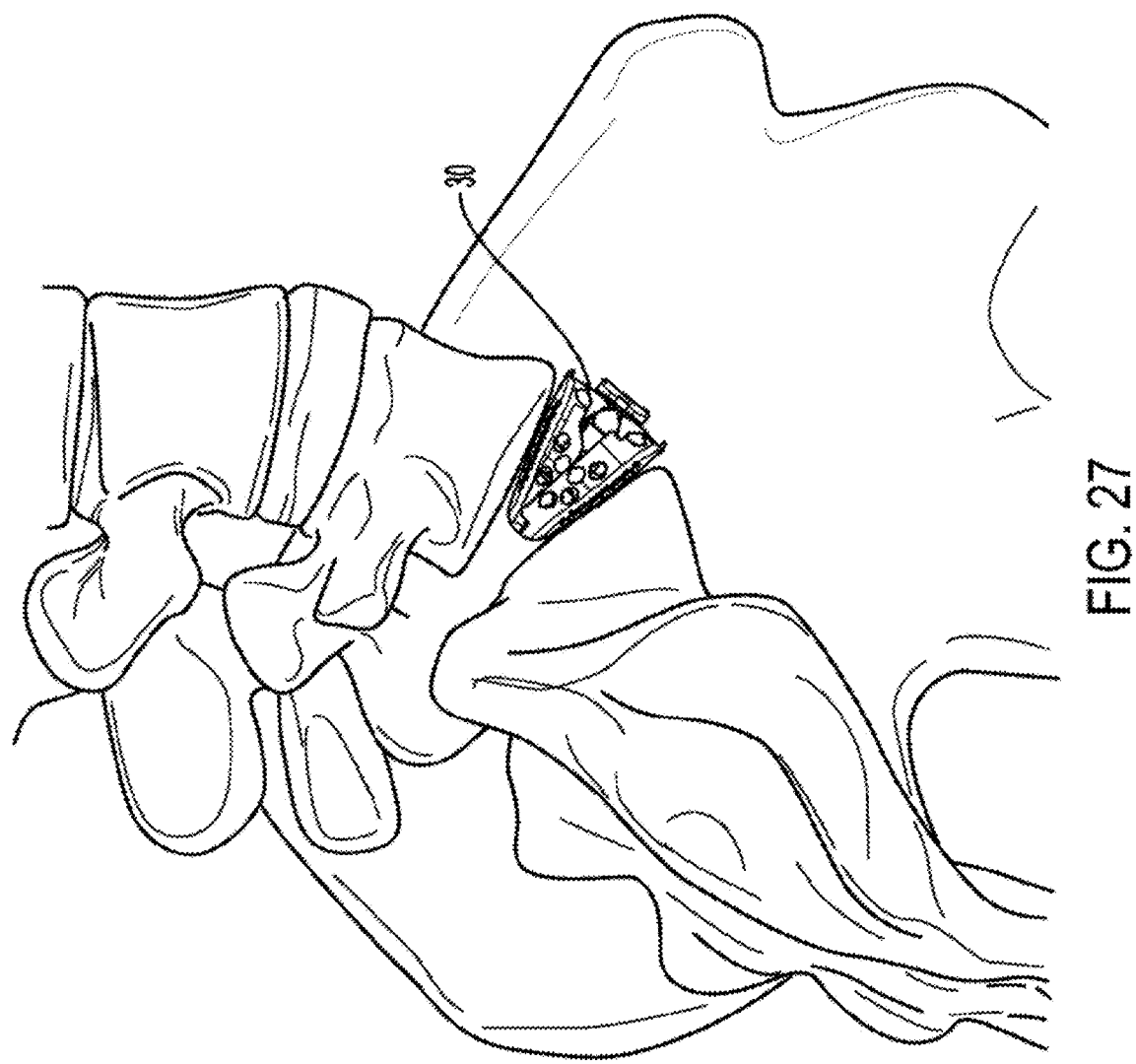
Figure 28:
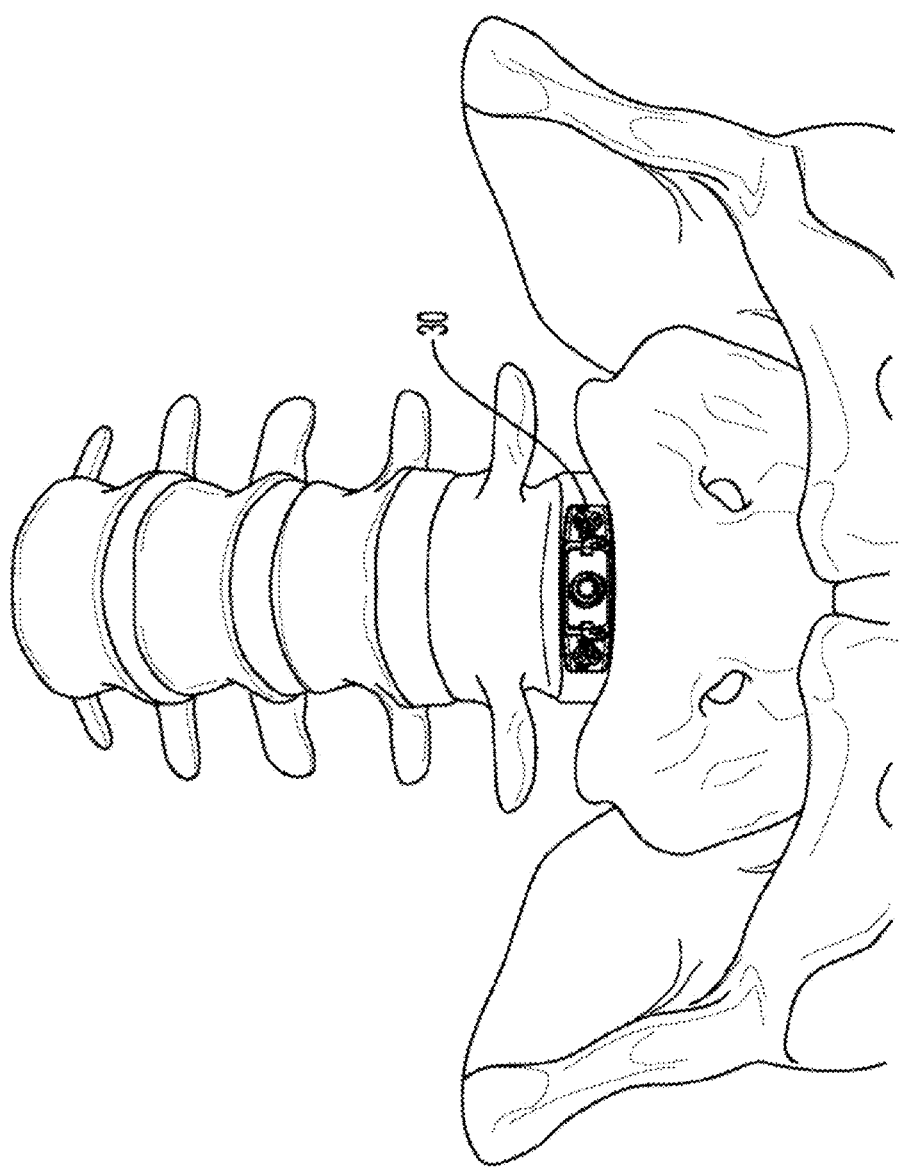

FIGS. 26-28 illustrate a left side view, right side view, and front side view, respectively, of an installed expandable spinal implant 100 positioned between adjacent vertebral bodies according to various surgical techniques, e.g., anterior techniques, oblique techniques, lateral techniques. For example, FIGS. 26-28 show spinal implant 100 after being installed according to an anterior lumbar interbody fusion (ALIF) technique.

Spinal implant systems of the present disclosure can be employed with a surgical arthrodesis procedure, such as, for example, an interbody fusion for treatment of an applicable condition or injury of an affected section of a spinal column and adjacent areas within a body, such as, for example, intervertebral disc space between adjacent vertebrae, and with additional surgical procedures and methods. In some embodiments, spinal implant systems can include an intervertebral implant that can be inserted between adjacent vertebral bodies to space apart articular joint surfaces, provide support for and maximize stabilization of vertebrae. In some embodiments, spinal implant systems may be employed with one or a plurality of vertebra.

Consistent with the disclosed embodiments herein, a medical practitioner may obtain access to a surgical site including vertebrae such as through incision and retraction of tissues. Spinal implant systems of the present disclosure can be used in any existing surgical method or technique including open surgery, mini-open surgery, minimally invasive surgery and percutaneous surgical implantation, whereby vertebrae are accessed through a mini-incision, retractor, tube or sleeve that provides a protected passageway to the area, including, for example, an expandable retractor wherein the sleeve is formed from multiple portions that may be moved apart or together and may be inserted with the portions closed or together and then expanded to allow for insertion of implants of larger size than the closed cross section of the unexpanded retractor portions. In one embodiment, the components of the spinal implant system are delivered through a surgical pathway to the surgical site along a surgical approach into intervertebral disc space between vertebrae. Various surgical approaches and pathways may be used.

As will be appreciated by one of skill in the art, a preparation instrument (not shown) may be employed to remove disc tissue, fluids, adjacent tissues and/or bone, and scrape and/or remove tissue from endplate surfaces of a first vertebra and/or endplate surface of a second vertebra in preparation for or as part of the procedures utilizing a system of the present disclosure. In some embodiments, the footprint of spinal implant 100 is selected after trialing using trialing instruments (not shown) that may approximate the size and configuration of spinal implant 100. In some embodiments, such trials may be fixed in size and/or be fitted with moving mechanisms 250 similar to embodiments described herein. In some embodiments, spinal implant 100 may be visualized by fluoroscopy and oriented before introduction into intervertebral disc space. Furthermore, first and second surgical tools 400, 500, and spinal implant 100 may be fitted with fiducial markers to enable image guided surgical navigation to be used prior to and/or during a procedure.

Components of a spinal implant systems of the present disclosure can be delivered or implanted as a pre-assembled device or can be assembled in situ. In one embodiment, spinal implant 100 is made of a single piece construction that may not be disassembled without destroying the device. In other embodiments, spinal implant 100 may comprise removable parts. Components of spinal implant system including implant 10, 20, 30 may be expanded, contracted, completely or partially revised, removed or replaced in situ. In some embodiments, spinal implant 100 can be delivered to the surgical site via mechanical manipulation and/or a free hand technique.

Additionally, components of spinal implant 100 can include radiolucent materials, e.g., polymers. Radiopaque markers may be included for identification under x-ray, fluoroscopy, CT or other imaging techniques. Furthermore, first and second surgical tools 400, 500 may be radiolucent and may optionally include markers added at a tip portion thereof to permit them to be seen on fluoroscopy/x-ray while advancing into the patient. At least one advantage to having spinal implant 100 is that a medical practitioner can verify the positioning of spinal implant 100 relative to adjacent vertebral bodies and make further adjustments to the spacing between endplates 110, 120, angle of inclination between endplates 110, 120, and the overall positioning of the device within a patient's body. In this way, spinal implant 100 may correct alignment of a patient's spine in a sagittal plane.

Figure 29A:
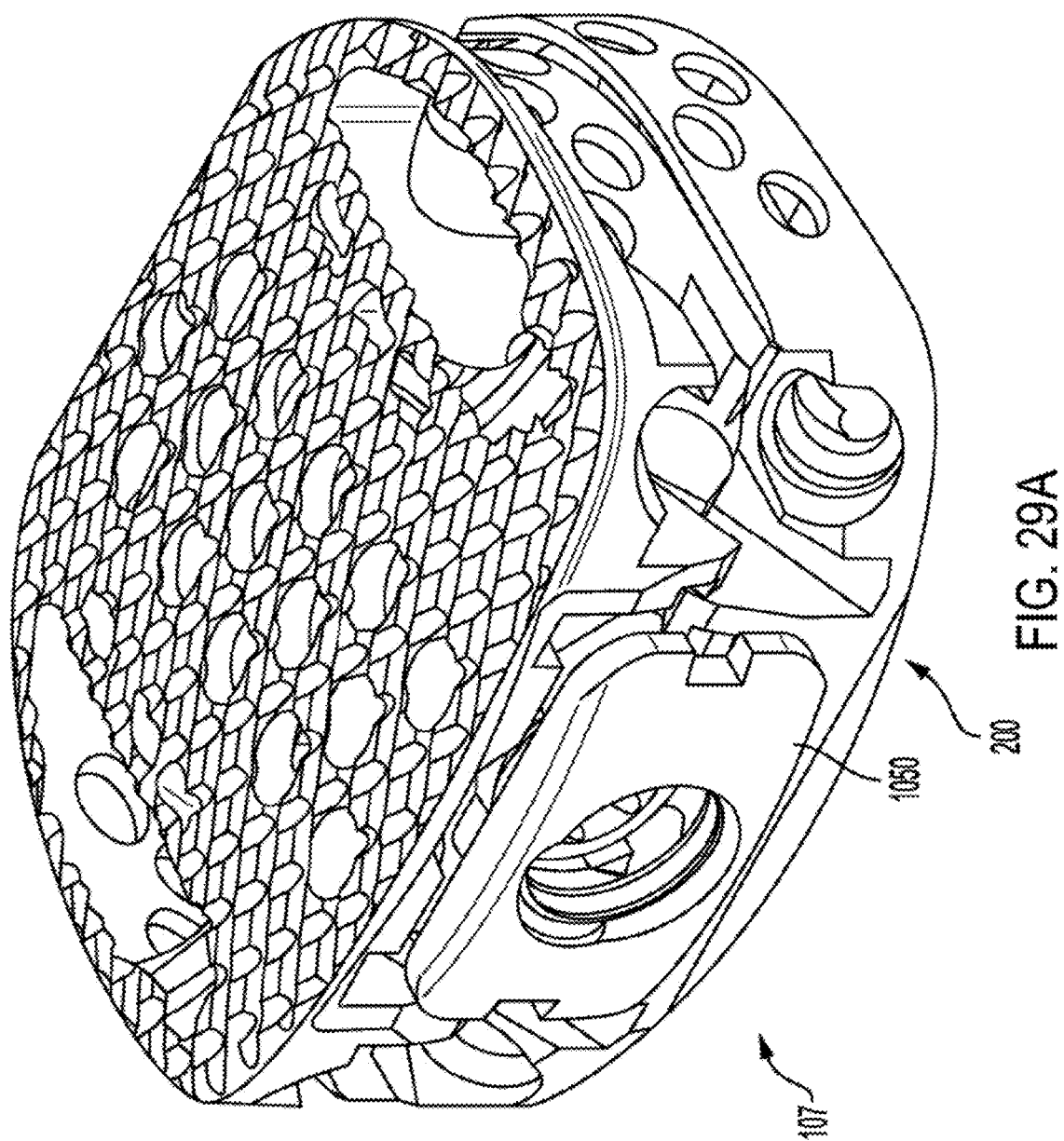
FIG. 29A is a perspective view of one embodiment of an expandable spinal implant in accordance with the principles of the present disclosure.

FIG. 29A is a perspective view of a second embodiment of an expandable spinal implant 200 in accordance with the principles of the present disclosure. Aspects of second spinal implant 100 may be the same as, substantially the same as, or similar to spinal implant 100. Additionally, second spinal implant 200 may be used in previously disclosed systems and methods. Accordingly, duplicative description thereof will be omitted.

Figure 29B:
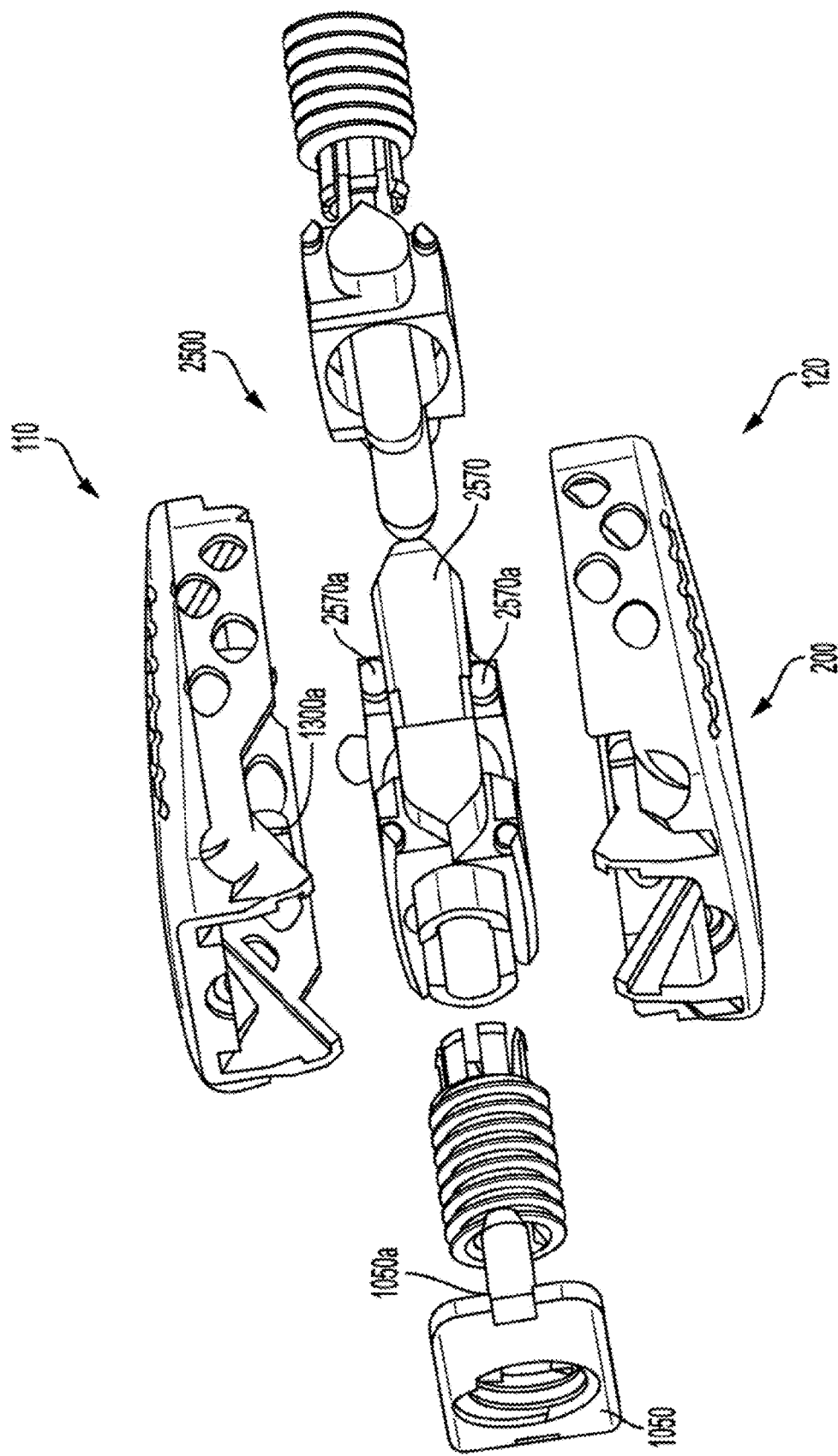
FIG. 29B is an exploded view of the embodiment of FIG. 29A in accordance with the principles of the present disclosure.

FIG. 29B is an exploded view illustrating second spinal implant 200. Second spinal implant 200 a top endplate 110 (first endplate) and a bottom endplate 120 (second endplate) and a moving mechanism 2500, which will be described in greater detail below. The proximal end 101 includes a screw guide endplate 1050 disposed between endplates 110 and 120. In some embodiments, screw guide endplate 1050 may be pivotable left-right and up-down to accommodate insertion of first surgical tool 400 from an off angle position. For example, screw guide endplate 1050 may accommodate a surgical tool that is insert off angle (not axially aligned) in a range of about 1° to 20°, and more particularly about 1° to 15° in the horizontal and vertical directions. At least one advantage of this arrangement is that first surgical tool 400 may be inserted off angle with respect to guide aperture 107 of spinal implant 200.

In the exemplary embodiment, moving mechanism 2500 is operably coupled to top endplate 110 and bottom endplate 120 similarly as explained above. Moving mechanism 2500 differs from moving mechanism 250 in that moving mechanism 2500 may be miss aligned, for example by about 5°, 10°, 15°, or 20° when compared to moving mechanism 250 of the first embodiment. In at least one embodiment, moving mechanism 2500 is misaligned about 15° to facilitate insertion and posterior adjustment by reconnection posteriorly. In the exemplary embodiment, moving mechanism 2500 operates by the same principles as moving mechanism 250 although the interior contours of top endplate 110 and bottom endplate 120 are shifted to allow moving mechanism 2500 to be miss aligned.

FIG. 30A is a top down view of spinal implant 200 contrasting an embodiment where moving mechanism 2500 is miss aligned. As illustrated, spinal implant 200 has a first reference axis $B_1$ and a second reference axis $B_2$. First reference axis $B_1$ may be understood as a projection where moving mechanism 2500 is not miss aligned and where moving mechanism 2500 is in a centered position. Second reference axis $B_2$ may be understood as a projection passing through a central portion of guide aperture 107 through moving mechanism 2500 when moving mechanism 2500 is miss aligned inside of endplates 110, 120 to an off-centered position.

Referring generally to FIGS. 30B-30F, a modified embodiment of spinal implant 200 where moving mechanism 2500 is miss aligned is disclosed. In the disclosed embodiment, moving mechanism 2500 features the same parts as moving mechanism 250 and operates under the same principles as explained previously. In the disclosed embodiment, moving mechanism 2500 is miss aligned by about 15° when compared with moving mechanism 250 of spinal implant 100. In other embodiments, moving mechanism 2500 may be miss aligned within any suitable range, e.g., from about 5° to 25°. FIG. 30C is a perspective view of the embodiment of FIG. 30B with a top endplate 110 removed for ease of understanding. As illustrated, moving mechanism 2500 is misaligned and the top and bottom endplates 110, 120 have a different geometry to accommodate the miss aligned moving mechanism 2500. Top and bottom endplates 110, 120 may feature the same or substantially the same characteristics as previously disclosed. FIG. 30D is an alternate perspective view of the embodiment of FIG. 30B with a top endplate 110 removed for ease of understanding. FIG. 30E is a top down view of an exemplary top endplate 110 for use with the embodiment of FIG. 30B and FIG. 30F is a top down view of an exemplary bottom endplate 120 for use with the embodiment of FIG. 30B.

FIG. 31 is a perspective view of spinal implant 200 in an installed position between vertebral bodies and three alternate positions of first surgical tool 400. FIG. 31 shows how first surgical tool 400 may be inserted into guide aperture 107 off angle with respect to first reference axis $B_1$. Reference ring RR represents the extent of viable offset positions that first surgical tool 400 may be operably inserted in guide aperture 107. In some embodiments, first surgical tool 400 may be bent at a midsection area at 15° to enable a surgeon to adjust spinal implant 200 in such a way as to avoid anatomical features and organs, such as, for example the pelvic ring and iliac crest. Additionally, this advantage is further expanded upon when using a miss-aligned moving mechanism 2500 that is miss aligned by, for example, about 15°. Therefore, disclosed systems of spinal implant 200 are able to be manipulated by a surgeon via surgical tool 400 at the combined total angular extent the moving mechanism 2500 is offset and the angular extent the surgical tool is bent. In at least one embodiment, the total angular extent is about 30° on account of the moving mechanism 2500 being offset about 15° and the surgical tool 400 being bent about 15°.

Figure 32A:
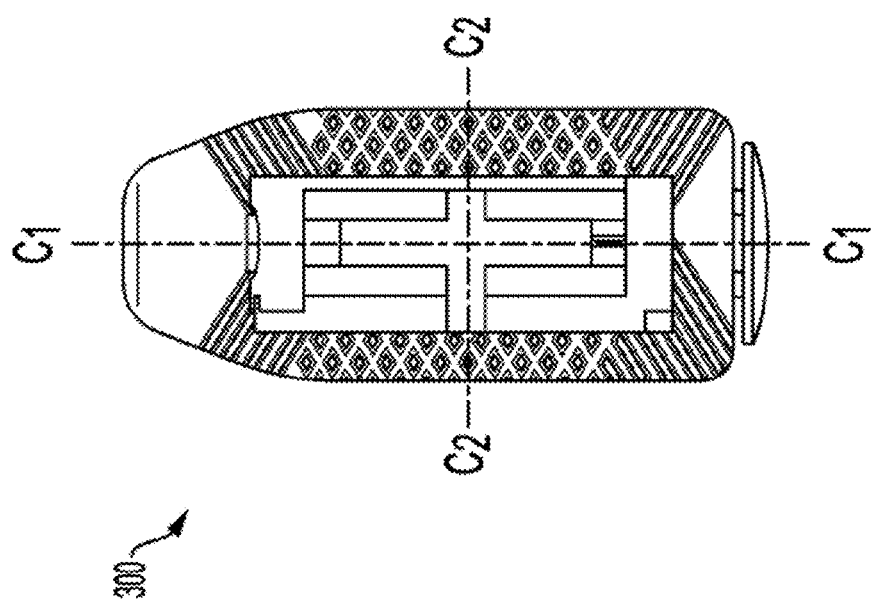
FIG. 32A is a top down view of one embodiment of an expandable spinal implant in accordance with the principles of the present disclosure.
Figure 32B:
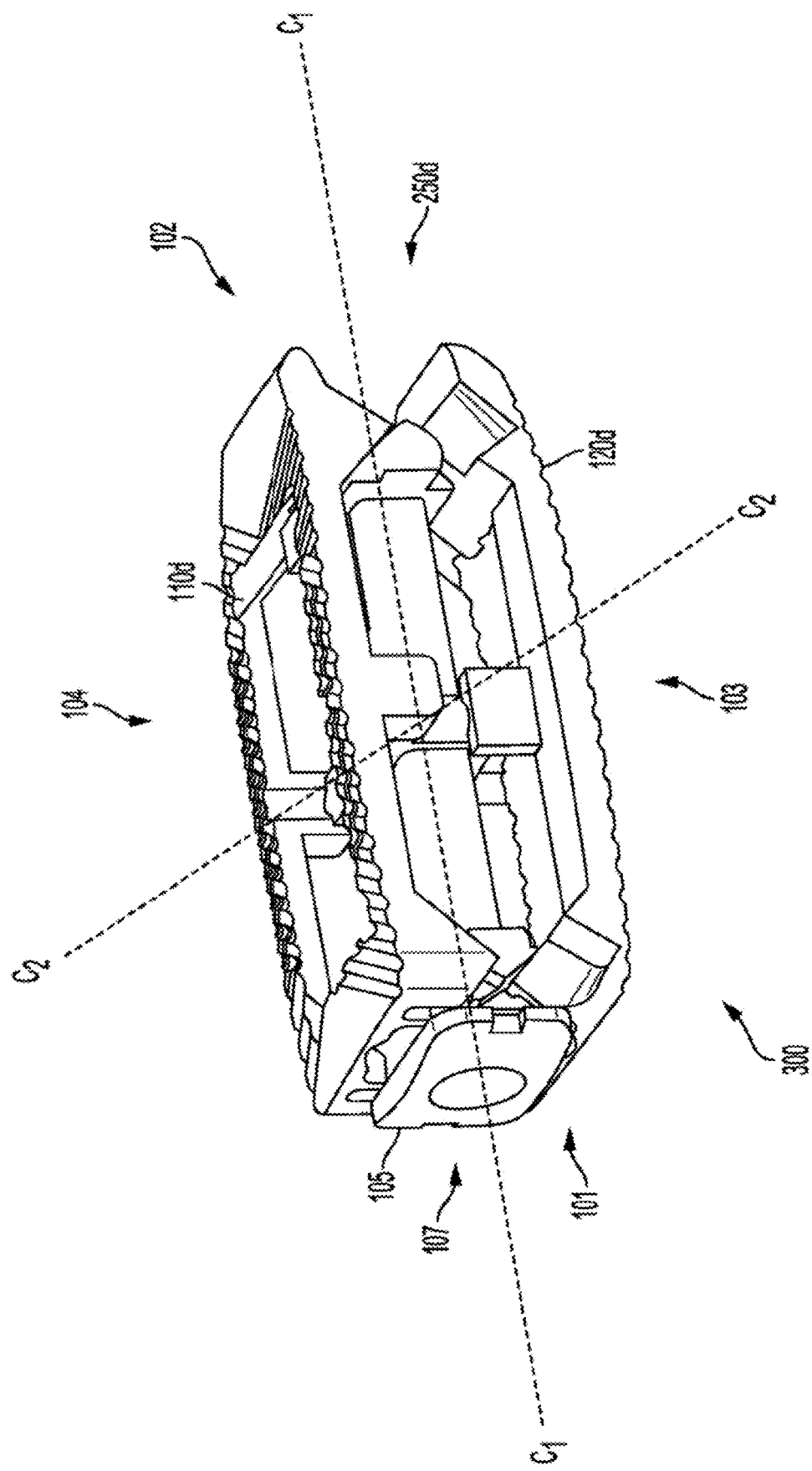
FIG. 32B is a perspective view of the embodiment of FIG. 32A in accordance with the principles of the present disclosure.

FIG. 32A is a top down view of a third embodiment of an expandable spinal implant 300 in accordance with the principles of the present disclosure. FIG. 32B shows spinal implant 300 in a perspective view. Aspects of spinal implant 300 may be the same as, substantially the same as, or similar to spinal implant 100. Additionally, spinal implant 300 may be used in previously disclosed systems and methods. Accordingly, duplicative description thereof will be omitted.

In some embodiments, the sizing and orientation of top and bottom endplates 110, 120 and the sizing and orientation of moving mechanism 250d is particularly advantageous for lateral insertion techniques. Spinal implant 300 includes a first reference axis $C_1$ and a second reference axis $C_2$. Different than previous embodiments, first reference axis $C_1$ may span a longitudinal length of spinal implant 300 and pass directly through a rotation axis of moving mechanism 250d. Second reference axis $C_2$ may bisect spinal implant 300 transversely across the center thereof. Additionally, second reference axis $C_2$ may intersect first reference axis $C_1$ and project through a center of buttress block 257.

Spinal implant 300 may include a top endplate 110d and a bottom endplate 120d and a moving mechanism 250, which may be the same as or substantially the same as described above. Spinal implant 300 includes a proximal end 101 and a distal end 102 opposite the proximal end 101, and a first lateral end 103 and a second lateral end 104 opposite the first lateral end 103. The first and second lateral ends 103, 104 extend between the proximal end 101 and the distal end 102. The proximal end 101 includes an exposed screw guide endplate 105 defining a corresponding screw guide aperture 107, which are disposed between endplates 110d and 120d. The screw guide endplate 105 and guide aperture 107 may be the same as or substantially the same as described above.

Top endplate 110 may include a first outside surface 111d and a first inside surface 112d opposite the first outside surface 111d. Similarly, bottom endplate 120d may include a second outside surface 121d and a second inside surface 122d. The outside surfaces 111d, 121d may be configured to be positioned between and/or contact vertebral bodies in a patients spine and have various surface characteristics similar to those described above with reference to spinal implant 100. In some embodiments, outside surfaces 111d and 122d may have a substantially linear surface profile across faces of textured surfaces thereof. In other embodiments, outside surfaces 111d and 122d may have curved surface profiles across faces of textured surfaces thereof. Further details of endplates 110d, 120d will be described in greater detail below.

Inside surfaces 111d, 122d, may surround moving mechanism 250 and have various contours, guides, cavities, and other operable characteristics that facilitate movement and/or provide mechanical advantage to other operable and movable corresponding parts to facilitate contraction, angular adjustment, lateral bending, absorption of compression forces, shear forces, etc. as will be explained in greater detail below.

In the exemplary embodiment, top endplate 110d includes a pair of first proximal ramps 114d and a pair of first distal ramps 116d opposite the first proximal ramps 114d. Each ramp of the first proximal ramps 114d includes an inclined surface extending away from inside surface 112d and moving mechanism 250d. Similarly, each ramp of first distal ramps 116*d* includes an inclined surface extending away from inside surface 112*d* and moving mechanism 250*d*. Bottom endplate 120*d* includes a pair of second proximal ramps 124*d* and a pair of second distal ramps 126*d* opposite the second proximal ramps 124*d*. Each ramp of the second proximal ramps 124*d* includes an inclined surface extending away from inside surface 122*d* and moving mechanism 250*d*. Similarly, each ramp of second distal ramps 126*d* includes an inclined surface extending away from inside surface 11*d*1 and moving mechanism 250*d*.

Exemplary spinal implant 300 includes a moving mechanism 250*d* that is operably coupled to top endplate 110*d* and bottom endplate 120*d*, similarly as explained above with reference to spinal implant 100. Accordingly, duplicative description will not be repeated. A first functional feature of moving mechanism 250*d* is that it is further configured to increase and decrease a spacing between the top and bottom endplates 110*d*, 120*d* upon simultaneous rotation of first and second set screws 252, 254 in a clockwise and counterclockwise direction, respectively. A second functional feature of moving mechanism 250*d* is that it is further configured to increase and decrease an angle of inclination between top and bottom endplates 110*d*, 120*d* upon rotation of the first set screw 252 in a clockwise and counterclockwise direction, respectively.

Figure 33A:
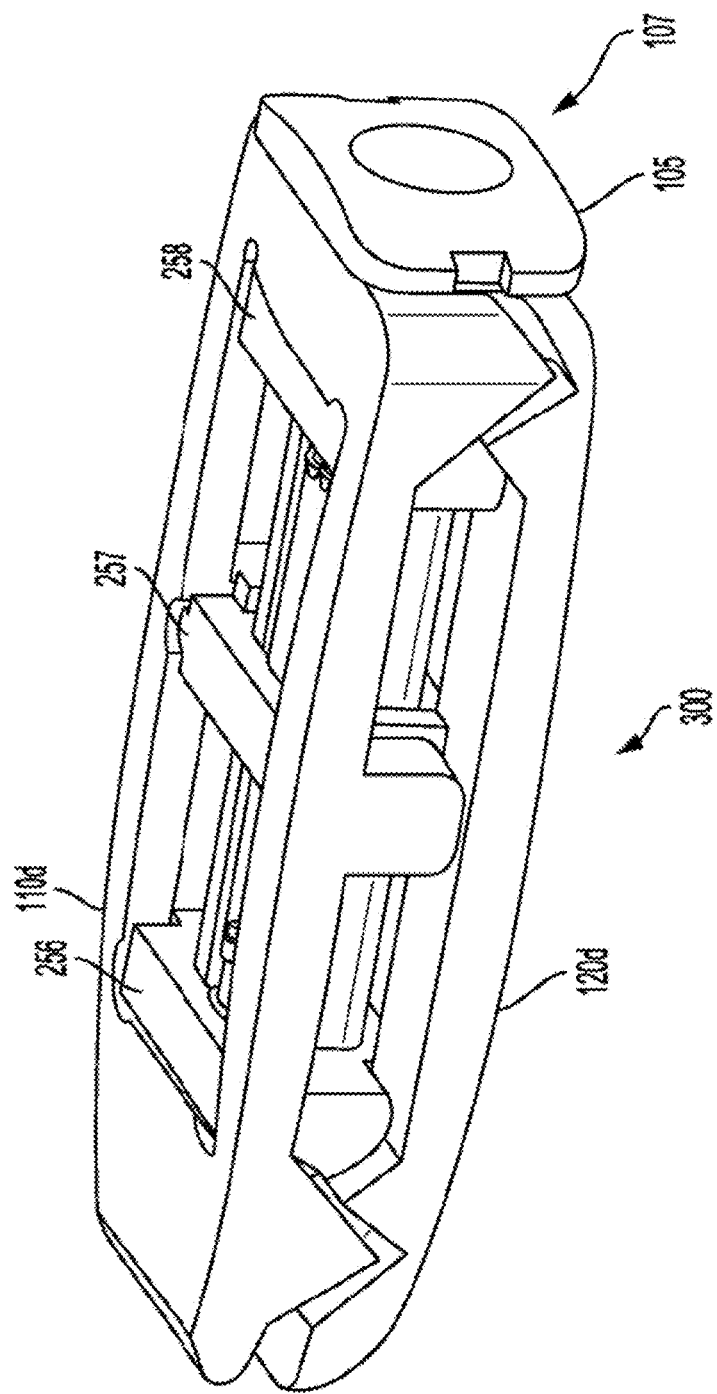
FIG. 33A is a perspective view of one embodiment of an expandable spinal implant in accordance with the principles of the present disclosure.
Figure 33B:
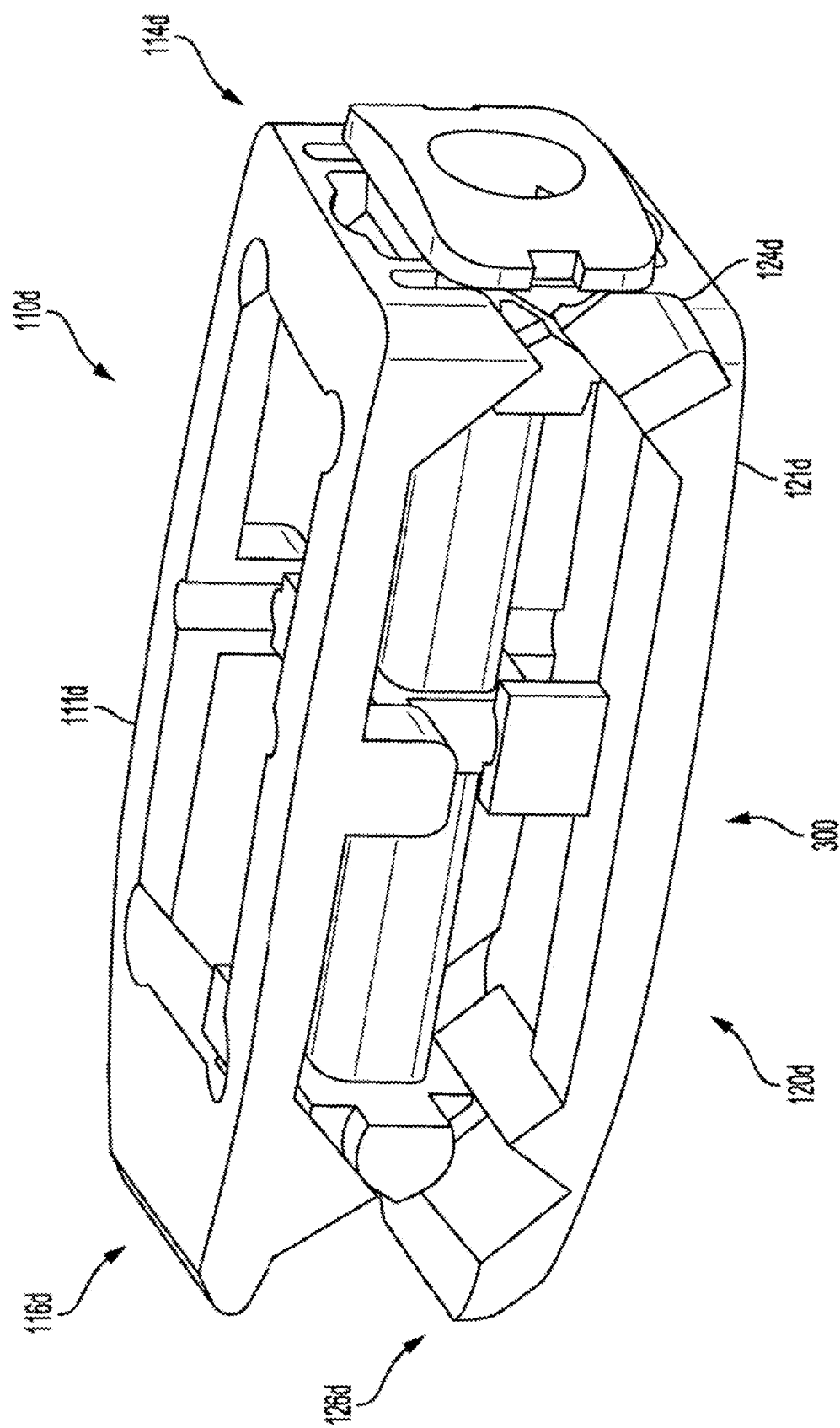
FIG. 33B is a perspective view of the embodiment of FIG. 33A in an expanded position in accordance with the principles of the present disclosure.
Figure 33C:
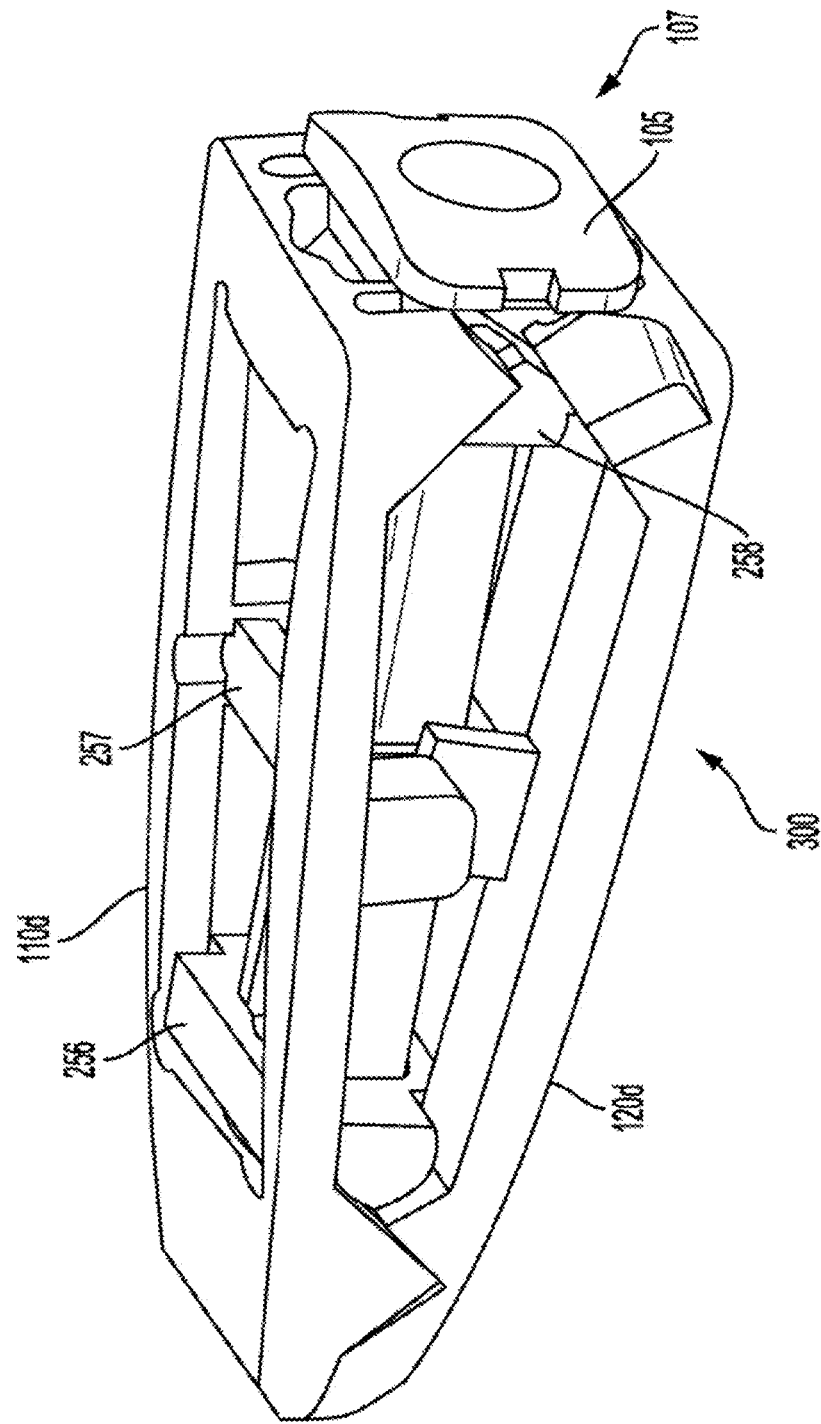
FIG. 33C is a perspective view of the embodiment of FIG. 33A in a first tilted position in accordance with the principles of the present disclosure.
Figure 33D:
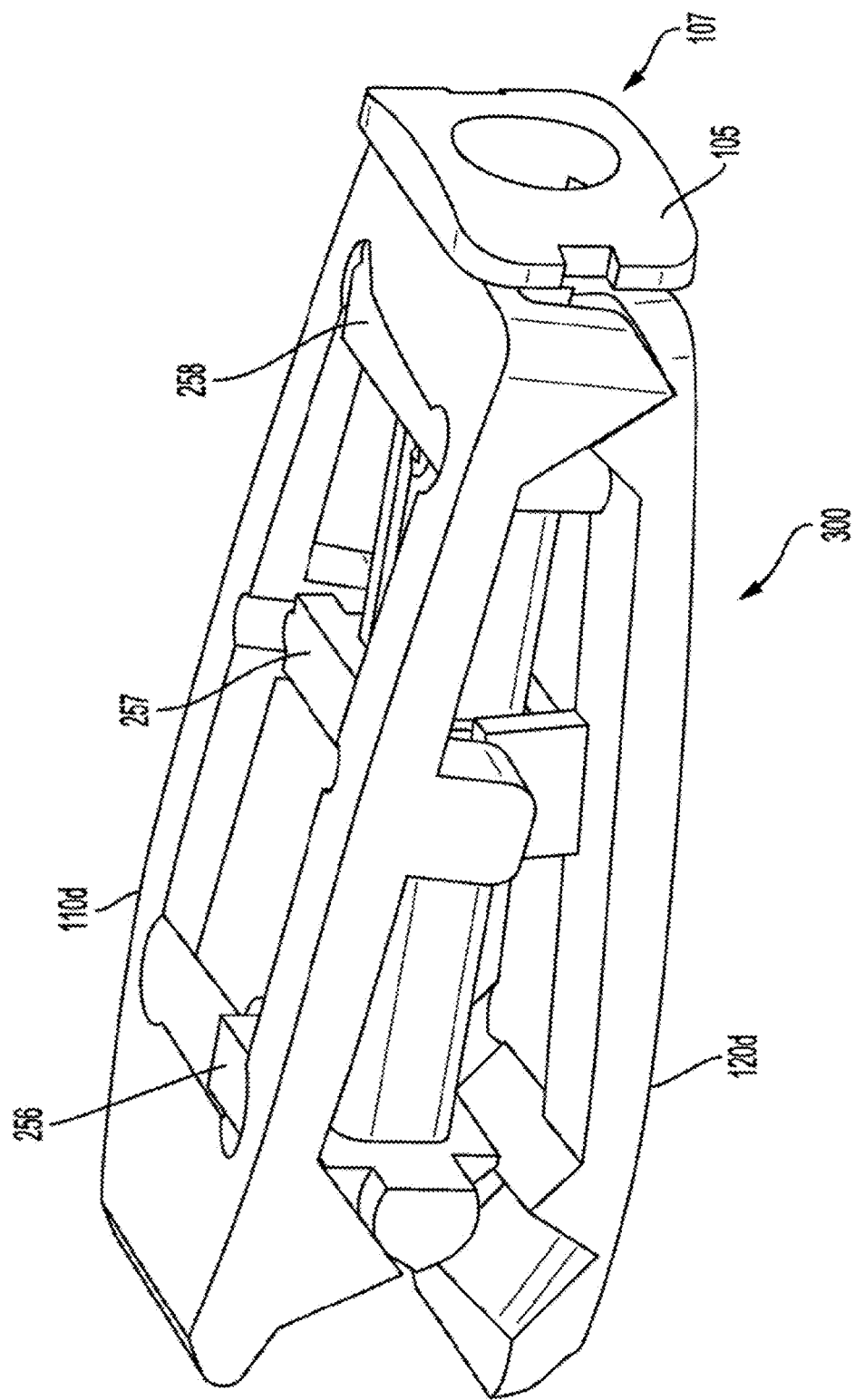
FIG. 33D is a perspective view of the embodiment of FIG. 33A in a second tilted position in accordance with the principles of the present disclosure.

FIG. 33A is a perspective view of spinal implant 300 in a contracted position and FIG. 33B is a perspective view of spinal implant 300 in an expanded position. In the contracted position of FIG. 33A, top endplate 110*d* and bottom endplate 120*d* are contracted to a fully closed position. In the expanded position of FIG. 33B, top endplate 110*d* and bottom endplate 120*d* are expanded an equal amount. Similarly as explained above with reference to spinal implant 100 and FIGS. 9A-9B when first surgical tool 400 is inserted in guide aperture 107 in a first position and rotated in a first direction (clockwise direction) the first and second trolleys 256, 258 move away from one another an equal amount in opposite directions. In turn, the first and second trolleys 256, 258 cause the top and bottom endplates 110*d*, 120*d* to move apart from one another an equal amount. Likewise, when first surgical tool 400 is rotated in a second direction (counter-clockwise direction) first and second trolleys 256, 258 cause the top and bottom endplates 110*d*, 120*d* to move towards one another an equal amount in a contraction direction (not illustrated). In summary, when positioning the first surgical tool 400 in the first position and rotating the first surgical tool 400 in either the first or second direction the moving mechanism 250*d* operably adjusts a spacing between the top and bottom endplates 110*d*, 120*d*. FIG. 33C is a perspective view of spinal implant 300 in a first angled position and FIG. 33D is a perspective view of spinal implant 300 in a second angled position. Spinal implant 300 may have the same or similar features as explained above with respect to spinal implants 100, 200. Spinal implant 300 may be capable of (1) expanding/contracting the proximal end while the distal end remains stationary, (2) expanding/contracting the distal end while the proximal end remains stationary, and (3) expanding/contracting both the proximal end and distal end simultaneously. Similarly as explained above with reference to spinal implant 100 and FIGS. 10A-10B when first surgical tool 400 is inserted in guide aperture 107 in a second position, and rotated in a first direction (clockwise direction) the first trolley 256 moves away from the proximal end 101 of spinal implant 100 and the second trolley 258 remains stationary in place. In effect, the top and bottom endplates 110*d*, 120*d* move towards one another at the distal end 102 (not shown) and move away from one another at the proximal end 101 thereby decreasing an angle of inclination between the top and bottom endplates 110, 120.

Likewise, when first surgical tool 400 is in the second position and is rotated in the second direction (counter-clockwise direction) the first trolley 256 moves towards the stationary second trolley 258. In effect, the top and bottom endplates 110*d*, 120*d* move towards one another at the proximal end 101 (not shown) thereby decreasing an angle of inclination between the top and bottom endplates 110*d*, 120*d*. In summary, when positioning the first surgical tool 400 in the second position and rotating the first surgical tool 400 in either the first or second direction the moving mechanism 250 operably adjusts an angle of inclination between the top and bottom endplates 110, 120 upon rotating the first set screw along the rotation axis.

In the contracted position of FIG. 33A, a first height between top endplate 110*d* and bottom endplate 120*d* on the proximal side 101 and distal side 102 is about 9 mm. In the first expanded position of FIG. 33B, a second height of spinal implant 300 between top endplate 110*d* and bottom endplate 120*d* on the proximal side 101 and distal side 102 is about 9 mm. Additionally, in the first expanded position of FIG. 33B, top endplate 110*d* is parallel with respect to bottom endplate 110*d*. In the first angled position of FIG. 33C, the top and bottom endplates 110*d*, 120*d* are contacting each other at the distal side 102 and are spaced apart from one another at the proximal side 101. For example, at the distal side 102, the height between top endplate 110*d* and bottom endplate 120*d* is about 9 mm. For example still, at the proximate side 101, the height between top endplate 110*d* and bottom endplate 120*d* is about 16 mm. Accordingly, an angle of inclination between top endplate 110*d* and bottom endplate 120*d* at the distal side 101 is about 11°. In the second angled position of FIG. 33D, the top and bottom endplates 110*d*, 120*d* are contacting each other at the proximal side 102 and are spaced apart from one another at the distal side 101. For example, at the proximal side 102, the height between top endplate 110*d* and bottom endplate 120*d* is about 9 mm. For example still, at the distal side 101, the height between top endplate 110*d* and bottom endplate 120*d* is about 16 mm. Accordingly, an angle of inclination between top endplate 110*d* and bottom endplate 120*d* at the proximal side 101 is about 11°.

In some embodiments, spinal implant 300 may comprise a three position inner drive shaft (not illustrated) complimentary to or in place of components of moving mechanism 250. The three position inner drive shaft may enable the first and second set screws 252, 254 to be adjusted independently from one another as well as enabling the first and second set screws 252, 254 to be adjusted concurrently or simultaneously. For example, first surgical tool 400 may have a relatively short circumferential surface 456 that will only engage one of the internal circumferential surfaces of first or second set screws 252, 254 at a time. For example still, another first surgical tool 400 having a relatively longer circumferential surface 456 may engage both of the internal circumferential surfaces of the first and second set screws 252, 254 at the same time. Consistent with disclosed embodiments, a surgeon can use a first surgical tool 400 having a relatively shorter circumferential surface 456 to perform angular adjustments of spinal implant 300 and then use a first surgical tool 400 having a relatively longer circumferential surface 456 to perform height adjustments of spinal implant 300. In other embodiments, spinal implant 300 may include a screw guide aperture 107 on both sides of the spinal implant 300 thereby providing access to the first set screw 252 independently from second set screw 254.

FIG. 34 is a perspective view of a spinal implant system utilizing spinal implant 300 and first surgical tool 400. In the exemplary system, spinal implant 300 is positioned in an installed position between vertebral bodies by first surgical tool 400 according to lateral insertion techniques as explained in greater detail above. First surgical tool 400 may operably adjust spinal implant 300 in situ between vertebral bodies as explained in greater above. For example, first surgical tool 400 may operably expand spinal implant 300 at a proximal side 101 and/or a distal side 102 thereof. In this way, spinal implant 300 may correct alignment of a patient's spine in a coronal plane.

Figure 35:
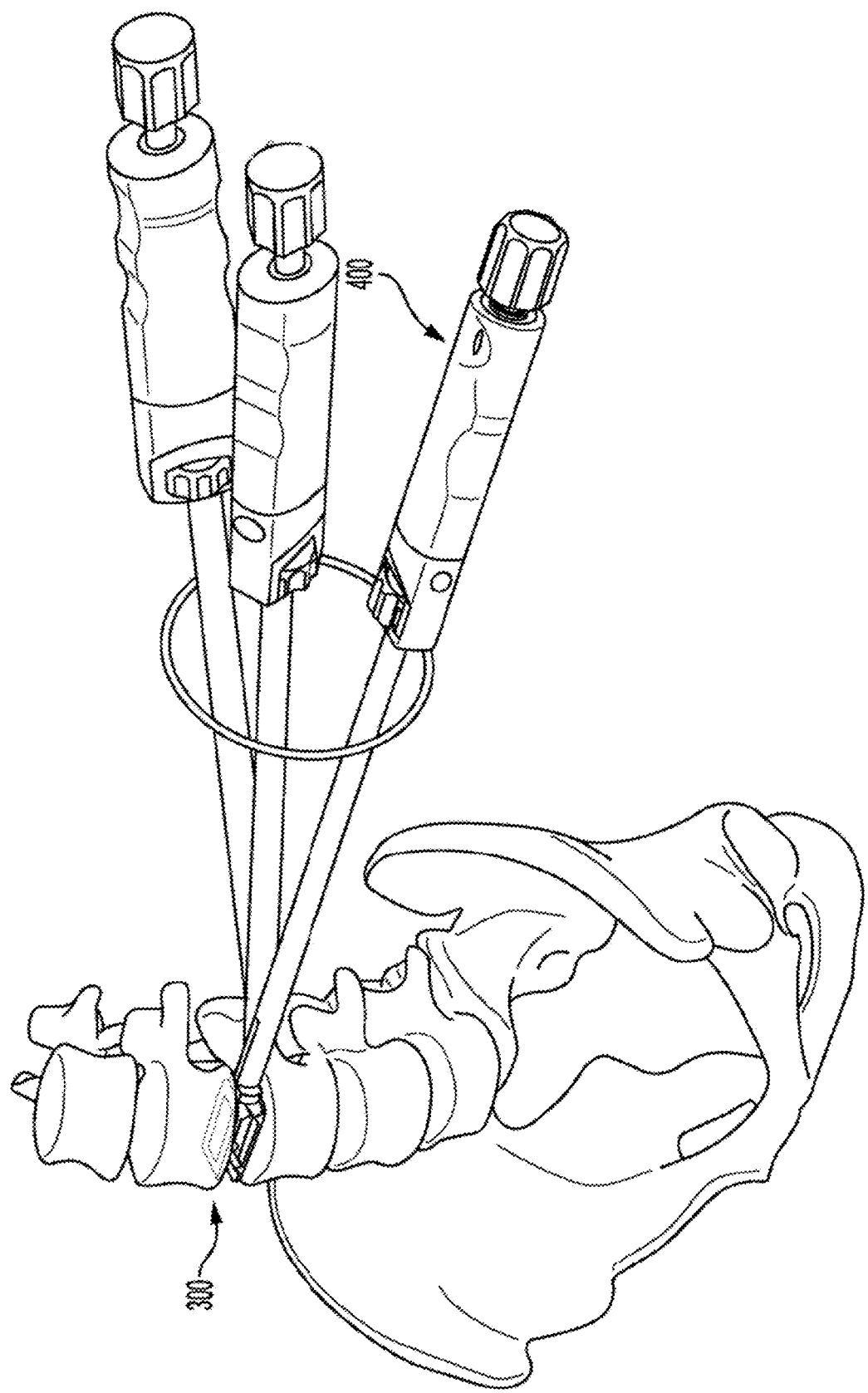
FIG. 35 is a perspective view of one embodiment of an expandable spinal implant system illustrating three alternate angular positions of an insertion tool in accordance with the principles of the present disclosure.
Figure 36:
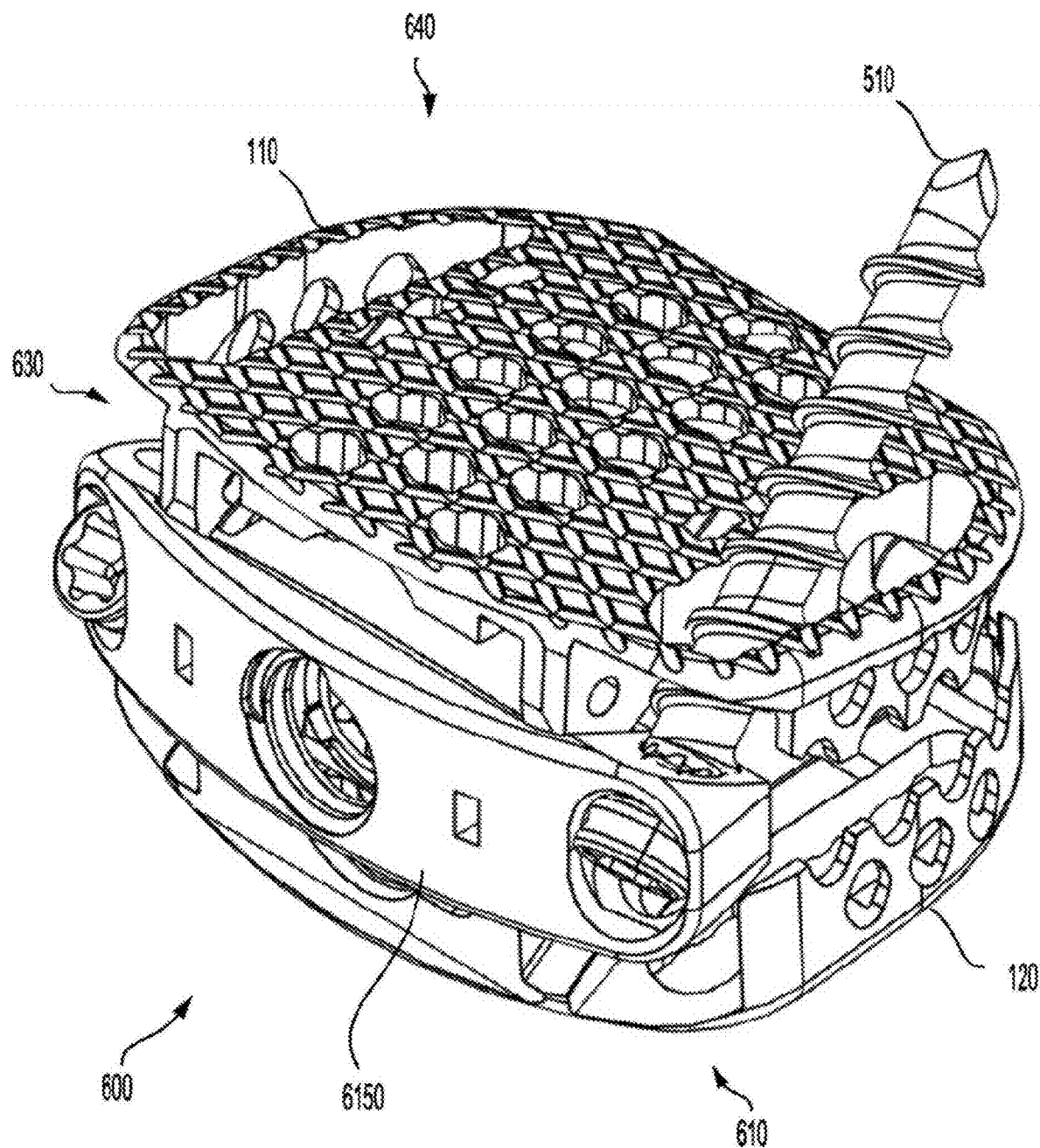
FIG. 36 is a perspective view of one embodiment of an expandable spinal implant including a screw guide endplate having at least one aperture configured to receive a anchoring screw therein.

FIG. 35 is a perspective view of a spinal implant system utilizing spinal implant 300 highlighting how first surgical tool 400 may manipulate spinal implant 300 from various angles. For example, spinal implant 300 may include the same, substantially the same, or similar components to moving mechanism 2500 as explained above. In the exemplary embodiment, first surgical tool 400 may be inserted into guide aperture 107 off angle with respect to first reference axis B 1. Reference ring RR represents the extent of viable offset positions that first surgical tool 400 may be operably inserted in guide aperture 107. In some embodiments, first surgical tool 400 may be bent at a midsection area at 15° (not illustrated) to enable a surgeon to adjust spinal implant 300 in such a way as to avoid anatomical features and organs, such as, for example the pelvic ring and iliac crest.

Referring generally to FIGS. 36-39B an additional expandable spinal implant 600 is disclosed. Expandable spinal implant 600 may have the same, substantially the same, and/or similar components and attributes as spinal implants 100, 200, and 300 including general applicability with other relevant systems and surgical tools disclosed hereinabove. Spinal implant 600 may include a screw guide endplate 6150 having at least one aperture 610 configured to receive an anchoring screw 510 therein. Screw guide endplate 6150 may be relatively longer in length than screw guide endplate 150 discussed above and screw guide endplate 6150 may be operably coupled with moving mechanism 250 similarly as explained above with respect to spinal implants 100, 200, and 300.

In the illustrated embodiment, top endplate 110 and bottom endplate 120 may each have an accommodating portion 630 having a corresponding size and geometry to the end portions of screw guide endplate 6150 such that when spinal implant 600 is in the fully collapsed position the end portions of screw guide endplate 6150 will not increase a relative height of implant 600 in a fully collapsed position. For example, endplates 110, 120 may fully close without being impacted by screw guide endplate 6150 and therefore maintain a relatively compact size.

Figure 38A:
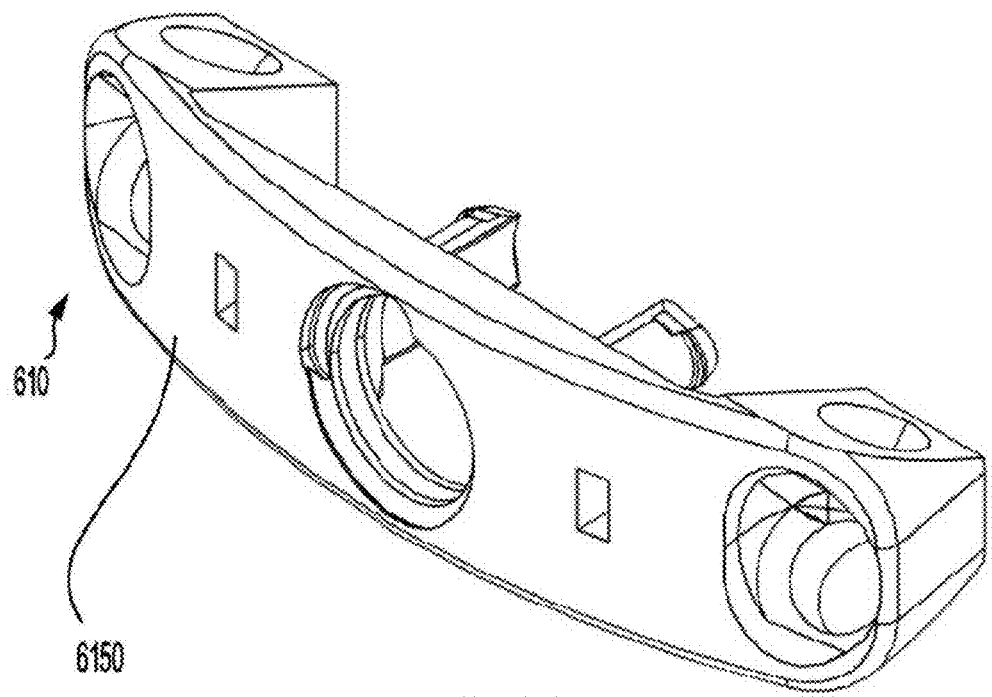
FIGS. 38A and 38B are various perspective views of a screw guide endplate having at least one aperture configured to receive a anchoring screw therein.
Figure 38B:
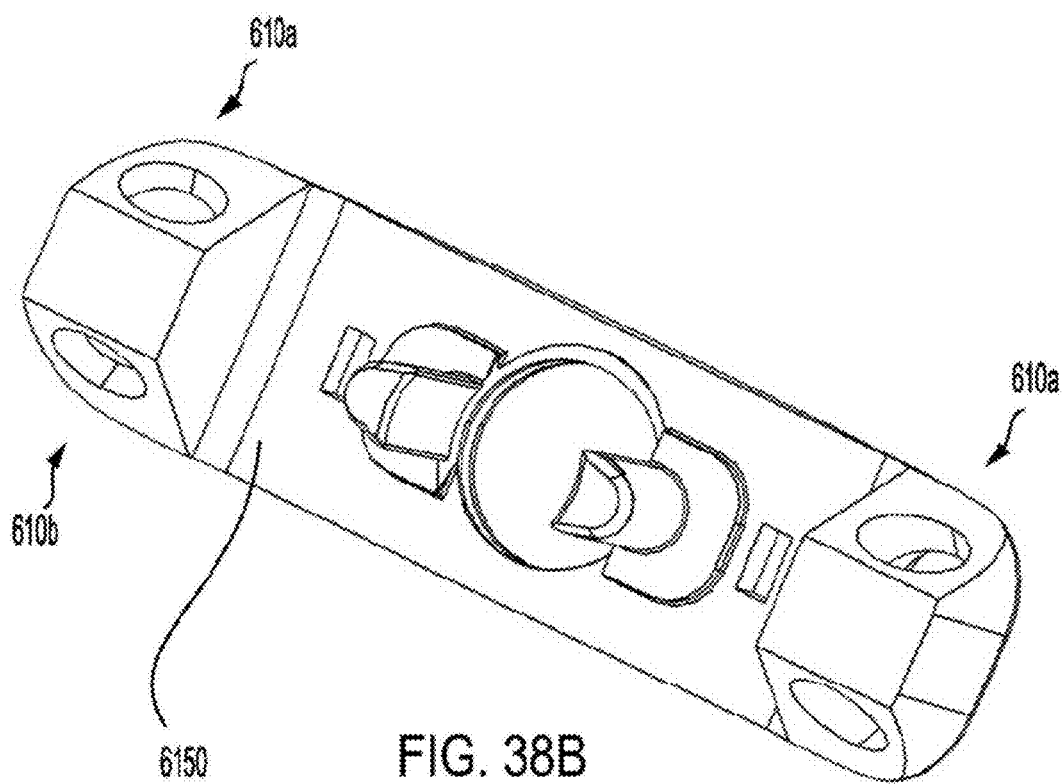
Figure 39A:
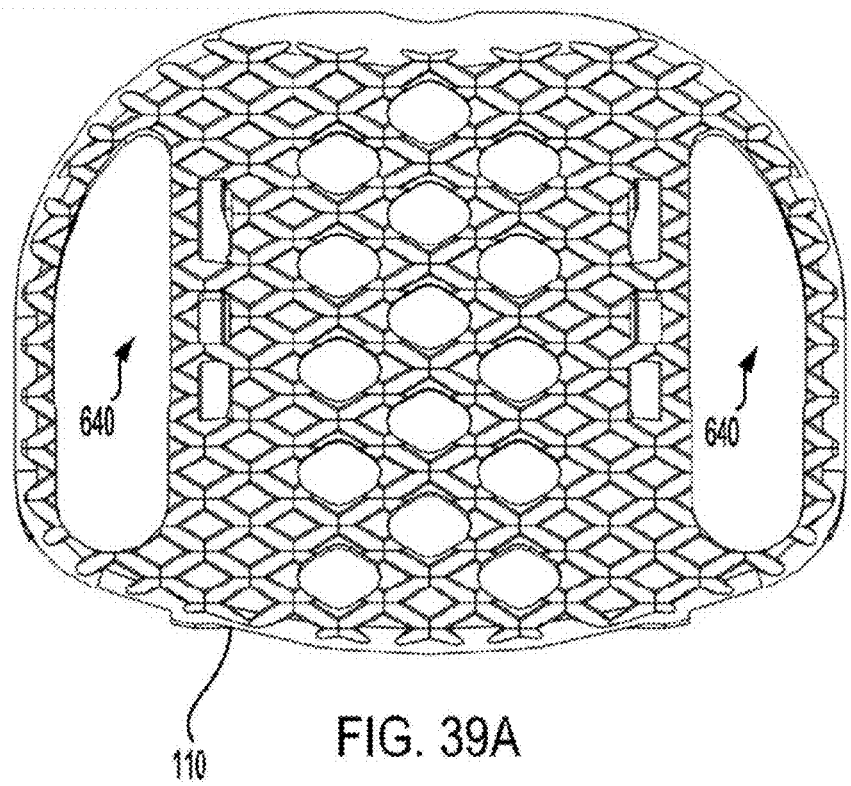
FIGS. 39A and 39B are top down view of a top endplate and a bottom endplate including at least one slotted aperture configured to receive a anchoring screw therein.
Figure 39B:
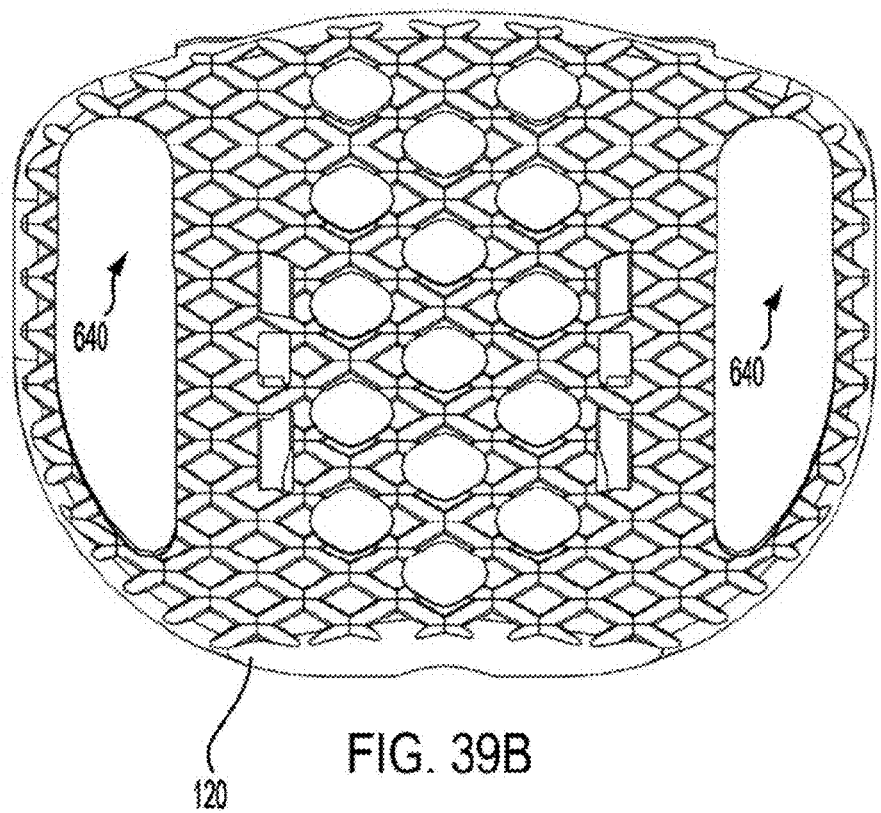

FIGS. 38A and 38B illustrate a front perspective view and a rear perspective view of an exemplary screw guide endplate 6150 having at least one aperture 610 configured to receive an anchoring screw 510 therein. In the illustrated embodiment, two apertures 610 are shown although embodiments in accordance with the principles of this disclosure may have any number of apertures 610. As illustrated, each aperture 610 may be configured to selectively receive a corresponding anchoring screw therein. The outside entrance to each aperture 610 may define two alternate guided paths. For example, a first guided path may be defined by the entrance to aperture 610 and a first exit aperture 610a and a second guided path may be defined by the entrance to aperture 610 and a second exit aperture 610b. In this way aperture 610 may be configured to orient one corresponding anchoring screw 510 at a time in either of a first orientation or a second orientation.

Figure 37:
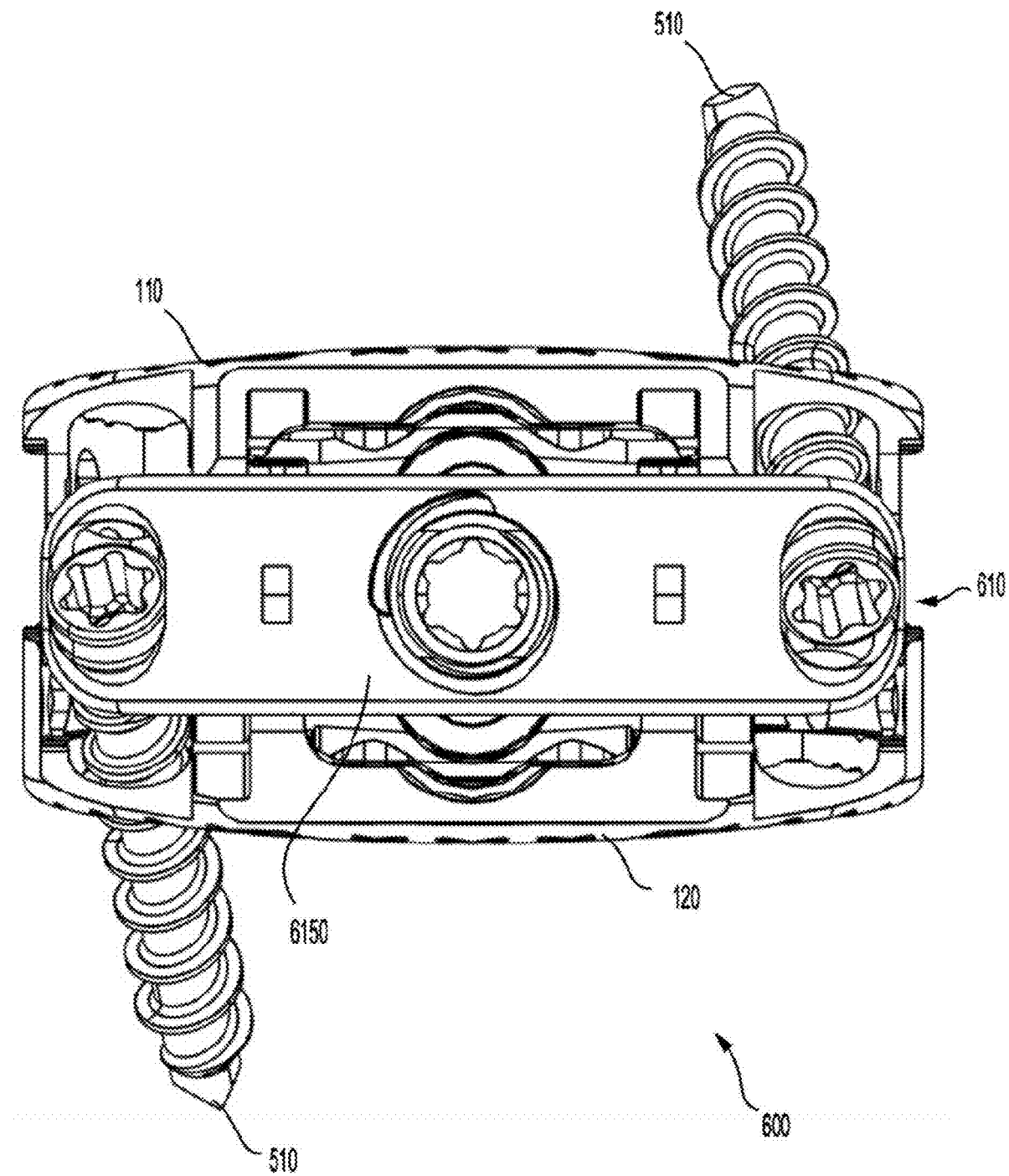
FIG. 37 is a front view of the embodiment of FIG. 36.

Corresponding exemplary first and second orientations are illustrated in FIG. 37 which shows a first anchoring screw 510 (right anchoring screw) oriented upward at an inclined angle with respect to top endplate 110 and a second anchoring screw 510 (left anchoring screw) oriented downward at an inclined angle with respect to bottom endplate 120. Additionally, the first orientation may align a corresponding anchoring screw 510 such that it projects through a corresponding slotted aperture 640 of the first endplate 110 (see FIGS. 36 and 39A). Similarly, the second orientation may align a corresponding anchoring screw 510 such that it projects through a corresponding slotted aperture 640 of the second endplate 120 (see FIGS. 36 and 39B).

At least one advantage of the disclosed spinal implant 600 is that screw guide endplate 6150 and moving mechanism 250 may be configured such that the moving mechanism 250 can selectively adjust a spacing between the first and second endplates 110, 120 and adjust an angle of inclination between the first and second endplates while the at least one corresponding anchoring screw 510 is anchored within a corresponding vertebrae. For example, a surgeon may initially position spinal implant 600 between adjacent vertebrae of a patient and install a corresponding first anchoring screw 510 in a first orientation projecting through slotted aperture 640 of first endplate 110 and a corresponding second anchoring screw 510 in a second orientation projecting through slotted aperture 640 of second endplate 120. Next, the surgeon may continue to adjust the spacing and/or angle of inclination between endplates 110, 120 until the endplates 110, 120 are in the desired position. This is possible, at least partly, because the relative location of the screw guide endplate 6150 remains fixed due to the anchored anchoring screws 510 and the first and second endplates can freely expand/contract and/or incline/decline via moving mechanism 250 while anchoring screws 510 extend through slotted aperture 640 (which has a geometry such that the anchored anchoring screws 510 do not interfere with the movement of endplates 110, 120). For example, the endplates 110, 120 may freely move while anchoring screws 510 remain anchored in place in the corresponding vertebrae while also changing a relative positioning with respect to the slotted aperture 640 due to movement of endplates 110, 120.

Referring generally to FIGS. 40-44B an additional expandable spinal implant 700 is disclosed. Expandable spinal implant 700 may have the same, substantially the same, and/or similar components and attributes as spinal implants 100, 200, 300, and 600 including general applicability with other relevant systems and surgical tools disclosed hereinabove. Spinal implant 700 may include a screw guide endplate 7150 having at least one aperture 710 configured to receive an anchoring screw 510 therein. Screw guide endplate 7150 may be relatively longer in length than screw guide endplate 150 discussed above and screw guide endplate 7150 may be operably coupled with moving mechanism 250 similarly as explained above with respect to spinal implants 100, 200, and 300.

In the illustrated embodiment, top endplate 110 and bottom endplate 120 may each have an accommodating portion 730 having a corresponding size and geometry to the end portions of screw guide endplate 7150 such that when spinal implant 700 is in the fully collapsed position the end portions of screw guide endplate 7150 will not increase a relative height of implant 700 in a fully collapsed position.

For example, endplates 110, 120 may fully close without being impacted by screw guide endplate 7150 and therefore maintain a relatively compact size.

Figure 42A:
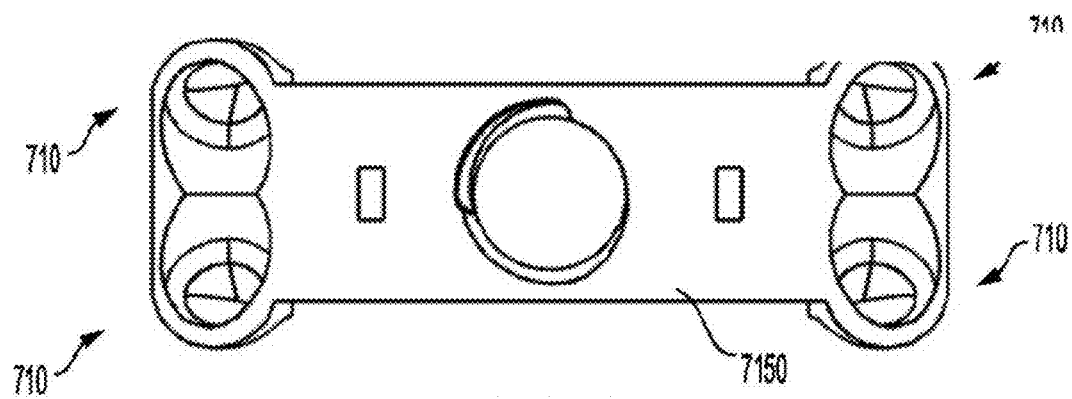
FIG. 42A is a front views of a screw guide endplate having at least one aperture configured to receive a anchoring screw therein.
Figure 42B:
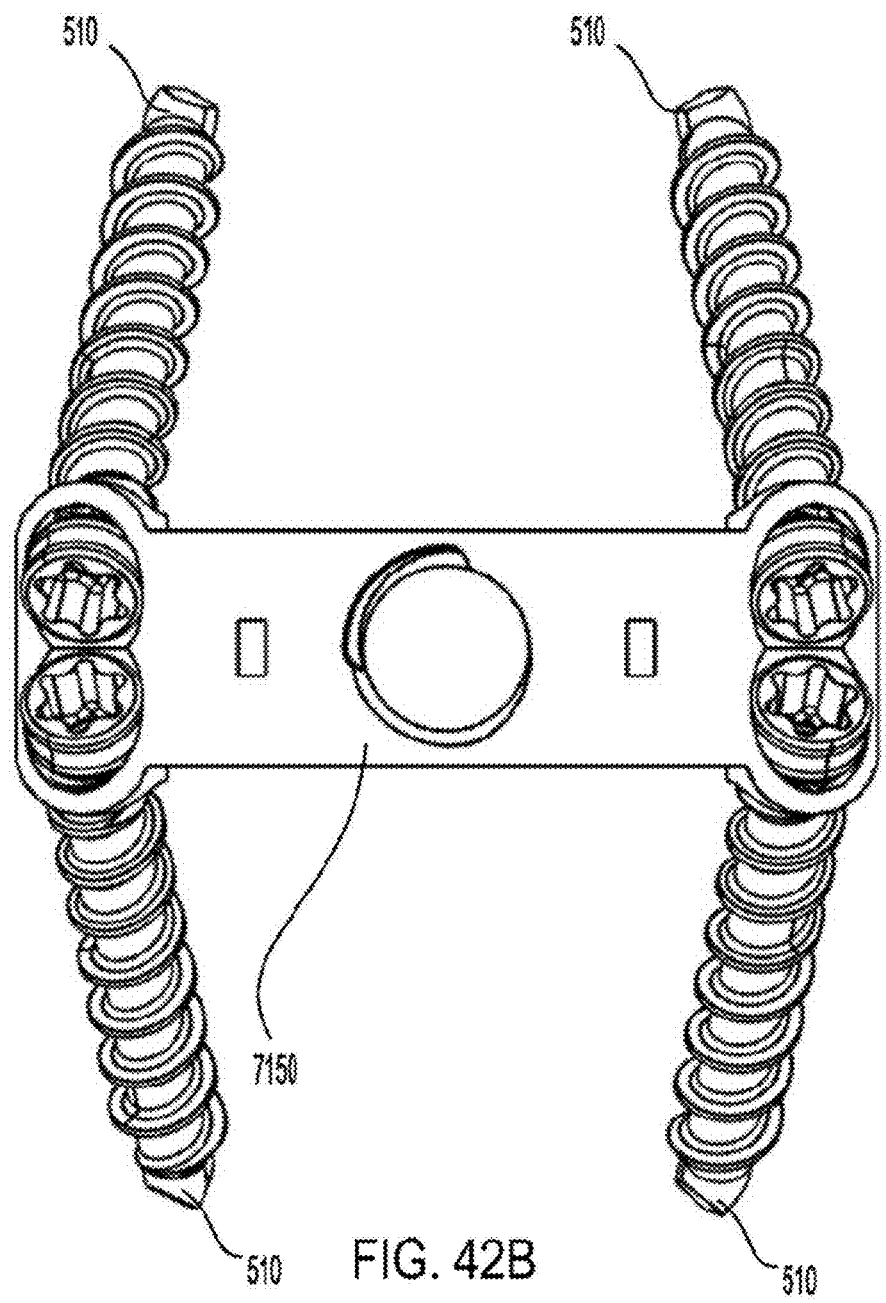
FIG. 42B is a front view of the screw guide endplate of FIG. 42A including anchoring screws installed in each of the corresponding apertures.
Figure 43A:
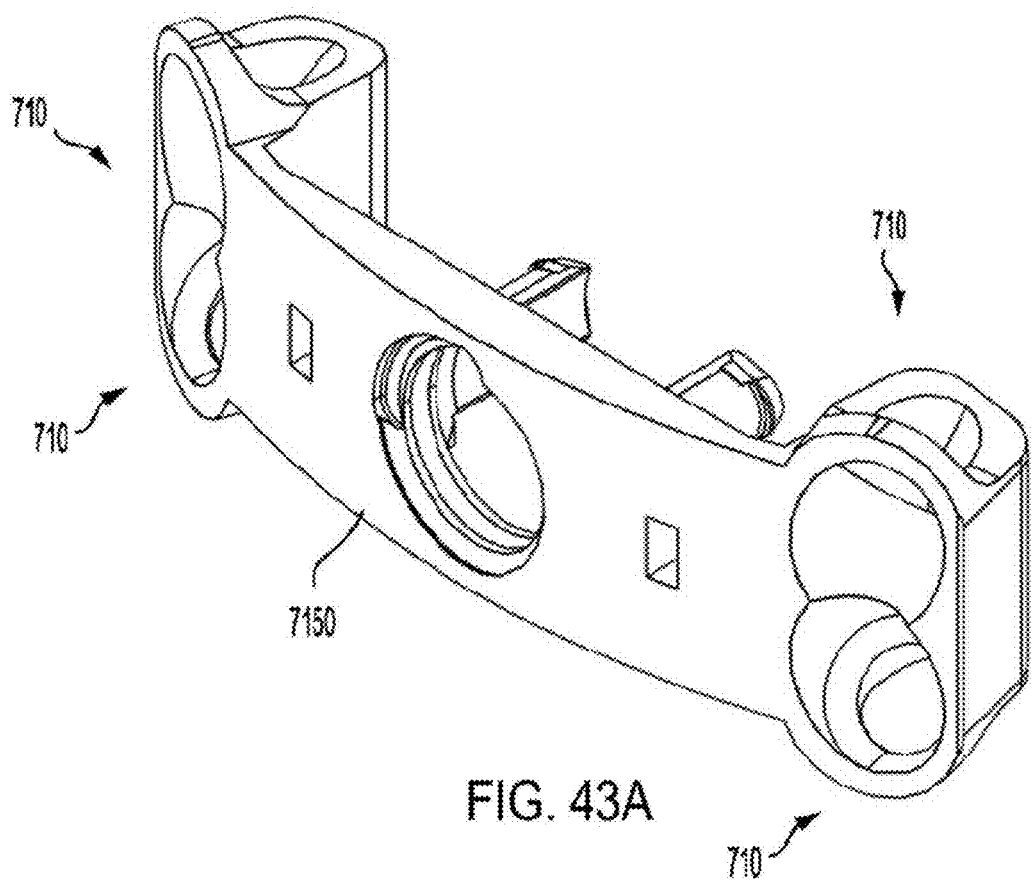
FIG. 43A and FIG. 43B are various perspective views of a screw guide endplate having at least one aperture configured to receive a anchoring screw therein.
Figure 43B:
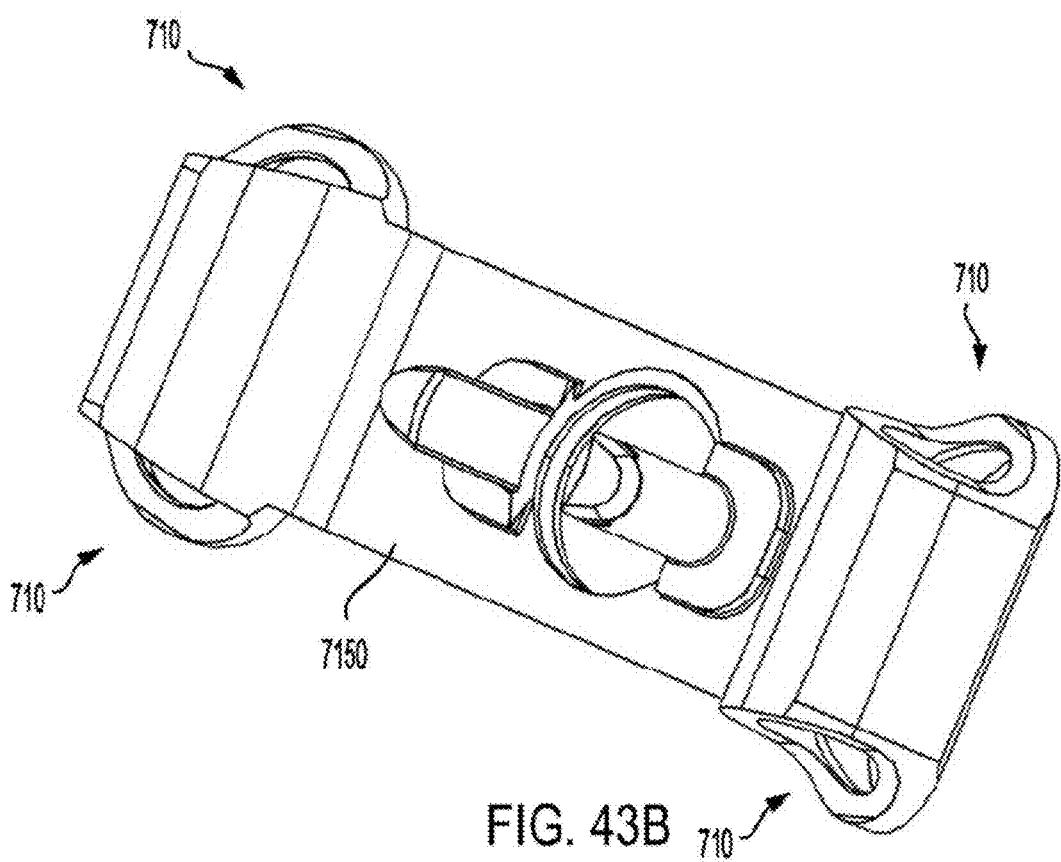

FIGS. 42A and 42B illustrate an exemplary screw guide endplate 7150 with and without corresponding anchoring screws 510, respectively. FIGS. 43A and 43B illustrate a front perspective view and a rear perspective view of an exemplary screw guide endplate 7150 having at least one aperture 710 configured to receive an anchoring screw 510 therein. In the illustrated embodiment, four apertures 710 are shown, although embodiments in accordance with the principles of this disclosure may have any number of apertures 710.

Figure 40:
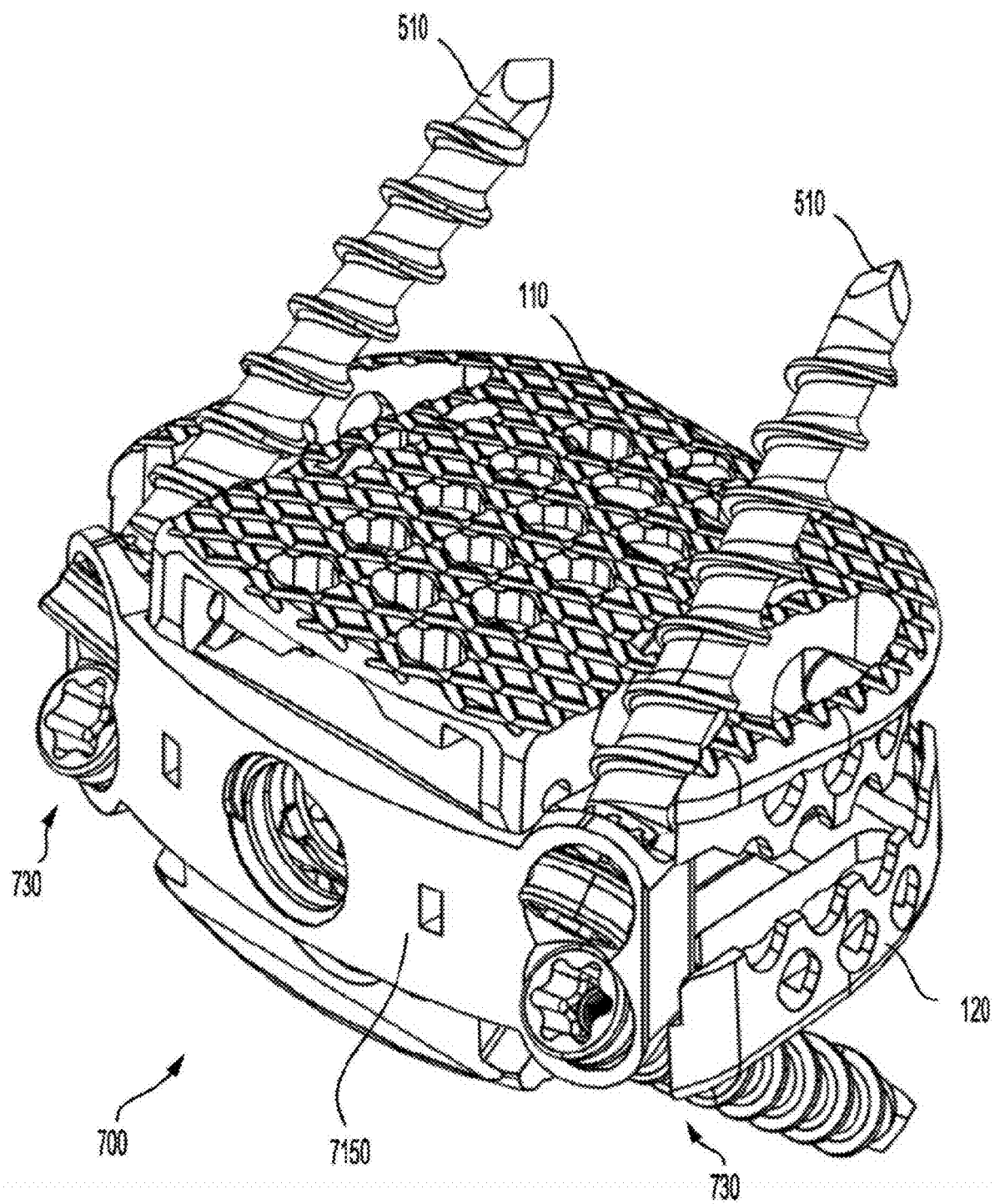
FIG. 40 is a perspective view of one embodiment of an expandable spinal implant including a screw guide endplate having at least one aperture configured to receive a anchoring screw therein.
Figure 41:
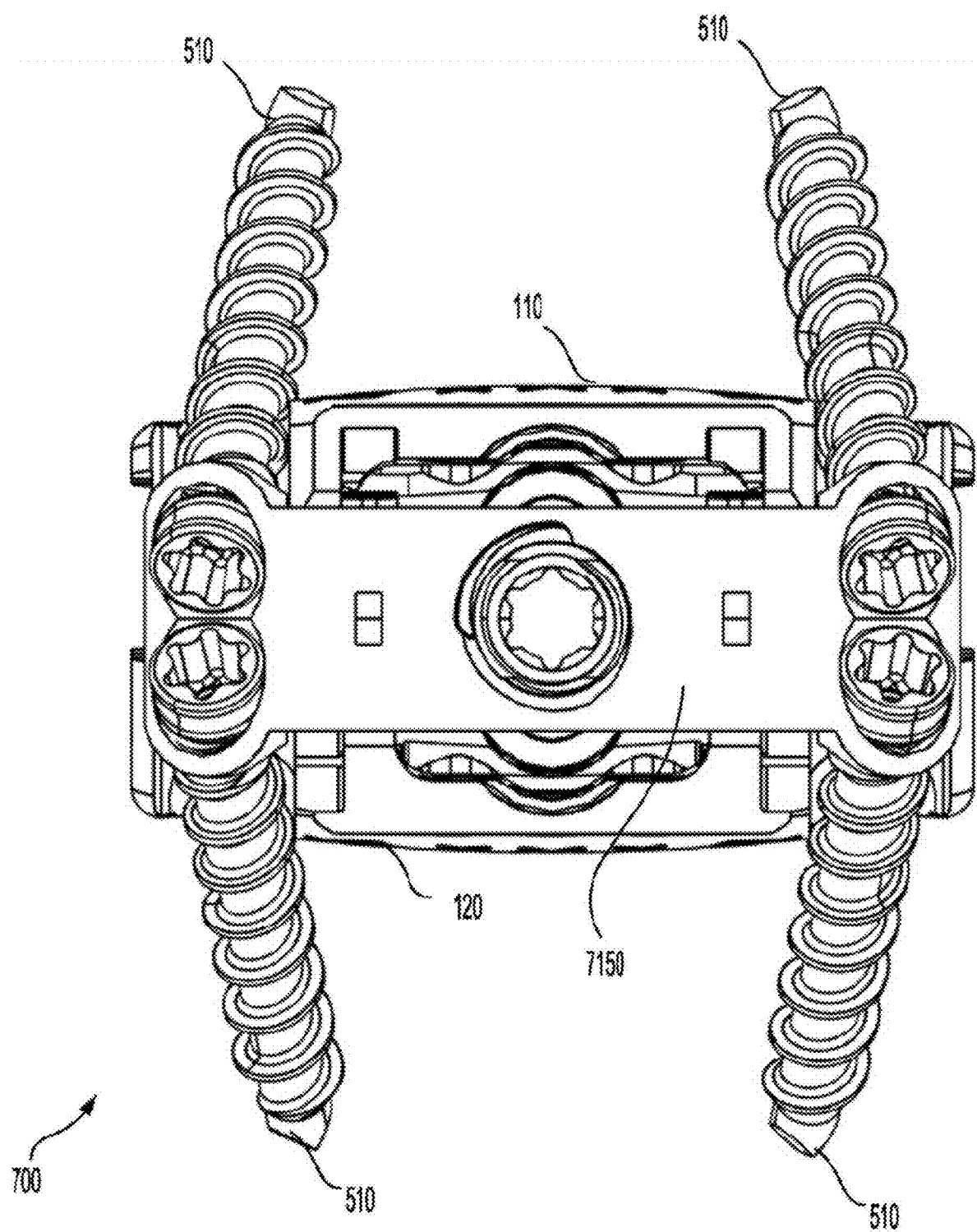
FIG. 41 is a front view of the embodiment of FIG. 40.

As illustrated, each aperture 710 may be configured to selectively receive a corresponding anchoring screw 510 therein. The outside entrance to each aperture 710 may define a guided path configured to orient a corresponding anchoring screw 510 in an inclined position extending away from a proximal side of a corresponding endplate 110 or 120. For example, screw guide endplate 7150 may include a total of four apertures 710, and the four apertures 710 may include two top most apertures 710 and two bottom most apertures 710. In the disclosed embodiment, the two top most apertures 710 may be configured to incline a corresponding anchoring screw 510 with respect to top endplate 110 that extends away from a proximal side of implant 700 towards a distal side of implant 700. Similarly, the two bottom most apertures 710 may be configured to incline a corresponding anchoring screw 510 with respect to bottom endplate 120 that extends from a proximal side of implant 700 towards a distal side of implant 700. Corresponding orientations are illustrated in FIGS. 40, 41, and 42B which show two top anchoring screws 510 oriented upward at an inclined angle with respect to top endplate 110 and two bottom anchoring screws 510 oriented downward at an inclined angle with respect to bottom endplate 120. Alternatively, the screw holes in the plate may be arranged and numbered in various alternative designs including, instead of two holes on top and bottom, presenting a single hole in the center or on one side or the other on top and bottom, or two holes on one of the top or bottom and one hole on the opposite side, top or bottom. These screw holes may further include protrusions, threads or other features to control, guide, and/or retain the screws in place or include features such as retaining clips, springs, or covers to retain the screws in place once inserted. The screw holes may be of various shapes including cylindrical, conical, or designed to receive a bulbous or spherical screw head.

Figure 44A:
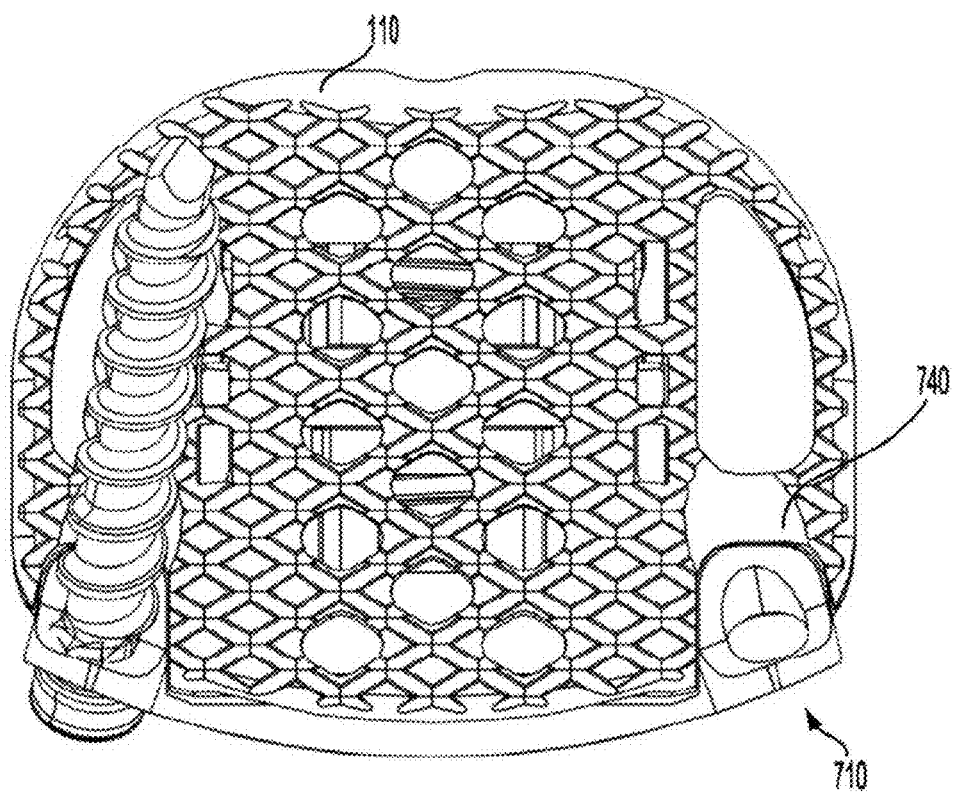
FIGS. 44A and 44B are top down views of a top endplate and a bottom endplate including at least one recessed portion configured to accommodate a anchoring screw.
Figure 44B:
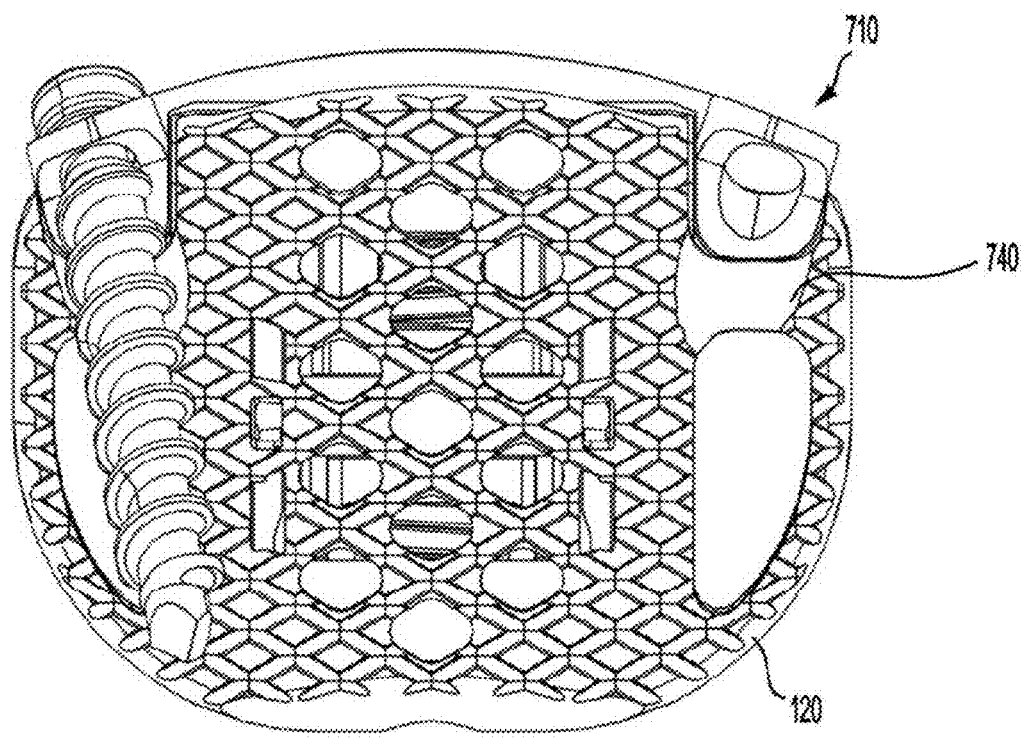

FIGS. 44A and 44B may illustrate a top endplate 110 and a bottom endplate 120, respectively, with an anchoring screw 510 in one corresponding aperture 710 and without an anchoring screw 510 in the other corresponding aperture 710 for ease of explanation. As illustrated, the top endplate 110 may include at least one anchoring screw 510 such that it projects through or across a corresponding recess 740 of the first endplate 110. Similarly, the bottom endplate 120 may include at least one anchoring screw 510 such that it projects through or across a corresponding recess 740 of the first endplate 110.

At least one advantage of the disclosed spinal implant 700 is that screw guide endplate 7150 and moving mechanism 250 may be configured such that the moving mechanism 250 can selectively adjust a spacing between the first and second endplates 110, 120 and adjust an angle of inclination between the first and second endplates while the at least one corresponding anchoring screw 510 is anchored within a corresponding vertebrae. For example, a surgeon may initially position spinal implant 700 between adjacent vertebrae of a patient and install at least one corresponding anchoring screw 510 in a first orientation projecting through or across a corresponding recess 740 of first endplate 110 and at least one corresponding anchoring screw 510 in a second orientation projecting through or across recess 740 of second endplate 120. Next, the surgeon may continue to adjust the spacing and/or angle of inclination between endplates 110, 120 until the endplates 110, 120 are in the desired position. This is possible, at least partly, because the relative location of the screw guide endplate 7150 remains fixed due to the anchored anchoring screws 510 and the first and second endplates can freely expand/contract and/or incline/decline via moving mechanism 250 while anchoring screws 510 extend through or across recess 740 (which has a geometry such that anchored anchoring screws 510 do not interfere with the movement of endplates 110, 120). For example, the endplates 110, 120 may freely move while anchoring screws 510 remain anchored in place in the corresponding vertebrae.

Figure 45:
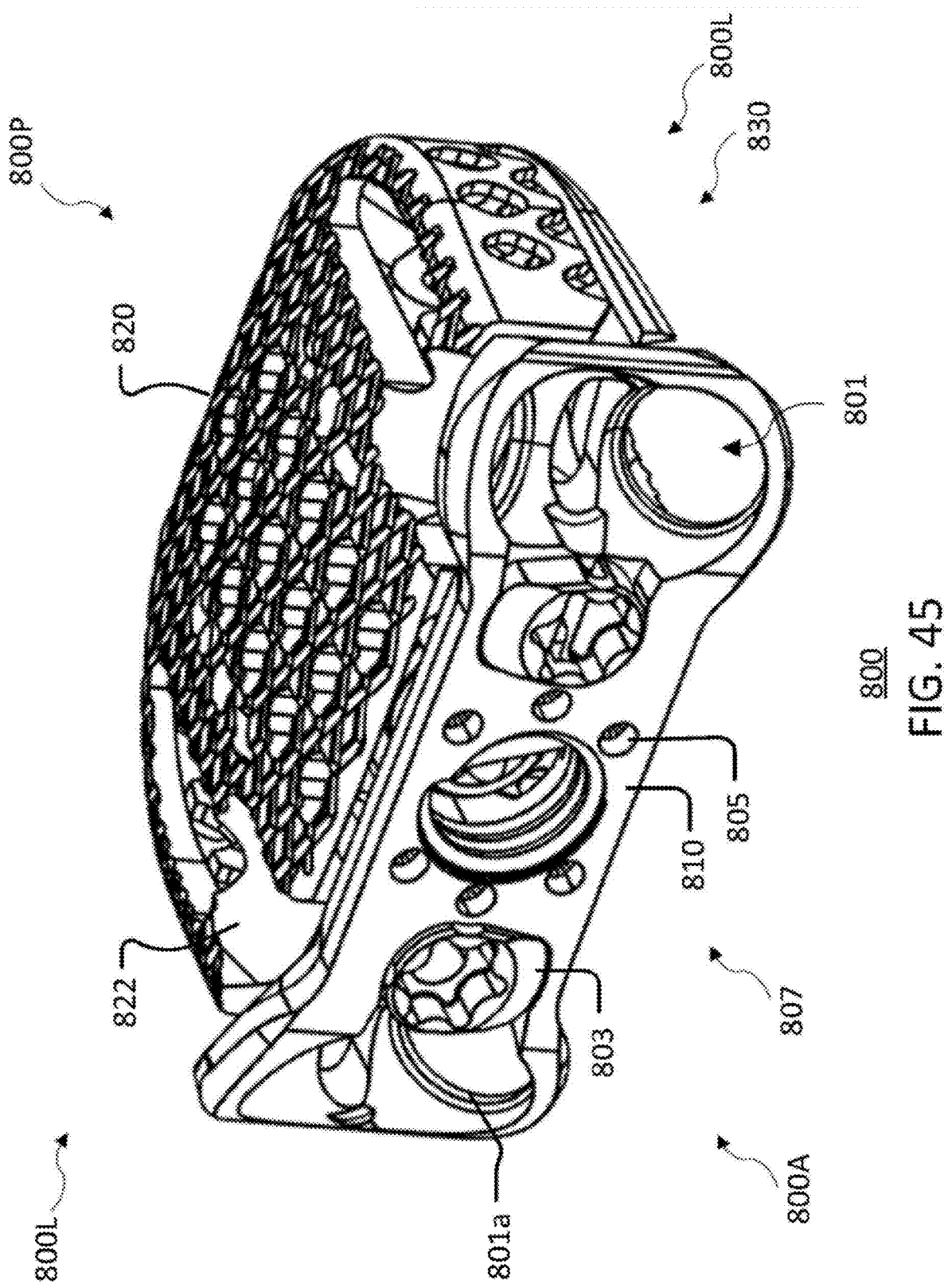
FIG. 45 is a perspective view of an additional embodiment of an expandable spinal implant including an anterior endplate in accordance with the principles of the present disclosure.
Figure 46:
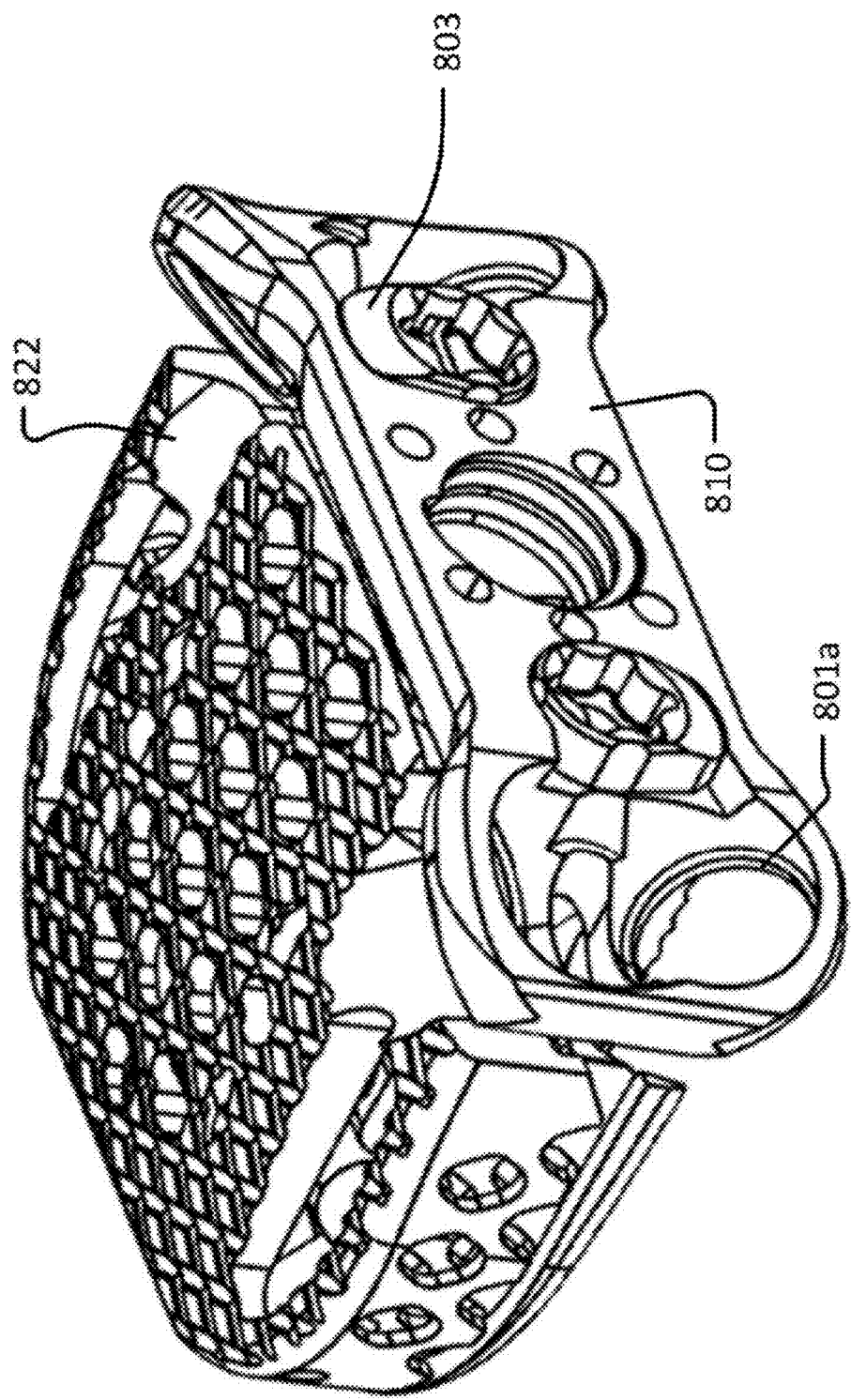
FIG. 46 is an alternate perspective view of the embodiment of FIG. 45 in accordance with the principles of the present disclosure.
Figure 47:
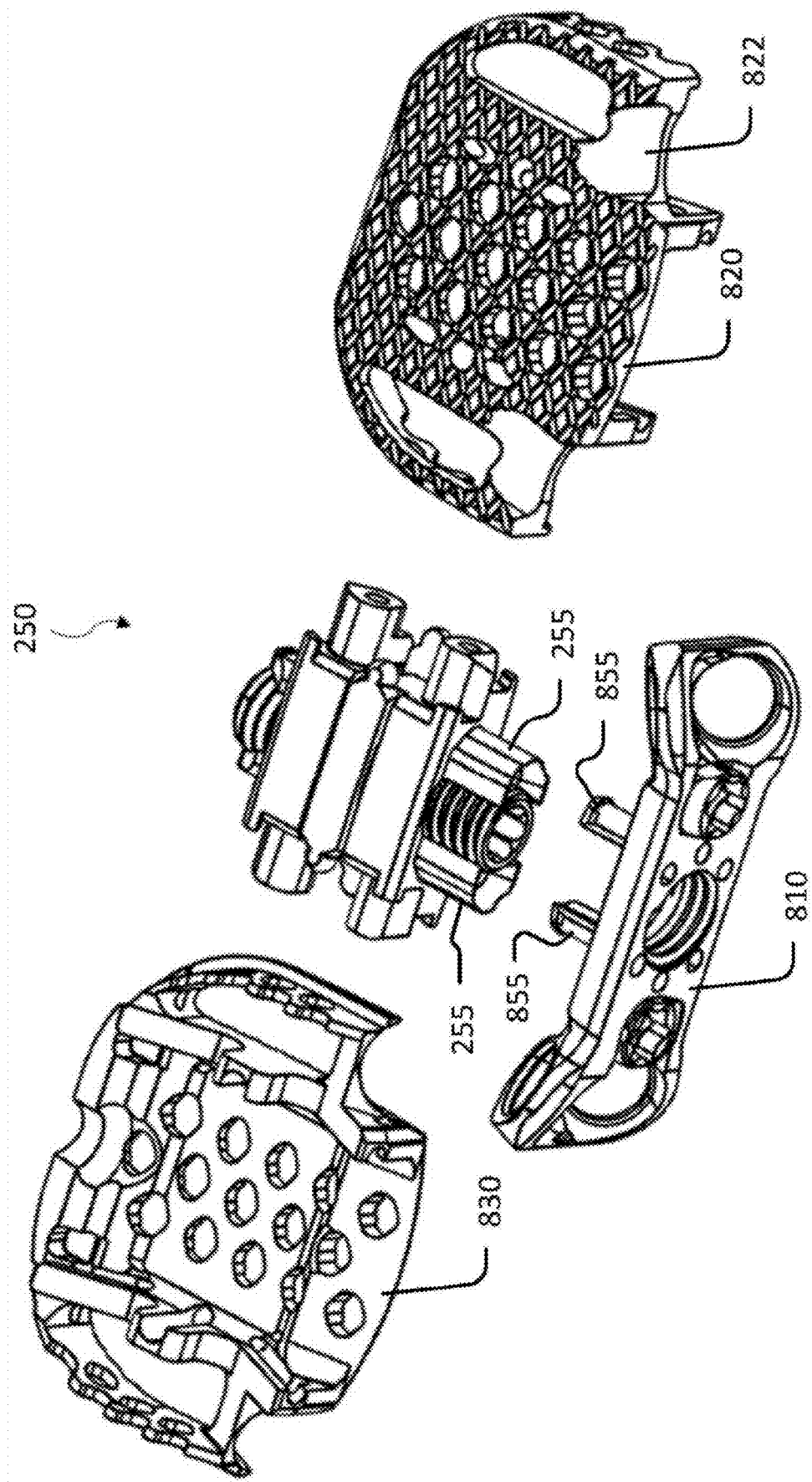
FIG. 47 is an exploded parts view diagram of the embodiment of FIG. 45 in accordance with the principles of the present disclosure.

FIGS. 45 and 46 are perspective views of an additional embodiment of an expandable spinal implant 800 including an anterior endplate 810 in accordance with the principles of the present disclosure. In some embodiments, anterior endplate 810 may be referred to as a third endplate, or may be referred to as a medial, lateral, or posterior endplate depending upon orientation or approach employed and the specific configuration and shape of the implant and the location, side or end to which the third plate is affixed or located. FIG. 47 is an exploded parts view diagram of the embodiment of FIG. 45 in accordance with the principles of the present disclosure. Expandable spinal implant 800 may include the same, substantially the same, and/or similar features as the various above disclosed embodiments. For example, moving mechanism 250 may operate in the same, substantially the same, and/or similar manner as explained above. However, implant 800 may include an anterior endplate 810, a top endplate 820 (superior endplate), and a bottom endplate 830 (inferior endplate) having different characteristics as will be explained in further detail below.

Implant 800 may include an anterior side 800a, a posterior side 800p and two opposing lateral sides 8001, for example. Additionally, the outside contours of implant 800 may include a top endplate 820 (superior endplate), bottom endplate 830 (inferior endplate) and an anterior endplate 810 (front endplate), for example. In various embodiments, the top endplate 820 and bottom endplate 830 may collectively define the posterior side 800p (rear side) of implant 800. Anterior endplate 810 may include a plurality of circular bone screw apertures 801, for example. In the example embodiment, four circular bone screw apertures 801 are disclosed although in other embodiments the number of bone screw apertures 801 may be more or less. For example, in some embodiments there may be an additional 5$^{th}$ and 6$^{th}$ bone screw aperture in the medial location of anterior endplate 810. In other embodiments, there may be a total of two bone screw apertures 801 including a left bone screw aperture 801 diagonally projecting over the top endplate 820 and a right bone screw aperture 801 diagonally projecting over the bottom endplate 820.

In various embodiments, each bone screw aperture 801 may include at least one circular ring portion 801a that facilitates seating of a bone screw 511 (see FIG. 52) and/or facilitates the alignment of a drill in a coaxial relationship, e.g., surgical tool 500 as disclosed above. For example, the ring portion 801a may define a bearing surface for seating an inclined surface 512 of an outdented rail 513 of a head portion of a bone screw 511, for example. In various embodiments, the ring portion 801*a* may have a size and shape generally corresponding to a size and shape of the inclined surface 512 and define an interior diameter that is less than a cross sectional diameter of the outdented rail 513. Additionally, in various embodiments, the ring portion 801*a* of bone screw apertures 801 may allow about +/−10° and in some embodiments about +/−5° of freedom to the corresponding bone screw 511 due to the inclined surface 512, for example.

Anterior endplate 810 may include at least one bone screw lock 803 for preventing bone screws 511 from backing out. For example, bone screw lock 803 may be a rotatable lock that may rotate about 90° between an open position and a closed position to prevent bone screws 511 from backing out, for example. In various embodiments, anterior endplate 810 may include at least one attachment point 805 for connecting implant 800 with a surgical tool. In the disclosed embodiment, a plurality of attachment points 805 are distributed around screw guide aperture 807. In the disclosed embodiment, six attachment points 805 are radially distributed around screw guide aperture 807 although other embodiments may have more or less, e.g. 2, 3, 4, 5, 7 or 8.

As understood best with reference to FIG. 47, anterior endplate 810, top endplate 820, and bottom endplate 830 may be operably coupled to moving mechanism 250. For example, moving mechanism 250 serves as a central attachment location for each of the endplates 810, 820, 830 and each of the endplates 810, 820, 830 may interact independently with moving mechanism 250, for example. In the disclosed embodiment, anterior endplate 810 may be operably coupled to moving mechanism 250 by inserting posts 855 into a corresponding post retaining aperture 255 having a size and shape configured to securely couple the two together. In various embodiments, posts 855 may extend from an inside surface of anterior endplate 810 in a direction towards the posterior side 800*p* of implant 800 and towards moving mechanism 250. In this way, anterior endplate 810 is independently secured to moving mechanism 250 from top endplate 820 and bottom endplate 830, for example.

Figure 48B:
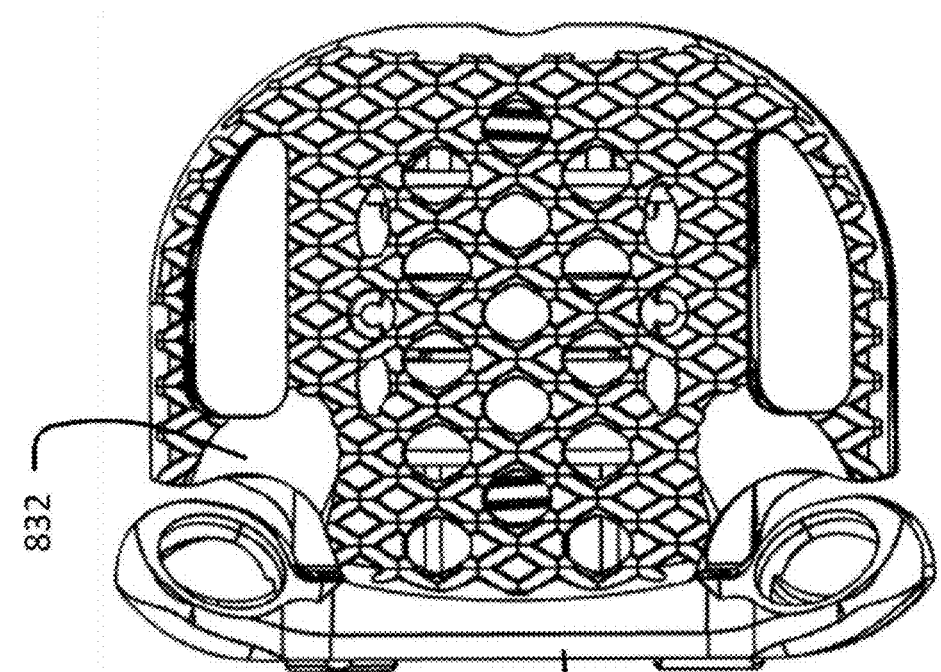
FIG. 48B is a second view of a bottom endplate of the embodiment of FIG. 45 in accordance with the principles of the present disclosure.
Figure 48A:
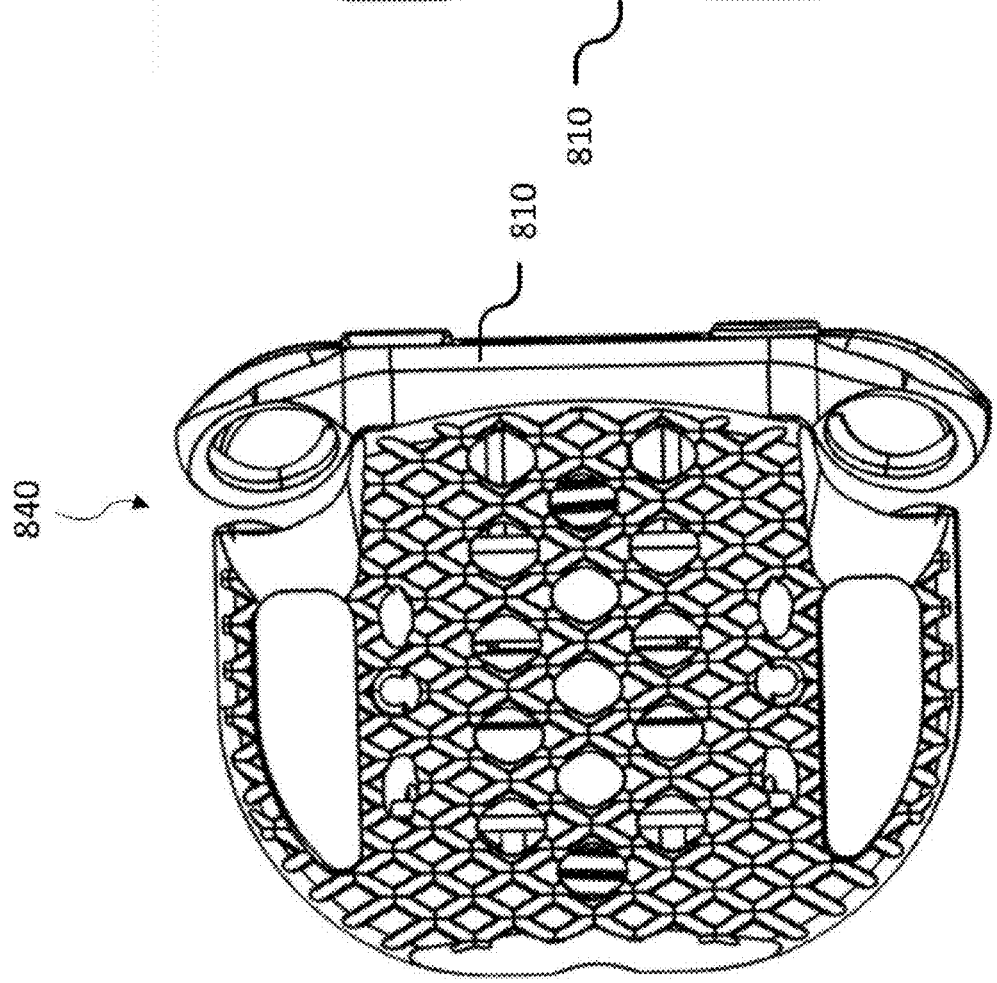
FIG. 48A is a first view of a bottom endplate of the embodiment of FIG. 45 in accordance with the principles of the present disclosure.
Figure 48C:
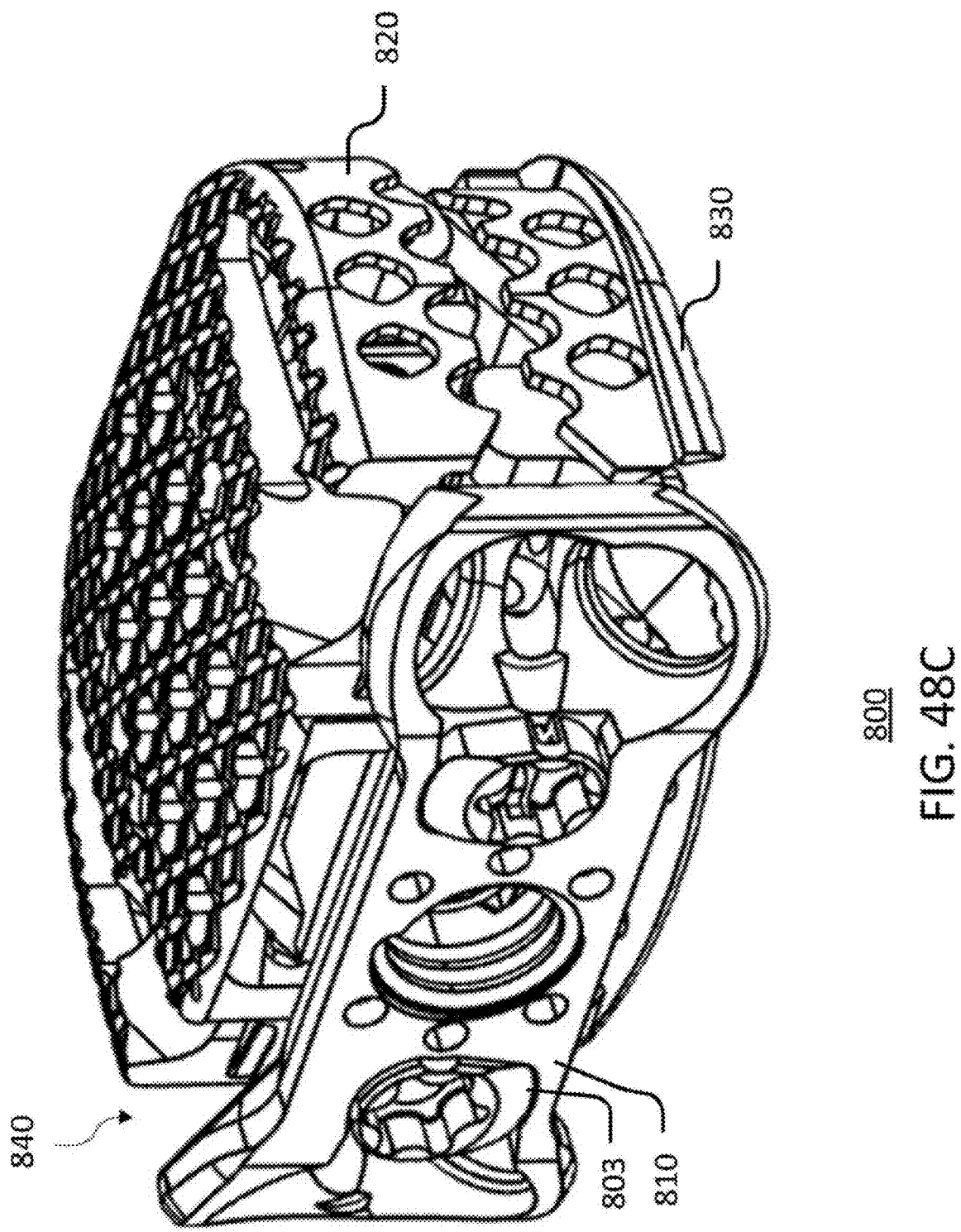
FIG. 48C is a perspective view of the embodiment of FIG. 45 in the expanded position in accordance with the principles of the present disclosure.

FIGS. 48A and 48B are top down views of an example bottom endplate 830 of spinal implant 800. In various embodiments, bottom endplate 830 and top endplate 820 may include the same, substantially the same, and/or similar characteristics. In the example illustration, bottom endplate 830 may include a bone screw relief 832 for each corresponding bone screw aperture 801. For example, bone screw relief 832 comprises an arcuate channel and/or conical channel defining a portion of the outside surface of endplate 830. In some embodiments, the number of bone screw reliefs 832 may be more or less. For example, a single bone screw relief 832 or three bone screw reliefs 832. In some embodiments, the top endplate 820 may include a first bone screw relief 822 and the bottom endplate 830 may include a second bone screw relief 832 that project oppositely from one another in a diametrically opposed direction. Additionally, in the top down views of FIGS. 48A and 48B it is shown that a gap 840 (void space) exists between anterior endplate 810 and bottom endplate 830. The gap 840 between anterior endplate 810 and endplates 820, 830 may be present in both the expanded and contracted position. For example, as shown in FIG. 48C implant 800 is in an expanded position and a gap 840 is present between anterior endplate 810, top endplate 820, and bottom endplate 830. For example still, gap 840 may define a continuous discontinuity between the posterior side of the anterior endplate 810 and the anterior side of the top endplate 820 and bottom endplate 830.

Figure 49:
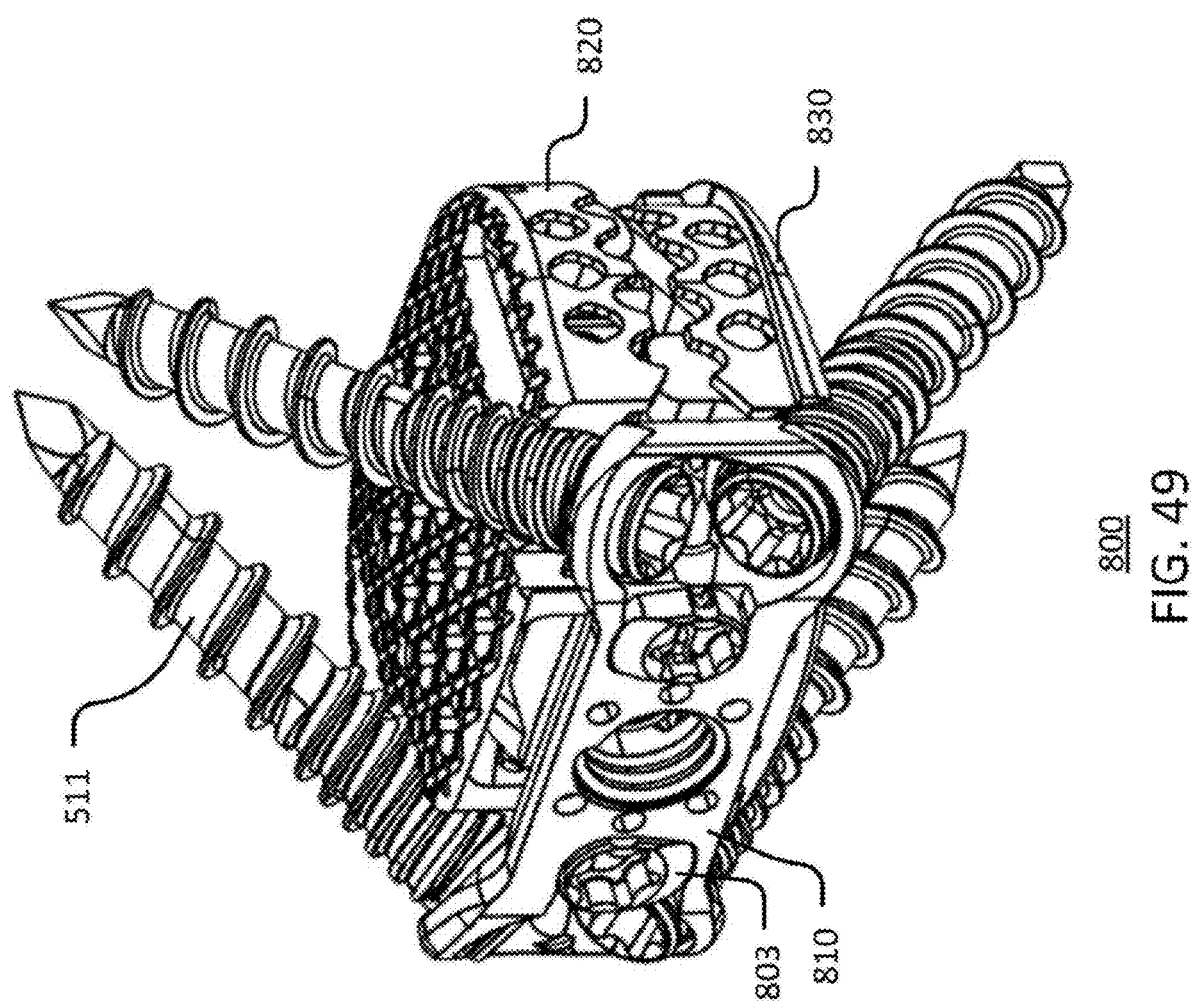
FIG. 49 is a perspective view of the embodiment of FIG. 45 including a plurality of bone screws in accordance with the principles of the present disclosure.

FIG. 49 is a perspective view of spinal implant 800 in an expanded configuration including a plurality of bone screws 511 extending over corresponding bone screw apertures 801. In the example embodiment, when implant 800 is in the fully expanded position a trajectory of the bone screws 511 is unaffected by the top endplate 820 and/or bottom endplate 830. For example, the bone screw reliefs 822, 832 allow the implant 800 to fully expand without interfering with bone screws 511. For example still, bone screws 511 may be secured to a boney surface and only anchor implant 800 via bone screw apertures 801 of anterior endplate 810.

Figure 50:
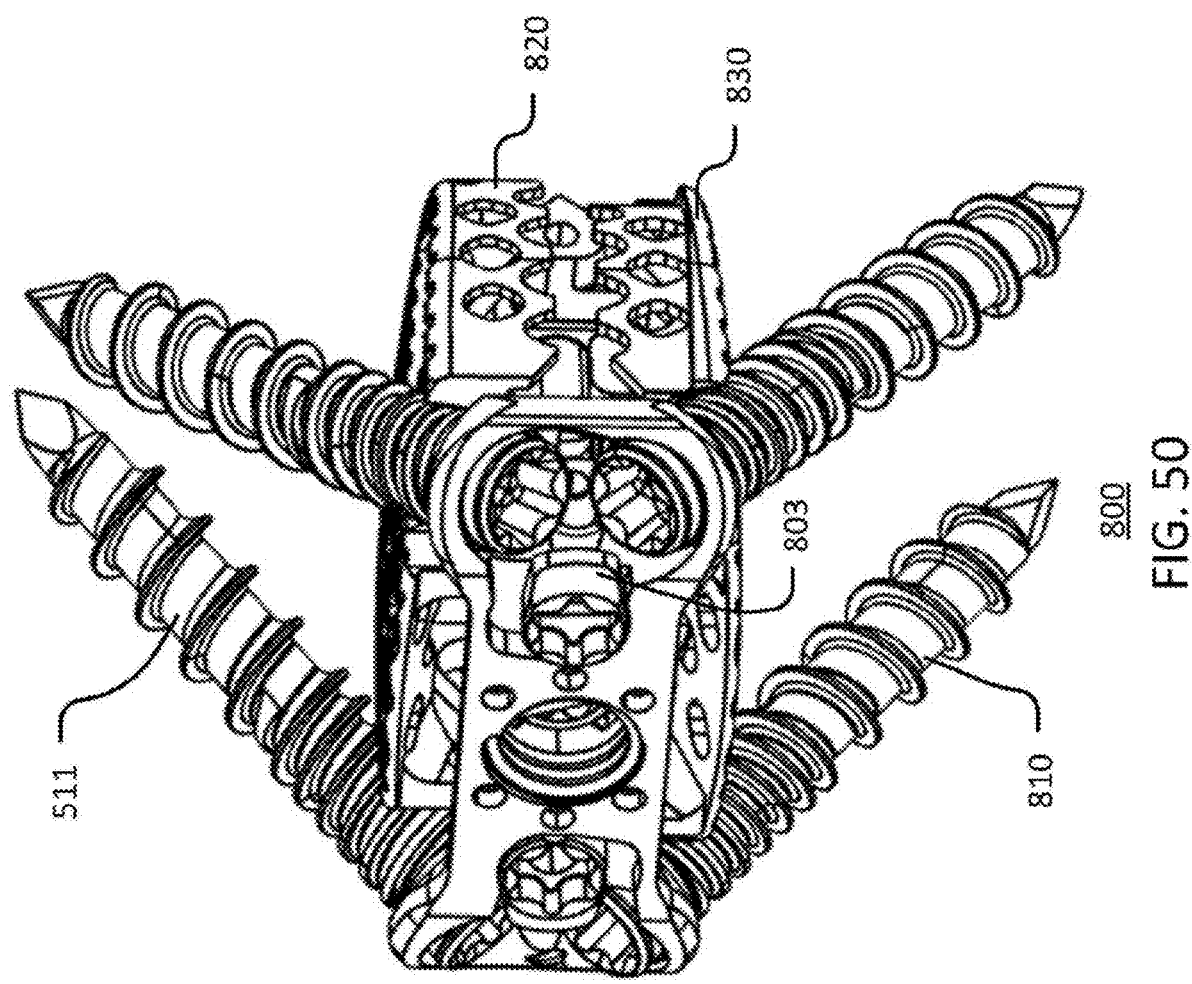
FIG. 50 is an alternate perspective view of the embodiment of FIG. 45 including a plurality of bone screws in accordance with the principles of the present disclosure.
Figure 51:
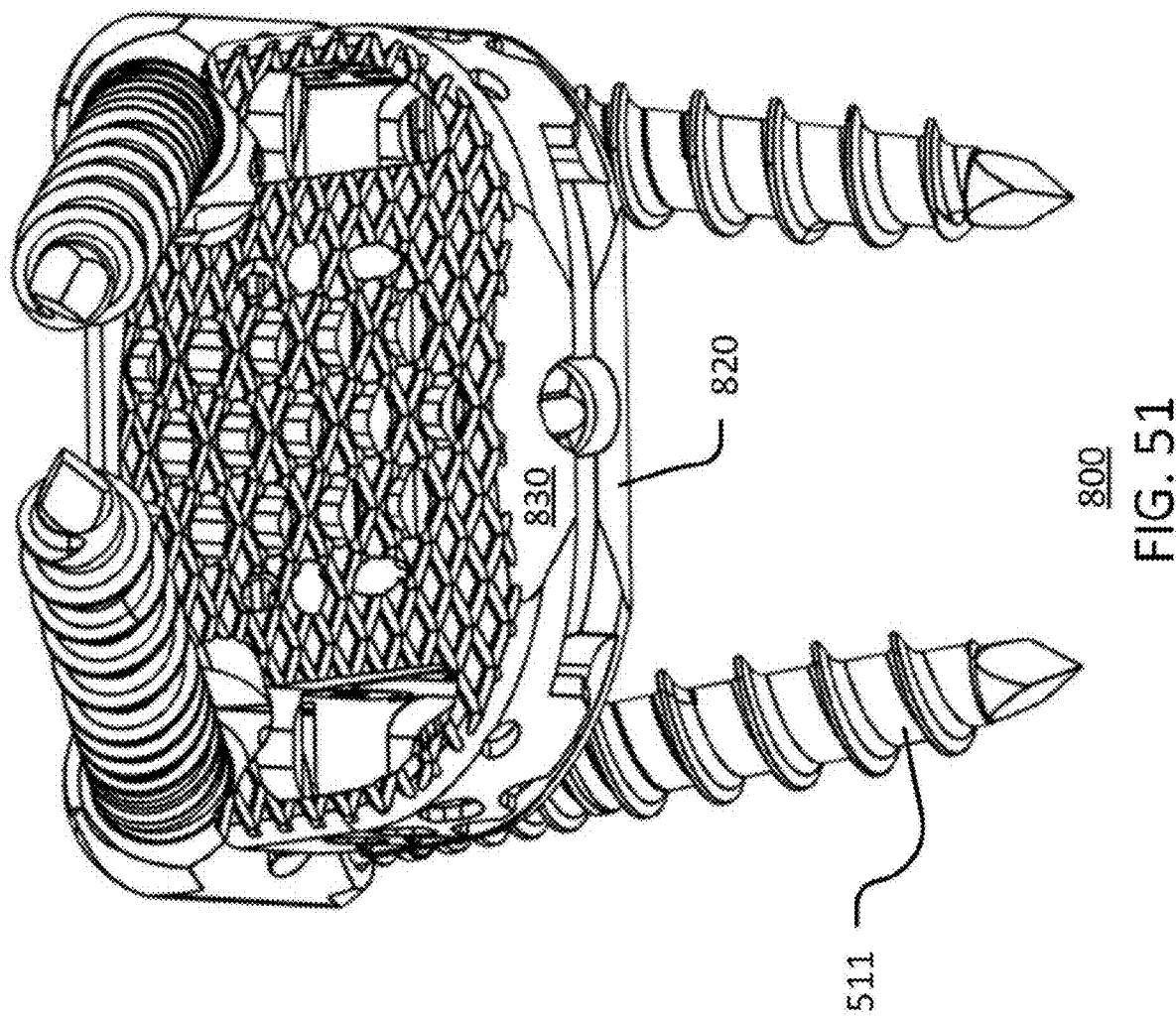
FIG. 51 is a rear perspective view of the embodiment of FIG. 45 including a plurality of bone screws in accordance with the principles of the present disclosure.

FIG. 50 is an alternate perspective view of the embodiment of FIG. 45 including a plurality of bone screws 511 that are prevented and/or suppressed from backing out due to bone screw locks 803. Bone screw locks 803 may be toggled between an unlocked position shown in FIG. 49 to a locked position shown in FIG. 50 by rotating the bone screw lock 803 about 90°. In operation, an end user such as a surgeon may place bone screws 511 through bone screw aperture 801 after the implant 800 is expanded to the desired height and inclination. Thereafter, the surgeon may move bone screw lock 803 from the unlocked position to the locked position to prevent bone screws 511 from backing out. In various embodiments, even after the bone screw lock 803 is engaged in the locked position the surgeon may drive bone screws 511. FIG. 51 is a rear perspective view of implant 800 including a plurality of bone screws 511.

Figure 52:
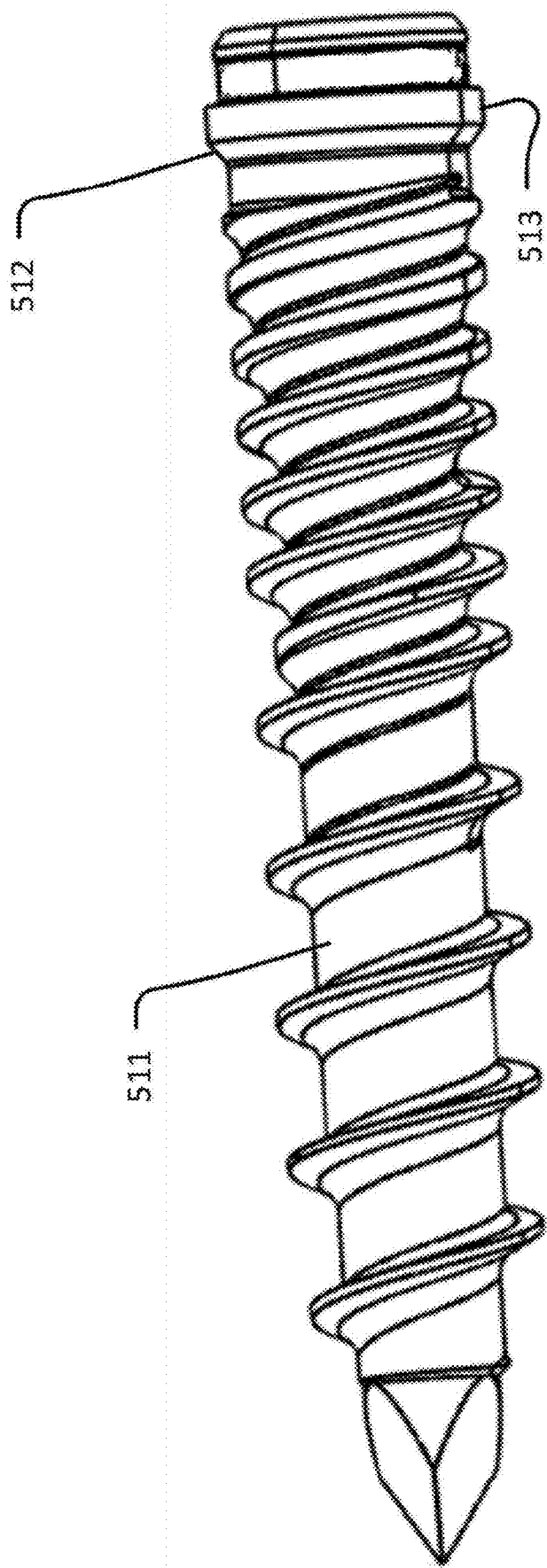
FIG. 52 is a side view of an example bone screw.

FIG. 52 is an example side view of a bone screw 511. As illustrated in the embodiment of FIG. 52, bone screw 511 may include an inclined surface 512 extending around the circumference of bone screw 511 and terminating into a ring portion 513. In various embodiments, the ring portion 513 may have a size and shape generally corresponding to a size and shape of circular ring portions 801*a* of bone screw aperture 801, for example. Additionally, in various embodiments the cooperation between the circular ring portions 801*a*, inclined surface 512 and ring portion 513 may allow about +/−5° of freedom to the corresponding bone screw 511, for example.

FIG. 53 is a reference diagram illustrating various cardinal directions and planes with respect to a patient that various spinal implants disclosed herein may operate, adjust, and/or move along in accordance with the principles of the present disclosure.

Additional Plate/Expandable Plate Embodiments

Referring generally to FIGS. 54-69 various plates, including expandable plate embodiments for coupling to various spinal implants are disclosed. FIGS. 54-61 illustrate a first expandable plate 1500 embodiment; FIGS. 62-67 illustrate a second expandable plate 1600 embodiment, and FIGS. 68-73 illustrate a third expandable plate 1700 embodiment. The various expandable plates 1500, 1600, 1700 may have the same, similar, and/or substantially the same components and functionality unless the context clearly indicates otherwise. For example, the various expandable plates 1500, 1600, and 1700 may each be designed for connecting and/or coupling to the various spinal implants disclosed herein, and may be used in conjunction with anterior endplate 810, for example. However, the principles of the disclosed expandable plates 1500, 1600, 1700 are not necessarily limited to the specific implants disclosed herein and can, of course, be coupled and/or connected to other implants in the same, similar, and/or substantially the same manner.

Figure 54:
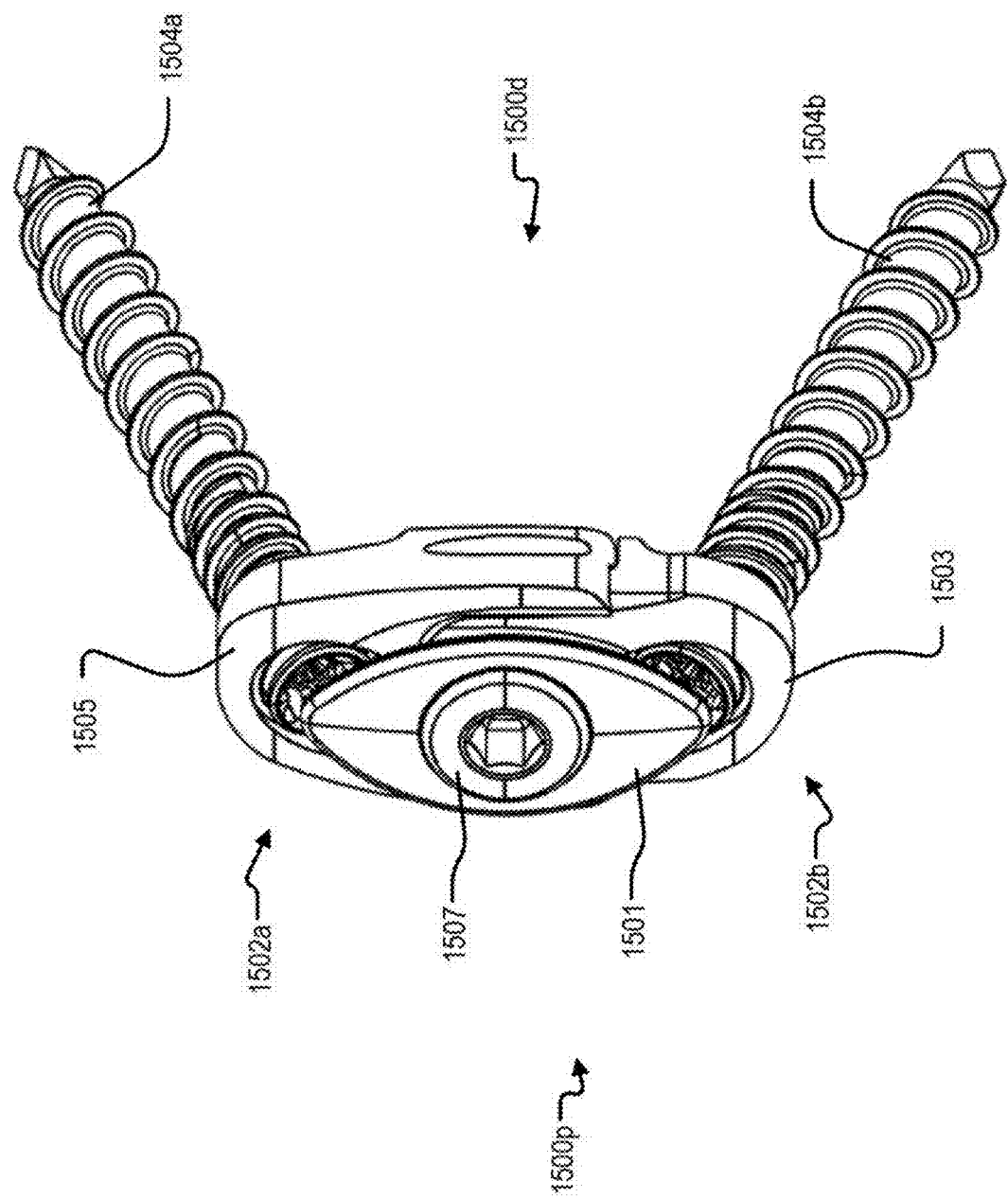
FIG. 54 is a perspective view of a first expandable plate embodiment for coupling to disclosed spinal implants.
Figure 55:
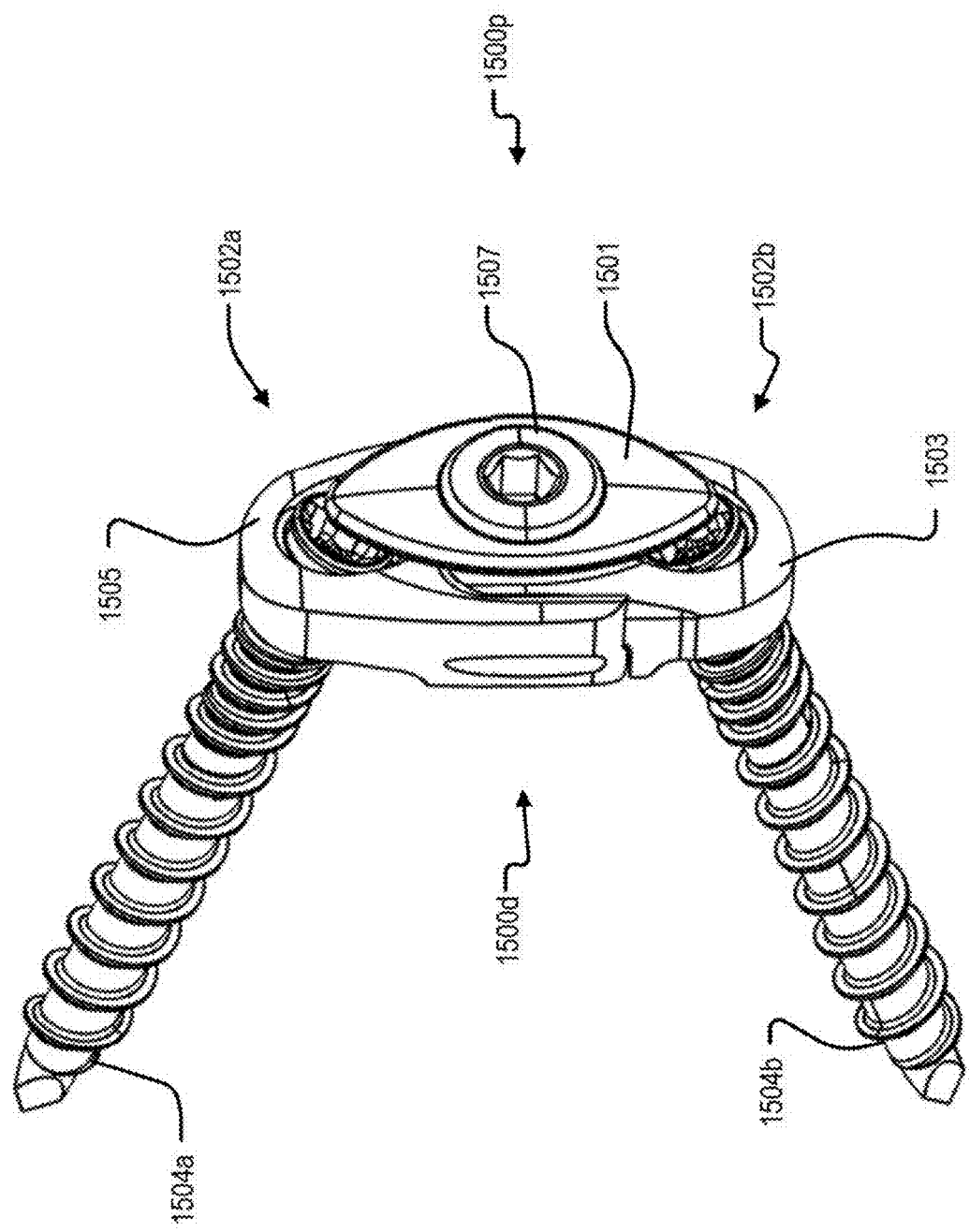
FIG. 55 is an alternate perspective view of a first expandable plate embodiment for coupling to disclosed spinal implants.

FIGS. 54-55 are various perspective views of a first expandable plate 1500 embodiment for coupling to disclosed spinal implants. Expandable plate 1500 may include a superior portion 1505 (may also be referred to as superior plate) and an inferior portion 1503 (may also be referred to as an inferior plate) that are expandable and contractible relative to one another, for example. Superior portion 1505 may include a first bone screw aperture 1502a for supporting a first bone screw 1504a in a target trajectory and inferior portion 1503 may include a second bone screw aperture 1502b for supporting a second bone screw 1504b in a target trajectory, for example. Expandable plate 1500 may include an end cap 1501 that is rotatable between a locked position where the first and second bone screw apertures 1502a, 1502b are covered such that the first and second bone screws 1504a, 1504b are prevented and/or suppressed from backing out. Expandable plate 1500 may include a set screw 1507 for securing the superior portion 1505 and inferior portion 1503 at a particular positon relative to one another. For example, the superior portion 1505 and inferior portion 1503 are expandable in a vertical direction away from one another and set screw 1507 may lock the superior portion 1505 and inferior portion 1503 at any one of the various expanded positions.

Figure 56:
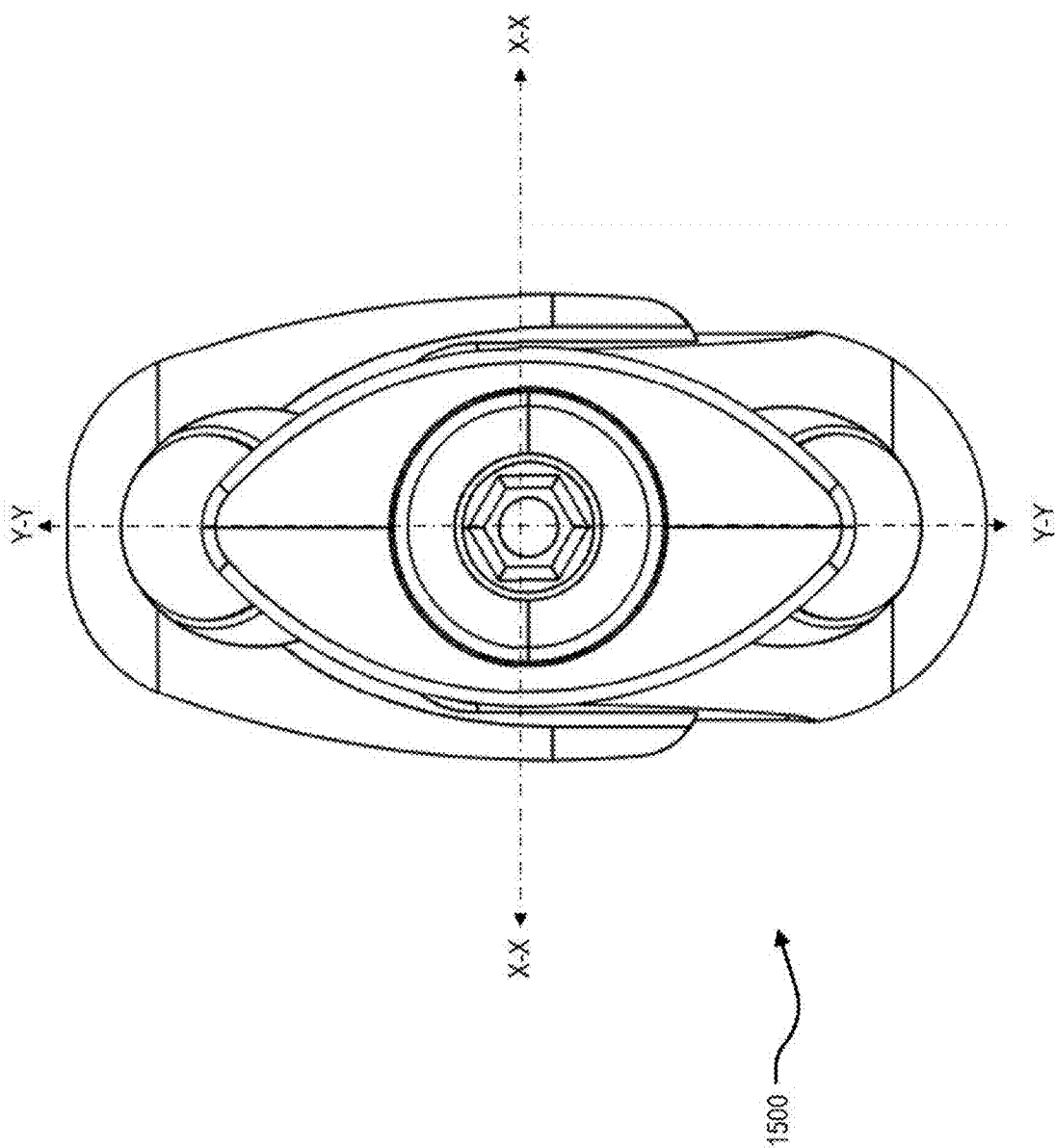
FIG. 56 is a front view of a first expandable plate embodiment for coupling to disclosed spinal implants.

FIG. 56 is a front view of a first expandable plate 1500 showing various axes and reference directions. Expandable plate 1500 may extend in a lengthwise direction along axis Y-Y (may also be referred to as the vertical direction depending on orientation), for example. In various embodiments, expandable plate 1500 may be roughly considered symmetrical on either side of axis Y-Y and/or at least because bone screw apertures 1502a and 1502b are vertically aligned. Additionally, expandable plate 1500 may extend in a widthwise direction along axis X-X (may also be referred to as a lateral direction depending on orientation), for example. In various embodiments, a thickness of expandable plate 1500 may extend in a proximal-to-distal direction. For example, as shown in FIG. 54, a thickness may be measured in a proximal-to-distal direction from proximal side 1500p to distal side 1500d.

Figure 57:
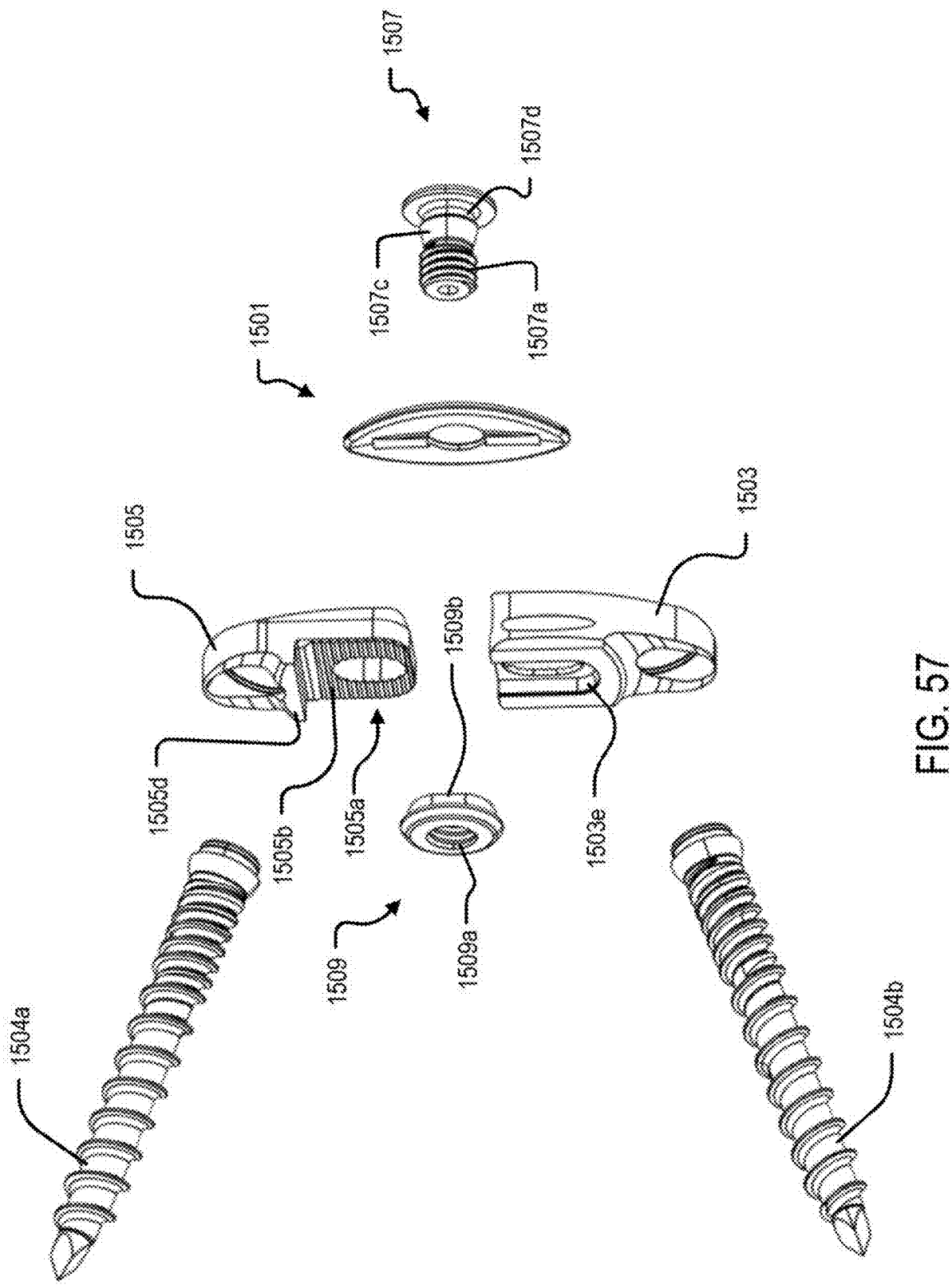
FIG. 57 is a perspective exploded parts view of a first expandable plate embodiment for coupling to disclosed spinal implants.
Figure 58:
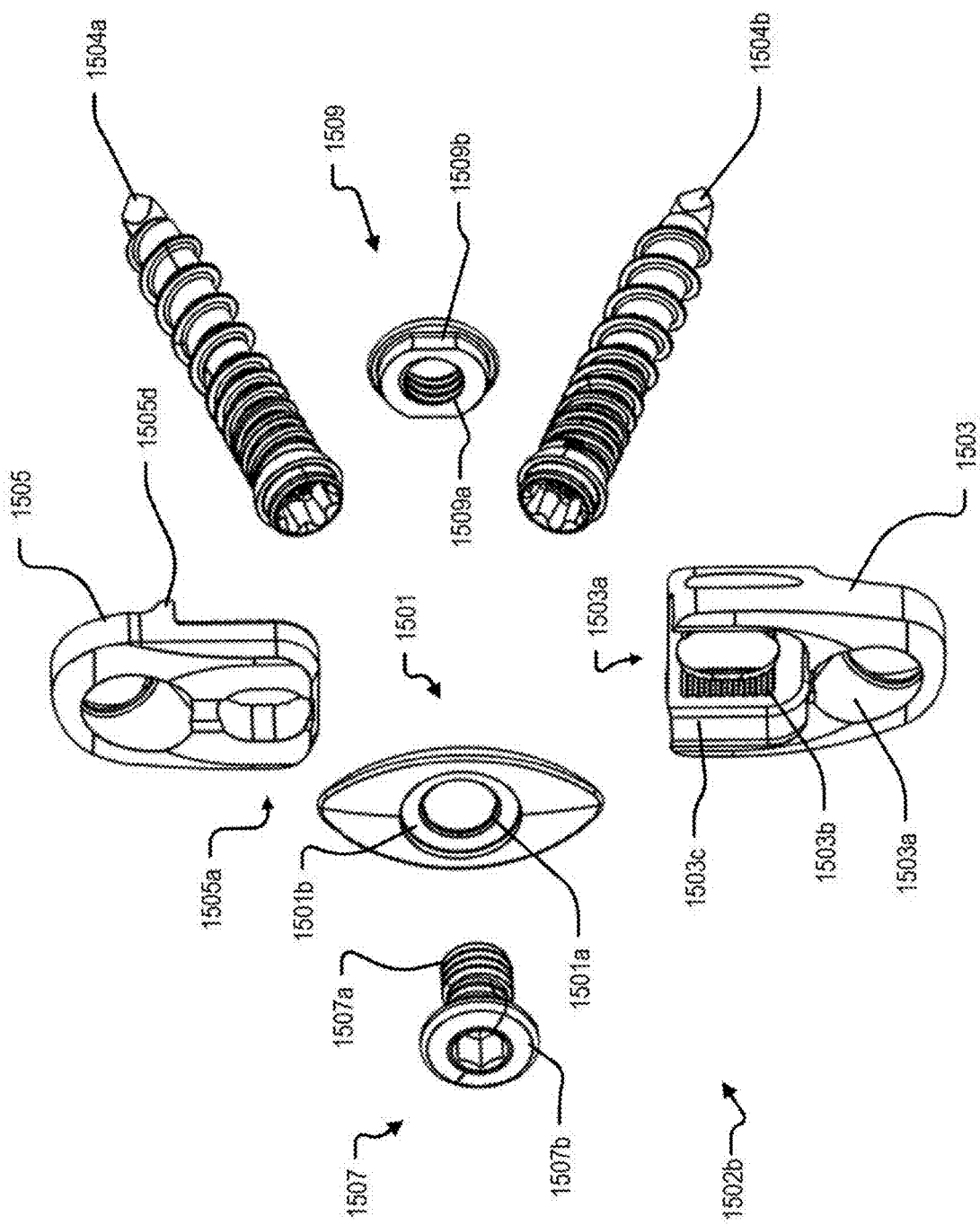
FIG. 58 is an alternate perspective exploded parts view of a first expandable plate embodiment for coupling to disclosed spinal implants.
Figure 59:
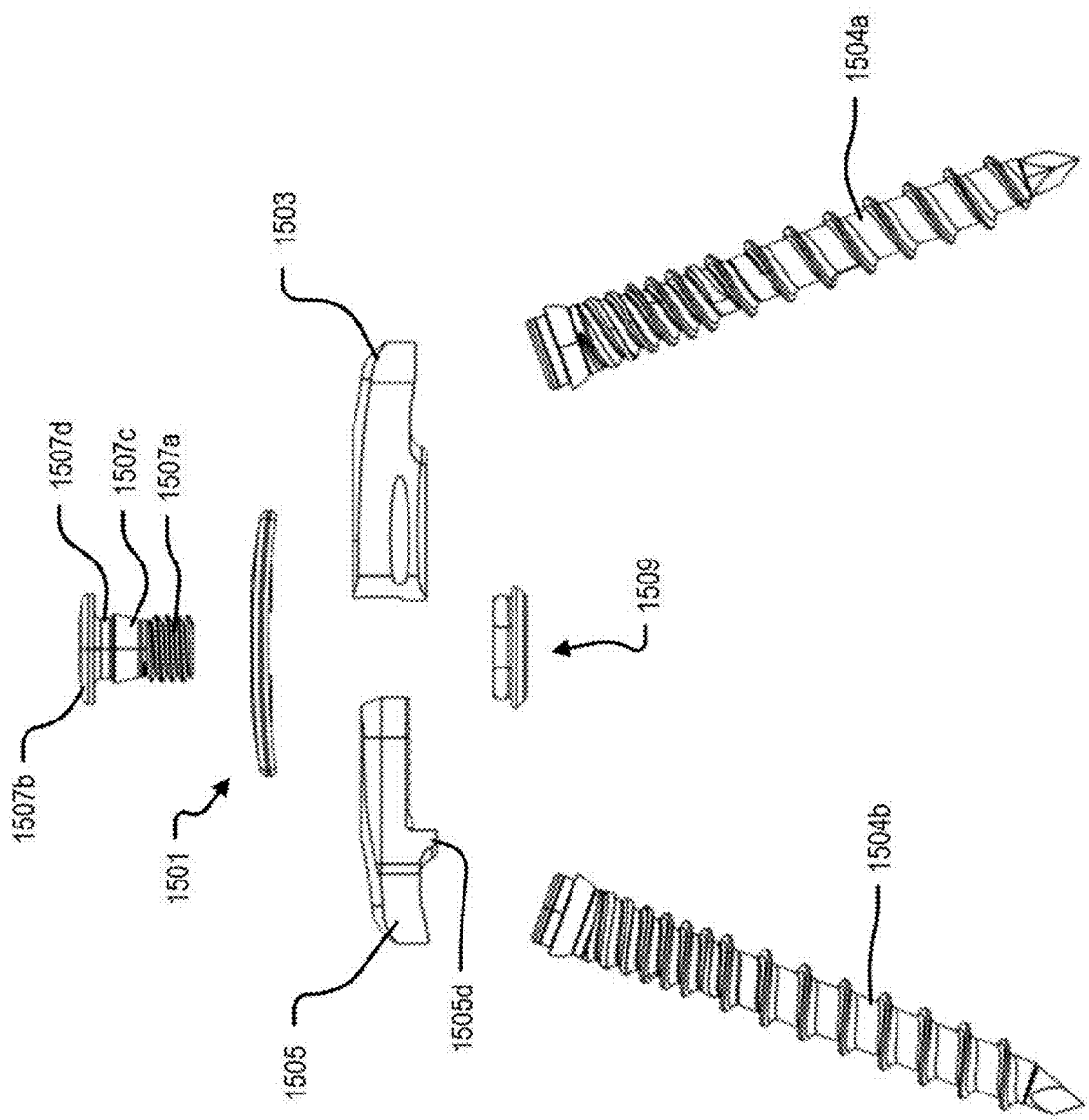
FIG. 59 is an alternate perspective exploded parts view of a first expandable plate embodiment for coupling to disclosed spinal implants.

FIGS. 57-59 are various exploded parts views of a first expandable plate 1500. In the example embodiment, it is shown that set screw 1507 extends in a proximal to distal direction and includes a thread pattern 1507a on an outside circumferential surface at the distal end and a head portion 1507b at the proximate end that is relatively larger than the maximum diameter of the thread pattern 1507a, for example. In various embodiments, set screw 1507 may include a hollow interior such that a rotation instrument such as a driver may extend through set screw 1507 in the proximal-to-distal direction. Set screw 1507 may extend through aperture 1501a of cover 1501, aperture 1503a of inferior portion 1503, aperture 1505a of superior portion 1505, and thread into the threaded aperture 1509a of nut 1509, for example. Additionally, in various embodiments head portion 1507b may be nested and/or seated within a circumferential indent 1501b such that the outside surfaces of head portion 1507b and the outside portion of end cap 1501 are flush and/or substantially flush, for example. Additionally, upper portion 1505 may include a lip 1505d projecting from a distal side of upper portion 1505 and extending in a widthwise direction. In various embodiments, lip 1505d may be positioned to sit on an apophyseal ring of an adjacent vertebrae and be utilized for determining an appropriate expansion setting of the upper portion 1505 relative to the lower portion 1503, for example.

As seen best in FIG. 58, lower portion 1503 may include a receiving cavity 1503c having a size and shape that corresponds to a lower end of upper portion 1505, for example. Receiving cavity 1503c may have a size and shape generally corresponding to a size and shape of a lower end of the upper portion 1505. Lower portion 1503 may include a rack portion 1503b comprising a plurality of raised rails and indented grooves that extend in a widthwise direction, for example. In various embodiments, rack portion 1503b may be disposed within cavity 1503c proximate to and on both sides of aperture 1503a. Additionally, rack portion 1503b may face the proximal direction of expandable plate 1500. As seen best in FIG. 57, upper portion 1505 may include a rack portion 1505b comprising a plurality of raised rails and indented grooves that extend in a widthwise direction, for example. In various embodiments, rack portion 1505b may be disposed on a distal end of upper portion 1505 such that when upper portion 1505 is insert within receiving cavity 1503c rack portion 1505b faces rack portion 1503b, for example. In this way, rack portion 1505b may mesh with rack portion 1503b within any of the various plurality of positions defined by the plurality of raised rails and indented grooves, for example.

In various embodiments, upper portion 1505 may move up and down in a vertical direction within receiving cavity 1503c such that expandable plate 1500 may be selectively expanded and contracted. Additionally, nut 1509 may nest within channel 1503e of lower portion 1503, for example. In the example embodiment, channel 1503e may be understood as a slotted channel that extends in a vertical direction for a distance greater than the diameter of nut 1509 and extends in the widthwise direction for a distance approximating a width of nut 1509. For example, nut 1509 may include planar side surfaces 1509b and a distance in the widthwise direction of channel 1503e may correspond to the distance between the two planar side surfaces 1509b. Additionally, planar side surfaces 1509b may prevent the nut 1509 from rotating while set screw 1507 is tightened to nut 1509. Accordingly, an end user such as a surgeon may expand the top portion 1505 relative to the bottom portion 1503 (or vice versa) and tighten set screw 1507 to nut 1509 such that rack portions 1505b and 1503b are urged together and/or directly engage with one another. In this way, an end user can securely couple the top portion 1505 to the bottom portion 1503 in any one of the various viable expanded positions.

Figure 61:
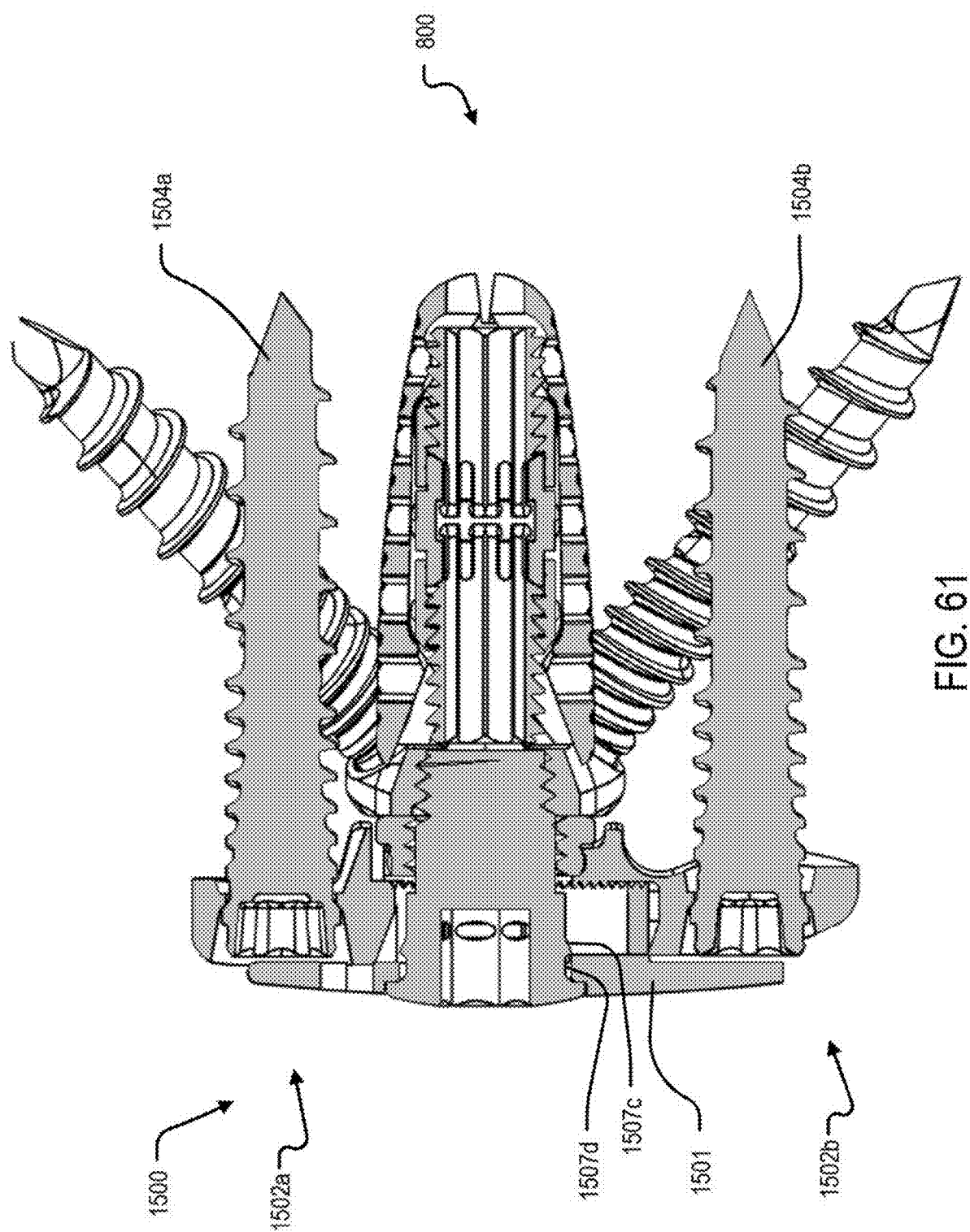
FIG. 61 is a cross section view of FIG. 60.

With reference to FIGS. 59 and 61, set screw 1507 may include a tapered portion 1507c disposed between a circumferential indent 1507d at a proximal side and a threaded portion 1507a, for example. In some embodiments, tapered portion 1507c may be referred to as a conical tapered portion, for example. Tapered portion 1507c may be widest at a proximal end of screw 1507 and narrowest at an end thereof closest to a distal side and before and/or adjoining threaded portion 1507a, for example. In various embodiments, tapered portion 1507c, In various embodiments, engagement surfaces of the upper portion 1505 and/or lower portion 1503 may be seated within circumferential indent 1507d (see FIG. 61). Additionally, in various embodiments tapered portion 1507c may interfere with aperture 1505a such that set screw 1507 may rotate therein while also remaining coupled to nut 1509, for example. Additionally, tapered portion 1507c may facilitate and/or allow the upper portion 1505 and lower portion 1503 to expand and contract while also allowing the cover 1501 to rotate. For example, cover 1501 may rotate around tapered portion 1507c between a locked position and an unlocked position.

Figure 60:
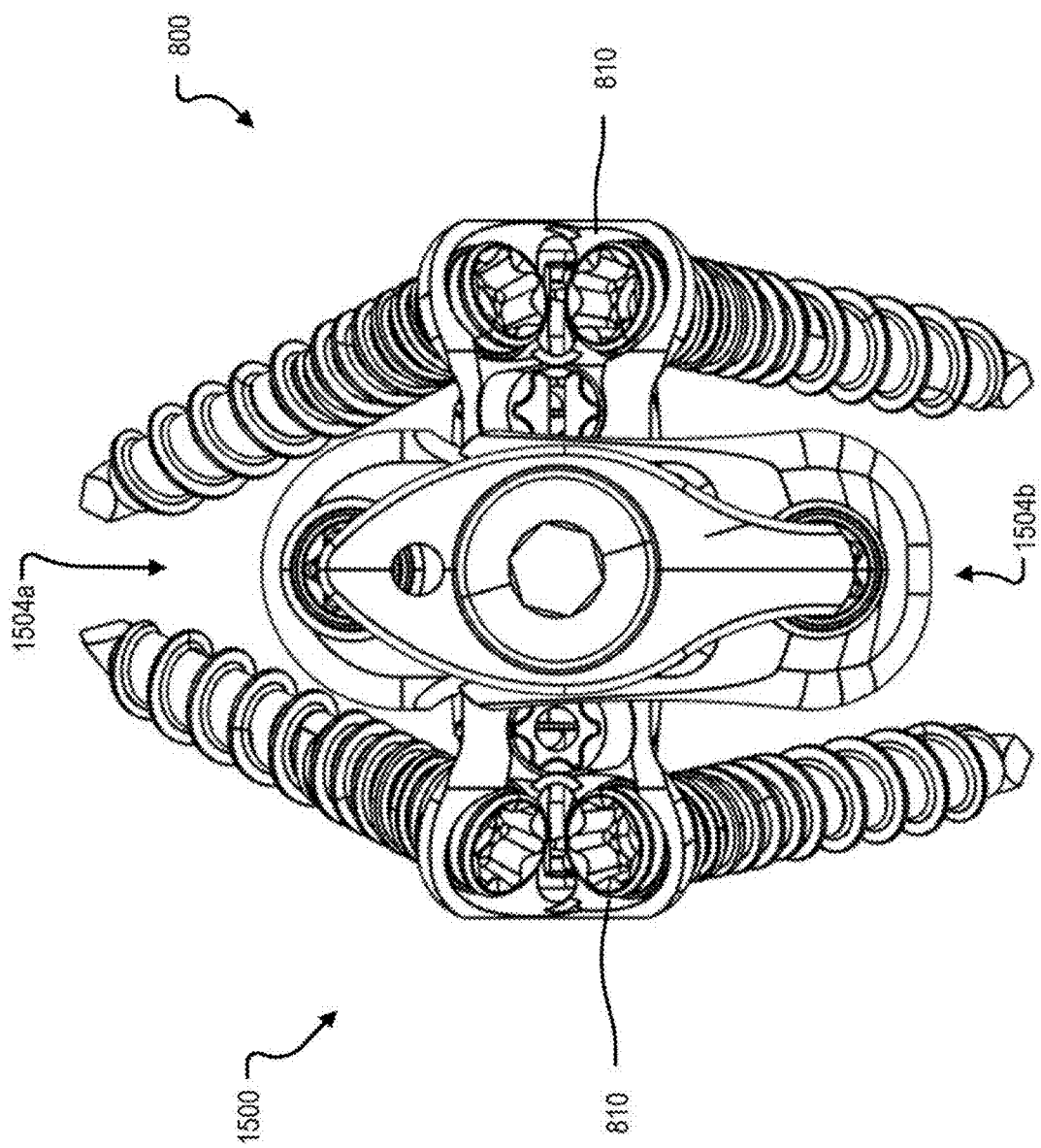
FIG. 60 is a front view of a first expandable plate embodiment coupled to a spinal implant.

FIG. 60 is a front view of a first expandable plate 1500 embodiment coupled to an endplate 810 of a spinal implant 800 and FIG. 61 is a cross section view of FIG. 60. In the example embodiment, it is shown that the distal side of expandable plate 1500 is in contact with the proximal side of endplate 810. Additionally, it is shown that the first and second set screws 252, 254 of moving mechanism 250 are accessible through an aperture of set screw 1507 of expandable plate 1500. Furthermore, it is shown that a target trajectory of the first and second bone screws 1504a, 1504b extends substantially perpendicular to the face of expandable plate 1500 in a proximal-to-distal-direction. For example, the first and second bone screws 1504a, 1504b extend straight back from the proximal end towards the distal end in a plane that approximates the centerline of implant 800 and expandable plate 1500. Furthermore, in various embodiments the first bone screw aperture 1502a and second bone screw aperture 1502b may be conically shaped, tapered, and/or cylindrical with or without a retaining lip and may also allow for about +/−9 degrees of relative freedom of movement. In various embodiments, in a contracted position, a vertical distance between the first bone screw aperture 1502a and second bone screw aperture 1502b may be about 15 mm to about 25 mm and in some embodiments about 21.5 mm, for example. In various embodiments, in an expanded position, a vertical distance between the first bone screw aperture 1502a and second bone screw aperture 1502b may about 20 mm to about 35 mm and in some embodiments about 27.5 mm, for example.

Figure 62:
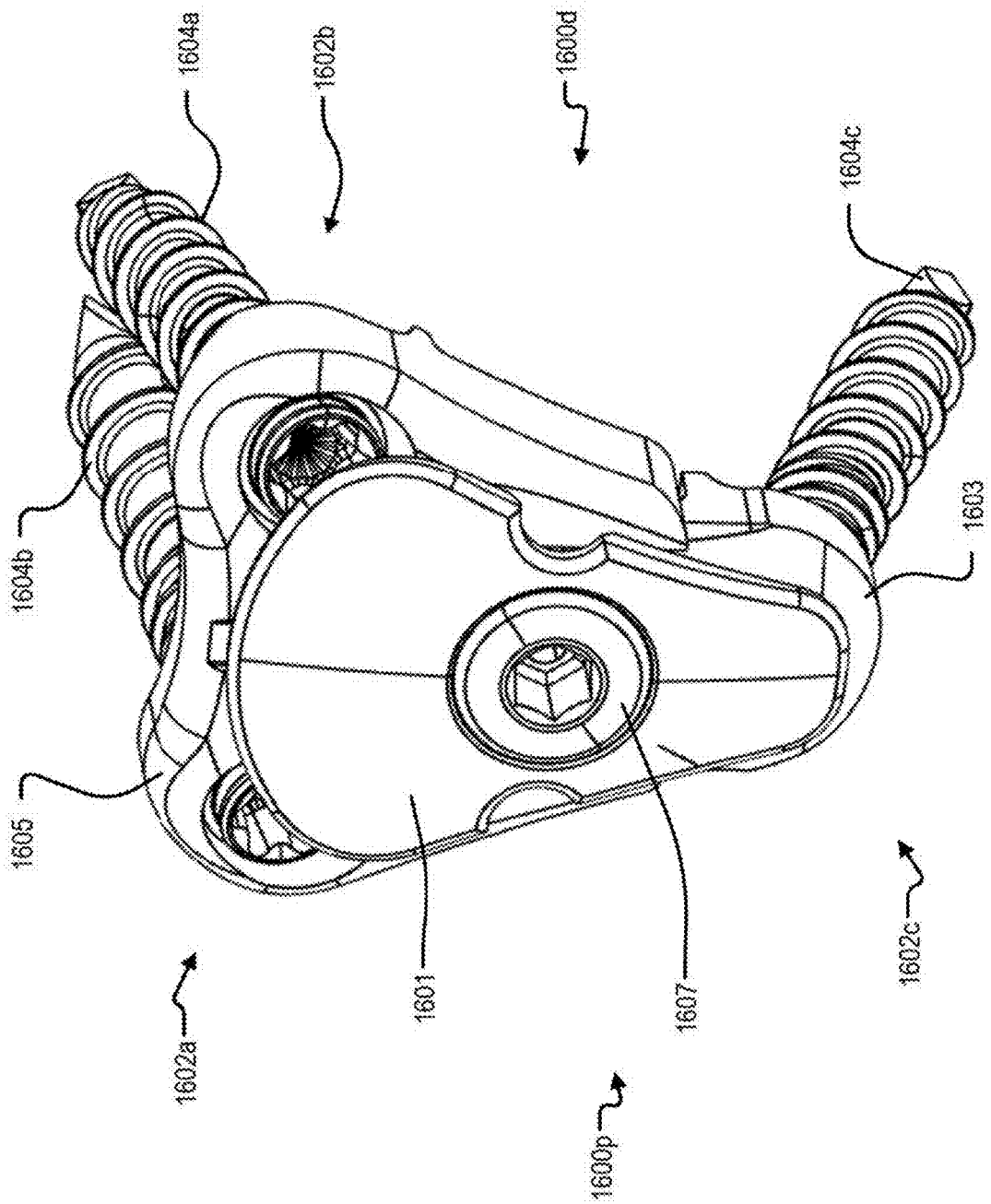
FIG. 62 is a perspective view of a second expandable plate embodiment for coupling to disclosed spinal implants.
Figure 63:
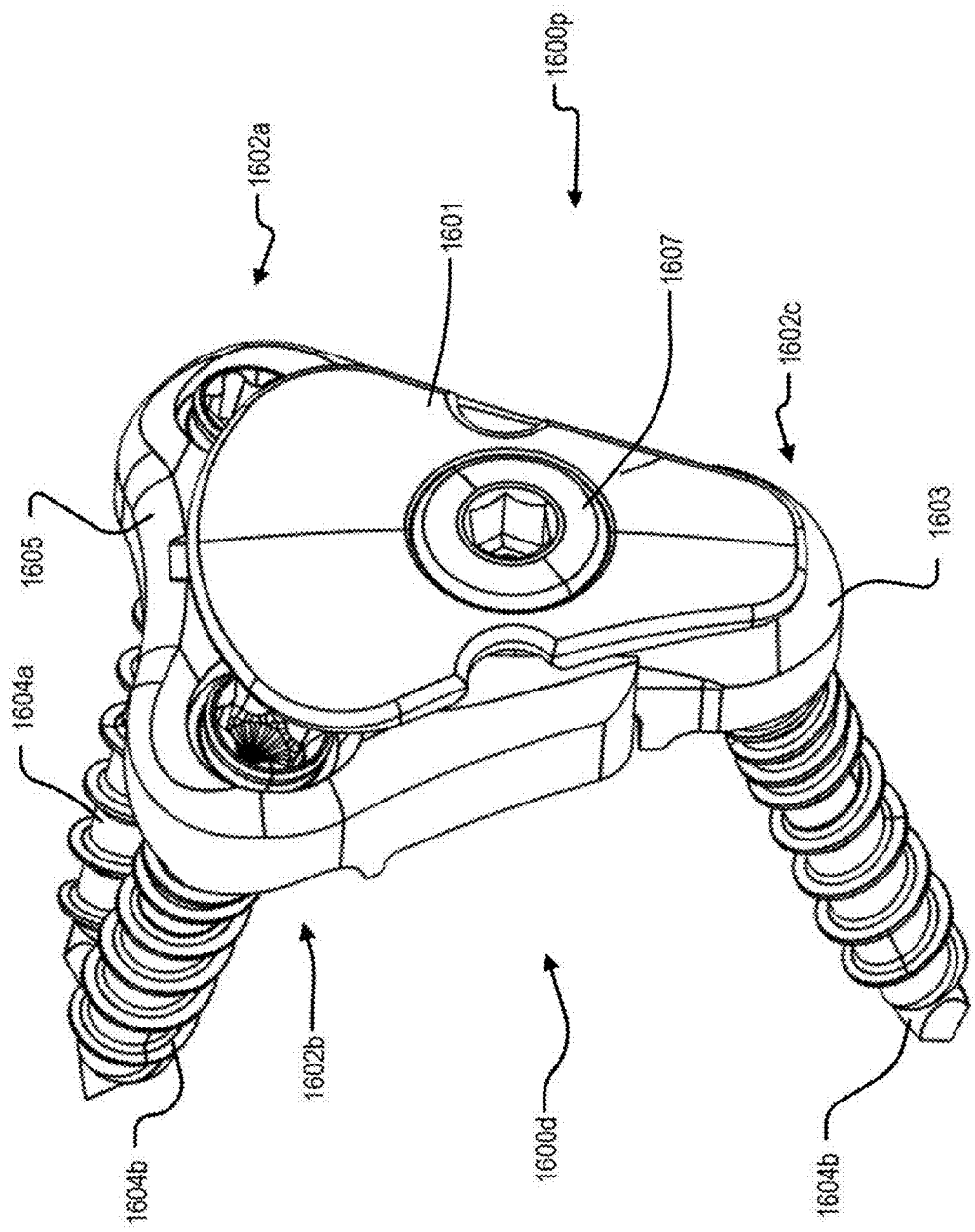
FIG. 63 is an alternate perspective view of a second expandable plate embodiment for coupling to disclosed spinal implants.

FIGS. 62-63 are various perspective views of a second expandable plate 1600 embodiment for coupling to disclosed spinal implants. Expandable plate 1600 may include a superior portion 1605 (may also be referred to as superior plate) and an inferior portion 1603 (may also be referred to as an inferior plate) that are expandable and contractible relative to one another, for example. Superior portion 1605 may include a first bone screw aperture 1602a for supporting a first bone screw 1604a in a target trajectory and a second bone screw aperture 1602b for supporting a second bone screw 1604b in a target trajectory, for example. Additionally, inferior portion 1603 may include a third bone screw aperture 1602c for supporting a third bone screw 1604c in a target trajectory, for example. Expandable plate 1600 may include an end cap 1601 that is rotatable between a locked position where the first, second, and third bone screw apertures 1602a, 1602b, and 1602c are covered such that the first, second, and third bone screws 1604a, 1604b, 1604c are prevented and/or suppressed from backing out. Expandable plate 1600 may include a set screw 1607 for securing the superior portion 1605 and inferior portion 1603 at a particular positon relative to one another. For example, the superior portion 1605 and inferior portion 1603 are expandable in a vertical direction away from one another and set screw 1607 may lock the superior portion 1605 and inferior portion 1603 at any one of the various expanded positions as will be explained in further detail below.

Figure 64:
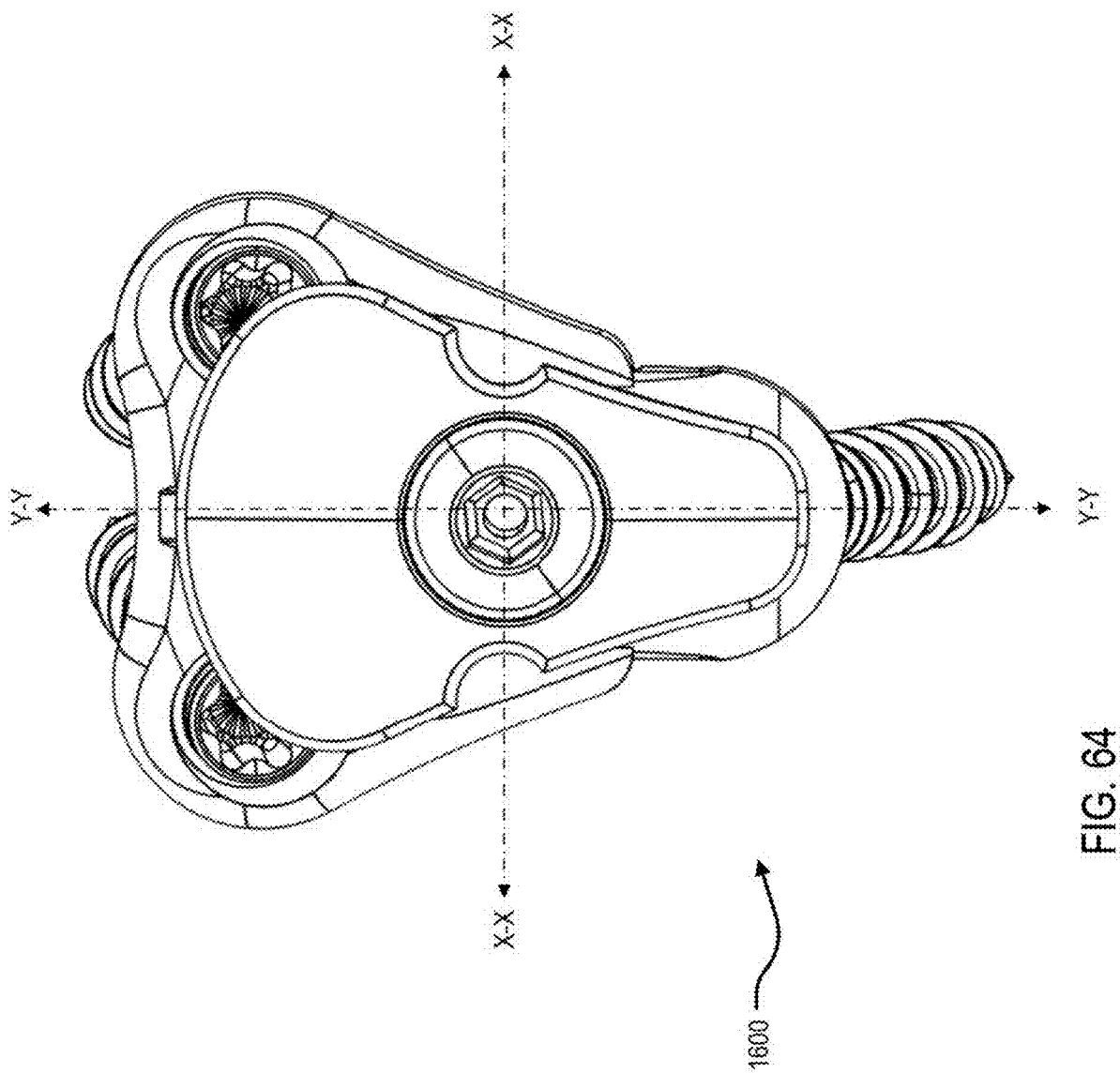
FIG. 64 is a front view of a second expandable plate embodiment for coupling to disclosed spinal implants.

FIG. 64 is a front view of a second expandable plate 1600 showing various axes and reference directions. Expandable plate 1600 may extend in a lengthwise direction along axis Y-Y (may also be referred to as the vertical direction depending on orientation), for example. In various embodiments, expandable plate 1600 may be roughly considered symmetrical on either side of axis Y-Y. For example, a left side of expandable plate 1700 may be symmetrical with respect to a right side of expandable plate 1700. Additionally, expandable plate 1600 may extend in a widthwise direction along axis X-X (may also be referred to as a lateral direction depending on orientation), for example. In various embodiments, a thickness of expandable plate 1600 may extend in a proximal-to-distal direction. For example, as shown in FIG. 62, a thickness may be measured in a proximal-to-distal direction from proximal side 1600p to distal side 1600d.

Figure 65:
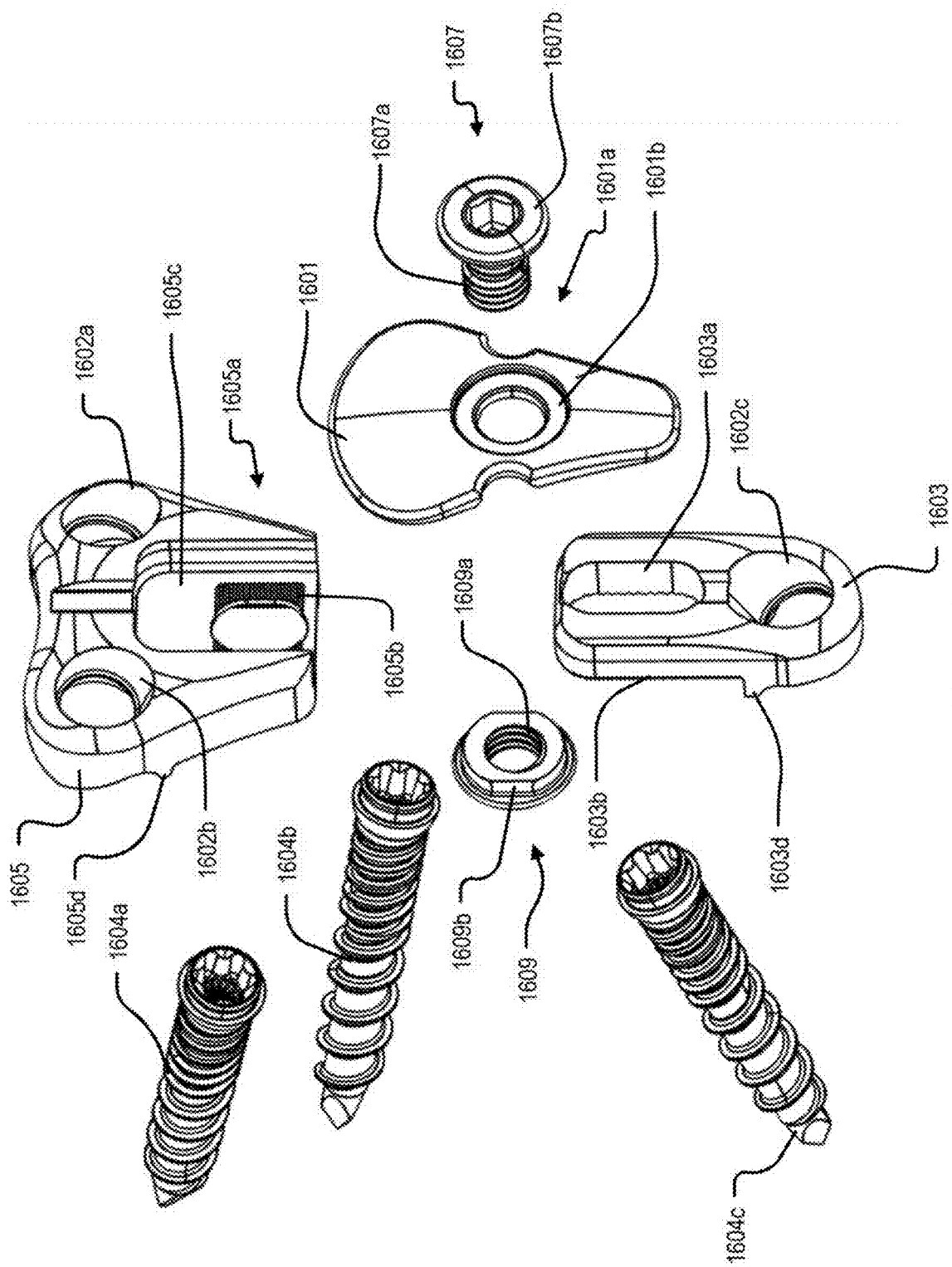
FIG. 65 is a perspective exploded parts view of a second expandable plate embodiment for coupling to disclosed spinal implants.

FIG. 65 is an exploded parts view of a second expandable plate 1600. In the example embodiment, it is shown that set screw 1607 extends in a proximal-to-distal direction and includes a thread pattern 1607a on an outside circumferential surface at the distal end and a head portion 1607b at the proximate end that is relatively larger than the maximum diameter of the thread pattern 1607a, for example. Set screw 1607 may extend through aperture 1601a of cover 1601, aperture 1603a of inferior portion 1603, aperture 1605a of superior portion 1605, and thread into the threaded aperture 1609a of nut 1609, for example. In various embodiments, set screw 1607 may include a hollow interior such that a rotation instrument such as a driver may extend through set screw 1607 in the proximal-to-distal direction. Additionally, in various embodiments head portion 1607b may be nested and/or seated within a circumferential indent 1601b such that the outside surfaces of head portion 1607b and the outside surface of end cap 1601 are flush and/or substantially flush, for example. Furthermore, upper portion 1605 may include a lip 1605d projecting from a distal side of upper portion 1605 and extending in a widthwise direction. Similarly, lower portion 1603 may include a lip 1603d projecting from a distal side of lower portion 1603 and extending in a widthwise direction. In various embodiments, lips 1605d, 1603d may be positioned to sit on an apophyseal ring of an adjacent vertebrae, respectively, and be utilized for determining an appropriate expansion setting of the upper portion 1605 relative to the lower portion 1603, for example. For example, an end user such as a surgeon may position lip 1605d to sit and/or contact an apophyseal ring of a superior vertebrae and position lip 1603d to sit and/or contact an apophyseal ring of an inferior vertebrae. In doing so, an appropriate expansion and/or relative height of expandable plate 1600 may be established.

As seen best in FIG. 65, upper portion 1605 may include a receiving cavity 1605c having a size and shape that corresponds to an upper end of lower portion 1603, for example. Receiving cavity 1605c may have a size and shape generally corresponding to a size and shape of an upper end of the lower portion 1603. Upper portion 1605 may include a rack portion 1605b comprising a plurality of raised rails and indented grooves that extend in a widthwise direction, for example. In various embodiments, rack portion 1605b may be disposed within cavity 1605c proximate to and on both sides of aperture 1605a. Additionally, rack portion 1605b may face the proximal direction of expandable plate 1600. As seen best in FIG. 65 and FIG. 67, lower portion 1603 may include a rack portion 1603b comprising a plurality of raised rails and indented grooves that extend in a widthwise direction, for example. In various embodiments, rack portion 1603b may be disposed on a distal end of lower portion 1603 such that when lower portion 1603 is insert within receiving cavity 1605c, rack portion 1603b faces rack portion 1605b, for example. In this way, rack portion 1603b may mesh with rack portion 1605b within any of the various plurality of positions defined by the plurality of raised rails and indented grooves, for example.

In various embodiments, lower portion 1603 may move up and down in a vertical direction within receiving cavity 1605c such that expandable plate 1600 may be selectively expanded and contracted. Additionally, nut 1609 may nest within channel 1605e of upper portion 1605, for example as seen best in FIG. 67. In the example embodiment, channel 1605e may be understood as a slotted channel that extends in a vertical direction for a distance greater than the diameter of nut 1609 and extends in the widthwise direction for a distance approximating a width of nut 1609. For example, nut 1609 may include planar side surfaces 1609b and a distance in the widthwise direction of channel 1605e may correspond to the distance between the two planar side surfaces 1609b. Additionally, planar side surfaces 1609b may prevent the nut 1609 from rotating while set screw 1607 is tightened to nut 1609. Accordingly, an end user such as a surgeon may expand the bottom portion 1603 relative to the top portion 1605 (or vice versa) and tighten set screw 1607 to nut 1609 such that rack portions 1605b and 1603b are urged together and/or directly engage with one another. In this way, an end user can securely couple the top portion 1605 to the bottom portion 1603 in any one of the various viable expanded positions.

Figure 66:
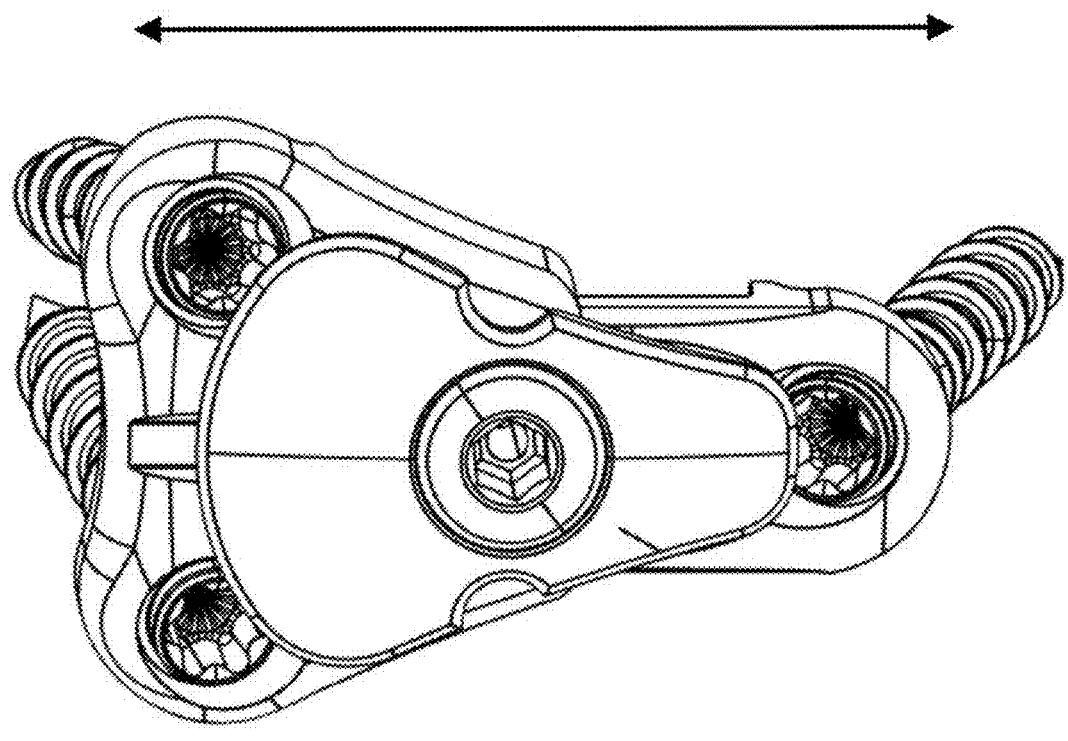
FIG. 66 is a perspective view of a second expandable plate embodiment in an expanded position.
Figure 67:
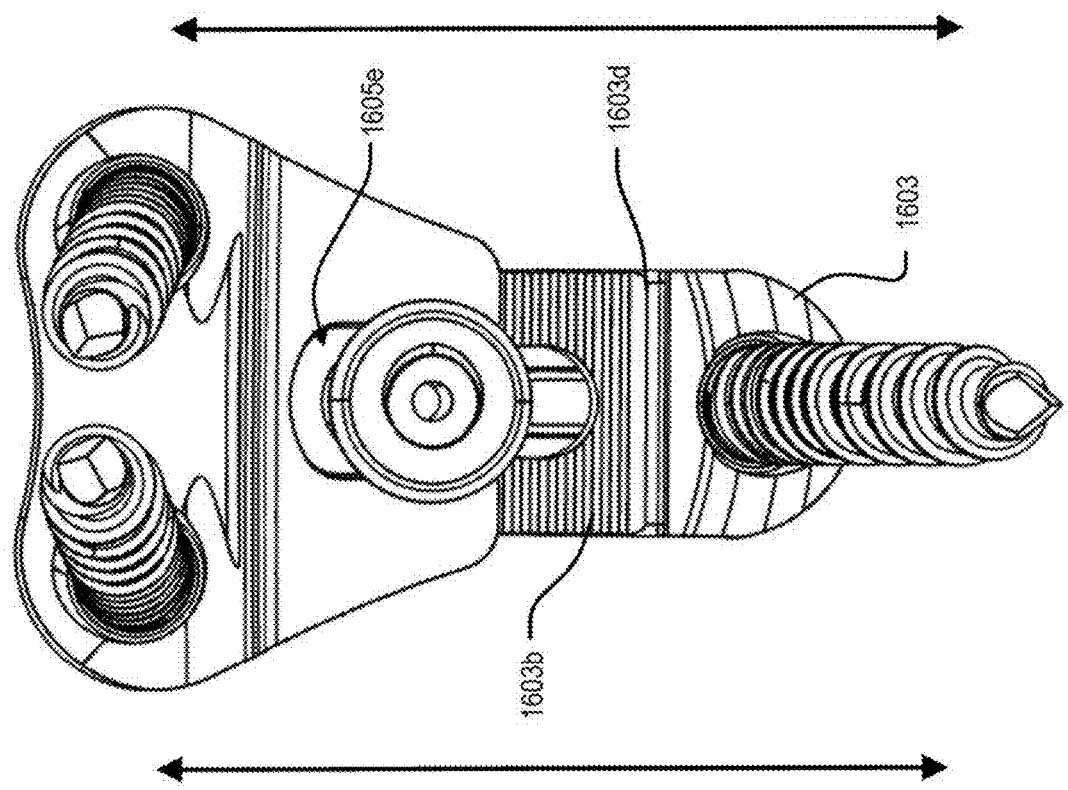
FIG. 67 is an alternate perspective view of a second expandable plate embodiment in an expanded position.

FIGS. 66 and 67 are various perspective views of a second expandable plate 1600 embodiment in an expanded position. Although not illustrated, second expandable plate 1600 may couple to an implant and/or endplate 810 in the same, substantially the same, and/or similar manner as explained above in reference to first expandable plate 1500. Accordingly, duplicative description will be omitted. In the example embodiment, it is shown that the first, second, and third bone screws 1604a, 1604b, 1604c extend from the proximal end towards the distal end in a diverging pattern. Additionally, in various embodiments, the first and second bone screws may converge towards one another, at least partially. Furthermore, in various embodiments the first bone screw aperture 1602a, second bone screw aperture 1602b, and third bone screw aperture 1602c may be conically shaped, tapered, and/or cylindrical with or without a retaining lip and may also allow for about +/−9 degrees of relative freedom of movement. In various embodiments, in a contracted position, a vertical distance between the first bone screw aperture 1602a and second bone screw aperture 1602b may be about 16 mm to about 25 mm and in some embodiments about 21.5 mm, for example. In various embodiments, in an expanded position, a vertical distance between the first bone screw aperture 1602a and second bone screw aperture 1602b may be about 20 mm to about 35 mm and in some embodiments about 27.5 mm, for example.

Figure 68:
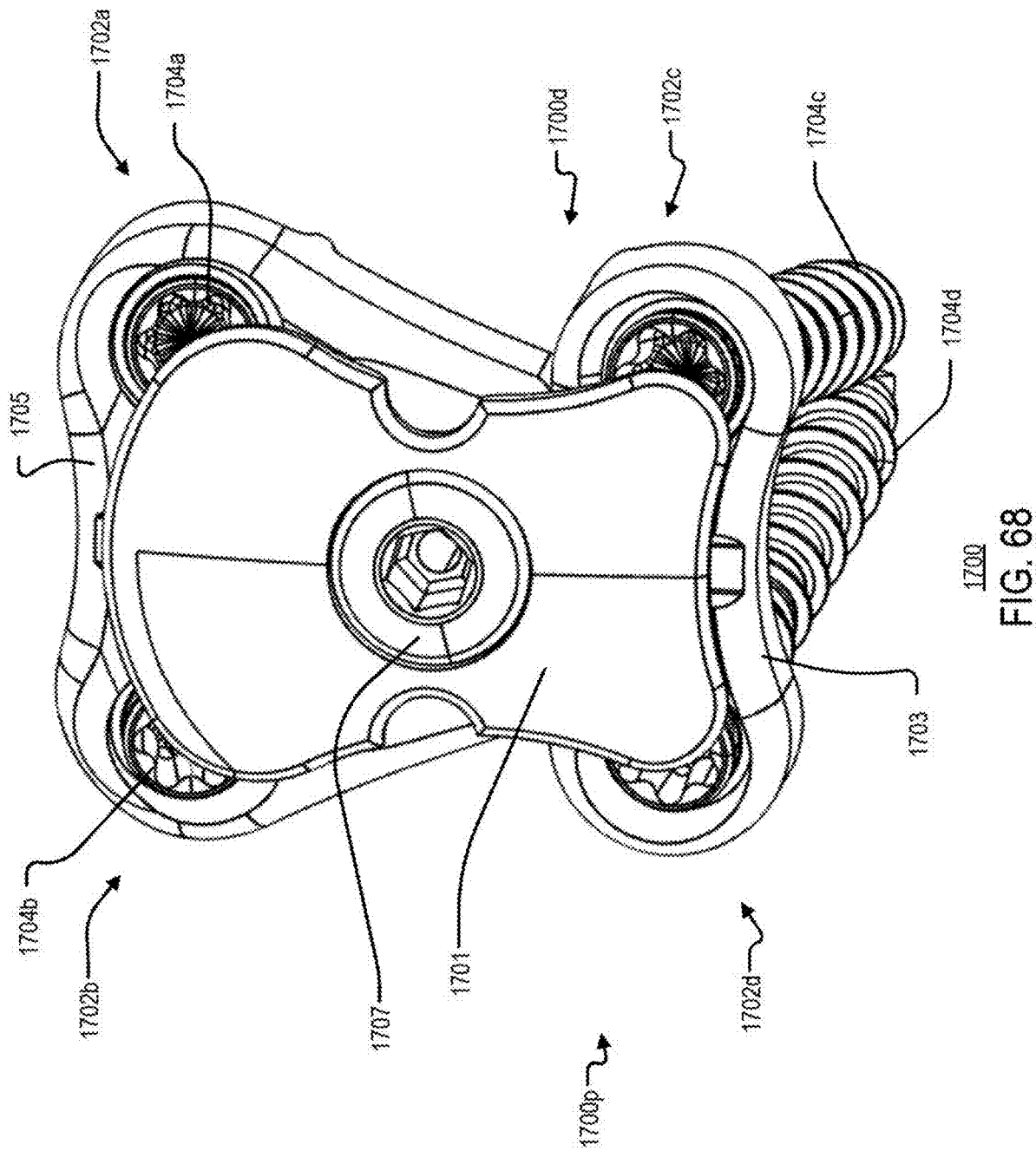
FIG. 68 is a perspective view of a third expandable plate embodiment for coupling to disclosed spinal implants.
Figure 69:
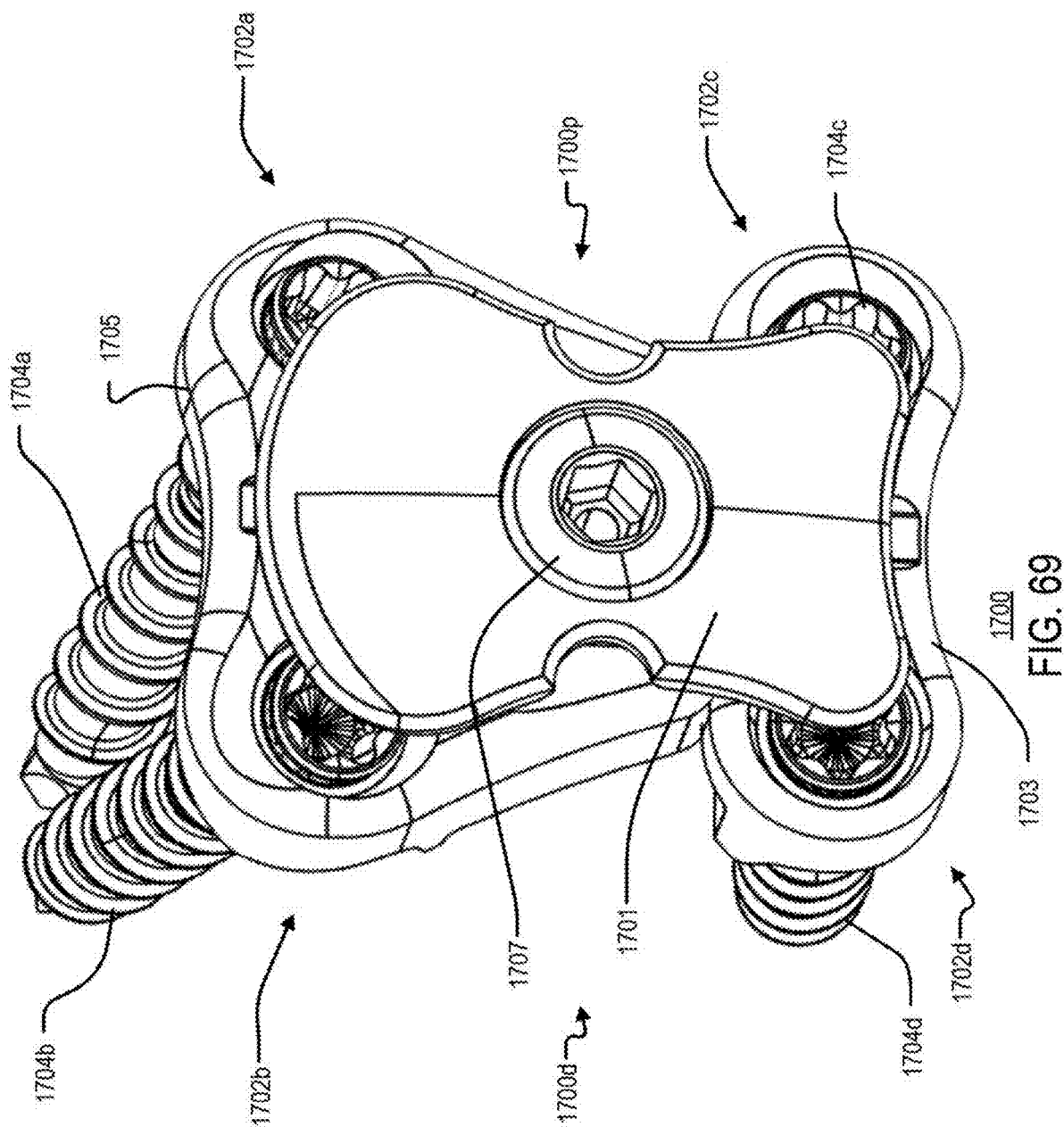
FIG. 69 is an alternate perspective view of a third expandable plate embodiment for coupling to disclosed spinal implants.

FIGS. 68-73 are various perspective views of a third expandable plate 1700 embodiment for coupling to disclosed spinal implants. With reference to FIGS. 68 and 69, expandable plate 1700 may include a superior portion 1705 (may also be referred to as superior plate) and an inferior portion 1703 (may also be referred to as an inferior plate) that are expandable and contractible relative to one another, for example. Superior portion 1705 may include a first bone screw aperture 1702a for supporting a first bone screw 1704a in a target trajectory and a second bone screw aperture 1702b for supporting a second bone screw 1704b in a target trajectory, for example. Additionally, inferior portion 1703 may include a third bone screw aperture 1702c for supporting a third bone screw 1704c in a target trajectory, and a fourth bone screw aperture 1702d for supporting a fourth bone screw 1704d, for example. Expandable plate 1700 may include an end cap 1701 that is rotatable between a locked position where the first, second, third, and fourth bone screw apertures 1702a, 1702b, 1702c, and 1702d, are covered such that the first, second, third, and fourth bone screws 1704a, 1704b, 1704c, and 1702d are prevented and/or suppressed from backing out. Expandable plate 1700 may include a set screw 1707 for securing the superior portion 1705 and inferior portion 1703 at a particular positon relative to one another. For example, the superior portion 1705 and inferior portion 1703 are expandable in a vertical direction away from one another and set screw 1707 may lock the superior portion 1705 and inferior portion 1703 at any one of the various expanded positions as will be explained in further detail below.

Figure 70:
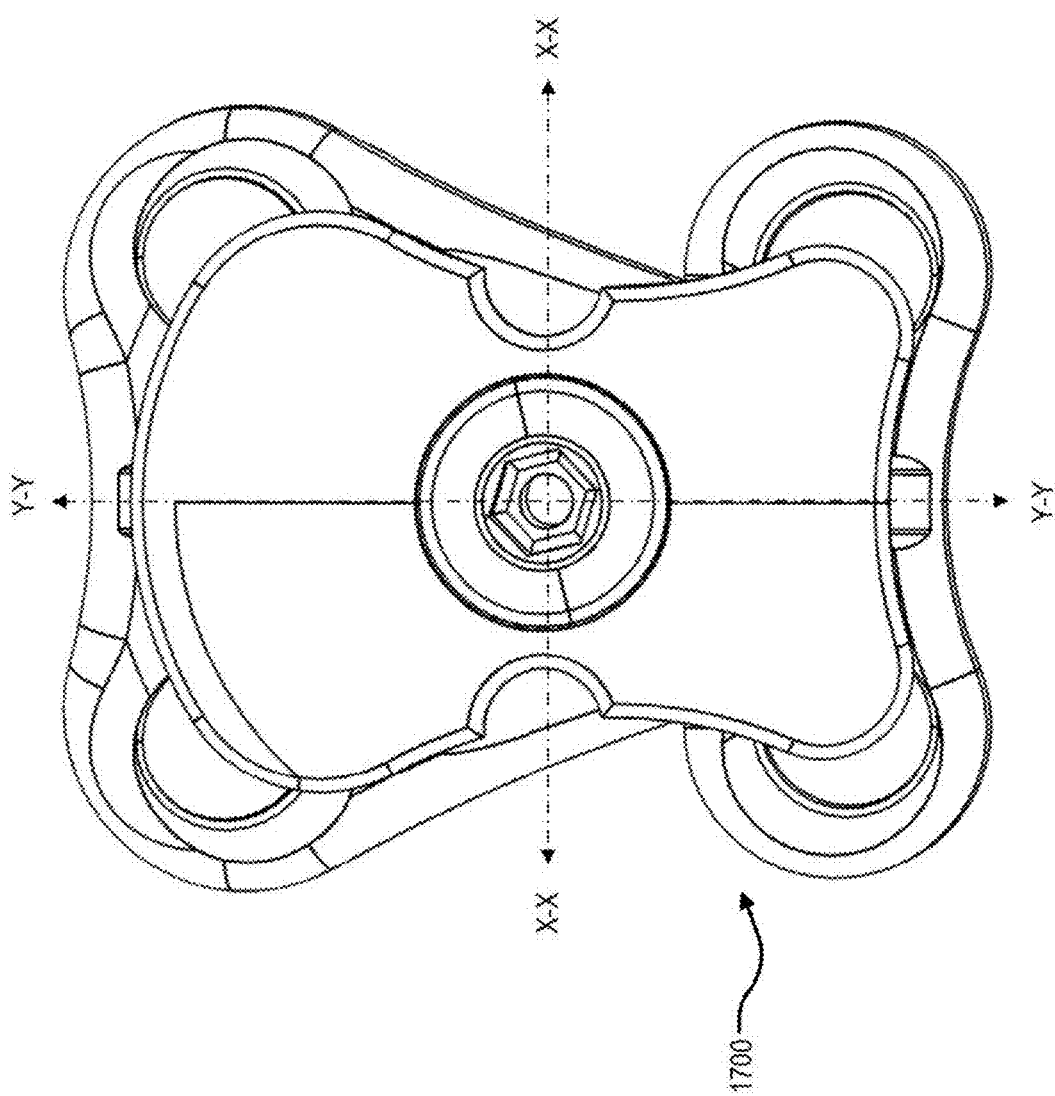
FIG. 70 is a front view of a third expandable plate embodiment for coupling to disclosed spinal implants.

FIG. 70 is a front view of a third expandable plate 1700 showing various axes and reference directions. Expandable plate 1700 may extend in a lengthwise direction along axis Y-Y (may also be referred to as the vertical direction depending on orientation), for example. In various embodiments, expandable plate 1700 may be roughly considered symmetrical on either side of axis Y-Y. For example, a left side of expandable plate 1700 may be symmetrical with respect to a right side of expandable plate 1700. Additionally, expandable plate 1700 may extend in a widthwise direction along axis X-X (may also be referred to as a lateral direction depending on orientation), for example. In various embodiments, a thickness of expandable plate 1700 may extend in a proximal-to-distal direction. For example, as shown in FIG. 68, a thickness may be measured in a proximal-to-distal direction from proximal side 1700p to distal side 1700d.

Figure 71:
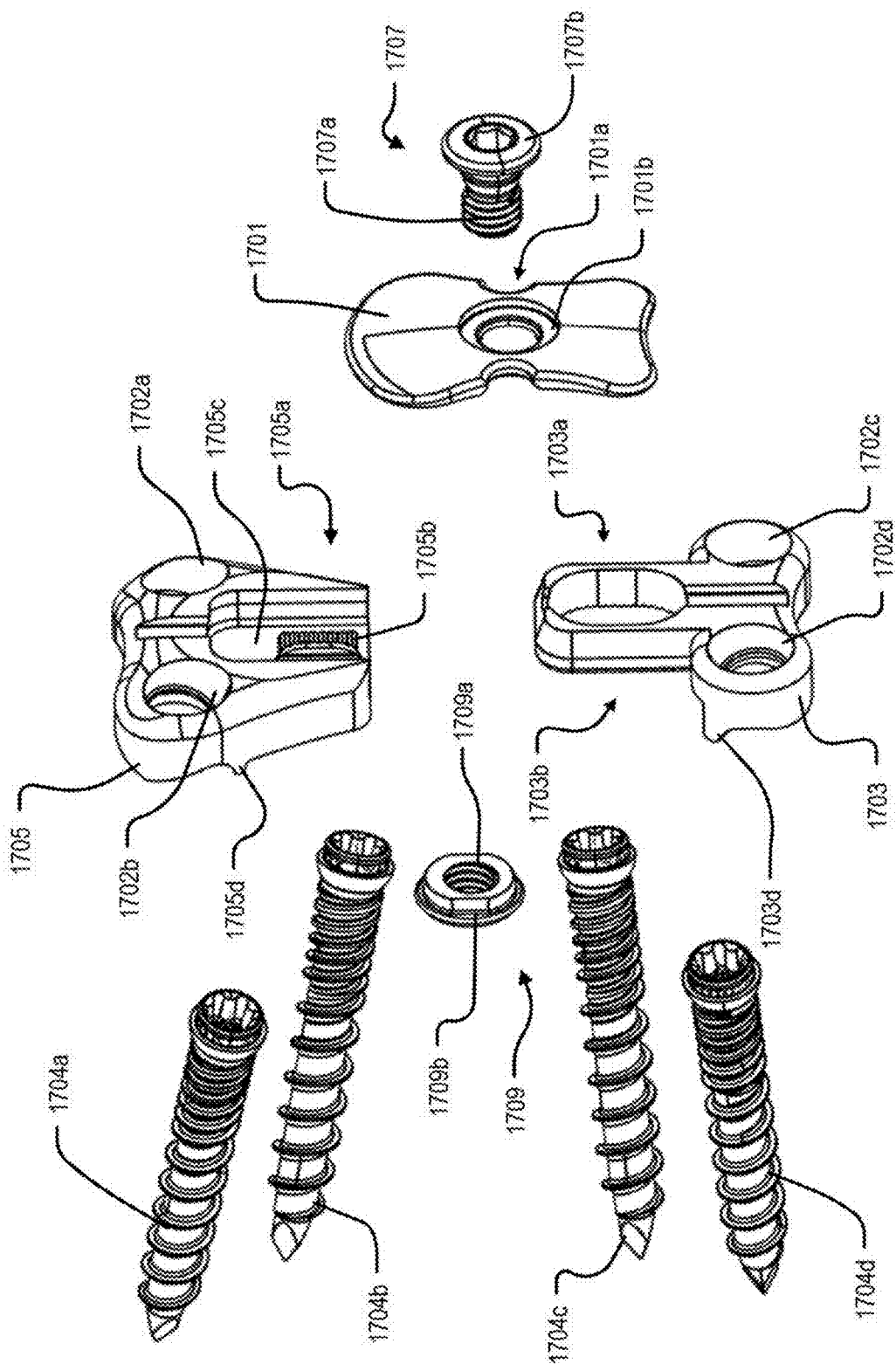
FIG. 71 is a perspective exploded parts view of a third expandable plate embodiment for coupling to disclosed spinal implants.

FIG. 71 is an exploded parts view of a third expandable plate 1700. In the example embodiment, it is shown that set screw 1707 extends in a proximal-to-distal direction and includes a thread pattern 1707a on an outside circumferential surface at the distal end and a head portion 1707b at the proximate end that is relatively larger than the maximum diameter of the thread pattern 1707a, for example. Set screw 1707 may extend through aperture 1701a of cover 1701, aperture 1703a of inferior portion 1703, aperture 1705a of superior portion 1705, and thread into the threaded aperture 1709a of nut 1709, for example. In various embodiments, set screw 1707 may include a hollow interior such that a rotation instrument such as a driver may extend through set screw 1707 in the proximal-to-distal direction. Additionally, in various embodiments head portion 1707b may be nested and/or seated within a circumferential indent 1701b such that the outside surfaces of head portion 1707b and the outside portion of end cap 1701 are flush and/or substantially flush, for example. Furthermore, upper portion 1705 may include a lip 1705d projecting from a distal side of upper portion 1705 and extending in a widthwise direction. Similarly, lower portion 1703 may include a lip 1703d projecting from a distal side of lower portion 1703 and extending in a widthwise direction. In various embodiments, lips 1705d, 1703d may be positioned to sit on an apophyseal ring of an adjacent vertebrae, respectively, and be utilized for determining an appropriate expansion setting of the upper portion 1705 relative to the lower portion 1703, for example. For example, an end user such as a surgeon may position lip 1705d to sit and/or contact an apophyseal ring of a superior vertebrae and position lip 1703d to sit and/or contact an apophyseal ring of an inferior vertebrae. In doing so, an appropriate expansion and/or relative height of expandable plate 1700 may be established.

As seen best in FIG. 71, upper portion 1705 may include a receiving cavity 1705c having a size and shape that corresponds to an upper end of lower portion 1703, for example. Receiving cavity 1705c may have a size and shape generally corresponding to a size and shape of a lower end of the upper portion 1705. Upper portion 1705 may include a rack portion 1705b comprising a plurality of raised rails and indented grooves that extend in a widthwise direction, for example. In various embodiments, rack portion 1705b may be disposed within cavity 1705c proximate to and on both sides of aperture 1705a. Additionally, rack portion 1705b may face the proximal direction of expandable plate 1700. As seen best in FIG. 71, lower portion 1703 may include a rack portion 1703b comprising a plurality of raised rails and indented grooves that extend in a widthwise direction, for example. In various embodiments, rack portion 1703b may be disposed on a distal end of lower portion 1703 such that when lower portion 1703 is insert within receiving cavity 1705c, rack portion 1703b faces rack portion 1705b, for example. In this way, rack portion 1703b may mesh with rack portion 1705b within any of the various plurality of positions defined by the plurality of raised rails and indented grooves, for example.

Figure 73:
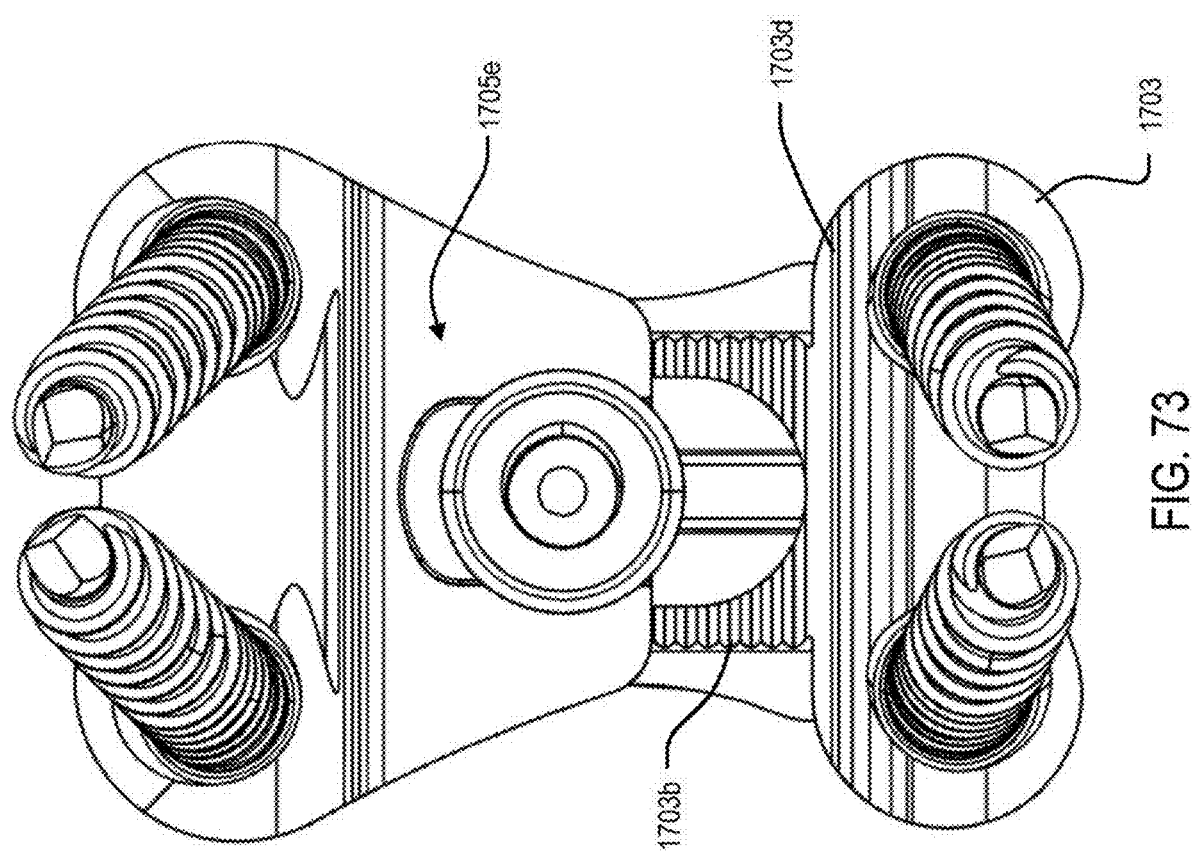
FIG. 73 is a perspective view of a third expandable plate embodiment in an expanded position.

In various embodiments, lower portion 1703 may move up and down in a vertical direction within receiving cavity 1705c such that expandable plate 1700 may be selectively expanded and contracted. Additionally, nut 1709 may nest within channel 1705e of upper portion 1705, for example as shown in FIG. 73. In the example embodiment, channel 1705e may be understood as a slotted channel that extends in a vertical direction for a distance greater than the diameter of nut 1709 and extends in the widthwise direction for a distance approximating a width of nut 1709. For example, nut 1709 may include planar side surfaces 1709b and a distance in the widthwise direction of channel 1705e may correspond to the distance between the two planar side surfaces 1709b. Additionally, planar side surfaces 1709b may prevent the nut 1709 from rotating while set screw 1707 is tightened to nut 1709. Accordingly, an end user such as a surgeon may expand the bottom portion 1703 relative to the top portion 1705 (or vice versa) and tighten set screw 1707 to nut 1709 such that rack portions 1705b and 1703b are urged together and/or directly engage with one another. In this way, an end user can securely couple the top portion 1705 to the bottom portion 1703 in any one of the various viable expanded positions.

Figure 72:
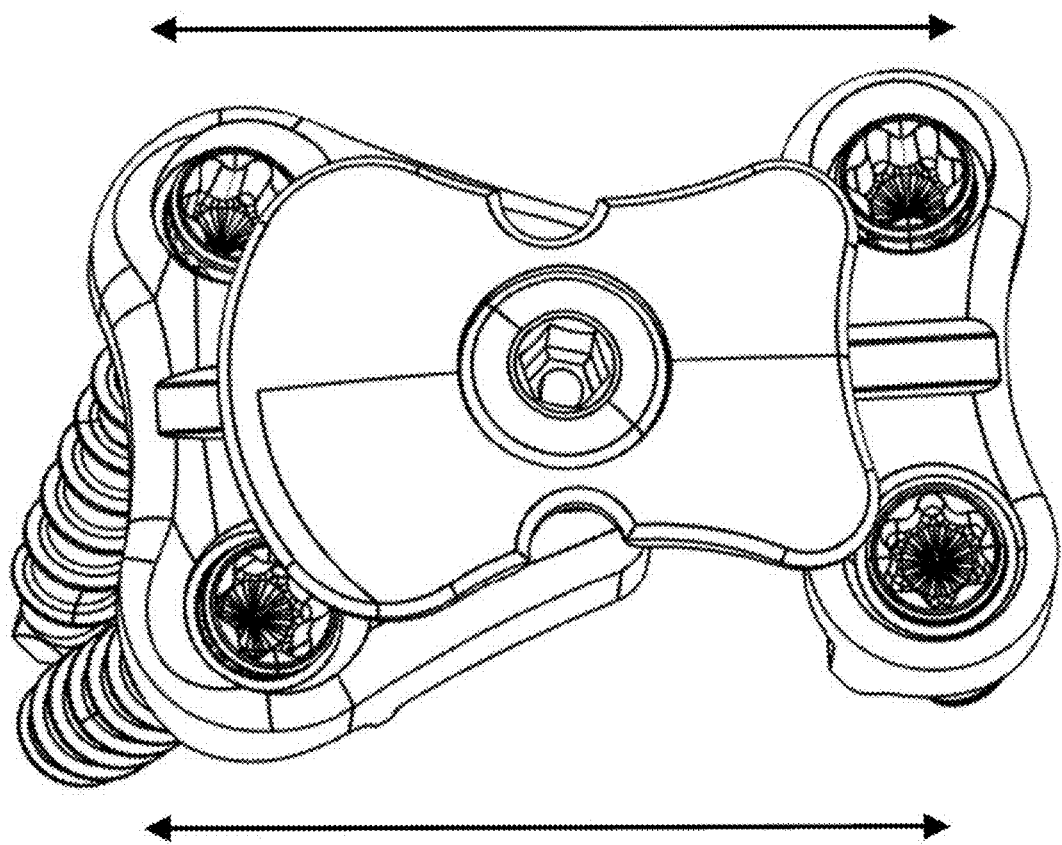
FIG. 72 is a perspective view of a third expandable plate embodiment in an expanded position.

FIGS. 72 and 73 are various perspective views of a third expandable plate 1700 embodiment in an expanded position. Although not illustrated, third expandable plate 1700 may couple to an implant and/or endplate 810 in the same, substantially the same, and/or similar manner as explained above in reference to first expandable plate 1500. Accordingly, duplicative description will be omitted. In the example embodiment, it is shown that the first, second, third and fourth bone screws 1704a, 1704b, 1704c, 1704d extend from the proximal end towards the distal end in a converging pattern. Furthermore, in various embodiments the first bone screw aperture 1702a, second bone screw aperture 1702b, third bone screw aperture 1702c, and fourth bone screw aperture 1702d may be conically shaped, tapered, and/or cylindrical with or without a retaining lip and may also allow for about +/−9 degrees of relative freedom of movement. In various embodiments, in a contracted position, a vertical distance between the first bone screw aperture 1702a and third bone screw aperture 1702b may be about 17 mm to about 25 mm and in some embodiments about 21.5 mm, for example. Similarly, in various embodiments, in a contracted position, a vertical distance between the second bone screw aperture 1702b and fourth bone screw aperture 1702d may be about 17 mm to about 25 mm and in some embodiments about 21.5 mm, for example. In various embodiments, in an expanded position, a vertical distance between the first bone screw aperture 1702a and third bone screw aperture 1702c may about 20 mm to about 35 mm and in some embodiments about 27.5 mm, for example. Similarly, in various embodiments, in an expanded position, a vertical distance between the second bone screw aperture 1702b and fourth bone screw aperture 1702d may about 20 mm to about 35 mm and in some embodiments about 27.5 mm, for example.

Figure 74:
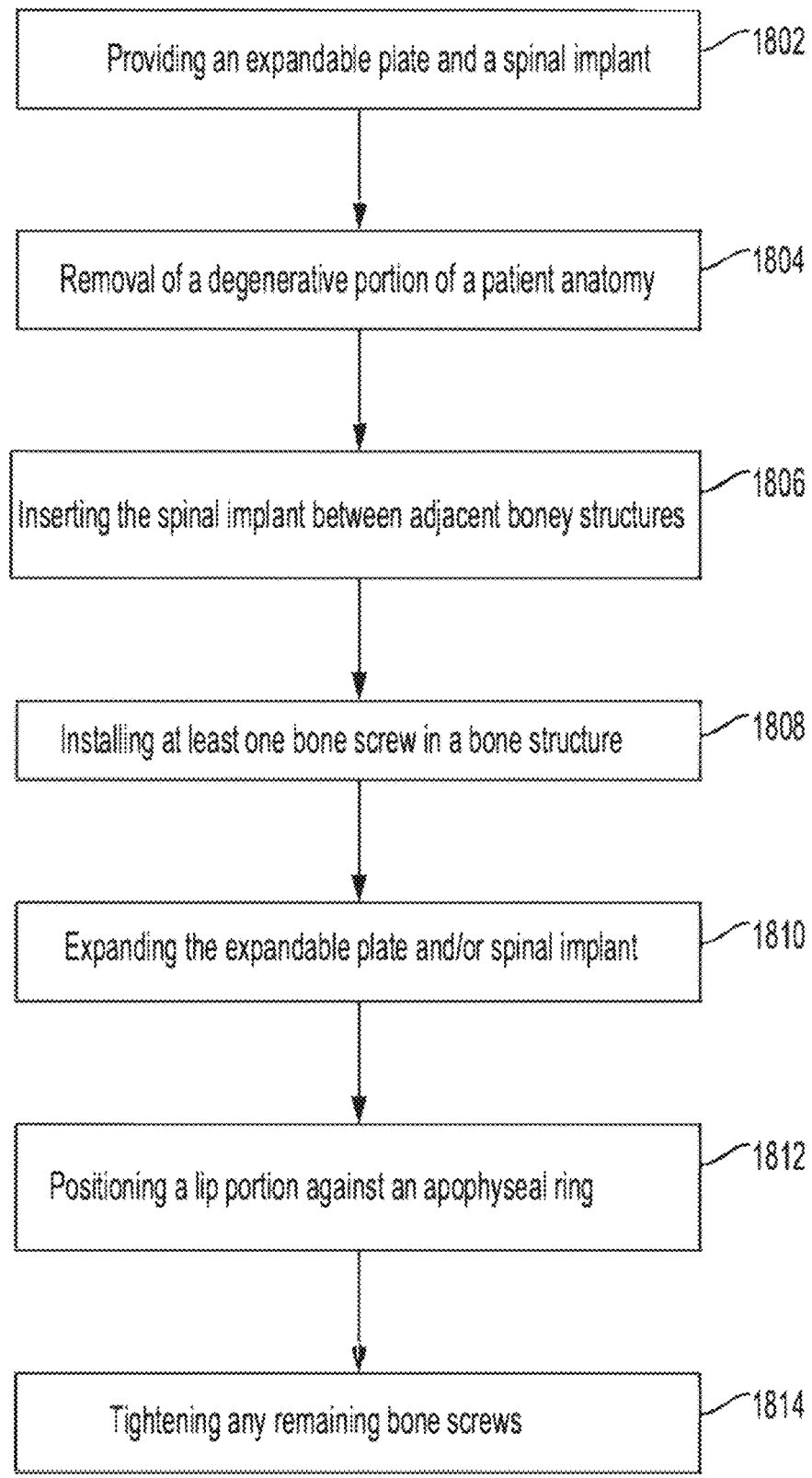
FIG. 74 is a flow chart of a method of operation of various expandable plates.

FIG. 74 is a flow chart method of operation 1800 for installing an expandable plate and an expandable implant between adjacent vertebrae of a patient. The various method steps below may be explained in the context of the various disclosed expandable plates 1500, 1600, and 1700. Although the various expandable plates 1500, 1600, 1700 and the various spinal implants disclosed herein may be used to perform the method of operation 18000 the method of operation is not limited to the embodiments disclosed herein. Furthermore, the following steps need not be performed in sequence and can be performed in any alternate sequence with or without all of the disclosed method steps.

At step 1802 an expandable plate and/or an expandable spinal implant may be provided, for example. At step 1804, an end user may prepare a space between adjacent boney structures by removal and/or cleaning of the space. For example, an end user may remove a degenerative disc between a superior vertebrae and an inferior vertebrae. At step 1806, an end user may insert the spinal implant between the superior vertebrae and inferior vertebrae. In some embodiments, the spinal implant and expandable plate may be simultaneously insert into the patient anatomy, although the spinal implant may be insert within the disc space between the superior and inferior vertebrae while the expandable plate remains on the outside of the disc space. At step 1808, an end user may install at least one bone screw in a boney structure. For example, an end user may install a bone screw that extends through an upper portion and/or lower portion of an expandable plate. In various embodiments, the at least one bone screw may be partially installed, i.e., the one screw may not be fully tightened into the patient anatomy. At step 1810, an end user may expand the expandable plate and/or spinal implant. For example, an end user may insert an inserter through a set screw of the expandable plate and activate an expansion mechanism inside of the spinal implant to effectuate expansion of the spinal implant within the disc space. Additionally, an end user may move the upper portion and/or lower portion to expand the expandable plate on the outside of the disc space. At step 1812, an end user may position a portion of the expandable plate against an apophyseal ring. For example, an end user may ensure that a lip portion of at least one of the upper portion and/or lower portion abuts an apophyseal ring of a corresponding vertebrae. At step 1814, an end user may fully tighten any remaining bone screws to be installed. For example, an end user may tighten any remaining bone screws of an expandable plate and/or any remaining bone screws of a spinal implant.

What is claimed is:

1. An expandable plate deployable between a contracted position and an expanded position, comprising:
an expandable body having a thickness in a proximal-to-distal direction between a proximal end and a distal end, a width in a widthwise direction, and a height in a longitudinal direction, the expandable body comprising a first portion and a second portion;
wherein the first portion includes:
a receiving cavity facing the proximal end, and
a first through aperture extending in the proximal-to-distal direction,
wherein the second portion includes:
a lower end having a size and shape that corresponds to the receiving cavity, and a second through aperture extending in the proximal-to-distal direction, a locking screw; and a nut, wherein, in a locked position, the locking screw extends through the first through aperture and the second through aperture, and is secured to the nut, and wherein the expandable plate is configured to couple to a proximal face of an intervertebral spinal implant via the locking screw.

2. The expandable plate of claim 1, wherein:

the receiving cavity comprises a first rack portion comprising a plurality of raised rails and indented grooves; and a distal end of the second portion comprises a second rack portion comprising a plurality of raised rails and indented grooves.

3. The expandable plate of claim 2, wherein, in the locked position, the first rack portion and second rack portion are directly engaged.

4. The expandable plate of claim 1, wherein the first portion comprises a first bone screw aperture and the second portion comprises a second bone screw aperture.

5. The expandable plate of claim 4, wherein the locking screw comprises a tapered portion.

6. The expandable plate of claim 1, wherein a distal end of the second portion comprises a slotted aperture.

7. The expandable plate of claim 6, wherein the nut is disposed within the slotted aperture.

8. The expandable plate of claim 7, wherein the nut comprises a first planar side surface and a second planar side surface opposite the first planar side surface.

9. The expandable plate of claim 8, wherein:

a first distance of the slotted aperture extends in the widthwise direction;

a second distance of the nut extends between the first planar side surface and the second planar side surface; and the first distance approximates the second distance.

10. The expandable plate of claim 1, wherein:

the receiving cavity comprises a first rack portion comprising a plurality of raised rails and indented grooves; and the first through aperture extends through the first rack portion.

11. The expandable plate of claim 10, wherein:

a distal end of the second portion comprises a second rack portion comprising a plurality of raised rails and indented grooves; and the second through aperture extends through the second rack portion.

12. The expandable plate of claim 1, comprising:

a rotatable end cap, and wherein the first portion comprises a first bone screw aperture configured to orient a first bone screw in a target trajectory and the second portion comprises a second bone screw aperture configured to orient a second bone screw in a target trajectory.

13. The expandable plate of claim 12, wherein, in a first position, the end cap is positioned such that the first bone screw aperture and second bone screw aperture are accessible.

14. The expandable plate of claim 13, wherein, in a second position, the end cap is positioned such that the first bone screw aperture and second bone screw aperture are blocked.

15. The expandable plate of claim 1, wherein:

the expandable body comprises a longitudinal axis crossing over a center of the expandable body in the longitudinal direction, and the expandable body is substantially symmetrical with respect to the longitudinal axis.

16. The expandable plate of claim 1, wherein:

the intervertebral spinal implant comprises an expansion mechanism including at least one set screw configured to expand the intervertebral spinal implant, and the locking screw includes a central aperture extending therethrough and being configured to allow a drive tool to extend through the central aperture for rotating the at least one set screw.

17. A method for installing an expandable plate and an expandable spinal implant, comprising:

providing an expandable spinal implant;

providing an expandable plate, the expandable plate including:

an expandable body having a thickness in a proximal-to-distal direction between a proximal end and a distal end, a width in a widthwise direction, and a height in a longitudinal direction, the expandable body comprising a first portion and a second portion;

wherein the first portion includes:

a receiving cavity facing the proximal end, a first bone screw aperture, and a first through aperture extending in the proximal-to-distal direction, wherein the second portion includes:

a lower end having a size and shape that corresponds to the receiving cavity, a second bone screw aperture, and a second through aperture extending in the proximal-to-distal direction, a locking screw; and a nut, wherein, in a locked position, the locking screw extends through the first through aperture and second through aperture, and is secured to the nut, and wherein the expandable plate is configured to couple to a face of the expandable spinal implant via the locking screw;

inserting the expandable spinal implant between adjacent boney structures;

installing a first bone screw that extends through either one of the first bone screw aperture and second bone screw aperture; and coupling the expandable plate to the face of the expandable spinal implant via the locking screw.

18. The method of claim 17, further comprising:

expanding the expandable plate; and expanding the expandable spinal implant.

19. The method of claim 17, further comprising positioning a lip portion of the expandable plate against an apophyseal ring of a patient.

20. The method of claim 17, further comprising removing a degenerative portion of a patient anatomy.

* * * * *